(12) United States Patent
Van Eenennaam et al.

(10) Patent No.: US 10,808,030 B2
(45) Date of Patent: Oct. 20, 2020

(54) ANTI-HCTLA-4 ANTIBODIES

(71) Applicant: ADURO BIOTECH HOLDINGS, EUROPE B.V., Oss (NL)

(72) Inventors: Hans Van Eenennaam, Oss (NL); Andrea Van Elsas, Oss (NL); Joost Kreijtz, Oss (NL); David Lutje Hulsik, Oss (NL); Paul Vink, Oss (NL)

(73) Assignee: ADURO BIOTECH HOLDINGS, EUROPE B.V., Oss (NL)

( * ) Notice: Subject to any disclaimer, the term of this patent is extended or adjusted under 35 U.S.C. 154(b) by 248 days.

(21) Appl. No.: 15/665,858

(22) Filed: Oct. 2, 2017

(65) Prior Publication Data

US 2018/0037654 A1 Feb. 8, 2018

(30) Foreign Application Priority Data

Aug. 2, 2016 (NL) ...................... 2017270

(51) Int. Cl.
*A61K 39/00* (2006.01)
*C07K 16/28* (2006.01)
*C07K 16/30* (2006.01)

(52) U.S. Cl.
CPC .......... *C07K 16/2818* (2013.01); *C07K 16/30* (2013.01); *A61K 39/00* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/732* (2013.01); *C07K 2317/734* (2013.01); *C07K 2317/76* (2013.01); *C07K 2317/92* (2013.01)

(58) Field of Classification Search
CPC ................................................ A61K 2039/505
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | Decant, Jr. et al. | |
| 4,447,233 A | 5/1984 | Mayfield | |
| 4,487,603 A | 12/1984 | Harris | |
| 4,596,556 A | 6/1986 | Morrow et al. | |
| 4,790,824 A | 12/1988 | Morrow et al. | |
| 4,816,567 A | 3/1989 | Cabilly et al. | |
| 4,941,880 A | 7/1990 | Burns | |
| 4,946,778 A | 8/1990 | Ladner et al. | |
| 5,064,413 A | 11/1991 | McKinnon et al. | |
| 5,225,539 A | 7/1993 | Winter | |
| 5,260,203 A | 11/1993 | Ladner et al. | |
| 5,312,335 A | 5/1994 | McKinnon et al. | |
| 5,383,851 A | 1/1995 | McKinnon et al. | |
| 5,399,163 A | 3/1995 | Peterson et al. | |
| 5,413,923 A | 5/1995 | Kucherlapati et al. | |
| 5,530,101 A | 6/1996 | Queen et al. | |
| 5,532,210 A | 7/1996 | Shen | |
| 5,545,806 A | 8/1996 | Lonberg et al. | |
| 5,569,825 A | 10/1996 | Lonberg et al. | |
| 5,571,698 A | 11/1996 | Ladner et al. | |
| 5,585,089 A | 12/1996 | Queen et al. | |
| 5,624,821 A | 4/1997 | Winter et al. | |
| 5,625,126 A | 4/1997 | Lonberg et al. | |
| 5,633,425 A | 5/1997 | Lonberg et al. | |
| 5,637,483 A | 6/1997 | Dranoff et al. | |
| 5,648,260 A | 7/1997 | Winter et al. | |
| 5,661,016 A | 8/1997 | Lonberg et al. | |
| 5,677,425 A | 10/1997 | Bodmer et al. | |
| 5,693,762 A | 12/1997 | Queen et al. | |
| 5,714,350 A | 2/1998 | Co et al. | |
| 5,807,715 A | 9/1998 | Morrison et al. | |
| 5,814,318 A | 9/1998 | Lonberg et al. | |
| 5,869,046 A | 2/1999 | Presta et al. | |
| 5,904,920 A | 5/1999 | Dranoff et al. | |
| 5,932,448 A | 8/1999 | Tso et al. | |
| 5,939,598 A | 8/1999 | Kucherlapati et al. | |
| 5,985,290 A | 11/1999 | Jaffee et al. | |
| 6,005,079 A | 12/1999 | Casterman et al. | |
| 6,033,674 A | 3/2000 | Jaffee et al. | |
| 6,057,098 A | 5/2000 | Buechler et al. | |
| 6,096,002 A | 8/2000 | Landau | |
| 6,121,022 A | 9/2000 | Presta et al. | |
| 6,129,914 A | 10/2000 | Weiner et al. | |
| 6,165,745 A | 12/2000 | Ward et al. | |
| 6,194,551 B1 | 2/2001 | Idusogie et al. | |
| 6,277,368 B1 | 8/2001 | Hiserodt et al. | |

(Continued)

FOREIGN PATENT DOCUMENTS

EP 0154316 A2 9/1985
EP 0256055 B1 8/1991

(Continued)

OTHER PUBLICATIONS

Barber et al. (Sci Transl Med. Jan. 16, 2019; 11 (475); pp. 1-7).*
Yshii et al. (Brain. Nov. 1, 2016; 139 (11): 2923-2934).*
Michot et al. (Eur. J. Cancer. Feb. 2016.; 54: 139-148).*
AlFadhli et al. (Gene. Jan. 25, 2014; 534 (2): 307-12).*
Chang et al., A Phase I Trial of Tumor Lysate-Pulsed Dendritic Cells in the Treatment of Advanced Cancer. Clin Cancer Res. Apr. 2002;8(4):1021-1032.
Chappel et al, Identification of a Secondary Fc gamma RI Binding Site within a Genetically Engineered Human IgG Antibody. J Biol Chem. Nov. 25, 1993;268(33):25124-25131.

(Continued)

*Primary Examiner* — Stephen L Rawlings
(74) *Attorney, Agent, or Firm* — Acuity Law Group, PC; Michael A. Whittaker

(57) ABSTRACT

The invention relates to new anti-hCTLA-4 antibodies that bind to a different epitope than prior art anti-CTLA4 antibodies, methods to produce these antibodies and therapeutic and diagnostic uses of these antibodies. These antibodies show a similar affinity for the CTLA4 antigen and they are also able to block the binding of CTLA4 to CD80 and/or CD86.

10 Claims, 7 Drawing Sheets

Specification includes a Sequence Listing.

(56) References Cited

U.S. PATENT DOCUMENTS

| | | |
|---|---|---|
| 6,277,375 B1 | 8/2001 | Ward |
| 6,329,511 B1 | 12/2001 | Vasquez et al. |
| 6,331,415 B1 | 12/2001 | Cabilly et al. |
| 6,350,445 B1 | 2/2002 | Jaffee et al. |
| 6,350,861 B1 | 2/2002 | Co et al. |
| 6,620,135 B1 | 9/2003 | Weston et al. |
| 6,946,292 B2 | 9/2005 | Kanda et al. |
| 7,029,872 B2 | 4/2006 | Gerngross |
| 7,125,689 B2 | 10/2006 | Carr et al. |
| 7,214,775 B2 | 5/2007 | Hanai et al. |
| 7,449,308 B2 | 11/2008 | Gerngross et al. |
| 7,592,326 B2 | 9/2009 | Karaolis |
| 7,709,458 B2 | 5/2010 | Karaolis et al. |
| 2002/0086014 A1 | 7/2002 | Korman et al. |
| 2002/0150588 A1 | 10/2002 | Allison et al. |
| 2005/0281783 A1 | 12/2005 | Kinch et al. |
| 2006/0040887 A1 | 2/2006 | Karaolis |
| 2008/0286296 A1 | 11/2008 | Ebensen et al. |
| 2010/0150946 A1 | 6/2010 | Jooss et al. |
| 2012/0041057 A1 | 2/2012 | Jones et al. |
| 2014/0205653 A1 | 7/2014 | Dubensky et al. |
| 2015/0056224 A1 | 2/2015 | Dubensky et al. |

FOREIGN PATENT DOCUMENTS

| | | |
|---|---|---|
| EP | 0323997 B1 | 4/1993 |
| EP | 0338841 b1 | 3/1995 |
| EP | 0216846 B2 | 4/1995 |
| EP | 0401384 B1 | 3/1996 |
| EP | 404097 B1 | 9/1996 |
| EP | 1229125 A1 | 8/2002 |
| WO | 8801649 A1 | 3/1988 |
| WO | 9311161 A1 | 6/1993 |
| WO | 940678 A1 | 3/1994 |
| WO | 9425591 A1 | 11/1994 |
| WO | 9429351 A2 | 12/1994 |
| WO | 9633735 A1 | 10/1996 |
| WO | 9634093 A1 | 10/1996 |
| WO | 9824893 A2 | 6/1998 |
| WO | 0042072 A2 | 7/2000 |
| WO | 0061739 A1 | 10/2000 |
| WO | 0114424 A2 | 3/2001 |
| WO | 0231140 A1 | 4/2002 |
| WO | 03011878 A2 | 2/2003 |
| WO | 03086310 A2 | 10/2003 |
| WO | 2005120571 A2 | 12/2005 |
| WO | 2006014679 A1 | 2/2006 |
| WO | 2006066568 A2 | 6/2006 |
| WO | 2007054279 A2 | 5/2007 |
| WO | 2007113648 A2 | 10/2007 |
| WO | 2009100140 A1 | 8/2009 |
| WO | 2012068360 A1 | 5/2012 |
| WO | 2014093936 A1 | 6/2014 |
| WO | 2014179335 A1 | 11/2014 |
| WO | 2014179760 A1 | 11/2014 |
| WO | 2014189805 A1 | 11/2014 |
| WO | 2016096174 A1 | 6/2016 |
| WO | 2017011444 A1 | 1/2017 |
| WO | 2017027645 A1 | 2/2017 |
| WO | 2017027646 A1 | 2/2017 |

OTHER PUBLICATIONS

Chen et al., Immunodominant CD4+ responses identified in a patient vaccinated with full-length NY-ESO-1 formulated with ISCOMATRIX adjuvant. Proc Natl Acad Sci U S A. Jan. 22, 2004;101(25):9363-9368.

Chen et al., Influence of Histidine on the Stability and Physical Properties of a Fully Human Antibody in Aqueous and Solid Forms. Pharm Res. Dec. 2003;20(12):1952-1960.

Chern et al., Glycoprotein B Subtyping of Cytomegalovirus (CMV) in the Vitreous of Patients with AIDS and CMV Retinitis. J Infect Dis. Oct. 1998;178(4):1149-1153.

Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.

Choi et al., Use of combinatorial genetic libraries to humanize N-linked glycosylation in the yeast *Pichia pastoris*. Proc Natl Acad Sci U S A. Apr. 29, 2003;100(9):5022-5027 (incl correction page for 7 pages total).

Chothia and Lesk, Canonical Structures for the Hypervariable Regions of Immunoglobulins. J Mol Biol. Aug. 20, 1987;196(4):901-917.

Chothia et al., Conformations of immunoglobulin hypervariable regions. Nature. Dec. 21-28, 1989;342(6252):877-883.

Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.

Clements et al., Adenomatous Polyposis Coli/ß-Catenin Interaction and Downstream Targets: Altered Gene Expression in Gastrointestinal Tumors. Clin Colorectal Cancer. Aug. 2003;3(2):113-120.

Clifton et al., A chlamydial type III translocated protein is tyrosine-phosphorylated at the site of entry and associated with recruitment of actin. Proc Natl Acad Sci USA. Jul. 6, 2004;101(27):10166-10171.

Clinton et al., A Comparative Study of Four Serological Tumor Markers for the Detection of Breast Cancer. Biomed Sci Instrum. 2003;39:408-414.

Cobaleda et al., A primitive hematopoietic cell is the target for the leukemic transformation in human Philadelphia-positive acute lymphoblastic leukemia. Blood. Feb. 1, 2000;95(3):1007-1013.

Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.

Colbere-Garapin et al., A New Dominant Hybrid Selective Marker for Higher Eukaryotic Cells. J Mol Biol. Jul. 25, 1981;150(1):1-14.

Collins et al., The Interaction Properties of Costimulatory Molecules Revisited. Immunity. Aug. 2002;17(2):201-210.

Conrath et al., Camel Single-domain Antibodies as Modular Building Units in Bispecific and Bivalent Antibody Constructs. J Biol Chem. Mar. 9, 2001;276(10):7346-7350.

Crouse et al., Expression and Amplification of Engineered Mouse Dihydrofolate Reductase Minigenes, Mol Cell Biol. Feb. 1983;3(2):257-266.

Cwirla et al., Peptides on phage: A vast library of peptides for identifying ligands. Proc Natl Acad Sci U S A. Aug. 1990;87(16):6378-6382.

Dalerba et al., MAGE, BAGE and GAGE gene expression in human rhabdomyosarcomas. Int J Cancer. Jul. 1, 2001;93(1):85-90.

Damasus-Awatai and Freeman-Wang, Human papilloma virus and cervical screening. Curr Opin Obstet Gynecol. Dec. 2003;15(6):473-477.

Das et al., Evaluation of a Western Equine Encephalitis recombinant E1 protein for protective immunity and diagnostics. Antiviral Res. Nov. 2004;64(2):85-92.

David and Reisfeld, Protein Iodination with Solid State Lactoperoxidase. Biochemistry. Feb. 26, 1974;13(5):1014-1021.

Davies et al., Characterisation of a recombinant Fv fragment of anti-MUC1 antibody HMFG1. Cancer Lett. Jul. 29, 1994;82(2):179-184.

Dayhoff et al., A Model of Evolutionary Change in Proteins. Atlas of Protein Sequence and Structure, M.O. Dayhoff (ed.), 1978; 5(suppl. 3): 345-352.

De Backer et al., Characterization of the GAGE Genes That Are Expressed in Various Human Cancers and in Normal Testis. Cancer Res. Jul. 1, 1999;59(13):3157-3165.

De Bruin et al., Selection of high-affinity phage antibodies from phage display libraries. Nat Biotechnol. Apr. 1999;17(4):397-399.

De Villiers et al., Classification of papillomaviruses. Virology. Jun. 20, 2004;324(1):17-24.

Dembo et al., Limit distribution of Maximal Non-Aligned Two-Sequence Segmental Score. Ann Prob. 1994;22:2022-2039 (pp. 1-16).

(56) References Cited

OTHER PUBLICATIONS

Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64(10):3653-3660.
Desmyter et al., Antigen Specificity and High Affinity Binding Provided by One Single Loop of a Camel Single-domain Antibody. J Biol Chem. Jul. 13, 2001;276(28):26285-26290.
Devlin et al., Random Peptide Libraries: A Source of Specific Protein Binding Molecules. Science. Jul. 27, 1990;249 (4967):404-406.
Disis and Cheever, HER-2/Neu Protein: A Target for Antigen-Specific Immunotherapy of Human Cancer. Adv Cancer Res. 1997;71:343-371.
Disis et al., Humoral Epitope-Spreading Following Immunization with a HER-2/neu Peptide Based Vaccine in Cancer Patients. J Clin Immunol. Sep. 2004;24(5):571-578.
Dosaka-Akita et al., Expression of N-Acetylglucosaminyltransferase V Is Associated with Prognosis and Histology in Non-Small Cell Lung Cancers. Clin Cancer Res. Mar. 1, 2004;10(5):1773-1779.
Duxbury et al., CEACAM6 as a novel target for indirect type 1 immunotoxin-based therapy in pancreatic adenocarcinoma. Biochem Biophys Res Commun. May 7, 2004;317(3):837-843.
Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbiol. May 1997;35(5):1122-1130.
Engels et al., Serologic Evidence for Exposure to Simian Virus 40 in North American Zoo Workers. J Infect Dis. Dec. 15, 2004;190(12):2065-2069.
Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.
Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.
Estrada-Franco et al., Venezuelan Equine Encephalitis Virus, Southern Mexico. Emerg Infect Dis. Dec. 2004;10(12):2113-2121.
Eton et al., Active Immunotherapy With Ultraviolet B-Irradiated Autologous Whole Melanoma Cells Plus DETOX in Patients With Metastatic Melanoma. Clin Cancer Res. Mar. 1998;4(3):619-627.
Everts et al., Selective Intracellular Delivery of Dexamethasone into Activated Endothelial Cells Using an E-Selectin-Directed Immunoconjugate. J Immunol. Jan. 15, 2002;168(2):883-889.
Fang et al., Expression of Dnmt1, demethylase, MeCP2 and methylation of tumor-related genes in human gastric cancer. World J Gastroenterol. Dec. 1, 2004;10(23):3394-3398.
Faure et al., Inducible Hsp70 as Target of Anticancer Immunotherapy: Identification of HLA-A*0201-Restricted Epitopes. Int J Cancer. Mar. 1, 2004;108(6):863-870.
Fleishhauer et al., The DAM Gene Family Encodes a New Group of Tumor-specific Antigens Recognized by Human Leukocyte Antigen A1-restricted Cytotoxic T Lymphocytes. Cancer Res. Jul. 15, 1998;58(14):2969-2972.
Fong et al., Altered peptide ligand vaccination with Flt3 ligand expanded dendritic cells for tumor immunotherapy. Proc Natl Acad Sci U S A. Jul. 17, 2001;98(15):8809-8814.
Foote and Winter, Antibody framework residues affecting the conformation of the hypervariable loops. J Mol Biol. Mar. 20, 1992;224(2):487-499.
Frankle et al., Neuroreceptor Imaging in Psychiatry: Theory and Applications. Int Rev Neurobiol. 2005;67:385-440.
Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.
Mack et al., A small bispecific antibody construct expressed as a functional single-chain molecule with high tumor cell cytotoxicity. Proc Natl Acad Sci U S A. Jul. 18, 1995;92(15):7021-7025.
Madden et al., Applications of Network BLAST Server. Methods Enzymol. 1996;266:131-141.
Malecki et al., Molecular immunolabeling with recombinant single-chain variable fragment (scFv) antibodies designed with metal-binding domains. Proc Natl Acad Sci U S A. Jan. 8, 2002;99(1):213-218.
Mandruzzato et al., A CASP-8 Mutation Recognized by Cytolytic T Lymphocytes on a Human Head and Neck Carcinoma. J Exp Med. Aug. 29, 1997;186(5):785-793.
Marshall, Glycoproteins. Annu Rev Biochem. 1972;41:673-702.
Matsumoto et al., Expression of the SART-1 antigens in uterine cancers. Jpn J Cancer Res. Dec. 1998;89(12):1292-1295.
Matsushita et al., Preferentially Expressed Antigen of Melanoma (PRAME) in the Development of Diagnostic and Therapeutic Methods for Hematological Malignancies. Leuk Lymphoma. Mar. 2003;44(3):439-444.
Mayo et al., Mdm-2 Phosphorylation by DNA-dependent Protein Kinase Prevents Interaction with p53. Cancer Res. Nov. 15, 1997;57(22):5013-5016.
McCool et al., Roles of calreticulin and calnexin during mucin synthesis in LS180 and HT29/A1 human colonic adenocarcinoma cells. Biochem J. Aug. 1, 1999;341 ( Pt 3):593-600.
Mendez et al., Functional transplant of megabase human immunoglobulin loci recapitulates human antibody response in mice. Nat Genet. Feb. 1997;15(2):146-156.
Menne et al., A comparison of signal sequence prediction methods using a test set of signal peptides.—Applications Note. Bioinformatics. Aug. 2000;16(8):741-742.
Merchant et al., The LMP2A ITAM Is Essential for Providing B Cells with Development and Survival Signals In Vivo. J Virol. Oct. 2000;74(19):9115-9124.
Meyaard et al., LAIR-1, a Novel Inhibitory Receptor Expressed on Human Mononuclear Leukocytes. Immunity. Aug. 1997;7(2):283-290.
Milgrom et al., Treatment of Allergic Asthma with Monoclonal Anti-IgE Antibody. For the rhuMAb-E25 Study Group. N Engl J Med. Dec. 23, 1999;341(26):1966-1973.
Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.
Mimura et al., The influence of glycosylation on the thermal stability and effector function expression of human IgG1-Fc: properties of a series of truncated glycoforms. Mol Immunol. Aug.-Sep. 2000;37(12-13):697-706.
Molijn et al., Molecular diagnosis of human papillomavirus (HPV) infections. J Clin Virol. Mar. 2005;32 Suppl 1: S43-51.
Moreau-Aubry et al., A Processed Pseudogene Codes for a New Antigen Recognized by a Cd8+ T Cell Clone on Melanoma. J Exp Med. May 1, 2000;191(9):1617-1624.
Morgan and Anderson, Human gene therapy. Annu Rev Biochem. 1993;62:191-217.
Morrison et al., Chimeric human antibody molecules: mouse antigen-binding domains with human constant region domains. Proc Natl Acad Sci USA. Nov. 1984;81(21):6851-6855.
Morrison, Transfectomas Provide Novel Chimeric Antibodies. Science. Sep. 20, 1985;229(4719):1202-1207.
Morse et al., A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen. Clin Cancer Res. Jun. 1999;5(6):1331-1338.
Mukhopadhyay et al., A structural perspective of the flavivirus life cycle. Nat Rev Microbiol. Jan. 2005;3(1):13-22.
Mulders et al., Tumor antigens and markers in renal cell carcinoma. Urol Clin North Am. Aug. 2003;30(3):455-465.
Muller et al., MeCP2 and MBD2 expression in human neoplastic and non-neoplastic breast tissue and its association with oestrogen receptor status. Br J Cancer Nov. 17, 2003;89(10):1934-1939.
Mulligan et Berg, Selection for animal cells that express the *Escherichia coli* gene coding for xanthine-guanine phosphoribosyltransferase. Proc Natl Acad Sci U S A. Apr. 1981;78(4):2072-2076.

(56) References Cited

OTHER PUBLICATIONS

Mulligan, The Basic Science of Gene Therapy. Science. May 14, 1993;260(5110):926-932.
Muminova et al., Characterization of human mesothelin transcripts in ovarian and pancreatic cancer. BMC Cancer May 12, 2004;4:19.
Murray et al., Epitope Affinity Chromatography and Biophysical Studies of Monoclonal Antibodies and Recombinant Antibody Fragments. J Chromatogr Sci. Jul. 2002;40(6):343-349.
Muyldermans et al., Recognition of antigens by single-domain antibody fragments: the superfluous luxury of paired domains. Trends Biochem Sci. Apr. 2001;26(4):230-235.
Nair et al., Induction of cytotoxic T cell responses and tumor immunity against unrelated tumors using telomerase reverse transcriptase RNA transfected dendritic cells. Nat Med. Sep. 2000;6(9):1011-1017.
Nakatsura et al., Cellular and humoral immune responses to a human pancreatic cancer antigen, coactosin-like protein, originally defined by the SEREX method. Eur J Immunol. Mar. 2002;32(3):826-836.
Nakatsura et al., Glypican-3, overexpressed specifically in human hepatocellular carcinoma, is a novel tumor marker. Biochem Biophys Res Commun. Jun. 20, 2003;306(1):16-25.
Nakatsura et al., Identification of Glypican-3 as a Novel Tumor Marker for Melanoma. Clin Cancer Res. Oct. 1, 2004;10(19):6612-6621.
Nechansky et al., Compensation of endogenous IgG mediated inhibition of antibody-dependent cellular cytotoxicity by glyco-engineering of therapeutic antibodies. Mol Immunol. Mar. 2007;44(7):1815-1817.
Nett et al., A combinatorial genetic library approach to target heterologous glycosylation enzymes to the endoplasmic reticulum or the Golgi apparatus of Pichia pastoris. Yeast Mar. 2011;28(3):237-252.
Neumann et al., Identification of an HLA-DR-restricted peptide epitope with a promiscuous binding pattern derived from the cancer testis antigen HOM-MEL-40/SSX2. Int J Cancer. Nov. 20, 2004;112(4):661-668.
Nicoletto et al., BRCA-1 and BRCA-2 mutations as prognostic factors in clinical practice and genetic counselling. Cancer Treat Rev. Oct. 2001;27(5):295-304.
Nygren, Conjugation of Horseradish Peroxidase to Fab Fragments with Different Homobifunctional and Heterobifunctional Cross-Linking Reagents. A Comparative Study. J Histochem Cytochem. May 1982;30(5):407-412.
Obeid et al., Vaccines, Adjuvants, and Dendritic Cell Activators—Current Status and Future Challenges. Semin Oncol. Aug. 2015; 42(4): 549-561.
Oberste et al., Evidence for Frequent Recombination within Species Human Enterovirus B Based on Complete Genomic Sequences of All Thirty-Seven Serotypes. J Virol. Jan. 2004;78(2):855-867.
Oberthuer et al., The Tumor-Associated Antigen PRAME Is Universally Expressed in High-Stage Neuroblastoma and Associated with Poor Outcome. Clin Cancer Res. Jul. 1, 2004;10(13):4307-4313.
O'Hare et al., Transformation of mouse fibroblasts to methotrexate resistance by a recombinant plasmid expressing a prokaryotic dihydrofolate reductase. Proc Natl Acad Sci U S A. Mar. 1981;78(3):1527-1531.
Oliveira-Ferreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.
Orvell et al., Antigenic relationships between six genotypes of the small hydrophobic protein gene of mumps virus. J Gen Virol. Oct. 2002;83(Pt 10):2489-2496.
Otte et al., MAGE-A Gene Expression Pattern in Primary Breast Cancer. Cancer Res. Sep. 15, 2001;61(18):6682-6687.
Oyston and Quarry, Tularemia vaccine: past, present and future. Antonie Van Leeuwenhoek. May 2005;87(4):277-281.
Padilla et al., Imaging of the varicella zoster virion in the viral highways: Comparison with herpes simplex viruses 1 and 2, cytomegalovirus, pseudorabies virus, and human herpes viruses 6 and 7. J Med Virol. 2003;70 Suppl 1:S103-S110.
Pain and Surolia, Preparation of protein A-peroxidase monoconjugate using a heterobifunctional reagent, and its use in enzyme immunoassays. J Immunol Methods. 1981;40(2):219-230.
Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.
Isherwood et al., Vaccination strategies for Francisella tularensis. Adv Drug Deliv Rev. Jun. 17, 2005;57(9):1403-1414.
Ito et al., Prostate Carcinoma Detection and Increased Prostate-Specific Antigen Levels after 4 Years in Dutch and Japanese Males Who Had No Evidence of Disease at Initial Screening. Cancer. Jan. 15, 2005;103(2):242-250.
Jainkittivong and Langlais, Herpes B virus infection. Oral Surg Oral Med Oral Pathol Oral Radiol Endod. Apr. 1998;85(4):399-403.
Jamieson et al., Human Torovirus: A New Nosocomial Gastrointestinal Pathogen. J Infect Dis. Nov. 1998;178(5):1263-1269.
Jansen and Shaw, Human Papillomavirus Vaccines and Prevention of Cervical Cancer. Annu Rev Med. 2004;55:319-331.
Jansson et al., A Theoretical Framework for Quantitative Analysis of the Molecular Basis of Costimulation. J Immunol. Aug. 1, 2005;175(3):1575-1585.
Johnson et al., 3-O-Desacyl Monophosphoryl Lipid A Derivatives: Synthesis and Immunostimulant Activities. J Med Chem. Nov. 4, 1999;42(22):4640-4649.
Jung et al., Strategies Against Human Papillomavirus Infection and Cervical Cancer. J Microbiol. Dec. 2004;42(4):255-266.
Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.
Kabat et al., Unusual Distributions of Amino Acids in Complementarity determining (Hypervariable) Segments of Heavy and Light Chains of Immunoglobulins and Their Possible Roles in Specificity of Antibody-combining Sites. J Biol Chem. Oct. 10, 1977;252(19):6609-6616.
Kabat, The Structural Basis of Antibody Complementarity. Adv Protein Chem. 1978;32:1-75.
Kaithamana et al., Induction of Experimental Autoimmune Graves' Disease in BALB/c Mice. J Immunol. Nov. 1, 1999;163(9):5157-5164.
Karlin and Altschul, Applications and statistics for multiple high-scoring segments in molecular sequences. Proc Natl Acad Sci USA Jun. 15, 1993;90(12):5873-5877.
Karlin and Altschul, Methods for assessing the statistical significance of molecular sequence features by using general scoring schemes. Proc Natl Acad Sci U S A. Mar. 1990;87(6):2264-2268.
Kaufman et al., Parvovirus B19 does not bind to membrane-associated globoside in vitro. Virology. Feb. 5, 2005;332(1):189-198.
Kedl et al., Comparative Sequence Analysis of the Reovirus S4 Genes from 13 Serotype 1 and Serotype 3 Field Isolates. J Virol. Jan. 1995;69(1):552-559.
Kim et al., Comparison of HPV DNA vaccines employing intracellular targeting strategies. Gene Ther. Jun. 2004;11(12):1011-1018.
Kita et al., Does IgE Bind to and Activate Eosinophils from Patients with Allergy? J Immunol. Jun. 1, 1999;162(11):6901-6911.
Kohler, Immunoglobulin chain loss in hybridoma lines. Proc Natl Acad Sci U S A. Apr. 1980;77(4):2197-2199.
Kostelny et al., Formation of a bispecific antibody by the use of leucine zippers. J Immunol. Mar. 1, 1992;148(5):1547-1553.
Krishnamurthy and Manning, The Stability Factor: Importance in Formulation Development. Curr Pharm Biotechnol. Dec. 2002;3(4):361-371.
Krummel and Allison, CD28 and CTLA-4 have opposing effects on the response of T cells to stimulation. J Exp Med. Aug. 1, 1995;182(2):459-465.
Krzych et al., T lymphocytes from volunteers immunized with irradiated Plasmodium falciparum sporozoites recognize liver and blood stage malaria antigens. J Immunol. Oct. 15, 1995;155(8):4072-4077.

(56) References Cited

OTHER PUBLICATIONS

Kubuschok et al., Expression of cancer testis antigens in pancreatic carcinoma cell lines, pancreatic adenocarcinoma and chronic pancreatitis. Int J Cancer Apr. 20, 2004;109(4):568-575.

Kumamuru et al., T-cell receptor Vbeta gene usage by T cells reactive with the tumor-rejection antigen SART-1 in oral squamous cell carcinoma. Int J Cancer. Feb. 20, 2004;108(5):686-695.

Labrijn et al., Efficient generation of stable bispecific IgG1 by controlled Fab-arm exchange. Proc Natl Acad Sci U S A. Mar. 26, 2013;110(13):5145-5150.

Laheru and Jaffee, Immunotherapy for pancreatic cancer—science driving clinical progress. Nat Rev Cancer. Jun. 2005;5(6):459-467.

Larkin et al., Combined Nivolumab and Ipilimumab or Monotherapy in Untreated Melanoma. N Engl J Med. Jul. 2, 2015;373(1):13-34.

Lazar et al, Engineered antibody Fc variants with enhanced effector function. Proc Natl Acad Sci U S A. Mar. 14, 2006;103(11):4005-4010.

Le Doussal et al., Enhanced in vivo targeting of an asymmetric bivalent hapten to double-antigen-positive mouse B cells with monoclonal antibody conjugate cocktails. J Immunol. Jan. 1, 1991;146(1):169-175.

Lee et al., Immunomic analysis of human sarcoma Proc Natl Acad Sci U S A. Mar. 4, 2003;100(5):2651-2656.

Lee et al., Prolonged Circulating Lives of Single-Chain Fv Proteins Conjugated with Polyethylene Glycol: A Comparison of Conjugation Chemistries and Compounds. Bioconjug Chem. Nov.-Dec. 1999;10(6):973-981.

Lee et al., Structural basis of checkpoint blockade by monoclonal antibodies in cancer immunotherapy. Nat Commun. Oct. 31, 2016;7:13354 (10 Pages).

Lee, Mass spectrometric analysis of cross-linking sites for the structure of proteins and protein complexes. Mol Biosyst. Aug. 2008;4(8):816-823.

Lefranc et al., IMGT, the international ImMunoGeneTics database. Nucleic Acids Res. Jan. 1, 1999;27(1):209-212.

Li et al., Advanced Glycation End Products Induce Tubular Epithelial-Myofibroblast Transition through the RAGE-ERK1/2 MAP Kinase Signaling Pathway. Am J Pathol. Apr. 2004;164(4):1389-1397.

Li et al., Expression Profile of Cancer-Testis Genes in 121 Human Colorectal Cancer Tissue and Adjacent Normal Tissue. Clin Cancer Res. Mar. 1, 2005;11(5):1809-1814.

Li et al., Optimization of humanized IgGs in glycoengineered Pichia pastoris. Nat Biotechnol. Feb. 2006;24(2):210-215.

Liang et al., Microvessel density, cyclo-oxygenase 2 expression, K-ras mutation and p53 overexpression in colonic cancer Br J Surg. Mar. 2004;91(3):355-361.

Lim et al., Molecular and phenotypic spectrum of de novo Philadelphia positive acute leukemia. Int J Mol Med. Dec. 1999;4(6):665-667.

Lin et al., Melanoma-Associated Antigens in Esophageal Adenocarcinoma Identification of Novel MAGE-A10 Splice Variants. Clin Cancer Res. Sep. 1, 2004;10(17):5708-5716.

Lipsky, et al., Infliximab and methotrexate in the treatment of rheumatoid arthritis. Anti-Tumor Necrosis Factor Trial in Rheumatoid Arthritis with Concomitant Therapy Study Group. N Engl J Med. Nov. 30, 2000;343(22):1594-1602.

Liu and Blumhardt, Randomised, double blind, placebo controlled study of interferon β-1a in relapsing-remitting multiple sclerosis analysed by area under disability/time curves. J Neurol Neurosurg Psychiatry. Oct. 1999;67(4):451-456.

Lodmell et al., DNA vaccination of mice against rabies virus: effects of the route of vaccination and the adjuvant monophosphoryl lipid A (MPL). Vaccine. Jan. 6, 2000;18(11-12):1059-1066.

Logan and Shenk, Adenovirus tripartite leader sequence enhances translation of mRNAs late after infection. Proc Natl Acad Sci U S A. Jun. 1984;81(12):3655-3659.

Lonberg and Huszar, Human Antibodies From Transgenic Mice. Int Rev Immunol. 1995;13(1):65-93.

Long, Regulation of immune responses through inhibitory receptors. Annu Rev Immunol. 1999;17:875-904.

Lowy et al., Isolation of transforming DNA: Cloning the hamster aprt gene. Cell. Dec. 1980;22(3):817-823.

Lucas et al., MAGE-B5, MAGE-B6, MAGE-C2, and MAGE-C3: four new members of the MAGE family with tumor-specific expression. Int J Cancer. Jul. 1, 2000;87(1):55-60.

Abutaily et al., Cadherins, catenins and APC in pleural malignant mesothelioma. J Pathol. Nov. 2003;201(3):355-362.

Aguilar et al., Endemic Venezuelan equine encephalitis in northern Peru. Emerg Infect Dis. May 2004;10(5):880-888.

Ahn et al., All CVB Serotypes and Clinical Isolates Induce Irreversible Cytopathic Effects in Primary Cardiomyocytes. J Med Virol. Feb. 2005;75(2):290-294.

Alegre et al., T-cell regulation by CD28 and CTLA-4. Nat Rev Immunol. Dec. 2001;1(3):220-228.

Alexander and Hughes, Monitoring of IgG Antibody Thermal Stability by Micellar Electrokinetic Capillary Chromatography and Matrix-Assisted Laser Desorpt ion/Ionizat ion Mass Spectrometry. Anal Chem. Oct. 15, 1995;67(20):3626-3632.

Altschul et al., Basic Local Alignment Search Tool. J Mol Biol. Oct. 5, 1990;215(3):403-410.

Altschul et al., Gapped BLAST and PSI-BLAST: a new generation of protein database search programs. Nucleic Acids Res. Sep. 1, 1997;25(17):3389-3402.

Altschul et al., Protein database searches using compositionally adjusted substitution matrices. FEBS J. Oct. 2005;272(20):5101-5109.

Altschul, A Protein Alignment Scoring System Sensitive at All Evolutionary Distances. J Mol Evol. Mar. 1993;36(3):290-300.

Altschul, Amino Acid Substitution Matrices from an Information Theoretic Perspective. J Mol Biol. Jun. 5, 1991;219(3):555-565.

Altschul, Evaluating the statistical significance of multiple distinct local alignments. In Theoretical and Computational Methods in Genome Research (S. Suhai, ed.), 1997:1-14.

Altwein and Luboldt, Prognostic factors for carcinoma of the prostate. Urol Int. 1999;63(1):62-71.

Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. May 2005;64(5):780-782.

Andersen and thor Straten, Survivin—a universal tumor antigen. Histol Histopathol. Apr. 2002;17(2):669-675.

Angal et al., A single amino acid substitution abolishes the heterogeneity of chimeric mouse/human (IgG4) antibody. Mol Immunol. Jan. 1993;30(1):105-108.

Argani et al., Discovery of New Markers of Cancer through Serial Analysis of Gene Expression: Prostate Stem Cell Antigen Is Overexpressed in Pancreatic Adenocarcinoma. Cancer Res. Jun. 1, 2001;61(11):4320-4324.

Arora et al., Identification of Differentially Expressed Genes in Oral Squamous Cell Carcinoma. Mol Carcinog. Feb. 2005;42(2):97-108.

Attoui et al., Comparative sequence analysis of American, European and Asian isolates of viruses in the genus Coltivirus. J Gen Virol. Oct. 1998;79 ( Pt 10):2481-2489.

Azzoni et al., Differential Transcriptional Regulation of CD161 and a Novel Gene, 197/15a, by IL-2, IL-15, and IL-12 in NK and T Cells. J Immunol. Oct. 1, 1998;161(7):3493-3500.

Baca et al., Antibody Humanization Using Monovalent Phage Display. J Biol Chem. Apr. 18, 1997;272(16):10678-10684.

Baert et al., Influence of Immunogenicity on the Long-Term Efficacy of Infliximab in Crohn's Disease. N Engl J Med. Feb. 13, 2003;348(7):601-608.

Baldridge and Crane, Monophosphoryl Lipid A (MPL) Formulations for the Next Generation of Vaccines. Methods. Sep. 1999;19(1):103-107.

Barbanti-Brodano et al., Simian virus 40 infection in humans and association with human diseases: results and hypotheses. Virology. Jan. 5, 2004;318(1):1-9.

Barbas, Synthetic human antibodies. Nat Med. Aug. 1995;1(8):837-839.

Barthold et al., Infectivity, Disease Patterns, and Serologic Profiles of Reovirus Serotypes 1, 2, and 3 in Infant and Weanling Mice. Lab Anim Sci. Oct. 1993;43(5):425-430.

(56) References Cited

OTHER PUBLICATIONS

Baurain et al., High Frequency of Autologous Anti-Melanoma CTL Directed Against an Antigen Generated by a Point Mutation in a New Helicase Gene. J Immunol. Jun. 1, 2000;164(11):6057-6066.
Bebbington and Hentschel, "The Use of Vectors Based on Gene Amplification for the Expression of Cloned Genes in Mammalian Cells," in DNA Cloning, vol. 3. (Academic Press, New York), 1987 :163-188.
Beniaminovitz et al., Prevention of Rejection in Cardiac Transplantation by Blockade of the Interleukin-2 Receptor with a Monoclonal Antibody. N Engl J Med. Mar. 2, 2000;342(9):613-619.
Benson et al., GenBank. Nucleic Acids Res. Jan. 2013;41(D1):D36-42.
Bevanger et al., Competitive enzyme immunoassay for antibodies to a 43,000-molecular-weight Francisella tularensis outer membrane protein for the diagnosis of tularemia. J Clin Microbiol. May 1989;27(5):922-926.
Bhigjee et al., Sequence of the env gene of some KwaZulu-Natal, South African strains of HTLV type I. AIDS Res Hum Retroviruses. Sep. 1, 1999;15(13):1229-1233.
Biagini et al., Simultaneous measurement of specific serum IgG responses to five select agents. Anal Bioanal Chem. Jun. 2005;382(4):1027-1034.
Bieg et al., GAD65 and Insulin B Chain Peptide (9-23) Are Not Primary Autoantigens in the Type 1 Diabetes Syndrome of the BB Rat. Autoimmunity. 1999;31(1):15-24.
Bischoff and Kolbe, Deamidation of asparagine and glutamine residues in proteins and peptides: structural determinants and analytical methodology. J Chromatogr B Biomed Appl. Dec. 9, 1994;662(2):261-278.
Bitter et al., Expression and Secretion Vectors for Yeast. Methods Enzymol. 1987;153:516-544.
Bondurant et al., Definition of an Immunogenic Region Within the Ovarian Tumor Antigen Stratum Corneum Chymotryptic Enzyme. Clin Cancer Res. May 1, 2005;11(9):3446-3454.
Brennan et al., Preparation of Bispecific Antibodies by Chemical Recombination of Monoclonal Immunoglobulin G1 Fragments. Science. Jul. 5, 1985;229(4708):81-83.
Bretscher, A two-step, two-signal model for the primary activation of precursor helper T cells. Proc Natl Acad Sci U S A. Jan. 5, 1999;96(1):185-190.
Brezniceanu et al., HMGB1 inhibits cell death in yeast and mammalian cells and is abundantly expressed in human breast carcinoma. FASEB J. Jul. 2003;17(10):1295-1297.
Brian and Baric, Coronavirus Genome Structure and Replication. Curr Top Microbiol Immunol. 2005;287:1-30.
Brinkmann et al., Novel Genes in the PAGE and GAGE Family of Tumor Antigens Found by Homology Walking in the dbEST Database. Cancer Res. Apr. 1, 1999;59(7):1445-1448.
Bronte et al., Genetic Vaccination with "Self" Tyrosinase-related Protein 2 Causes Melanoma Eradication but not Vitiligo. Cancer Res. Jan. 15, 2000;60(2):253-258.
Brown et al., Complete Genomic Sequencing Shows that Polioviruses and Members of Human Enterovirus Species C Are Closely Related in the Noncapsid Coding Region. J Virol. Aug. 2003;77(16):8973-8984.
Brown, Variants of B19. Dev Biol (Basel). 2004;118:71-77.
Capdepont et al., New Insights in HTLV-I Phylogeny by Sequencing and Analyzing the Entire Envelope Gene. AIDS Res Hum Retroviruses. Jan. 2005;21(1):28-42.
Capurro et al., Glypican-3: A Novel Serum and Histochemical Marker for Hepatocellular Carcinoma. Gastroenterology. Jul. 2003;125(1):89-97.
Carbone et al., New developments about the association of SV40 with human mesothelioma. Oncogene. Aug. 11, 2003;22(33):5173-5180.
Carpenter et al., Non-Fc Receptor-Binding Humanized Anti-CD3 Antibodies Induce Apoptosis of Activated Human T Cells. J Immunol. Dec. 1, 2000;165(11):6205-6213.
Carter, Bispecific human IgG by design. J Immunol Methods. Feb. 1, 2001;248(1-2):7-15.
Chan et al., In Situ Hybridization Study of PSP94 (Prostatic Secretory Protein of 94 Amino Acids) Expression in Human Prostates. Prostate. Oct. 1, 1999;41(2):99-109.
Pandey et al., Identification of a Novel Immunoreceptor Tyrosine-based Activation Motif-containing Molecule, STAM2, by Mass Spectrometry and Its Involvement in Growth Factor and Cytokine Receptor Signaling Pathways. J Biol Chem. Dec. 8, 2000;275(49):38633-38639.
Parekh et al., Association of rheumatoid arthritis and primary osteoarthritis with changes in the glycosylation pattern of total serum IgG. Nature. Aug. 1-7, 1985;316(6027):452-7.
Patel et al., Development of a simple restriction fragment length polymorphism assay for subtyping of coxsackie B viruses. J Virol Methods. Sep. 15, 2004;120(2):167-172.
Peggs et al., Blockade of CTLA-4 on both effector and regulatory T cell compartments contributes to the antitumor activity of anti-CTLA-4 antibodies. J Exp Med. Aug. 3, 2009;206(8):1717-1725.
Peh et al., Frequent presence of subtype A virus in Epstein-Barr virus-associated malignancies. Pathology. Oct. 2002;34(5):446-450.
Pisarev et al., Full-length dominant-negative survivin for cancer immunotherapy. Clin Cancer Res. Dec. 15, 2003;9(17):6523-6533.
Ziyaeyan et al., The Seroprevalence of Parvovirus B19 Infection among To-Be-Married Girls, Pregnant Women, and Their Neonates in Shiraz, Iran. Jpn J Infect Dis. Apr. 2005;58(2):95-97.
Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. Nov. 2004;11(6):1008-1015.
Portielji et al., IL-12: a promising adjuvant for cancer vaccination. Cancer Immunol Immunother. Mar. 2003;52(3):133-144.
Presta, Selection, design, and engineering of therapeutic antibodies. J Allergy Clin Immunol. Oct. 2005;116(4):731-736.
Propst et al., Proinflammatory and Th2-Derived Cytokines Modulate CD40-Mediated Expression of Inflammatory Mediators in Airway Epithelia: Implications for the Role of Epithelial CD40 in Airway Inflammation. J Immunol. Aug. 15, 2000;165(4):2214-2221.
Fuessel et al., Multiple tumor marker analyses (PSA, hK2, PSCA, trp-p8) in primary prostate cancers using quantitative RT-PCR. Int J Oncol. Jul. 2003;23(1):221-228.
Gala and Morrison, V Region Carbohydrate and Antibody Expression. J Immunol. May 1, 2004;172(9):5489-5494.
Gambus et al., Epitope mapping of a mouse monoclonal anti-MUC2 antibody suggests the existence of an Immunodominant region in the COOH terminus of the MUC2 tandem-repeat sequence. Int J Cancer. Jan. 3, 1995;60(1):146-148.
Geisbert and Jahrling, Differentiation of filoviruses by electron microscopy. Virus Res. Dec. 1995;39(2-3):129-150.
Ghazizadeh et al., Role of cdk4, p16INK4, and Rb Expression in the Prognosis of Bronchioloalveolar Carcinomas. Respiration. Jan.-Feb. 2005;72(1):68-73.
Ghirlando et al., Glycosylation of human IgG-Fc: influences on structure revealed by differential scanning micro-calorimetry. Immunol Lett. May 3, 1999;68(1):47-52.
Ghosh et al., Natalizumab for Active Crohn's Disease. N Engl J Med. Jan. 2, 2003;348(1):24-32.
Gibellini et al., Extracellular HIV-1 Tat Protein Induces the Rapid Ser133 Phosphorylation and Activation of CREB Transcription Factor in Both Jurkat Lymphoblastoid T Cells and Primary Peripheral Blood Mononuclear Cells. J Immunol. Apr. 15, 1998;160(8):3891-3898.
Gilliam et al., A phase II study of G17DT in gastric carcinoma. Eur J Surg Oncol. Jun. 2004;30(5):536-543.
Gish and States, Identification of protein coding regions by database similarity search. Nat Genet. Mar. 1993;3(3):266-272.
Giudicelli et al., IMGT/GENE-DB: a comprehensive database for human and mouse immunoglobulin and T cell receptor genes. Nucleic Acids Res. Jan. 1, 2005;33(Database issue):D256-61-D261.

(56) References Cited

OTHER PUBLICATIONS

Gonzalez et al., A comparative sequence analysis to revise the current taxonomy of the family Coronaviridae. Arch Virol. Nov. 2003;148(11):2207-2235.
Good et al., Development and regulation of cell-mediated immune responses to the blood stages of malaria: Implications for vaccine research. Annu Rev Immunol. 2005;23:69-99.
Good et al., The immunological challenge to developing a vaccine to the blood stages of malaria parasites. Immunol Rev. Oct. 2004;201:254-267.
Götze et al., StavroX—A Software for Analyzing Crosslinked Products in Protein Interaction Studies. J Am Soc Mass Spectrom. Jan. 2012;23(1):76-87.
Grimm et al., Mouse alpha-fetoprotein-specific DNA-based immunotherapy of hepatocellular carcinoma leads to tumor regression in mice. Gastroenterology. Oct. 2000;119(4):1104-1112.
Groh et al., Efficient cross-priming of tumor antigen-specific T cells by dendritic cells sensitized with diverse anti-MICA opsonized tumor cells. Proc Natl Acad Sci USA. May 3, 2005;102(18):6461-6466.
Gueguen et al., An Antigen Recognized by Autologous CTLs on a Human Bladder Carcinoma. J Immunol. Jun. 15, 1998;160(12):6188-6194.
Gulmann et al., Adenomatous *Polyposis coli* Gene, beta-Catenin, and E-Cadherin Expression in Proximal and Distal Gastric Cancers and Precursor Lesions. Appl Immunohistochem Mol Morphol. Sep. 2003;11(3):230-237.
Guo et al., Therapeutic Cancer Vaccines: Past, Present and Future. Adv Cancer Res. 2013;119:421-475.
Gupta and Siber, adjuvants for human vaccines—current status, problems and future prospects. Vaccine. Oct. 1995;13(14):1263-1276.
Gupta et al., Refolding, purification, and crystallization of apical membrane antigen 1 from Plasmodium falciparum. Protein Expr Purif. May 2005;41(1):186-198.
Haddad et al., Novel antigen identification method for discovery of protective malaria antigens by rapid testing of DNA vaccines encoding exons from the parasite genome. Infect Immun. Mar. 2004;72(3):1594-1602.
Hakansson et al., Establishment and phenotypic characterization of human U937 cells with inducible P210 BCR/ABL expression reveals upregulation of CEACAM1 (CD66a). (2004) Leukemia 18:538-547.
Hamilton and Gerngross, Glycosylation engineering in yeast: the advent of fully humanized yeast. Curr Opin Biotechnol. Oct. 2007;18(5):387-392.
Hamilton et al., Humanization of Yeast to Produce Complex Terminally Sialylated Glycoproteins. Science. Sep. 8, 2006;313(5792):1441-1443.
Hamilton et al., Production of Complex Human Glycoproteins in Yeast. Science. Aug. 29, 2003;301(5637):1244-1246.
Hancock and Armstrong, SIMPLE34: an improved and enhanced implementation for VAX and Sun computers of the SIMPLE algorithm for analysis of clustered repetitive motifs in nucleotide sequences. Comput Appl Biosci. Feb. 1994;10(1):67-70.
Harris et al., The Biological and Therapeutic Importance of Gastrin Gene Expression in Pancreatic Adenocarcinomas. Cancer Res. Aug. 15, 2004;64(16):5624-5631.
Hashido et al., Evaluation of an enzyme-linked immunosorbent assay based on binding inhibition for type-specific quantification of poliovirus neutralization-relevant antibodies. Microbiol Immunol. 1999;43(1):73-77.
Havlasova et al., Mapping of immunoreactive antigens of Francisella tularensis live vaccine strain. Proteomics. Jul. 2002;2(7):857-867.
Havlasova et al., Proteomic analysis of anti-Francisella tularensis LVS antibody response in murine model of tularemia. Proteomics. May 2005;5(8):2090-2103.
He et al., Complexes of Poliovirus Serotypes with Their Common Cellular Receptor, CD155. J Virol. Apr. 2003;77(8):4827-4835.
He et al., Humanization and Pharmacokinetics of a Monoclonal Antibody with Specificity for Both E- and P-Selectin. J Immunol. Jan. 15, 1998;160(2):1029-1035.
Henikoff and Henikoff, Amino acid substitution matrices from protein blocks. Proc Natl Acad Sci U S A. Nov. 15, 1992;89(22):10915-10919.
Herold et al., Anti-CD3 monoclonal antibody in new-onset type 1 diabetes mellitus. N Engl J Med. May 30, 2002;346(22):1692-1698.
Hirose et al., Incidence of Diffuse Large B-Cell Lymphoma of Germinal Center B-Cell Origin in Whole Diffuse Large B-Cell Lymphoma: Tissue Fluorescence In Situ Hybridization Using t(14;18) Compared with Immunohistochemistry. Int J Hematol. Jan. 2005;81(1):48-57.
Hodi et al., Improved Survival with Ipilimumab in Patients with Metastatic Melanoma. N Engl J Med. Aug. 19, 2010;363(8):711-723.
Hoffman et al., Strategy for development of a pre-erythrocytic Plasmodium falciparum DNA vaccine for human use. Vaccine. Jun. 1997;15(8):842-845.
Hoke, History of U.S. Military Contributions to the Study of Viral Encephalitis. Mil Med. Apr. 2005;170(4 Suppl):92-105.
Holliger and Hudson, Engineered antibody fragments and the rise of single domains. Nat Biotechnol. Sep. 2005;23(9):1126-1136.
Holliger et al., "Diabodies": Small bivalent and bispecific antibody fragments. Proc Natl Acad Sci U S A. Jul. 15, 1993;90(14):6444-6448.
Hoogenboom and Chames, Natural and designer binding sites made by phage display technology. Immunol Today. Aug. 2000;21(8):371-378.
Hsing and Bishop, Requirement for Nuclear Factor-κB Activation by a Distinct Subset of CD40-Mediated Effector Functions in B Lymphocytes. J Immunol. Mar. 1, 1999;162(5):2804-2811.
Hudson and Kortt, High avidity scFv multimers; diabodies and triabodies. J Immunol Methods. Dec. 10, 1999;231(1-2):177-189.
Hunter and Greenwood, Preparation of iodine-131 labelled human growth hormone of high specific activity. Nature. May 5, 1962;194:495-496.
Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.
Hutchinson et al., Multiplex Analysis of Cytokines in the Blood of Cynomolgus Macaques Naturally Infected With Ebola Virus (Reston Serotype). J Med Virol. Nov. 2001;65(3):561-566.
Jacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 15, 2003;63(24):8614-8622.
Inouye and Inouye, Up-Promoter Mutations in the Lpp Gene of *Escherichia coli*. Nucleic Acids Res. May 10, 1985;13(9):3101-3110.
Pluckthun, Antibodies from *Escherichia coli*. in The Pharmacology of Monoclonal Antibodies, Rosenburg and Moore eds. Springer-Verlag, New York, 1994;113:269-315.
Proudfoot, Transcriptional interference and termination between duplicated alpha-globin gene constructs suggests a novel mechanism for gene regulation. Nature. Aug. 7-13, 1986;322(6079):562-565.
Raghunathan et al., Antigen-binding site anatomy and somatic mutations in antibodies that recognize different types of antigens. J Mol Recognit. Mar. 2012;25(3):103-113—incl supplemental data (25 pages total).
Ramagopal et al., Structural basis for cancer immunotherapy by the first-in-class checkpoint inhibitor ipilimumab. Proc Natl Acad Sci U S A. May 23, 2017;114(21):E4223-E4232.
Raso et al., Intracellular Targeting with Low pH-triggered Bispecific Antibodies. J Biol Chem. Oct. 31, 1997;272(44):27623-27628.
Reichmann and Muyldermans, Single domain antibodies: Comparison of camel VH and camelised human VH domains. J Immunol Methods. Dec. 10, 1999;231(1-2):25-38.
Reissner and Aswad, Deamidation and isoaspartate formation in proteins: unwanted alterations or surreptitious signals? Cell Mol Life Sci. Jul. 2003;60(7):1281-1295.

(56) References Cited

OTHER PUBLICATIONS

Renkvist et al., A listing of human tumor antigens recognized by T cells. Cancer Immunol Immunother. Mar. 2001;50(1):3-15.
Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.
Rezig et al., Molecular Characterization of Coxsackievirus B5 Isolates. J Med Virol. Feb. 2004;72(2):268-274.
Ribas et al., Phase III Randomized Clinical Trial Comparing Tremelimumab With Standard-of-Care Chemotherapy in Patients With Advanced Melanoma. J Clin Oncol. Feb. 10, 2013;31(5):616-622.
Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26(3):817-824.
Roden and Wu, Preventative and therapeutic vaccines for cervical cancer. Expert Rev Vaccines. Aug. 2003;2 (4):495-516.
Romano et al., Ipilimumab-dependent cell-mediated cytotoxicity of regulatory T cells ex vivo by nonclassical monocytes in melanoma patients. Proc Natl Acad Sci U S A. May 12, 2015;112(19):6140-6145.
Roner et al., Identification of signals required for the insertion of heterologous genome segments into the reovirus genome. Proc Natl Acad Sci U S A. Dec. 19, 1995;92(26):12362-12366.
Rossi et al., A Comparative Study Between a Novel Category of Immunoreagents and the Corresponding Mouse Monoclonal Antibodies. Am J Clin Pathol. Aug. 2005;124(2):295-302.
Ruther and Müller-Hill, Easy identification of cDNA clones. EMBO J. 1983;2(10):1791-1794.
Salazar-Onfray et al., Synthetic peptides derived from the melanocyte-stimulating hormone receptor MC1R can stimulate HLA-A2-restricted cytotoxic T lymphocytes that recognize naturally processed peptides on human melanoma cells. Cancer Res. Oct. 1, 1997;57(19):4348-4355.
Santerre et al Expression of prokaryotic genes for hygromycin B and G418 resistance as dominant-selection markers in mouse L cells. Gene. Oct. 1984;30(1-3):147-156.
Santin et al., The serine protease stratum corneum chymotryptic enzyme (kallikrein 7) is highly overexpressed in squamous cervical cancer cells. Gynecol Oncol. Aug. 2004;94(2):283-288.
Sarcevic et al., Expression of Cancer/Testis Tumor Associated Antigens in Cervical Squamous Cell Carcinoma. Oncology. 2003;64(4):443-449.
Sarobe et al., Carcinoembryonic Antigen as a Target to Induce Anti-Tumor Immune Responses. Curr Cancer Drug Targets. Aug. 2004;4(5):443-454.
Sasaki et al., SAGE mRNA expression in advanced-stage lung cancers. Eur J Surg Oncol. Dec. 2003;29(10):900-903.
Sasatomi et al., Expression of tumor rejection antigens in colorectal carcinomas. Cancer. Mar. 15, 2002;94(6):1636-1641.
Scanlan et al., Antigens recognized by autologous antibody in patients with renal-cell carcinoma. Int J Cancer. Nov. 12, 1999;83(4):456-464.
Scanlan et al., Cancer-related serological recognition of human colon cancer: identification of potential diagnostic and immunotherapeutic targets. Cancer Res. Jul. 15, 2002;62(14):4041-4047.
Scanlan et al., Expression of cancer-testis antigens in lung cancer: definition of bromodomain testis-specific gene (BRDT) as a new CT gene, CT9. Cancer Lett. Mar. 31, 2000;150(2):155-164.
Scanlan et al., Humoral immunity to human breast cancer: antigen definition and quantitative analysis of mRNA expression. Cancer Immun. Mar. 30, 2001;1:4.
Scanlan et al., The cancer/testis genes: review, standardization, and commentary. Cancer Immun. Jan. 23, 2004;4:1.
Scarcella et al., Expression of MAGE and GAGE in high-grade brain tumors: a potential target for specific immunotherapy and diagnostic markers. Clin Cancer Res. Feb. 1999;5(2):335-341.

Schadendorf et al., Pooled Analysis of Long-Term Survival Data From Phase II and Phase III Trials of Ipilimumab in Unresectable or Metastatic Melanoma. J Clin Oncol. Jun. 10, 2015;33(17):1889-1894.
Schmittgen et al., Expression of prostate specific membrane antigen and three alternatively spliced variants of PSMA in prostate cancer patients. Int J Cancer. Nov. 1, 2003;107(2):323-329.
Schwartz et al., Novel Targeted and Immunotherapeutic Strategies in Chronic Myeloid Leukemia. Semin Hematol. Jan. 2003;40(1):87-96.
Scott and Smith, Searching for Peptide Ligands with an Epitope Library. Science. Jul. 27, 1990;249(4967):386-388.
Scott et al., Antibody therapy of cancer. Nat Rev Cancer. Mar. 22, 2012;12(4):278-287.
Segal et al., Introduction: bispecific antibodies. J Immunol Methods. Feb. 1, 2001;248(1-2):1-6.
Selby et al., Anti-CTLA-4 Antibodies of IgG2a Isotype Enhance Antitumor Activity through Reduction of Intratumoral Regulatory T Cells. Cancer Immunol Res. Jul. 2013;1(1):32-42.
Sepehr et al., Distinct pattern of TP53 mutations in squamous cell carcinoma of the esophagus in Iran. Oncogene. Nov. 1, 2001;20(50):7368-7374.
Shields et al., High Resolution Mapping of the Binding Site on Human IgG1 for FcγRI, FcγRII, FcγRIII, and FcRn and Design of IgG1 Variants with Improved Binding to the FcγR R. J Biol Chem. Mar. 2, 2001;276(9):6591-6604.
Shigemasa et al., Expression of the protease inhibitor antileukoprotease and the serine protease stratum corneum chymotryptic enzyme (SCCE) is coordinated in ovarian tumors. Int J Gynecol Cancer. Nov.-Dec. 2001;11(6):454-461.
International Search Report and Written Opinion issued in PCT/IB2017/054697 dated Oct. 17, 2017—17 pages.
Chin et al., Immune Intervention with Monoclonal Antibodies Targeting CD152 (CTLA-4) for Autoimmune and Malignant Diseases. Chang Gung Med J. Jan.-Feb. 2008;31(1):1-15.
He et al., Remarkably similar CTLA-4 binding properties of therapeutic ipilimumab and tremelimumab antibodies. Oncotarget. May 19, 2017;8(40):67129-67139.
Ramagopal et al., Structural basis for cancer immunotherapy by the first-in-class checkpoint inhibitor ipilimumab. Proc Natl Acad Sci U S A. May 23, 2017;114(21):E4223-E4232 (incl supporting information—22 pages total).
Virok et al., Chlamydial Infection Induces Pathobiotype-Specific Protein Tyrosine Phosphorylation in Epithelial Cells. Infect Immun. Apr. 2005;73(4):1939-1946.
Volkel et al., Optimized linker sequences for the expression of monomeric and dimeric bispecific single-chain diabodies. Protein Eng. Oct. 2001;14(10):815-823.
Von Heijne, A new method for predicting signal sequence cleavage sites. Nucleic Acids Res. Jun. 11, 1986;14(11):4683-4690.
Von Heijne, Patterns of Amino Acids near Signal-Sequence Cleavage Sites. Eur J Biochem. Jun. 1, 1983;133(1):17-21.
Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4):1687-1697.
Wallick et al., Glycosylation of a VH residue of a monoclonal antibody against alpha (1-6) dextran increases its affinity for antigen. J Exp Med. Sep. 1, 1988;168(3):1099-1109.
Waltregny et al., Screening of histone deacetylases (HDAC) expression in human prostate cancer reveals distinct class I HDAC profiles between epithelial and stromal cells. Eur J Histochem. Jul.-Sep. 2004;48(3):273-290.
Walunas et al., Pillars Article: CTLA-4 Can Function as a Negative Regulator of T Cell Activation. Immunity. 1994. 1:405-413. J Immunol. Oct. 1, 2011;187(7):3466.
Wang et al., Alterations of APC, c-met, and p53 Genes in Tumor Tissue and Serum of Patients with Gastric Cancers. J Surg Res. Aug. 2004;120(2):242-248.
Wang et al., Cloning Genes Encoding MHC Class II—Restricted Antigens: Mutated CDC27 as a Tumor Antigen. Science. May 21, 1999;284(5418):1351-1354.

(56) References Cited

OTHER PUBLICATIONS

Wang et al., Identification of a Novel Major Histocompatibility Complex Class II—restricted Tumor Antigen Resulting from a Chromosomal Rearrangement Recognized by CD4+ T Cells. J Exp Med. May 17, 1999;189(10):1659-1668.
Weaver et al., Genetic determinants of Venezuelan equine encephalitis emergence. Arch Virol Suppl. 2004; (18):43-64.
Weaver et al., Venezuelan Equine Encephalitis. Annu Rev Entomol. 2004;49:141-174.
Weber, Review: Anti-CTLA-4 Antibody Ipilimumab: Case Studies of Clinical Response and Immune-Related Adverse Events. Oncologist. Jul. 2007;12(7):864-872.
Wells et al., Swine Influenza Virus Infections Transmission. From III Pigs to Humans at a Wisconsin Agricultural Fair and Subsequent Probable Person-to-Person Transmission. JAMA. Jan. 23-30, 1991;265(4):478-481.
Wen et al., Poly(ethylene glycol)-Conjugated Anti-EGF Receptor Antibody C225 with Radiometal Chelator Attached to the Termini of Polymer Chains. Bioconjug Chem. Jul.-Aug. 2001;12(4):545-553.
Wentworth et al., An Influenza A (HINI) Virus, Closely Related to Swine Influenza Virus, Responsible for a Fatal Case of Human Influenza. J Virol. Apr. 1994;68(4):2051-2058.
Wigler et al., Transfer of Purified Herpes Virus Thymidine Kinase Gene to Cultured Mouse Cells. Cell. May 1977;11(1):223-232.
Wigler et al., Transformation of mammalian cells with an amplifiable dominant-acting gene. Proc Natl Acad Sci U S A. Jun. 1980;77(6):3567-3570.
Wootton and Federhen, Statistics of local complexity in amino acid sequences and sequence databases. Comput Chem. 1993;17(2):149-163.
Wren et al., Signal-Sequence Information and GeNomic AnaLysis. Comput Methods Programs Biomed. May 2002;68(2):177-181.
Wright et al., Lymphoid/Neuronal Cell Surface OX2 Glycoprotein Recognizes a Novel Receptor on Macrophages Implicated in the Control of Their Function. Immunity. Aug. 2000;13(2):233-242.
Yamazaki et al., Cutting Edge: Tumor Secreted Heat Shock-Fusion Protein Elicits CD8 Cells for Rejection. J Immunol. Nov. 15, 1999;163(10):5178-5182.
Yan et al., Synthesis and immunostimulatory properties of the phosphorothioate analogues of cdiGMP. Bioorg Med Chem Lett. Oct. 15, 2008;18(20):5631-5634.
Yang, et al., A Randomized Trial of Bevacizumab, an Anti-Vascular Endothelial Growth Factor Antibody, for Metastatic Renal Cancer N Engl J Med. Jul. 31, 2003;349(5):427-434.
Ye et al., IgBLAST: an immunoglobulin variable domain sequence analysis tool. Nucleic Acids Res. Jul. 2013;41(Web Server issue):W34-40.
Zaremba et al., Identification of an Enhancer Agonist Cytotoxic T Lymphocyte Peptide from Human Carcinoembryonic Antigen. Cancer Res. Oct. 15, 1997;57(20):4570-4577.
Zeier et al., New Ecological Aspects of Hantavirus Infection: A Change of A Paradigm and a Challenge of Prevention—A Review. Virus Genes. Mar. 2005;30(2):157-180.
Zhang and Madden, PowerBLAST: A New Network BLAST Application for Interactive or Automated Sequence Analysis and Annotation. Genome Res. Jun. 1997;7(6):649-656.
Zheng et al., Expression of the Platelet Receptor GPVI Confers Signaling via the Fc Receptor γ-Chain in Response to the Snake Venom Convulxin but Not to Collagen. J Biol Chem. Apr. 20, 2001;276(16):12999-13006.
Zimmerman et al., Expression of annexin II in conventional renal cell carcinoma is correlated with Fuhrman grade and clinical outcome. Virchows Arch. Oct. 2004;445(4):368-374.
Shinkawa et al., The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity. J Biol Chem. Jan. 31, 2003;278(5):3466-3473.
Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.
Shirasawa et al., Receptor for advanced glycation end-products is a marker of type I lung alveolar cells. Genes Cells. Feb. 2004;9(2):165-174.
Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64(11):3757-3760.
Siegel et al., Induction of antitumour immunity using survivin peptide-pulsed dendritic cells in a murine lymphoma model. Br J Haematol. Sep. 2003;122(6):911-914.
Simon et al., Cervical response to vaccination against HPV16 E7 in case of severe dysplasia. Eur J Obstet Gynecol Reprod Biol. Aug. 15, 2003;109(2):219-223.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-1710.
Sjolander et al., Serological divergence of Dobrava and Saaremaa hantaviruses: evidence for two distinct serotypes. Epidemiol Infect. Feb. 2002;128(1):99-103.
Slager et al., Identification of multiple HLA-DR-restricted epitopes of the tumor-associated antigen CAMEL by CD4+ Th1/Th2 lymphocytes. J Immunol. Apr. 15, 2004;172(8):5095-5102.
Slager et al., Induction of CAMEL/NY-ESO-ORF2-specific CD8+ T cells upon stimulation with dendritic cells infected with a modified Ad5 vector expressing a chimeric Ad5/35 fiber. Cancer Gene Ther. Mar. 2004;11(3):227-236.
Slamon et al., Use of Chemotherapy plus a Monoclonal Antibody against HER2 for Metastatic Breast Cancer That Overexpresses HER2. N Engl J Med. Mar. 15, 2001;344(11):783-792.
Small et al., Immunotherapy of Hormone-Refractory Prostate Cancer With Antigen-Loaded Dendritic Cells. J Clin Oncol. Dec. 1, 2000;18(23):3894-3903.
Smith et al., Neutralization of HIV-1 Subtypes: Implications for Vaccine Formulations. J Med Virol. Nov. 1998;56(3):264-268.
Smits et al., Phylogenetic and Evolutionary Relationships among Torovirus Field Variants: Evidence for Multiple Intertypic Recombination Events. J Virol. Sep. 2003;77(17):9567-9577.
Songsivilai and Lachmann, Bispecific antibody: a tool for diagnosis and treatment of disease. Clin Exp Immunol. Mar. 1990;79(3):315-321.
Spiro, Protein glycosylation: nature, distribution, enzymatic formation, and disease implications of glycopeptide bonds. Glycobiology. Apr. 2002;12(4):43R-56R.
Stams et al., Expression Levels of TEL, AML1, and the Fusion ProductsTEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8):2974-2980.
States et al., Improved Sensitivity of Nucleic Acid Database Searches Using Application-Specific Scoring Matrices. Methods: A Compan Meth Enzymol. 1991;3(1):66-70.
Steenbakkers et al., A new approach to the generation of human or murine antibody producing hybridomas. J Immunol Methods. Jul. 31, 1992;152(1):69-77.
Steenbakkers et al., Efficient generation of monoclonal antibodies from preselected antigen-specific B cells. Efficient immortalization of preselected B cells. Mol Biol Rep. Mar. 1994;19(2):125-134.
Steffens et al., Immunohistochemical analysis of tumor antigen saturation following injection of monoclonal antibody G250. Anticancer Res. Mar.-Apr. 1999;19(2A):1197-1200.
Stirnadel et al., Assessment of different sources of variation in the antibody responses to specific malaria antigens in children in Papua New Guinea. Int J Epidemiol. Jun. 2000;29(3):579-586.
Stolier et al., Initial experience with surgical treatment planning in the newly diagnosed breast cancer patient at high risk for BRCA-1 or BRCA-2 mutation. Breast J. Nov.-Dec. 2004;10(6):475-480.
Strbo et al., Secreted heat shock protein gp96-Ig: next-generation vaccines for cancer and infectious diseases. Immunol Res. Dec. 2013;57(1-3):311-325.

(56) References Cited

OTHER PUBLICATIONS

Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.
Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.
Szybalska and Szybalski, Genetics of Human Cell Lines, IV. DNA-Mediated Heritable Transformation of a Biochemical Trait. Proc Natl Acad Sci U S A. Dec. 15, 1962;48:2026-2034.
Tachibana et al., Altered reactivity of immunoglobulin produced by human-human hybridoma cells transfected by pSV2-neo gene. Cytotechnology. Jul. 1991;6(3):219-226.
Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8):1363-1370.
Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.
Tanaka et al., Expression of Tumor-Rejection Antigens in Gynecologic Cancers. Jpn J Cancer Res. Nov. 2000;91(11):1177-1184.
Tang et al., Use of a Peptide Mimotope to Guide the Humanization of MRK-16, an Anti-P-glycoprotein Monoclonal Antibody. J Biol Chem, Sep. 24, 1999;274(39):27371-27378.
Tannapfel et al., BRAF Gene Mutations Are Rare Events in Gastroenteropancreatic Neuroendocrine Tumors. Am J Clin Pathol. Feb. 2005;123(2):256-2601.
Tolstoshev, Gene Therapy, Concepts, Current Trials and Future Directions. Annu Rev Pharmacol Toxicol. 1993;33:573-596.
Traunecker et al., Bispecific single chain molecules (Janusins) target cytotoxic lymphocytes on HIV infected cells. EMBO J. Dec. 1991;10(12):3655-3659.
Traunecker et al., Janusin: new molecular design for bispecific reagents. Int J Cancer Suppl. 1992;7:51-52.
Treurnicht et al., HHV-8 subtypes in South Africa: identification of a case suggesting a novel B variant. J Med Virol. Feb. 2002;66(2):235-240.
Trimble et al., Comparison of the CD8+ T cell responses and antitumor effects generated by DNA vaccine administered through gene gun, biojector, and syringe. Vaccine. Sep. 8, 2003;21(25-26):4036-4042.
Trincado et al., Human Cytomegalovirus Strains Associated With Congenital and Perinatal Infections. J Med Virol. Aug. 2000;61(4):481-487.
Tsang et al., Phenotypic Stability of a Cytotoxic T-Cell Line Directed Against an Immunodominant Epitope of Human Carcinoembryonic Antigen. Clin Cancer Res. Dec. 1997;3(12 Pt 1):2439-2449.
Tsao and Sober, Melanoma Treatment Update. Dermatol Clin. Apr. 2005;23(2):323-333.
Tsuruma et al., Phase I clinical study of anti-apoptosis protein, survivin-derived peptide vaccine therapy for patients with advanced or recurrent colorectal cancer. J Transl Med. Jun. 13, 2004;2(1):19 (11 pages).
Vallejo et al., Nucleotide Sequence and Restriction Fragment-Length Polymorphism Analysis of Human T-Cell Lymphotropic Virus Type II (HTLV-II) in Southern Europe: Evidence for the HTLV-IIa and HTLV-IIb Subtypes. J Acquir Immune Defic Syndr Hum Retrovirol. Dec. 1, 1996;13(4):384-391.
Van Den Eynde et al., A New Antigen Recognized by Cytolytic T Lymphocytes on a Human Kidney Tumor Results From Reverse Strand Transcription. J Exp Med. Dec. 20, 1999;190(12):1793-1800.
Van Heeke and Schuster, Expression of Human Asparagine Synthetase in *Escherichia coli*. J Biol Chem. Apr. 5, 1989;264(10):5503-5509.
Vance et al., Patterns of Pathogenesis: Discrimination of Pathogenic and Nonpathogenic Microbes by the Innate Immune System. Cell Host Microbe. Jul. 23, 2009;6(1):10-21.
Vandamme et al., African Origin of Human T-Lymphotropic Virus Type 2 (HTLV-2) Supported by a Potential New HTLV-2d Subtype in Congolese Bambuti Efe Pygmies. J Virol. May 1998;72(5):4327-4340.
Vaughan et al., Human Antibodies with Sub-nanomolar Affinities Isolated from a Large Non-immunized Phage Display Library. Nat Biotechnol. Mar. 1996;14(3):309-314.
Vilas Boas et al., Cytomegalovirus Glycoprotein B Genotypes and Central Nervous System Disease in AIDS Patients. J Med Virol. Nov. 2003;71(3):404-407.
Vilchez and Butel, Emergent Human Pathogen Simian Virus 40 and Its Role in Cancer. Clin Microbiol Rev. Jul. 2004;17(3):495-508.
Wykes et al., "Immune checkpoint blockade in infectious diseases", Nat Rev Immunol. Feb. 2018 ; 18(2): 91-104. doi:101038/nri.2017.112.

\* cited by examiner

SEQUENCE LISTING

```
<160> NUMBER OF SEQ ID NOS: 59

<210> SEQ ID NO 1
<211> LENGTH: 5
<212> TYPE: PRT
<213> ORGANISM: Artificial Sequence
<220> FEATURE:
<223> OTHER INFORMATION: CDR1 heavy chain

<400> SEQUENCE: 1

Thr Tyr Trp Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: CDR2 heavy chain
```

```
<400> SEQUENCE: 2

Met Ile His Pro Ser Asp Ser Glu Thr Ser Leu Asn Gln Ala Phe Lys
1               5                   10                  15

Asp

<210> SEQ ID NO 3
<211> LENGTH: 11
<212> TYPE: PRT
<213> ORGANISM: Artificial Sequence
<220> FEATURE:
<223> OTHER INFORMATION: CDR3 heavy chain

<400> SEQUENCE: 3

Met Gly Arg Arg Asn Pro Tyr Tyr Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDR1 light chain

<400> SEQUENCE: 4

Arg Pro Ser Glu Asn Leu Tyr Thr Asn Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR2 light chain

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: CDR3 light chain

<400> SEQUENCE: 6

Gln His Leu Trp Gly Thr Pro Phe Thr
1               5

<210> SEQ ID NO 7
<211> LENGTH: 120
<212> TYPE: PRT
<213> ORGANISM: Artificial Sequence
<220> FEATURE:
<223> OTHER INFORMATION: consensus heavy chain
<220> FEATURE:
<221> NAME/KEY: VARIANT
<222> LOCATION: (5)..(5)
<223> OTHER INFORMATION: May be Val or Leu
<220> FEATURE:
<221> NAME/KEY: VARIANT
<222> LOCATION: (6)..(6)
<223> OTHER INFORMATION: May be Gln or Glu
<220> FEATURE:
<221> NAME/KEY: VARIANT
<222> LOCATION: (7)..(7)
<223> OTHER INFORMATION: May be Ser or Ala
```

```
<220> FEATURE:
<221> NAME/KEY: VARIANT
<222> LOCATION: (9)..(9)
<223> OTHER INFORMATION: May be Phe or Ala
<220> FEATURE:
<221> NAME/KEY: VARIANT
<222> LOCATION: (10)..(10)
<223> OTHER INFORMATION: May be Val or Glu
<220> FEATURE:
<221> NAME/KEY: VARIANT
<222> LOCATION: (11)..(11)
<223> OTHER INFORMATION: May be Val or Leu
<220> FEATURE:
<221> NAME/KEY: VARIANT
<222> LOCATION: (12)..(12)
<223> OTHER INFORMATION: May be Val, Ala or Lys
<220> FEATURE:
<221> NAME/KEY: VARIANT
<222> LOCATION: (13)..(13)
<223> OTHER INFORMATION: May be Arg or Lys
<220> FEATURE:
<221> NAME/KEY: VARIANT
<222> LOCATION: (16)..(16)
<223> OTHER INFORMATION: May be Ala, Thr or Ser
<220> FEATURE:
<221> NAME/KEY: VARIANT
<222> LOCATION: (20)..(20)
<223> OTHER INFORMATION: May be Ile or Val
<220> FEATURE:
<221> NAME/KEY: VARIANT
<222> LOCATION: (38)..(38)
<223> OTHER INFORMATION: May be Lys or Arg
<220> FEATURE:
<221> NAME/KEY: VARIANT
<222> LOCATION: (40)..(40)
<223> OTHER INFORMATION: May be Ala or Arg
<220> FEATURE:
<221> NAME/KEY: VARIANT
<222> LOCATION: (43)..(43)
<223> OTHER INFORMATION: May be Lys or Gln
<220> FEATURE:
<221> NAME/KEY: VARIANT
<222> LOCATION: (48)..(48)
<223> OTHER INFORMATION: May be Ile or Met
<220> FEATURE:
<221> NAME/KEY: VARIANT
<222> LOCATION: (67)..(67)
<223> OTHER INFORMATION: May be Lys or Arg
<220> FEATURE:
<221> NAME/KEY: VARIANT
<222> LOCATION: (68)..(68)
<223> OTHER INFORMATION: May be Val or Ala
<220> FEATURE:
<221> NAME/KEY: VARIANT
<222> LOCATION: (69)..(69)
<223> OTHER INFORMATION: May be Lys or Thr
<220> FEATURE:
<221> NAME/KEY: VARIANT
<222> LOCATION: (70)..(70)
<223> OTHER INFORMATION: May be Leu, Ile or Met
<220> FEATURE:
<221> NAME/KEY: VARIANT
<222> LOCATION: (72)..(72)
<223> OTHER INFORMATION: May be Ala or Arg
<220> FEATURE:
<221> NAME/KEY: VARIANT
<222> LOCATION: (73)..(73)
<223> OTHER INFORMATION: May be Ala or Asp
<220> FEATURE:
<221> NAME/KEY: VARIANT
<222> LOCATION: (74)..(74)
<223> OTHER INFORMATION: May be Thr, Glu or Lys
<220> FEATURE:
<221> NAME/KEY: VARIANT
<222> LOCATION: (76)..(76)
<223> OTHER INFORMATION: May be Thr or Ala
<220> FEATURE:
<221> NAME/KEY: VARIANT
<222> LOCATION: (78)..(78)
```

<223> OTHER INFORMATION: May be Thr or Ile
<220> FEATURE:
<221> NAME/KEY: VARIANT
<222> LOCATION: (79)..(79)
<223> OTHER INFORMATION: May be Ala or Val
<220> FEATURE:
<221> NAME/KEY: VARIANT
<222> LOCATION: (81)..(81)
<223> OTHER INFORMATION: May be Leu or Met
<220> FEATURE:
<221> NAME/KEY: VARIANT
<222> LOCATION: (82)..(82)
<223> OTHER INFORMATION: May be Glu or Gln
<220> FEATURE:
<221> NAME/KEY: VARIANT
<222> LOCATION: (83)..(83)
<223> OTHER INFORMATION: May be Phe or Leu
<220> FEATURE:
<221> NAME/KEY: VARIANT
<222> LOCATION: (87)..(87)
<223> OTHER INFORMATION: May be Arg or Thr
<220> FEATURE:
<221> NAME/KEY: VARIANT
<222> LOCATION: (88)..(88)
<223> OTHER INFORMATION: May be Ser or Asn
<220> FEATURE:
<221> NAME/KEY: VARIANT
<222> LOCATION: (91)..(91)
<223> OTHER INFORMATION: May be Ser or Thr
<220> FEATURE:
<221> NAME/KEY: VARIANT
<222> LOCATION: (99)..(99)
<223> OTHER INFORMATION: May be Met or Ile
<220> FEATURE:
<221> NAME/KEY: VARIANT
<222> LOCATION: (115)..(115)
<223> OTHER INFORMATION: May be Leu or Thr

<400> SEQUENCE: 7

Glu Val Gln Leu Xaa Xaa Xaa Gly Xaa Xaa Xaa Xaa Pro Gly Xaa
1               5                   10                  15

Ser Val Lys Xaa Ser Cys Lys Ala Ser Gly Tyr Ser Phe Thr Thr Tyr
            20                  25                  30

Trp Met Asn Trp Val Xaa Gln Xaa Pro Gly Xaa Gly Leu Glu Trp Xaa
            35                  40                  45

Gly Met Ile His Pro Ser Asp Ser Glu Thr Ser Leu Asn Gln Ala Phe
    50                  55                  60

Lys Asp Xaa Xaa Xaa Xaa Thr Xaa Xaa Xaa Ser Xaa Ser Xaa Xaa Tyr
65                  70                  75                  80

Xaa Xaa Xaa Ser Ser Leu Xaa Xaa Glu Asp Xaa Ala Val Tyr Tyr Cys
                85                  90                  95

Ala Arg Xaa Gly Arg Arg Asn Pro Tyr Tyr Phe Asp Tyr Trp Gly Gln
            100                 105                 110

Gly Thr Xaa Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: consensus light chain
<220> FEATURE:
<221> NAME/KEY: VARIANT
<222> LOCATION: (7)..(7)
<223> OTHER INFORMATION: May be Ser or Ala
<220> FEATURE:
<221> NAME/KEY: VARIANT
<222> LOCATION: (18)..(18)
<223> OTHER INFORMATION: May be Arg or Thr

```
<220> FEATURE:
<221> NAME/KEY: VARIANT
<222> LOCATION: (48)..(48)
<223> OTHER INFORMATION: May be Leu or Ile
<220> FEATURE:
<221> NAME/KEY: VARIANT
<222> LOCATION: (70)..(70)
<223> OTHER INFORMATION: May be Asp or Glu
<220> FEATURE:
<221> NAME/KEY: VARIANT
<222> LOCATION: (71)..(71)
<223> OTHER INFORMATION: May be Tyr or Phe
<220> FEATURE:
<221> NAME/KEY: VARIANT
<222> LOCATION: (72)..(72)
<223> OTHER INFORMATION: May be Thr or Ser
<220> FEATURE:
<221> NAME/KEY: VARIANT
<222> LOCATION: (74)..(74)
<223> OTHER INFORMATION: May be Thr or Ser
<220> FEATURE:
<221> NAME/KEY: VARIANT
<222> LOCATION: (80)..(80)
<223> OTHER INFORMATION: May be Pro, Ala or Ser
<220> FEATURE:
<221> NAME/KEY: VARIANT
<222> LOCATION: (100)..(100)
<223> OTHER INFORMATION: May be Gly or Gln
<220> FEATURE:
<221> NAME/KEY: VARIANT
<222> LOCATION: (104)..(104)
<223> OTHER INFORMATION: May be Leu or Val

<400> SEQUENCE: 8

Asp Ile Gln Met Thr Gln Xaa Pro Ser Ser Leu Ser Ala Ser Val Gly
1               5                   10                  15

Asp Xaa Val Thr Ile Thr Cys Arg Pro Ser Glu Asn Leu Tyr Thr Asn
            20                  25                  30

Leu Ala Trp Tyr Gln Gln Lys Pro Gly Lys Ala Pro Lys Leu Leu Xaa
        35                  40                  45

Tyr Gly Ala Thr Asn Leu Ala Asp Gly Val Pro Ser Arg Phe Ser Gly
    50                  55                  60

Ser Gly Ser Gly Thr Xaa Xaa Xaa Leu Xaa Ile Ser Ser Leu Gln Xaa
65                  70                  75                  80

Glu Asp Phe Ala Thr Tyr Tyr Cys Gln His Leu Trp Gly Thr Pro Phe
                85                  90                  95

Thr Phe Gly Xaa Gly Thr Lys Xaa Glu Ile Lys
            100                 105

<210> SEQ ID NO 9
<211> LENGTH: 360
<212> TYPE: DNA
<213> ORGANISM: Artificial Sequence
<220> FEATURE:
<223> OTHER INFORMATION: hCTLA4.27VH1
<220> FEATURE:
<221> NAME/KEY: CDS
<222> LOCATION: (1)..(360)

<400> SEQUENCE: 9 gag gtg cag ctg ctg cag tct ggc gct gtg ctg gcc aga cct ggc acc      48
Glu Val Gln Leu Leu Gln Ser Gly Ala Val Leu Ala Arg Pro Gly Thr
1               5                   10                  15 agc gtg aag atc agc tgc aag gcc agc ggc tac agc ttc acc acc tac      96
Ser Val Lys Ile Ser Cys Lys Ala Ser Gly Tyr Ser Phe Thr Thr Tyr
            20                  25                  30 tgg atg aac tgg gtc aag cag cgg cca ggc cag ggc ctg gaa tgg atc     144
Trp Met Asn Trp Val Lys Gln Arg Pro Gly Gln Gly Leu Glu Trp Ile
```

```
                      35                  40                  45
gga atg atc cac ccc agc gac agc gag aca agc ctg aac cag gcc ttc    192
Gly Met Ile His Pro Ser Asp Ser Glu Thr Ser Leu Asn Gln Ala Phe
         50                  55                  60 aag gac aag gcc aag ctg acc gcc gcc acc tct gcc tct atc gcc tac    240
Lys Asp Lys Ala Lys Leu Thr Ala Ala Thr Ser Ala Ser Ile Ala Tyr
 65                  70                  75                  80 ctg gaa ttt tcc agc ctg acc aac gag gac agc gcc gtg tac tac tgc    288
Leu Glu Phe Ser Ser Leu Thr Asn Glu Asp Ser Ala Val Tyr Tyr Cys
                 85                  90                  95 gcc cgg atg ggc aga cgg aac ccc tac tac ttc gac tac tgg ggc cag    336
Ala Arg Met Gly Arg Arg Asn Pro Tyr Tyr Phe Asp Tyr Trp Gly Gln
                100                 105                 110 ggc acc ctc gtg aca gtg tct agc                                    360
Gly Thr Leu Val Thr Val Ser Ser
                115                 120

<210> SEQ ID NO 10
<211> LENGTH: 120
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Leu Gln Ser Gly Ala Val Leu Ala Arg Pro Gly Thr
  1               5                  10                  15

Ser Val Lys Ile Ser Cys Lys Ala Ser Gly Tyr Ser Phe Thr Thr Tyr
                 20                  25                  30

Trp Met Asn Trp Val Lys Gln Arg Pro Gly Gln Gly Leu Glu Trp Ile
                 35                  40                  45

Gly Met Ile His Pro Ser Asp Ser Glu Thr Ser Leu Asn Gln Ala Phe
         50                  55                  60

Lys Asp Lys Ala Lys Leu Thr Ala Ala Thr Ser Ala Ser Ile Ala Tyr
 65                  70                  75                  80

Leu Glu Phe Ser Ser Leu Thr Asn Glu Asp Ser Ala Val Tyr Tyr Cys
                 85                  90                  95

Ala Arg Met Gly Arg Arg Asn Pro Tyr Tyr Phe Asp Tyr Trp Gly Gln
                100                 105                 110

Gly Thr Leu Val Thr Val Ser Ser
                115                 120

<210> SEQ ID NO 11
<211> LENGTH: 360
<212> TYPE: DNA
<213> ORGANISM: Artificial Sequence
<220> FEATURE:
<223> OTHER INFORMATION: hCTLA4.27VH2
<220> FEATURE:
<221> NAME/KEY: CDS
<222> LOCATION: (1)..(360)

<400> SEQUENCE: 11 gag gtg cag ctg gtg cag tct ggc gct gtg ctc gtg aaa cct ggc gcc     48
Glu Val Gln Leu Val Gln Ser Gly Ala Val Leu Val Lys Pro Gly Ala
  1               5                  10                  15 tcc gtg aag gtg tcc tgc aag gcc agc ggc tac agc ttc acc acc tac     96
Ser Val Lys Val Ser Cys Lys Ala Ser Gly Tyr Ser Phe Thr Thr Tyr
                 20                  25                  30 tgg atg aac tgg gtg cgc cag agg cct ggc aag ggc ctg gaa tgg atc    144
Trp Met Asn Trp Val Arg Gln Arg Pro Gly Lys Gly Leu Glu Trp Ile
```

```
                  35                  40                  45
ggc atg atc cac ccc agc gac agc gag aca agc ctg aac cag gcc ttc      192
Gly Met Ile His Pro Ser Asp Ser Glu Thr Ser Leu Asn Gln Ala Phe
        50                  55                  60 aag gac aaa gtg acc atc acc gcc gac gag agc acc agc acc gcc tac      240
Lys Asp Lys Val Thr Ile Thr Ala Asp Glu Ser Thr Ser Thr Ala Tyr
65                  70                  75                  80 atg cag ctg agc agc ctg aga agc gag gac acc gcc gtg tac tac tgc      288
Met Gln Leu Ser Ser Leu Arg Ser Glu Asp Thr Ala Val Tyr Tyr Cys
                85                  90                  95 gcc cgg atg ggc aga cgg aac ccc tac tac ttc gac tac tgg ggc cag      336
Ala Arg Met Gly Arg Arg Asn Pro Tyr Tyr Phe Asp Tyr Trp Gly Gln
            100                 105                 110 ggc acc acc gtg aca gtg tct agc                                      360
Gly Thr Thr Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Gln Ser Gly Ala Val Leu Val Lys Pro Gly Ala
1               5                   10                  15

Ser Val Lys Val Ser Cys Lys Ala Ser Gly Tyr Ser Phe Thr Thr Tyr
            20                  25                  30

Trp Met Asn Trp Val Arg Gln Arg Pro Gly Lys Gly Leu Glu Trp Ile
        35                  40                  45

Gly Met Ile His Pro Ser Asp Ser Glu Thr Ser Leu Asn Gln Ala Phe
    50                  55                  60

Lys Asp Lys Val Thr Ile Thr Ala Asp Glu Ser Thr Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Met Gly Arg Arg Asn Pro Tyr Tyr Phe Asp Tyr Trp Gly Gln
            100                 105                 110

Gly Thr Thr Val Thr Val Ser Ser
        115                 120

<210> SEQ ID NO 13
<211> LENGTH: 360
<212> TYPE: DNA
<213> ORGANISM: Artificial Sequence
<220> FEATURE:
<223> OTHER INFORMATION: hCTLA4.27VH3
<220> FEATURE:
<221> NAME/KEY: CDS
<222> LOCATION: (1)..(360)

<400> SEQUENCE: 13 gag gtg cag ctg gtg cag tct ggc gcc gtg gtg gcc aag cct ggc agc       48
Glu Val Gln Leu Val Gln Ser Gly Ala Val Val Ala Lys Pro Gly Ser
1               5                   10                  15 agc gtg aag gtg tcc tgt aaa gcc agc ggc tac agc ttc acc acc tac       96
Ser Val Lys Val Ser Cys Lys Ala Ser Gly Tyr Ser Phe Thr Thr Tyr
            20                  25                  30 tgg atg aac tgg gtg cgc cag gcc cct gga cag ggc ctg gaa tgg atg      144
Trp Met Asn Trp Val Arg Gln Ala Pro Gly Gln Gly Leu Glu Trp Met
```

```
                    35                  40                  45
ggc atg atc cac ccc agc gac agc gag aca agc ctg aac cag gcc ttc        192
Gly Met Ile His Pro Ser Asp Ser Glu Thr Ser Leu Asn Gln Ala Phe
         50                  55                  60 aag gac aga gtg acc atc acc gcc gac aag agc acc agc acc gcc tac        240
Lys Asp Arg Val Thr Ile Thr Ala Asp Lys Ser Thr Ser Thr Ala Tyr
 65                  70                  75                  80 atg gaa ctg agc agc ctg acc agc gag gac acc gcc gtg tac tac tgc        288
Met Glu Leu Ser Ser Leu Thr Ser Glu Asp Thr Ala Val Tyr Tyr Cys
                 85                  90                  95 gcc cgg atg ggc aga cgg aac ccc tac tac ttc gac tac tgg ggc cag        336
Ala Arg Met Gly Arg Arg Asn Pro Tyr Tyr Phe Asp Tyr Trp Gly Gln
            100                 105                 110 ggc acc acc gtg aca gtg tct agc                                        360
Gly Thr Thr Val Thr Val Ser Ser
        115                 120

<210> SEQ ID NO 14
<211> LENGTH: 120
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Gln Ser Gly Ala Val Ala Lys Pro Gly Ser
1               5                   10                  15

Ser Val Lys Val Ser Cys Lys Ala Ser Gly Tyr Ser Phe Thr Thr Tyr
            20                  25                  30

Trp Met Asn Trp Val Arg Gln Ala Pro Gly Gln Gly Leu Glu Trp Met
        35                  40                  45

Gly Met Ile His Pro Ser Asp Ser Glu Thr Ser Leu Asn Gln Ala Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Met Gly Arg Arg Asn Pro Tyr Tyr Phe Asp Tyr Trp Gly Gln
            100                 105                 110

Gly Thr Thr Val Thr Val Ser Ser
        115                 120

<210> SEQ ID NO 15
<211> LENGTH: 360
<212> TYPE: DNA
<213> ORGANISM: Artificial Sequence
<220> FEATURE:
<223> OTHER INFORMATION: hCTLA4.27VH4
<220> FEATURE:
<221> NAME/KEY: CDS
<222> LOCATION: (1)..(360)

<400> SEQUENCE: 15 gag gtg cag ctg gtg cag tct ggc gcc gaa gtg aag aaa cca ggc gcc        48
Glu Val Gln Leu Val Gln Ser Gly Ala Glu Val Lys Lys Pro Gly Ala
1               5                   10                  15 agc gtg aag gtg tcc tgc aag gcc agc ggc tac agc ttc acc acc tac        96
Ser Val Lys Val Ser Cys Lys Ala Ser Gly Tyr Ser Phe Thr Thr Tyr
            20                  25                  30 tgg atg aac tgg gtg cgc cag gcc cct gga cag ggc ctg gaa tgg atg       144
Trp Met Asn Trp Val Arg Gln Ala Pro Gly Gln Gly Leu Glu Trp Met
```

```
                      35                  40                  45
ggc atg atc cac ccc agc gac agc gag aca agc ctg aac cag gcc ttc      192
Gly Met Ile His Pro Ser Asp Ser Glu Thr Ser Leu Asn Gln Ala Phe
        50                  55                  60 aag gac aga gtg acc atg acc cgg gac acc agc acc tcc acc gtg tac      240
Lys Asp Arg Val Thr Met Thr Arg Asp Thr Ser Thr Ser Thr Val Tyr
 65                  70                  75                  80 atg gaa ctg agc agc ctg cgg agc gag gac acc gcc gtg tac tac tgc      288
Met Glu Leu Ser Ser Leu Arg Ser Glu Asp Thr Ala Val Tyr Tyr Cys
                 85                  90                  95 gcc cgg atg ggc aga cgg aac ccc tac tac ttc gac tac tgg ggc cag      336
Ala Arg Met Gly Arg Arg Asn Pro Tyr Tyr Phe Asp Tyr Trp Gly Gln
            100                 105                 110 ggc acc ctc gtg aca gtg tct agc                                      360
Gly Thr Leu Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Synthetic Construct

<400> SEQUENCE: 16

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Thr Tyr
            20                  25                  30

Trp Met Asn Trp Val Arg Gln Ala Pro Gly Gln Gly Leu Glu Trp Met
        35                  40                  45

Gly Met Ile His Pro Ser Asp Ser Glu Thr Ser Leu Asn Gln Ala Phe
    50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Met Gly Arg Arg Asn Pro Tyr Tyr Phe Asp Tyr Trp Gly Gln
            100                 105                 110

Gly Thr Leu Val Thr Val Ser Ser
        115                 120

<210> SEQ ID NO 17
<211> LENGTH: 360
<212> TYPE: DNA
<213> ORGANISM: Artificial Sequence
<220> FEATURE:
<223> OTHER INFORMATION: hCTLA4.27VH5
<220> FEATURE:
<221> NAME/KEY: CDS
<222> LOCATION: (1)..(360)

<400> SEQUENCE: 17 gag gtg cag ctg ctg cag gct ggc gct gtg ctg gct aga cct ggc acc       48
Glu Val Gln Leu Leu Gln Ala Gly Ala Val Leu Ala Arg Pro Gly Thr
 1               5                  10                  15 agc gtg aag atc agc tgc aag gcc agc ggc tac agc ttc acc acc tac       96
Ser Val Lys Ile Ser Cys Lys Ala Ser Gly Tyr Ser Phe Thr Thr Tyr
            20                  25                  30 tgg atg aac tgg gtc aag cag agg ccc ggc aag ggc ctg gaa tgg atc      144
Trp Met Asn Trp Val Lys Gln Arg Pro Gly Lys Gly Leu Glu Trp Ile
```

```
                  35                  40                  45
ggc atg atc cac ccc agc gac agc gag aca agc ctg aac cag gcc ttc      192
Gly Met Ile His Pro Ser Asp Ser Glu Thr Ser Leu Asn Gln Ala Phe
         50                  55                  60 aag gac aag gcc aag ctg acc gcc gcc acc tct gcc tct atc gcc tac      240
Lys Asp Lys Ala Lys Leu Thr Ala Ala Thr Ser Ala Ser Ile Ala Tyr
 65                  70                  75                  80 ctg gaa ttt tcc agc ctg acc aac gag gac agc gcc gtg tac tac tgc      288
Leu Glu Phe Ser Ser Leu Thr Asn Glu Asp Ser Ala Val Tyr Tyr Cys
                 85                  90                  95 gcc cgg atc ggc aga cgg aac ccc tac tac ttc gac tac tgg ggc cag      336
Ala Arg Ile Gly Arg Arg Asn Pro Tyr Tyr Phe Asp Tyr Trp Gly Gln
            100                 105                 110 ggc acc ctc gtg aca gtg tct agc                                       360
Gly Thr Leu Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Leu Gln Ala Gly Ala Val Leu Ala Arg Pro Gly Thr
 1               5                  10                  15

Ser Val Lys Ile Ser Cys Lys Ala Ser Gly Tyr Ser Phe Thr Thr Tyr
            20                  25                  30

Trp Met Asn Trp Val Lys Gln Arg Pro Gly Lys Gly Leu Glu Trp Ile
        35                  40                  45

Gly Met Ile His Pro Ser Asp Ser Glu Thr Ser Leu Asn Gln Ala Phe
    50                  55                  60

Lys Asp Lys Ala Lys Leu Thr Ala Ala Thr Ser Ala Ser Ile Ala Tyr
 65                  70                  75                  80

Leu Glu Phe Ser Ser Leu Thr Asn Glu Asp Ser Ala Val Tyr Tyr Cys
                 85                  90                  95

Ala Arg Ile Gly Arg Arg Asn Pro Tyr Tyr Phe Asp Tyr Trp Gly Gln
            100                 105                 110

Gly Thr Leu Val Thr Val Ser Ser
        115                 120

<210> SEQ ID NO 19
<211> LENGTH: 360
<212> TYPE: DNA
<213> ORGANISM: Artificial Sequence
<220> FEATURE:
<223> OTHER INFORMATION: hCTLA4.27VH6
<220> FEATURE:
<221> NAME/KEY: CDS
<222> LOCATION: (1)..(360)

<400> SEQUENCE: 19 gag gtg cag ctg ctg gaa tct ggc cct gaa ctc gtg cgg cct ggc agc       48
Glu Val Gln Leu Leu Glu Ser Gly Pro Glu Leu Val Arg Pro Gly Ser
 1               5                  10                  15 agc gtg aag atc agc tgt aaa gcc agc ggc tac agc ttc acc acc tac       96
Ser Val Lys Ile Ser Cys Lys Ala Ser Gly Tyr Ser Phe Thr Thr Tyr
            20                  25                  30 tgg atg aac tgg gtc aag cag agg ccc ggc aag ggc ctg gaa tgg atc      144
Trp Met Asn Trp Val Lys Gln Arg Pro Gly Lys Gly Leu Glu Trp Ile
```

```
                35                  40                  45
ggc atg atc cac ccc agc gac agc gag aca agc ctg aac cag gcc ttc     192
Gly Met Ile His Pro Ser Asp Ser Glu Thr Ser Leu Asn Gln Ala Phe
         50                  55                  60 aag gac aaa gtg aag ctg acc gcc gcc acc agc gcc tct atc gcc tac     240
Lys Asp Lys Val Lys Leu Thr Ala Ala Thr Ser Ala Ser Ile Ala Tyr
 65                  70                  75                  80 ctg gaa ttt tcc agc ctg cgg aac gag gac agc gcc gtg tac tac tgc     288
Leu Glu Phe Ser Ser Leu Arg Asn Glu Asp Ser Ala Val Tyr Tyr Cys
                 85                  90                  95 gcc cgg atg ggc aga cgg aac ccc tac tac ttc gac tac tgg ggc cag     336
Ala Arg Met Gly Arg Arg Asn Pro Tyr Tyr Phe Asp Tyr Trp Gly Gln
            100                 105                 110 ggc acc ctc gtg aca gtg tct agc                                     360
Gly Thr Leu Val Thr Val Ser Ser
        115                 120

<210> SEQ ID NO 20
<211> LENGTH: 120
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Leu Glu Ser Gly Pro Glu Leu Val Arg Pro Gly Ser
1               5                   10                  15

Ser Val Lys Ile Ser Cys Lys Ala Ser Gly Tyr Ser Phe Thr Thr Tyr
            20                  25                  30

Trp Met Asn Trp Val Lys Gln Arg Pro Gly Lys Gly Leu Glu Trp Ile
        35                  40                  45

Gly Met Ile His Pro Ser Asp Ser Glu Thr Ser Leu Asn Gln Ala Phe
    50                  55                  60

Lys Asp Lys Val Lys Leu Thr Ala Ala Thr Ser Ala Ser Ile Ala Tyr
65                  70                  75                  80

Leu Glu Phe Ser Ser Leu Arg Asn Glu Asp Ser Ala Val Tyr Tyr Cys
                85                  90                  95

Ala Arg Met Gly Arg Arg Asn Pro Tyr Tyr Phe Asp Tyr Trp Gly Gln
            100                 105                 110

Gly Thr Leu Val Thr Val Ser Ser
        115                 120

<210> SEQ ID NO 21
<211> LENGTH: 321
<212> TYPE: DNA
<213> ORGANISM: Artificial Sequence
<220> FEATURE:
<223> OTHER INFORMATION: hCTLA4.27VL1
<220> FEATURE:
<221> NAME/KEY: CDS
<222> LOCATION: (1)..(321)

<400> SEQUENCE: 21 gac atc cag atg acc cag agc ccc agc agc ctg tct gcc agc gtg ggc      48
Asp Ile Gln Met Thr Gln Ser Pro Ser Ser Leu Ser Ala Ser Val Gly
1               5                   10                  15 gac aga gtg acc atc acc tgt cgg ccc agc gag aac ctg tac acc aac      96
Asp Arg Val Thr Ile Thr Cys Arg Pro Ser Glu Asn Leu Tyr Thr Asn
            20                  25                  30 ctg gcc tgg tat cag cag aag ccc ggc aag gcc ccc aaa ctg ctg ctg     144
Leu Ala Trp Tyr Gln Gln Lys Pro Gly Lys Ala Pro Lys Leu Leu Leu
```

```
                   35                  40                  45 tac ggc gcc acc aat ctg gcc gat ggc gtg ccc agc aga ttt tcc ggc    192
Tyr Gly Ala Thr Asn Leu Ala Asp Gly Val Pro Ser Arg Phe Ser Gly
         50                  55                  60 tct ggc agc ggc acc gac tac acc ctg acc atc tct agc ctg cag ccc    240
Ser Gly Ser Gly Thr Asp Tyr Thr Leu Thr Ile Ser Ser Leu Gln Pro
 65                  70                  75                  80 gag gac ttc gcc acc tac tac tgt cag cac ctg tgg ggc acc ccc ttc    288
Glu Asp Phe Ala Thr Tyr Tyr Cys Gln His Leu Trp Gly Thr Pro Phe
                 85                  90                  95 acc ttt ggc cag ggc acc aag ctg gaa atc aag                        321
Thr Phe Gly Gln Gly Thr Lys Leu Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Synthetic Construct

<400> SEQUENCE: 22

Asp Ile Gln Met Thr Gln Ser Pro Ser Ser Leu Ser Ala Ser Val Gly
 1               5                  10                  15

Asp Arg Val Thr Ile Thr Cys Arg Pro Ser Glu Asn Leu Tyr Thr Asn
             20                  25                  30

Leu Ala Trp Tyr Gln Gln Lys Pro Gly Lys Ala Pro Lys Leu Leu Leu
         35                  40                  45

Tyr Gly Ala Thr Asn Leu Ala Asp Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Leu Trp Gly Thr Pro Phe
                 85                  90                  95

Thr Phe Gly Gln Gly Thr Lys Leu Glu Ile Lys
            100                 105

<210> SEQ ID NO 23
<211> LENGTH: 321
<212> TYPE: DNA
<213> ORGANISM: Artificial Sequence
<220> FEATURE:
<223> OTHER INFORMATION: hCTLA4.27VL2
<220> FEATURE:
<221> NAME/KEY: CDS
<222> LOCATION: (1)..(321)

<400> SEQUENCE: 23 gac atc cag atg acc cag agc ccc agc agc ctg tct gcc agc gtg ggc    48
Asp Ile Gln Met Thr Gln Ser Pro Ser Ser Leu Ser Ala Ser Val Gly
 1               5                  10                  15 gac aga gtg acc atc acc tgt cgg ccc agc gag aac ctg tac acc aac    96
Asp Arg Val Thr Ile Thr Cys Arg Pro Ser Glu Asn Leu Tyr Thr Asn
             20                  25                  30 ctg gcc tgg tat cag cag aag ccc ggc aag gcc ccc aag ctg ctg atc    144
Leu Ala Trp Tyr Gln Gln Lys Pro Gly Lys Ala Pro Lys Leu Leu Ile
         35                  40                  45 tac ggc gcc acc aat ctg gcc gat ggc gtg ccc agc aga ttt tcc ggc    192
Tyr Gly Ala Thr Asn Leu Ala Asp Gly Val Pro Ser Arg Phe Ser Gly
     50                  55                  60 tct ggc agc ggc acc gag ttc agc ctg agc atc tct agc ctg cag ccc    240
```

-continued

```
Ser Gly Ser Gly Thr Glu Phe Ser Leu Ser Ile Ser Ser Leu Gln Pro
 65                  70                  75                  80 gag gac ttc gcc acc tac tac tgt cag cac ctg tgg ggc acc ccc ttc        288
Glu Asp Phe Ala Thr Tyr Tyr Cys Gln His Leu Trp Gly Thr Pro Phe
                 85                  90                  95 acc ttt ggc ggc gga aca aag gtg gaa atc aag                            321
Thr Phe Gly Gly Gly Thr Lys Val Glu Ile Lys
            100                 105
```

<210> SEQ ID NO 24
<211> LENGTH: 107
<212> TYPE: PRT
<213> ORGANISM: Artificial Sequence
<220> FEATURE:
<223> OTHER INFORMATION: Synthetic Construct

<400> SEQUENCE: 24

```
Asp Ile Gln Met Thr Gln Ser Pro Ser Ser Leu Ser Ala Ser Val Gly
  1               5                  10                  15

Asp Arg Val Thr Ile Thr Cys Arg Pro Ser Glu Asn Leu Tyr Thr Asn
                 20                  25                  30

Leu Ala Trp Tyr Gln Gln Lys Pro Gly Lys Ala Pro Lys Leu Leu Ile
             35                  40                  45

Tyr Gly Ala Thr Asn Leu Ala Asp Gly Val Pro Ser Arg Phe Ser Gly
 50                  55                  60

Ser Gly Ser Gly Thr Glu Phe Ser Leu Ser Ile Ser Ser Leu Gln Pro
 65                  70                  75                  80

Glu Asp Phe Ala Thr Tyr Tyr Cys Gln His Leu Trp Gly Thr Pro Phe
                 85                  90                  95

Thr Phe Gly Gly Gly Thr Lys Val Glu Ile Lys
            100                 105
```

<210> SEQ ID NO 25
<211> LENGTH: 321
<212> TYPE: DNA
<213> ORGANISM: Artificial Sequence
<220> FEATURE:
<223> OTHER INFORMATION: hCTLA4.27VL3
<220> FEATURE:
<221> NAME/KEY: CDS
<222> LOCATION: (1)..(321)

<400> SEQUENCE: 25

```
gac atc cag atg acc cag agc ccc agc agc ctg tct gcc agc gtg ggc        48
Asp Ile Gln Met Thr Gln Ser Pro Ser Ser Leu Ser Ala Ser Val Gly
  1               5                  10                  15 gat acc gtg acc atc acc tgt cgg ccc agc gag aac ctg tac acc aac        96
Asp Thr Val Thr Ile Thr Cys Arg Pro Ser Glu Asn Leu Tyr Thr Asn
                 20                  25                  30 ctg gcc tgg tat cag cag aag ccc ggc aag gcc ccc aaa ctg ctg ctg       144
Leu Ala Trp Tyr Gln Gln Lys Pro Gly Lys Ala Pro Lys Leu Leu Leu
             35                  40                  45 tac ggc gcc acc aat ctg gcc gat ggc gtg ccc agc aga ttt tcc ggc       192
Tyr Gly Ala Thr Asn Leu Ala Asp Gly Val Pro Ser Arg Phe Ser Gly
 50                  55                  60 tct ggc agc ggc acc gac tac acc ctg acc atc tct agc ctg cag agc       240
Ser Gly Ser Gly Thr Asp Tyr Thr Leu Thr Ile Ser Ser Leu Gln Ser
 65                  70                  75                  80 gag gac ttc gcc acc tac tac tgt cag cac ctg tgg ggc acc ccc ttc       288
Glu Asp Phe Ala Thr Tyr Tyr Cys Gln His Leu Trp Gly Thr Pro Phe
                 85                  90                  95
```

```
acc ttt ggc cag ggc acc aag ctg gaa atc aag                          321
Thr Phe Gly Gln Gly Thr Lys Leu Glu Ile Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: Synthetic Construct

<400> SEQUENCE: 26

Asp Ile Gln Met Thr Gln Ser Pro Ser Ser Leu Ser Ala Ser Val Gly
1               5                   10                  15

Asp Thr Val Thr Ile Thr Cys Arg Pro Ser Glu Asn Leu Tyr Thr Asn
            20                  25                  30

Leu Ala Trp Tyr Gln Gln Lys Pro Gly Lys Ala Pro Lys Leu Leu Leu
        35                  40                  45

Tyr Gly Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Ser
65                  70                  75                  80

Glu Asp Phe Ala Thr Tyr Tyr Cys Gln His Leu Trp Gly Thr Pro Phe
                85                  90                  95

Thr Phe Gly Gln Gly Thr Lys Leu Glu Ile Lys
            100                 105

<210> SEQ ID NO 27
<211> LENGTH: 321
<212> TYPE: DNA
<213> ORGANISM: Artificial Sequence
<220> FEATURE:
<223> OTHER INFORMATION: hCTLA4.27VL4
<220> FEATURE:
<221> NAME/KEY: CDS
<222> LOCATION: (1)..(321)

<400> SEQUENCE: 27 gac atc cag atg acc cag agc ccc agc agc ctg tct gcc agc gtg ggc     48
Asp Ile Gln Met Thr Gln Ser Pro Ser Ser Leu Ser Ala Ser Val Gly
1               5                   10                  15 gac aga gtg acc atc acc tgt cgg ccc agc gag aac ctg tac acc aac     96
Asp Arg Val Thr Ile Thr Cys Arg Pro Ser Glu Asn Leu Tyr Thr Asn
            20                  25                  30 ctg gcc tgg tat cag cag aag ccc ggc aag gcc cct aag ctg ctg ctg    144
Leu Ala Trp Tyr Gln Gln Lys Pro Gly Lys Ala Pro Lys Leu Leu Leu
        35                  40                  45 tac ggc gcc acc aat ctg gcc gat ggc gtg ccc agc aga ttt tcc ggc    192
Tyr Gly Ala Thr Asn Leu Ala Asp Gly Val Pro Ser Arg Phe Ser Gly
    50                  55                  60 tct ggc agc ggc acc gac tac acc ctg acc atc tct agc ctg cag ccc    240
Ser Gly Ser Gly Thr Asp Tyr Thr Leu Thr Ile Ser Ser Leu Gln Pro
65                  70                  75                  80 gag gac ttc gcc acc tac tac tgc cag cac ctg tgg ggc acc ccc ttc    288
Glu Asp Phe Ala Thr Tyr Tyr Cys Gln His Leu Trp Gly Thr Pro Phe
                85                  90                  95 aca ttt ggc gga ggc acc aag ctg gaa atc aag                         321
Thr Phe Gly Gly Gly Thr Lys Leu Glu Ile Lys
            100                 105

<210> SEQ ID NO 28
<211> LENGTH: 107
```

<212> TYPE: PRT
<213> ORGANISM: Artificial Sequence
<220> FEATURE:
<223> OTHER INFORMATION: Synthetic Construct

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Pro Ser Glu Asn Leu Tyr Thr Asn
            20                  25                  30

Leu Ala Trp Tyr Gln Gln Lys Pro Gly Lys Ala Pro Lys Leu Leu Leu
        35                  40                  45

Tyr Gly Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Leu Trp Gly Thr Pro Phe
                85                  90                  95

Thr Phe Gly Gly Gly Thr Lys Leu Glu Ile Lys
            100                 105

<210> SEQ ID NO 29
<211> LENGTH: 321
<212> TYPE: DNA
<213> ORGANISM: Artificial Sequence
<220> FEATURE:
<223> OTHER INFORMATION: hCTLA4.27VL5
<220> FEATURE:
<221> NAME/KEY: CDS
<222> LOCATION: (1)..(321)

<400> SEQUENCE: 29 gac atc cag atg acc cag gcc cct agc agc ctg tct gcc agc gtg ggc        48
Asp Ile Gln Met Thr Gln Ala Pro Ser Ser Leu Ser Ala Ser Val Gly
1               5                   10                  15 gac aga gtg acc atc acc tgt cgg ccc agc gag aac ctg tac acc aac        96
Asp Arg Val Thr Ile Thr Cys Arg Pro Ser Glu Asn Leu Tyr Thr Asn
            20                  25                  30 ctg gcc tgg tat cag cag aag ccc ggc aag gcc ccc aaa ctg ctg ctg       144
Leu Ala Trp Tyr Gln Gln Lys Pro Gly Lys Ala Pro Lys Leu Leu Leu
        35                  40                  45 tac ggc gcc acc aat ctg gcc gat ggc gtg ccc agc aga ttt tcc ggc       192
Tyr Gly Ala Thr Asn Leu Ala Asp Gly Val Pro Ser Arg Phe Ser Gly
    50                  55                  60 tct ggc agc ggc acc gac tac acc ctg aca atc agc tcc ctg cag gcc       240
Ser Gly Ser Gly Thr Asp Tyr Thr Leu Thr Ile Ser Ser Leu Gln Ala
65                  70                  75                  80 gag gac ttc gcc acc tac tac tgt cag cac ctg tgg ggc acc ccc ttc       288
Glu Asp Phe Ala Thr Tyr Tyr Cys Gln His Leu Trp Gly Thr Pro Phe
                85                  90                  95 acc ttt ggc ggc gga aca aag ctg gaa atc aag                           321
Thr Phe Gly Gly Gly Thr Lys Leu Glu Ile Lys
            100                 105

<210> SEQ ID NO 30
<211> LENGTH: 107
<212> TYPE: PRT
<213> ORGANISM: Artificial Sequence
<220> FEATURE:
<223> OTHER INFORMATION: Synthetic Construct

<400> SEQUENCE: 30

```
Asp Ile Gln Met Thr Gln Ala Pro Ser Ser Leu Ser Ala Ser Val Gly
 1               5                  10                  15

Asp Arg Val Thr Ile Thr Cys Arg Pro Ser Glu Asn Leu Tyr Thr Asn
             20                  25                  30

Leu Ala Trp Tyr Gln Gln Lys Pro Gly Lys Ala Pro Lys Leu Leu Leu
         35                  40                  45

Tyr Gly Ala Thr Asn Leu Ala Asp Gly Val Pro Ser Arg Phe Ser Gly
     50                  55                  60

Ser Gly Ser Gly Thr Asp Tyr Thr Leu Thr Ile Ser Ser Leu Gln Ala
 65                  70                  75                  80

Glu Asp Phe Ala Thr Tyr Tyr Cys Gln His Leu Trp Gly Thr Pro Phe
             85                  90                  95

Thr Phe Gly Gly Gly Thr Lys Leu Glu Ile Lys
            100                 105
```

<210> SEQ ID NO 31
<211> LENGTH: 360
<212> TYPE: DNA
<213> ORGANISM: Mus musculus
<220> FEATURE:
<221> NAME/KEY: CDS
<222> LOCATION: (1)..(360)

<400> SEQUENCE: 31

```
cag gtc caa ctg cag cag cct ggg gct gta ctg gtg agg cct gga gtt      48
Gln Val Gln Leu Gln Gln Pro Gly Ala Val Leu Val Arg Pro Gly Val
 1               5                  10                  15 tca gtg aag ctg tcc tgc aag gct tct ggc tac tcc ttc acc acc tac      96
Ser Val Lys Leu Ser Cys Lys Ala Ser Gly Tyr Ser Phe Thr Thr Tyr
             20                  25                  30 tgg atg aac tgg gtg aag cag agg cct gga caa ggc ctt gag tgg att     144
Trp Met Asn Trp Val Lys Gln Arg Pro Gly Gln Gly Leu Glu Trp Ile
         35                  40                  45 ggc atg att cat cct tcc gat agt gaa act agt tta aat cag gcg ttc     192
Gly Met Ile His Pro Ser Asp Ser Glu Thr Ser Leu Asn Gln Ala Phe
     50                  55                  60 aag gac aag gcc aca ttg act ata gac aaa tcc tcc agc aca gcc tac     240
Lys Asp Lys Ala Thr Leu Thr Ile Asp Lys Ser Ser Ser Thr Ala Tyr
 65                  70                  75                  80 atg caa ctc agc agc ccg aca tct gaa gac tct gcg gtc tat ttc tgt     288
Met Gln Leu Ser Ser Pro Thr Ser Glu Asp Ser Ala Val Tyr Phe Cys
             85                  90                  95 gca aga atg gga cgt cgt aat ccc tat tac ttt gac tac tgg ggc caa     336
Ala Arg Met Gly Arg Arg Asn Pro Tyr Tyr Phe Asp Tyr Trp Gly Gln
            100                 105                 110 ggc acc act ctc aca gtc tcc tca                                     360
Gly Thr Thr Leu Thr Val Ser Ser
        115                 120
```

<210> SEQ ID NO 32
<211> LENGTH: 120
<212> TYPE: PRT
<213> ORGANISM: Mus musculus

<400> SEQUENCE: 32

```
Gln Val Gln Leu Gln Gln Pro Gly Ala Val Leu Val Arg Pro Gly Val
 1               5                  10                  15

Ser Val Lys Leu Ser Cys Lys Ala Ser Gly Tyr Ser Phe Thr Thr Tyr
             20                  25                  30

Trp Met Asn Trp Val Lys Gln Arg Pro Gly Gln Gly Leu Glu Trp Ile
         35                  40                  45
```

```
                35                  40                  45
Gly Met Ile His Pro Ser Asp Ser Glu Thr Ser Leu Asn Gln Ala Phe
     50                  55                  60
Lys Asp Lys Ala Thr Leu Thr Ile Asp Lys Ser Ser Thr Ala Tyr
65                  70                  75                  80
Met Gln Leu Ser Ser Pro Thr Ser Glu Asp Ser Ala Val Tyr Phe Cys
                85                  90                  95
Ala Arg Met Gly Arg Arg Asn Pro Tyr Tyr Phe Asp Tyr Trp Gly Gln
            100                 105                 110
Gly Thr Thr Leu Thr Val Ser Ser
        115                 120

<210> SEQ ID NO 33
<211> LENGTH: 321
<212> TYPE: DNA
<213> ORGANISM: Mus musculus
<220> FEATURE:
<221> NAME/KEY: CDS
<222> LOCATION: (1)..(321)

<400> SEQUENCE: 33 gac atc caa atg act cag tct cca gtc tcc cta tct gta tct gtg gga   48
Asp Ile Gln Met Thr Gln Ser Pro Val Ser Leu Ser Val Ser Val Gly
1               5                   10                  15 gaa act gtc acc atc aca tgt cga cca agt gag aat ctt tat act aat   96
Glu Thr Val Thr Ile Thr Cys Arg Pro Ser Glu Asn Leu Tyr Thr Asn
            20                  25                  30 tta gca tgg tat caa cag aaa cag gga aaa tct cct cag ctc ctg gtc  144
Leu Ala Trp Tyr Gln Gln Lys Gln Gly Lys Ser Pro Gln Leu Leu Val
        35                  40                  45 tat ggt gca aca aac cta gca gat ggt gtg cca tca agg ttc agt ggc  192
Tyr Gly Ala Thr Asn Leu Ala Asp Gly Val Pro Ser Arg Phe Ser Gly
    50                  55                  60 agt gga tca ggc aca cag tac tcc ctc agg atc aac agc ctg cag tct  240
Ser Gly Ser Gly Thr Gln Tyr Ser Leu Arg Ile Asn Ser Leu Gln Ser
65                  70                  75                  80 gaa gat ttc ggg act tat tac tgt caa cat ttg tgg ggt act cct ttc  288
Glu Asp Phe Gly Thr Tyr Tyr Cys Gln His Leu Trp Gly Thr Pro Phe
                85                  90                  95 acg ttc ggc tcg ggg aca aag ttg gaa cta aaa                      321
Thr Phe Gly Ser Gly Thr Lys Leu Glu Leu Lys
            100                 105

<210> SEQ ID NO 34
<211> LENGTH: 107
<212> TYPE: PRT
<213> ORGANISM: Mus musculus

<400> SEQUENCE: 34

Asp Ile Gln Met Thr Gln Ser Pro Val Ser Leu Ser Val Ser Val Gly
1               5                   10                  15

Glu Thr Val Thr Ile Thr Cys Arg Pro Ser Glu Asn Leu Tyr Thr Asn
            20                  25                  30

Leu Ala Trp Tyr Gln Gln Lys Gln Gly Lys Ser Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Thr Gln Tyr Ser Leu Arg Ile Asn Ser Leu Gln Ser
65                  70                  75                  80
```

```
Glu Asp Phe Gly Thr Tyr Tyr Cys Gln His Leu Trp Gly Thr Pro Phe
                85                  90                  95

Thr Phe Gly Ser Gly Thr Lys Leu Glu Leu Lys
            100                 105

<210> SEQ ID NO 35
<211> LENGTH: 669
<212> TYPE: DNA
<213> ORGANISM: Homo sapiens
<220> FEATURE:
<221> NAME/KEY: CDS
<222> LOCATION: (1)..(669)

<400> SEQUENCE: 35 atg gct tgc ctt gga ttt cag cgg cac aag gct cag ctg aac ctg gct       48
Met Ala Cys Leu Gly Phe Gln Arg His Lys Ala Gln Leu Asn Leu Ala
1               5                   10                  15 acc agg acc tgg ccc tgc act ctc ctg ttt ttt ctt ctc ttc atc cct       96
Thr Arg Thr Trp Pro Cys Thr Leu Leu Phe Phe Leu Leu Phe Ile Pro
            20                  25                  30 gtc ttc tgc aaa gca atg cac gtg gcc cag cct gct gtg gta ctg gcc      144
Val Phe Cys Lys Ala Met His Val Ala Gln Pro Ala Val Val Leu Ala
        35                  40                  45 agc agc cga ggc atc gcc agc ttt gtg tgt gag tat gca tct cca ggc      192
Ser Ser Arg Gly Ile Ala Ser Phe Val Cys Glu Tyr Ala Ser Pro Gly
    50                  55                  60 aaa gcc act gag gtc cgg gtg aca gtg ctt cgg cag gct gac agc cag      240
Lys Ala Thr Glu Val Arg Val Thr Val Leu Arg Gln Ala Asp Ser Gln
65                  70                  75                  80 gtg act gaa gtc tgt gcg gca acc tac atg atg ggg aat gag ttg acc      288
Val Thr Glu Val Cys Ala Ala Thr Tyr Met Met Gly Asn Glu Leu Thr
                85                  90                  95 ttc cta gat gat tcc atc tgc acg ggc acc tcc agt gga aat caa gtg      336
Phe Leu Asp Asp Ser Ile Cys Thr Gly Thr Ser Ser Gly Asn Gln Val
            100                 105                 110 aac ctc act atc caa gga ctg agg gcc atg gac acg gga ctc tac atc      384
Asn Leu Thr Ile Gln Gly Leu Arg Ala Met Asp Thr Gly Leu Tyr Ile
        115                 120                 125 tgc aag gtg gag ctc atg tac cca ccg cca tac tac ctg ggc ata ggc      432
Cys Lys Val Glu Leu Met Tyr Pro Pro Pro Tyr Tyr Leu Gly Ile Gly
    130                 135                 140 aac gga acc cag att tat gta att gat cca gaa ccg tgc cca gat tct      480
Asn Gly Thr Gln Ile Tyr Val Ile Asp Pro Glu Pro Cys Pro Asp Ser
145                 150                 155                 160 gac ttc ctc ctc tgg atc ctt gca gca gtt agt tcg ggg ttg ttt ttt      528
Asp Phe Leu Leu Trp Ile Leu Ala Ala Val Ser Ser Gly Leu Phe Phe
                165                 170                 175 tat agc ttt ctc ctc aca gct gtt tct ttg agc aaa atg cta aag aaa      576
Tyr Ser Phe Leu Leu Thr Ala Val Ser Leu Ser Lys Met Leu Lys Lys
            180                 185                 190 aga agc cct ctt aca aca ggg gtc tat gtg aaa atg ccc cca aca gag      624
Arg Ser Pro Leu Thr Thr Gly Val Tyr Val Lys Met Pro Pro Thr Glu
        195                 200                 205 cca gaa tgt gaa aag caa ttt cag cct tat ttt att ccc atc aat           669
Pro Glu Cys Glu Lys Gln Phe Gln Pro Tyr Phe Ile Pro Ile Asn
    210                 215                 220

<210> SEQ ID NO 36
<211> LENGTH: 223
<212> TYPE: PRT
<213> ORGANISM: Homo sapiens
```

<400> SEQUENCE: 36

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 37
<211> LENGTH: 669
<212> TYPE: DNA
<213> ORGANISM: Artificial Sequence
<220> FEATURE:
<223> OTHER INFORMATION: mutant CTLA4
<220> FEATURE:
<221> NAME/KEY: CDS
<222> LOCATION: (1)..(669)

<400> SEQUENCE: 37

```
atg gct tgc ctt gga ttt cag cgg cac aag gct cag ctg aac ctg gct    48
Met Ala Cys Leu Gly Phe Gln Arg His Lys Ala Gln Leu Asn Leu Ala
1               5                   10                  15 acc agg acc tgg ccc tgc act ctc ctg ttt ttt ctt ctc ttc atc cct    96
Thr Arg Thr Trp Pro Cys Thr Leu Leu Phe Phe Leu Leu Phe Ile Pro
            20                  25                  30 gtc ttc tgc aaa gca atg cac gtg gcc cag cct gct gtg gta ctg gcc   144
Val Phe Cys Lys Ala Met His Val Ala Gln Pro Ala Val Val Leu Ala
        35                  40                  45 agc agc cga ggc atc gcc agc ttt gtg tgt gag tat gca tct cca ggc   192
Ser Ser Arg Gly Ile Ala Ser Phe Val Cys Glu Tyr Ala Ser Pro Gly
    50                  55                  60 aaa gcc act gag gtc cgg gtg aca gtg ctt cgg cag gct gac agc cag   240
Lys Ala Thr Glu Val Arg Val Thr Val Leu Arg Gln Ala Asp Ser Gln
65                  70                  75                  80 gtg act gaa gtc tgt gcg gca acc tac atg atg ggg aat gag ttg acc   288
Val Thr Glu Val Cys Ala Ala Thr Tyr Met Met Gly Asn Glu Leu Thr
                85                  90                  95
```

```
                     85                  90                  95
ttc cta gat gat tcc atc tgc acg ggc acc tcc agt gga aat caa gtg        336
Phe Leu Asp Asp Ser Ile Cys Thr Gly Thr Ser Ser Gly Asn Gln Val
            100                 105                 110 aac ctc act atc caa gga ctg agg gcc atg gac acg gga ctc tac atc        384
Asn Leu Thr Ile Gln Gly Leu Arg Ala Met Asp Thr Gly Leu Tyr Ile
        115                 120                 125 tgc aag gtg gag ctc atg tac cca ccg cca tac tac ctg ggc ata ggc        432
Cys Lys Val Glu Leu Met Tyr Pro Pro Pro Tyr Tyr Leu Gly Ile Gly
    130                 135                 140 aac gga acc cag att tat gta att gat cca gaa ccg tgc cca gat tct        480
Asn Gly Thr Gln Ile Tyr Val Ile Asp Pro Glu Pro Cys Pro Asp Ser
145                 150                 155                 160 gac ttc ctc ctc tgg atc ctt gca gca gtt agt tcg ggg ttg ttt ttt        528
Asp Phe Leu Leu Trp Ile Leu Ala Ala Val Ser Ser Gly Leu Phe Phe
                165                 170                 175 tat agc ttt ctc ctc aca gct gtt tct ttg agc aaa atg cta aag aaa        576
Tyr Ser Phe Leu Leu Thr Ala Val Ser Leu Ser Lys Met Leu Lys Lys
            180                 185                 190 aga agc cct ctt aca aca ggg gtc ggt gtg aaa atg ccc cca aca gag        624
Arg Ser Pro Leu Thr Thr Gly Val Gly Val Lys Met Pro Pro Thr Glu
        195                 200                 205 cca gaa tgt gaa aag caa ttt cag cct ggt ttt att ccc atc aat            669
Pro Glu Cys Glu Lys Gln Phe Gln Pro Gly Phe Ile Pro Ile Asn
    210                 215                 220
```

<210> SEQ ID NO 38
<211> LENGTH: 223
<212> TYPE: PRT
<213> ORGANISM: Artificial Sequence
<220> FEATURE:
<223> OTHER INFORMATION: Synthetic Construct

<400> SEQUENCE: 38

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190
```

```
                Arg Ser Pro Leu Thr Thr Gly Val Gly Val Lys Met Pro Thr Glu
                    195                 200                 205
                Pro Glu Cys Glu Lys Gln Phe Gln Pro Gly Phe Ile Pro Ile Asn
                    210                 215                 220

<210> SEQ ID NO 39
<211> LENGTH: 669
<212> TYPE: DNA
<213> ORGANISM: Macaca fascicularis
<220> FEATURE:
<221> NAME/KEY: CDS
<222> LOCATION: (1)..(669)

<400> SEQUENCE: 39 atg gct tgc ctt gga ttt cag cgg cac aag gct cgg ctc aac ctg gct        48
Met Ala Cys Leu Gly Phe Gln Arg His Lys Ala Arg Leu Asn Leu Ala
1               5                   10                  15 acc agg acc cgg ccc tac act ctc ctg ttt tct ctt ctc ttc atc cct        96
Thr Arg Thr Arg Pro Tyr Thr Leu Leu Phe Ser Leu Leu Phe Ile Pro
                20                  25                  30 gtc ttc tcc aaa gca atg cac gtg gcc cag cct gct gtg gtg ctg gcc       144
Val Phe Ser Lys Ala Met His Val Ala Gln Pro Ala Val Val Leu Ala
            35                  40                  45 aac agc cga ggg atc gcc agc ttt gtg tgt gag tat gca tct cca ggc       192
Asn Ser Arg Gly Ile Ala Ser Phe Val Cys Glu Tyr Ala Ser Pro Gly
        50                  55                  60 aaa gcc act gag gtc cgg gtg aca gtg ctt cgg cag gcc gac agc cag       240
Lys Ala Thr Glu Val Arg Val Thr Val Leu Arg Gln Ala Asp Ser Gln
65                  70                  75                  80 gtg act gaa gtc tgt gcg gca acg tac atg atg ggg aat gag ttg acc       288
Val Thr Glu Val Cys Ala Ala Thr Tyr Met Met Gly Asn Glu Leu Thr
                85                  90                  95 ttc cta gat gat tcc atc tgc acg ggc acc tcc agt gga aat caa gtg       336
Phe Leu Asp Asp Ser Ile Cys Thr Gly Thr Ser Ser Gly Asn Gln Val
                100                 105                 110 aac ctc act atc caa gga ctg agg gct atg gac aca gga ctc tac atc       384
Asn Leu Thr Ile Gln Gly Leu Arg Ala Met Asp Thr Gly Leu Tyr Ile
            115                 120                 125 tgc aag gtg gag ctc atg tac cca cca cca tac tac atg ggc ata ggc       432
Cys Lys Val Glu Leu Met Tyr Pro Pro Pro Tyr Tyr Met Gly Ile Gly
        130                 135                 140 aat gga acc cag att tat gta att gat cca gaa ccg tgc cca gat tct       480
Asn Gly Thr Gln Ile Tyr Val Ile Asp Pro Glu Pro Cys Pro Asp Ser
145                 150                 155                 160 gac ttc ctc ctc tgg atc ctt gca gca gtt agt tcg ggg ttg ttt ttt       528
Asp Phe Leu Leu Trp Ile Leu Ala Ala Val Ser Ser Gly Leu Phe Phe
                165                 170                 175 tat agc ttt ctc ctc aca gct gtt tct ttg agc aaa atg cta aag aaa       576
Tyr Ser Phe Leu Leu Thr Ala Val Ser Leu Ser Lys Met Leu Lys Lys
                180                 185                 190 aga agc cct ctc aca aca ggg gtc tat gtg aaa atg ccc cca aca gag       624
Arg Ser Pro Leu Thr Thr Gly Val Tyr Val Lys Met Pro Pro Thr Glu
            195                 200                 205 cca gaa tgt gaa aag caa ttt cag cct tat ttt att ccc atc aat           669
Pro Glu Cys Glu Lys Gln Phe Gln Pro Tyr Phe Ile Pro Ile Asn
        210                 215                 220

<210> SEQ ID NO 40
<211> LENGTH: 223
<212> TYPE: PRT
<213> ORGANISM: Macaca fascicularis
```

-continued

<400> SEQUENCE: 40

Met Ala Cys Leu Gly Phe Gln Arg His Lys Ala Arg Leu Asn Leu Ala
1               5                   10                  15

Thr Arg Thr Arg Pro Tyr Thr Leu Leu Phe Ser Leu Leu Phe Ile Pro
            20                  25                  30

Val Phe Ser Lys Ala Met His Val Ala Gln Pro Ala Val Val Leu Ala
        35                  40                  45

Asn Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Met Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 41
<211> LENGTH: 669
<212> TYPE: DNA
<213> ORGANISM: Artificial Sequence
<220> FEATURE:
<223> OTHER INFORMATION: Human-mouse CTLA4
<220> FEATURE:
<221> NAME/KEY: CDS
<222> LOCATION: (1)..(669)

<400> SEQUENCE: 41 atg gcc tgc ctg ggc ttc cag aga cac aag gcc cag ctg aac ctg gcc      48
Met Ala Cys Leu Gly Phe Gln Arg His Lys Ala Gln Leu Asn Leu Ala
1               5                   10                  15 acc agg acc tgg cct tgt acc ctg ctg ttc ttc ctg ctg ttt atc ccc      96
Thr Arg Thr Trp Pro Cys Thr Leu Leu Phe Phe Leu Leu Phe Ile Pro
            20                  25                  30 gtg ttc tgc aag gcc atg cac gtg gcc cag cct gct gtg gtg ctg gcc    144
Val Phe Cys Lys Ala Met His Val Ala Gln Pro Ala Val Val Leu Ala
        35                  40                  45 tct tcc aga gga atc gcc tcc ttc gtg tgc gag tac gcc tcc ccc cac    192
Ser Ser Arg Gly Ile Ala Ser Phe Val Cys Glu Tyr Ala Ser Pro His
    50                  55                  60 aac acc gat gaa gtg cgc gtg acc gtg ctg cgg cag acc aac gac cag    240
Asn Thr Asp Glu Val Arg Val Thr Val Leu Arg Gln Thr Asn Asp Gln
65                  70                  75                  80 atg acc gaa gtg tgc gcc acc acc ttc acc gag aag aac gag ctg acc    288

```
                Met Thr Glu Val Cys Ala Thr Thr Phe Thr Glu Lys Asn Glu Leu Thr
                                85                  90                  95 ttc ctg gac gac tct atc tgc acc ggc acc tcc agc ggc aac caa gtg          336
Phe Leu Asp Asp Ser Ile Cys Thr Gly Thr Ser Ser Gly Asn Gln Val
            100                 105                 110 aac ctg aca atc cag ggc ctg cgg gcc atg gac acc ggc ctg tac ctg          384
Asn Leu Thr Ile Gln Gly Leu Arg Ala Met Asp Thr Gly Leu Tyr Leu
            115                 120                 125 tgc aag gtg gaa ctg atg tac ccc cct ccc tac ttc gtg ggc atg ggc          432
Cys Lys Val Glu Leu Met Tyr Pro Pro Pro Tyr Phe Val Gly Met Gly
        130                 135                 140 aac ggc acc cag atc tac gtg atc gac ccc gag cct tgc ccc gac tcc          480
Asn Gly Thr Gln Ile Tyr Val Ile Asp Pro Glu Pro Cys Pro Asp Ser
145                 150                 155                 160 gac ttt ctg ctg tgg atc ctg gct gcc gtg tcc tcc ggc ctg ttc ttc          528
Asp Phe Leu Leu Trp Ile Leu Ala Ala Val Ser Ser Gly Leu Phe Phe
                165                 170                 175 tac tct ttc ctg ctg acc gcc gtg tcc ctg tcc aag atg ctg aag aag          576
Tyr Ser Phe Leu Leu Thr Ala Val Ser Leu Ser Lys Met Leu Lys Lys
            180                 185                 190 cgg tcc ccc ctg acc acc ggc gtg gga gtg aaa atg cct ccc acc gag          624
Arg Ser Pro Leu Thr Thr Gly Val Gly Val Lys Met Pro Pro Thr Glu
            195                 200                 205 ccc gag tgc gag aag cag ttc cag ccc ggc ttc atc ccc atc aac              669
Pro Glu Cys Glu Lys Gln Phe Gln Pro Gly Phe Ile Pro Ile Asn
        210                 215                 220

<210> SEQ ID NO 42
<211> LENGTH: 223
<212> TYPE: PRT
<213> ORGANISM: Artificial Sequence
<220> FEATURE:
<223> OTHER INFORMATION: Synthetic Construct

<400> SEQUENCE: 42

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Leu
            115                 120                 125

Cys Lys Val Glu Leu Met Tyr Pro Pro Pro Tyr Phe Val Gly Met Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
```

```
                180              185              190
Arg Ser Pro Leu Thr Thr Gly Val Gly Val Lys Met Pro Thr Glu
        195              200              205

Pro Glu Cys Glu Lys Gln Phe Gln Pro Gly Phe Ile Pro Ile Asn
        210              215              220

<210> SEQ ID NO 43
<211> LENGTH: 669
<212> TYPE: DNA
<213> ORGANISM: Artificial Sequence
<220> FEATURE:
<223> OTHER INFORMATION: Mouse-Human CTLA4
<220> FEATURE:
<221> NAME/KEY: CDS
<222> LOCATION: (1)..(669)

<400> SEQUENCE: 43 atg gcc tgc ctg ggc ttc cag aga cac aag gcc cag ctg aac ctg gcc      48
Met Ala Cys Leu Gly Phe Gln Arg His Lys Ala Gln Leu Asn Leu Ala
1               5                  10                  15 acc agg acc tgg cct tgt acc ctg ctg ttc ttc ctg ctg ttt atc ccc      96
Thr Arg Thr Trp Pro Cys Thr Leu Leu Phe Phe Leu Leu Phe Ile Pro
                20                  25                  30 gtg ttc tgc gag gcc atc caa gtg acc cag ccc tct gtg gtg ctg gcc     144
Val Phe Cys Glu Ala Ile Gln Val Thr Gln Pro Ser Val Val Leu Ala
            35                  40                  45 tct tct cat ggc gtg gcc agc ttc cct tgc gag tac tcc cca tct ggc     192
Ser Ser His Gly Val Ala Ser Phe Pro Cys Glu Tyr Ser Pro Ser Gly
        50                  55                  60 aag gcc acc gaa gtg cgc gtg acc gtg ctg aga cag gcc gac tcc caa     240
Lys Ala Thr Glu Val Arg Val Thr Val Leu Arg Gln Ala Asp Ser Gln
65                  70                  75                  80 gtg aca gaa gtg tgc gcc gcc acc tac atg atg ggc aac acc gtg ggc     288
Val Thr Glu Val Cys Ala Ala Thr Tyr Met Met Gly Asn Thr Val Gly
                85                  90                  95 ttt ctg gac tac ccc ttc tgc tcc ggc acc ttc aac gag tcc aga gtg     336
Phe Leu Asp Tyr Pro Phe Cys Ser Gly Thr Phe Asn Glu Ser Arg Val
                100                 105                 110 aac ctg aca atc cag ggc ctg cgg gcc gtg gat acc ggc ctg tat atc     384
Asn Leu Thr Ile Gln Gly Leu Arg Ala Val Asp Thr Gly Leu Tyr Ile
            115                 120                 125 tgc aag gtg gaa ctg atg tac ccc cct ccc tac tac ctg ggc atc ggc     432
Cys Lys Val Glu Leu Met Tyr Pro Pro Pro Tyr Tyr Leu Gly Ile Gly
        130                 135                 140 aac ggc acc cag atc tac gtg atc gac ccc gag cct tgc ccc gac tcc     480
Asn Gly Thr Gln Ile Tyr Val Ile Asp Pro Glu Pro Cys Pro Asp Ser
145                 150                 155                 160 gac ttt ctg ctg tgg atc ctg gcc gcc gtg tcc tcc ggc ctg ttc ttc     528
Asp Phe Leu Leu Trp Ile Leu Ala Ala Val Ser Ser Gly Leu Phe Phe
                165                 170                 175 tac tct ttc ctg ctg acc gct gtg tcc ctg tcc aag atg ctg aag aag     576
Tyr Ser Phe Leu Leu Thr Ala Val Ser Leu Ser Lys Met Leu Lys Lys
            180                 185                 190 cgg tcc ccc ctg acc acc ggc gtg gga gtg aaa atg cct ccc acc gag     624
Arg Ser Pro Leu Thr Thr Gly Val Gly Val Lys Met Pro Pro Thr Glu
        195                 200                 205 ccc gag tgc gag aag cag ttc cag ccc ggc ttc atc ccc atc aac         669
Pro Glu Cys Glu Lys Gln Phe Gln Pro Gly Phe Ile Pro Ile Asn
        210                 215                 220

<210> SEQ ID NO 44
```

<211> LENGTH: 223
<212> TYPE: PRT
<213> ORGANISM: Artificial Sequence
<220> FEATURE:
<223> OTHER INFORMATION: Synthetic Construct

<400> SEQUENCE: 44

Met Ala Cys Leu Gly Phe Gln Arg His Lys Ala Gln Leu Asn Leu Ala
1               5                   10                  15

Thr Arg Thr Trp Pro Cys Thr Leu Leu Phe Leu Leu Phe Ile Pro
            20                  25                  30

Val Phe Cys Glu Ala Ile Gln Val Thr Gln Pro Ser Val Val Leu Ala
        35                  40                  45

Ser Ser His Gly Val Ala Ser Phe Pro Cys Glu Tyr Ser Pro Ser Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Gly Val Lys Met Pro Pro Thr Glu
        195                 200                 205

Pro Glu Cys Glu Lys Gln Phe Gln Pro Gly Phe Ile Pro Ile Asn
    210                 215                 220

<210> SEQ ID NO 45
<211> LENGTH: 669
<212> TYPE: DNA
<213> ORGANISM: Mus musculus
<220> FEATURE:
<221> NAME/KEY: CDS
<222> LOCATION: (1)..(669)

<400> SEQUENCE: 45 atg gct tgt ctt gga ctc cgg agg tac aaa gct caa ctg cag ctg cct     48
Met Ala Cys Leu Gly Leu Arg Arg Tyr Lys Ala Gln Leu Gln Leu Pro
1               5                   10                  15 tct agg act tgg cct ttt gta gcc ctg ctc act ctt ctt ttc atc cca     96
Ser Arg Thr Trp Pro Phe Val Ala Leu Leu Thr Leu Leu Phe Ile Pro
            20                  25                  30 gtc ttc tct gaa gcc ata cag gtg acc caa cct tca gtg gtg ttg gct    144
Val Phe Ser Glu Ala Ile Gln Val Thr Gln Pro Ser Val Val Leu Ala
        35                  40                  45 agc agc cat ggt gtc gcc agc ttt cca tgt gaa tat tca cca tca cac    192
Ser Ser His Gly Val Ala Ser Phe Pro Cys Glu Tyr Ser Pro Ser His
    50                  55                  60 aac act gat gag gtc cgg gtg act gtg ctg cgg cag aca aat gac caa    240
Asn Thr Asp Glu Val Arg Val Thr Val Leu Arg Gln Thr Asn Asp Gln

```
                    65                  70                  75                  80 atg act gag gtc tgt gcc acg aca ttc aca gag aag aat aca gtg ggc    288
Met Thr Glu Val Cys Ala Thr Thr Phe Thr Glu Lys Asn Thr Val Gly
                    85                  90                  95 ttc cta gat tac ccc ttc tgc agt ggt acc ttt aat gaa agc aga gtg    336
Phe Leu Asp Tyr Pro Phe Cys Ser Gly Thr Phe Asn Glu Ser Arg Val
                    100                 105                 110 aac ctc acc atc caa gga ctg aga gct gtt gac acg gga ctg tac ctc    384
Asn Leu Thr Ile Gln Gly Leu Arg Ala Val Asp Thr Gly Leu Tyr Leu
                    115                 120                 125 tgc aag gtg gaa ctc atg tac cca ccg cca tac ttt gtg ggc atg ggc    432
Cys Lys Val Glu Leu Met Tyr Pro Pro Pro Tyr Phe Val Gly Met Gly
                    130                 135                 140 aac ggg acg cag att tat gtc att gat cca gaa cca tgc ccg gat tct    480
Asn Gly Thr Gln Ile Tyr Val Ile Asp Pro Glu Pro Cys Pro Asp Ser
145                 150                 155                 160 gac ttc ctc ctt tgg atc ctt gtc gca gtt agc ttg ggg ttg ttt ttt    528
Asp Phe Leu Leu Trp Ile Leu Val Ala Val Ser Leu Gly Leu Phe Phe
                    165                 170                 175 tac agt ttc ctg gtc tct gct gtt tct ttg agc aag atg cta aag aaa    576
Tyr Ser Phe Leu Val Ser Ala Val Ser Leu Ser Lys Met Leu Lys Lys
                    180                 185                 190 aga agt cct ctt aca aca ggg gtc tat gtg aaa atg ccc cca aca gag    624
Arg Ser Pro Leu Thr Thr Gly Val Tyr Val Lys Met Pro Pro Thr Glu
                    195                 200                 205 cca gaa tgt gaa aag caa ttt cag cct tat ttt att ccc atc aac        669
Pro Glu Cys Glu Lys Gln Phe Gln Pro Tyr Phe Ile Pro Ile Asn
                    210                 215                 220

<210> SEQ ID NO 46
<211> LENGTH: 223
<212> TYPE: PRT
<213> ORGANISM: Mus musculus

<400> SEQUENCE: 46

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
                20                  25                  30

Val Phe Ser Glu Ala Ile Gln Val Thr Gln Pro Ser Val Val Leu Ala
            35                  40                  45

Ser Ser His Gly Val Ala Ser Phe Pro Cys Glu Tyr Ser Pro Ser His
        50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
                100                 105                 110

Asn Leu Thr Ile Gln Gly Leu Arg Ala Val Asp Thr Gly Leu Tyr Leu
            115                 120                 125

Cys Lys Val Glu Leu Met Tyr Pro Pro Pro Tyr Phe Val Gly Met Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175
```

```
Tyr Ser Phe Leu Val Ser Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 47
<211> LENGTH: 990
<212> TYPE: DNA
<213> ORGANISM: Artificial Sequence
<220> FEATURE:
<223> OTHER INFORMATION: human IgG1 constant domains
<220> FEATURE:
<221> NAME/KEY: CDS
<222> LOCATION: (1)..(990)

<400> SEQUENCE: 47 gcc agc aca aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc     336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgg gtg gtc agc gtc ctc acc gtc ctg     576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg     672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag     720
Gln Pro Arg Glu Pro Gln Val Tyr Thr Leu Pro Pro Ser Arg Asp Glu
```

```
Gln Pro Arg Glu Pro Gln Val Tyr Thr Leu Pro Ser Arg Asp Glu
225                 230                 235                 240 ctg acc aag aac cag gtc agc ctg acc tgc ctg gtc aaa ggc ttc tat        768
Leu Thr Lys Asn Gln Val Ser Leu Thr Cys Leu Val Lys Gly Phe Tyr
            245                 250                 255 ccc agc gac atc gcc gtg gag tgg gag agc aat ggg cag ccg gag aac        816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc        864
Asn Tyr Lys Thr Thr Pro Pro Val Leu Asp Ser Asp Gly Ser Phe Phe
            275                 280                 285 ctc tac agc aag ctc acc gtg gac aag agc agg tgg cag cag ggg aac        912
Leu Tyr Ser Lys Leu Thr Val Asp Lys Ser Arg Trp Gln Gln Gly Asn
            290                 295                 300 gtc ttc tca tgc tcc gtg atg cat gag gct ctg cac aac cac tac acg        960
Val Phe Ser Cys Ser Val Met His Glu Ala Leu His Asn His Tyr Thr
305                 310                 315                 320 cag aag agc ctc tcc ctg tct ccg ggt aaa                                 990
Gln Lys Ser Leu Ser Leu Ser Pro Gly Lys
                325                 330

<210> SEQ ID NO 48
<211> LENGTH: 330
<212> TYPE: PRT
<213> ORGANISM: Artificial Sequence
<220> FEATURE:
<223> OTHER INFORMATION: Synthetic Construct

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 49
<211> LENGTH: 981
<212> TYPE: DNA
<213> ORGANISM: Artificial Sequence
<220> FEATURE:
<223> OTHER INFORMATION: human IgG4 constant domains (including S228P)
<220> FEATURE:
<221> NAME/KEY: CDS
<222> LOCATION: (1)..(981)

<400> SEQUENCE: 49 gcc agc aca aag ggc ccc agc gtg ttc cct ctg gcc cct tgt agc aga       48
Ala Ser Thr Lys Gly Pro Ser Val Phe Pro Leu Ala Pro Cys Ser Arg
1               5                   10                  15 agc acc agc gag tct aca gcc gcc ctg ggc tgc ctc gtg aag gac tac       96
Ser Thr Ser Glu Ser Thr Ala Ala Leu Gly Cys Leu Val Lys Asp Tyr
                20                  25                  30 ttt ccc gag ccc gtg acc gtg tcc tgg aac tct ggc gct ctg aca agc      144
Phe Pro Glu Pro Val Thr Val Ser Trp Asn Ser Gly Ala Leu Thr Ser
            35                  40                  45 ggc gtg cac acc ttt cca gcc gtg ctg cag agc agc ggc ctg tac tct      192
Gly Val His Thr Phe Pro Ala Val Leu Gln Ser Ser Gly Leu Tyr Ser
    50                  55                  60 ctg agc agc gtc gtg act gtg ccc agc agc tct ctg ggc acc aag acc      240
Leu Ser Ser Val Val Thr Val Pro Ser Ser Ser Leu Gly Thr Lys Thr
65                  70                  75                  80 tac acc tgt aac gtg gac cac aag ccc agc aac acc aag gtg gac aag      288
Tyr Thr Cys Asn Val Asp His Lys Pro Ser Asn Thr Lys Val Asp Lys
                85                  90                  95 cgg gtg gaa tct aag tac ggc cct ccc tgc cct cct tgc cca gcc cct      336
Arg Val Glu Ser Lys Tyr Gly Pro Pro Cys Pro Pro Cys Pro Ala Pro
            100                 105                 110 gaa ttt ctg ggc gga ccc tcc gtg ttc ctg ttc ccc cca aag ccc aag      384
Glu Phe Leu Gly Gly Pro Ser Val Phe Leu Phe Pro Pro Lys Pro Lys
        115                 120                 125 gac acc ctg atg atc agc cgg acc ccc gaa gtg acc tgc gtg gtg gtg      432
Asp Thr Leu Met Ile Ser Arg Thr Pro Glu Val Thr Cys Val Val Val
    130                 135                 140 gat gtg tcc cag gaa gat cct gag gtg cag ttc aat tgg tac gtg gac      480
Asp Val Ser Gln Glu Asp Pro Glu Val Gln Phe Asn Trp Tyr Val Asp
145                 150                 155                 160 ggc gtg gaa gtg cac aac gcc aag acc aag cct aga gag gaa cag ttc      528
Gly Val Glu Val His Asn Ala Lys Thr Lys Pro Arg Glu Glu Gln Phe
                165                 170                 175 aac agc acc tac cgg gtg gtg tcc gtg ctg aca gtg ctg cac cag gac      576
Asn Ser Thr Tyr Arg Val Val Ser Val Leu Thr Val Leu His Gln Asp
```

-continued

```
                Asn Ser Thr Tyr Arg Val Val Ser Val Leu Thr Val Leu His Gln Asp
                            180                 185                 190 tgg ctg aac ggc aaa gag tac aag tgc aag gtg tcc aac aag gga ctg        624
Trp Leu Asn Gly Lys Glu Tyr Lys Cys Lys Val Ser Asn Lys Gly Leu
            195                 200                 205 ccc agc tcc atc gag aaa acc atc agc aag gcc aag ggc cag ccc cgc        672
Pro Ser Ser Ile Glu Lys Thr Ile Ser Lys Ala Lys Gly Gln Pro Arg
210                 215                 220 gaa ccc cag gtg tac aca ctg cct cca agc cag gaa gag atg acc aag        720
Glu Pro Gln Val Tyr Thr Leu Pro Pro Ser Gln Glu Glu Met Thr Lys
225                 230                 235                 240 aac cag gtg tcc ctg acc tgt ctc gtg aaa ggc ttc tac ccc tcc gat        768
Asn Gln Val Ser Leu Thr Cys Leu Val Lys Gly Phe Tyr Pro Ser Asp
                245                 250                 255 atc gcc gtg gaa tgg gag agc aac ggc cag ccc gag aac aac tac aag        816
Ile Ala Val Glu Trp Glu Ser Asn Gly Gln Pro Glu Asn Asn Tyr Lys
            260                 265                 270 acc acc ccc cct gtg ctg gac agc gac ggc tca ttc ttc ctg tac agc        864
Thr Thr Pro Pro Val Leu Asp Ser Asp Gly Ser Phe Phe Leu Tyr Ser
        275                 280                 285 aga ctg acc gtg gac aag agc cgg tgg cag gaa ggc aac gtg ttc agc        912
Arg Leu Thr Val Asp Lys Ser Arg Trp Gln Glu Gly Asn Val Phe Ser
290                 295                 300 tgc agc gtg atg cac gag gcc ctg cac aac cac tac acc cag aag tcc        960
Cys Ser Val Met His Glu Ala Leu His Asn His Tyr Thr Gln Lys Ser
305                 310                 315                 320 ctg tct ctg agc ctg ggc aaa                                             981
Leu Ser Leu Ser Leu Gly Lys
                325

<210> SEQ ID NO 50
<211> LENGTH: 327
<212> TYPE: PRT
<213> ORGANISM: Artificial Sequence
<220> FEATURE:
<223> OTHER INFORMATION: Synthetic Construct

<400> SEQUENCE: 50

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 51
<211> LENGTH: 321
<212> TYPE: DNA
<213> ORGANISM: Artificial Sequence
<220> FEATURE:
<223> OTHER INFORMATION: human kappa constant domain
<220> FEATURE:
<221> NAME/KEY: CDS
<222> LOCATION: (1)..(321)

<400> SEQUENCE: 51 cgg aca gtg gcc gct ccc agc gtg ttc atc ttc cca cct agc gac gag     48
Arg Thr Val Ala Ala Pro Ser Val Phe Ile Phe Pro Pro Ser Asp Glu
1               5                   10                  15 cag ctg aag tcc ggc aca gcc tct gtc gtg tgc ctg ctg aac aac ttc     96
Gln Leu Lys Ser Gly Thr Ala Ser Val Val Cys Leu Leu Asn Asn Phe
            20                  25                  30 tac ccc cgc gag gcc aag gtg cag tgg aag gtg gac aat gcc ctg cag    144
Tyr Pro Arg Glu Ala Lys Val Gln Trp Lys Val Asp Asn Ala Leu Gln
        35                  40                  45 agc ggc aac agc cag gaa agc gtg acc gag cag gac agc aag gac tcc    192
Ser Gly Asn Ser Gln Glu Ser Val Thr Glu Gln Asp Ser Lys Asp Ser
    50                  55                  60 acc tac agc ctg agc agc acc ctg aca ctg agc aag gcc gac tac gag    240
Thr Tyr Ser Leu Ser Ser Thr Leu Thr Leu Ser Lys Ala Asp Tyr Glu
65                  70                  75                  80 aag cac aag gtg tac gcc tgc gaa gtg acc cac cag ggc ctg tct agc    288
Lys His Lys Val Tyr Ala Cys Glu Val Thr His Gln Gly Leu Ser Ser
                85                  90                  95 ccc gtg acc aag agc ttc aac cgg ggc gag tgc                        321
Pro Val Thr Lys Ser Phe Asn Arg Gly Glu Cys
            100                 105

<210> SEQ ID NO 52
<211> LENGTH: 107
<212> TYPE: PRT
<213> ORGANISM: Artificial Sequence
```

```
<220> FEATURE:
<223> OTHER INFORMATION: Synthetic Construct

<400> SEQUENCE: 52

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 53
<211> LENGTH: 13
<212> TYPE: PRT
<213> ORGANISM: Homo sapiens

<400> SEQUENCE: 53

Ser Phe Val Cys Glu Tyr Ala Ser Pro Gly Lys Ala Thr
1               5                   10

<210> SEQ ID NO 54
<211> LENGTH: 25
<212> TYPE: PRT
<213> ORGANISM: Homo sapiens

<400> SEQUENCE: 54

Val Leu Ala Ser Ser Arg Gly Ile Ala Ser Phe Val Cys Glu Tyr Ala
1               5                   10                  15

Ser Pro Gly Lys Ala Thr Glu Val Arg
            20                  25

<210> SEQ ID NO 55
<211> LENGTH: 9
<212> TYPE: PRT
<213> ORGANISM: Homo sapiens

<400> SEQUENCE: 55

Ala Ser Ser Arg Gly Ile Ala Ser Phe
1               5

<210> SEQ ID NO 56
<211> LENGTH: 5
<212> TYPE: PRT
<213> ORGANISM: Homo sapiens

<400> SEQUENCE: 56

Ala Thr Glu Val Arg
1               5

<210> SEQ ID NO 57
<211> LENGTH: 8
<212> TYPE: PRT
<213> ORGANISM: Homo sapiens
```

<400> SEQUENCE: 57

Ala Ser Pro Gly Lys Ala Thr Glu
1               5

<210> SEQ ID NO 58
<211> LENGTH: 31
<212> TYPE: PRT
<213> ORGANISM: Homo sapiens

<400> SEQUENCE: 58

Val Leu Ala Ser Ser Arg Gly Ile Ala Ser Phe Val Cys Glu Tyr Ala
1               5                   10                  15

Ser Pro Gly Lys Ala Thr Glu Val Arg Val Thr Val Leu Arg Gln
            20                  25                  30

<210> SEQ ID NO 59
<211> LENGTH: 369
<212> TYPE: PRT
<213> ORGANISM: Artificial Sequence
<220> FEATURE:
<223> OTHER INFORMATION: rhCTLA-4/Fc/6His

<400> SEQUENCE: 59

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Leu Asp Asp
    50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp Phe Ile Glu
        115                 120                 125

Gly Arg Met Asp Pro Lys Ser Cys Asp Lys Thr His Thr Cys Pro Pro
    130                 135                 140

Cys Pro Ala Pro Glu Leu Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
            180                 185                 190

Trp Tyr Val Asp Gly Val Glu Val His Asn Ala Lys Thr Lys Pro Arg
        195                 200                 205

Glu Glu Gln Tyr Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Ala Leu Pro Ala Pro Ile Glu Lys Thr Ile Ser Lys Ala Lys
                245                 250                 255

Gly Gln Pro Arg Glu Pro Gln Val Tyr Thr Leu Pro Pro Ser Arg Asp
            260                 265                 270

```
Glu Leu Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
    290                 295                 300

Asn Asn Tyr Lys Thr Thr Pro Pro Val Leu Asp Ser Asp Gly Ser Phe
305                 310                 315                 320

Phe Leu Tyr Ser Lys Leu Thr Val Asp Lys Ser Arg Trp Gln Gln Gly
                325                 330                 335

Asn Val Phe Ser Cys Ser Val Met His Glu Ala Leu His Asn His Tyr
                340                 345                 350

Thr Gln Lys Ser Leu Ser Leu Ser Pro Gly Lys His His His His His
        355                 360                 365

His
```

ANTI-HCTLA-4 ANTIBODIES

The present application claims priority to Netherlands Patent Application No. 2017270, filed Aug. 2, 2016, which is hereby incorporated by reference in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Jul. 26, 2017, is named ABE_0003_UT_SeqListing.txt and is 98 kilobytes in size.

FIELD OF THE INVENTION

The present invention relates to treatments of conditions ameliorated by stimulation of an immune response, in particular by the stimulation of antigen-specific T-lymphocytes. More specifically, the present invention relates to anti-human CTLA-4 antibodies, as well as use of these antibodies in the treatment of diseases such as cancer and infectious disease.

BACKGROUND OF THE INVENTION

The following discussion of the background of the invention is merely provided to aid the reader in understanding the invention and is not admitted to describe or constitute prior art to the present invention.

T lymphocytes play a central role in the adaptive immune response to antigen. Naive T cells require two signals for their full activation (Bretscher 1999, Proc Natl Acad Sci USA 96:185-90). The first signal is antigen-specific and is provided by interaction of the T-cell receptor (TCR) with MHC/peptide complex on an antigen-presenting cell (APC). The second signal is a co-stimulatory signal provided by the interactions between receptors on the T cell and their ligands on the APC. Engagement of both TCR/MHC and co-stimulatory interactions leads to T-cell activation via a number of intracellular pathways, including calcium calcineurin and RAS mitogen-activated protein kinase, and subsequent activation of transcription factors for a number of effector compounds, including cytokines such as IL-2.

Although multiple positive and negative costimulatory pathways are involved in T-cell regulation, the most critical are between CD28 on T cells and B7-1 (CD80) and B7-2 (CD86) on APCs. CD28 promotes T-cell differentiation and enhances antibody production by B cells and activation of T cells. CD80 and CD86, expressed on APCs such as dendritic cells and B cells, have overlapping but distinct functions. CD86 is constitutively expressed and is rapidly upregulated on APCs coincident with TCR/MHC engagement. CD80 expression is very low on the resting cell, but is typically induced after prolonged T-cell stimulation. These differences suggest that while CD86 may be important in initialization of T-cell activation, CD80 may play a greater role in perpetuating the immune response.

Subsequent to T-cell activation, a negative regulatory receptor Cytotoxic T Lymphocyte Antigen 4 (CTLA-4 or CTLA-4, also called CD152), is upregulated on T cells (Alegre et al., 2001, Nat Rev Immunol 1:220-8). CTLA-4 is structurally homologous to CD28 but binds more tightly to both CD80 and CD86 ligands. CTLA-4 inhibits the immune response in two principal ways—it competes with CD28 for the CD80 and CD86 ligands and thus blocks co-stimulation, and it also signals in a negative way to inhibit T cell activation (Krummel and Allison, 1995, J Exp Med 182:459-465; Walunas et al., 1994, Immunity 1:405-413). It has further been shown that CD86 engages CD28 more than CTLA-4 at the immune synapse, while CD80 ligates more CTLA-4 than CD28 (Collins et al., 2002, Immunity 17:201-210; Jansson et al., 2005, J Immunol 175:1575-1585).

It has been reported that CTLA-4 blockade augments T cell responses in vitro and in vivo, exacerbates antitumor immunity, and enhances an induced autoimmune disease. It has also been reported that CTLA-4 has an alternative or additional impact on the initial character of the T cell immune response. This is consistent with the observation that some autoimmune patients have autoantibodies to CTLA-4. It is possible that CTLA-4 blocking autoantibodies play a pathogenic role in these patients. Furthermore, human antibodies against human CTLA-4 have been described as immunostimulation modulators in a number of disease conditions, such as treating or preventing viral and bacterial infection and for treating cancer. Ipilimumab is a human anti-human CTLA-4 antibody which blocks the binding of CTLA-4 to CD80 and CD86 expressed on APCs, blocking the negative downregulation of the immune responses elicited by the interaction of these molecules. Evidence of tumor regression with prolonged time to progression has been seen in patients with melanoma who received either ipilimumab (10D1) or another anti-CTLA-4 antibody, tremelimumab (CP-675,206) and durable responses have been observed with ipilimumab in patients with melanoma, ovarian cancer, prostate cancer and renal cell cancer. Interestingly, antitumor responses may be characterized by short-term progression followed by delayed regression, and an important, possibly unique, clinical characteristic of anti-CTLA-4 antibodies is that the duration of clinical responses and even stable disease is often quite prolonged. Preclinical and early clinical studies of patients with advanced melanoma show that ipilimumab promotes antitumor activity as monotherapy and in combination with treatments such as chemotherapy, antibodies, vaccines, or cytokines (Weber, J., The Oncologist, 12(7):864-872, 2007; Scott, A. M. et al., Nature Reviews (Cancer) 12:278-287, 2012; Hodi, F. S. et al., New Eng. J. Med. 363(8):711-723, 2010; Schadendorf, D. et al., J. Clin. Oncol. 33(17):1889-1894, 2015; Larkin, J. V. et al., New Eng. J. Med. 2015; Ribas, A. et al., J. Clin. Oncol. 31(5):616-622, 2013)).

A second proposed mechanism of CTLA-4 targeting by ipilimumab is depletion of CTLA-4+ regulatory T cells (Tregs), which has been shown to be a critical driver behind the efficacy of CTLA-4 targeting in mice (Peggs et al, J Exp Med, 2009, DOI: 10.1084/jem.20082492; Simpson et al, J Exp med, 2013, DOI: 10.1084/jem.20130579; Selby et al Cancer Immunol, 2013 DOI: 10.1158/2326-6066.CIR-13-0013).

Although ipilimumab is already on the market for some cancer therapies and is being tested for other anti-cancer indications, and although tremelimumab is also advanced in the clinical test phase, there still is a need for alternative anti-CTLA-4 antibodies, especially where they have an activity that can be differentiated from the activities of the known anti-CTLA-4 antibodies.

SUMMARY OF THE INVENTION

In a first aspect, the present invention relates to antibodies or antigen binding fragments thereof that binds to human CTLA-4, wherein the antibody or antigen binding fragment comprises one or more, and optionally each, of:

a heavy chain variable region CDR1 comprising the
amino acid sequence of SEQ ID NO: 1 or an amino acid
sequence differing from SEQ ID NO: 1 by 1, 2, 3, or
more conservative substitutions,
a heavy chain variable region CDR2 comprising the
amino acid sequence of SEQ ID NO: 2 or an amino acid
sequence differing from SEQ ID NO: 2 by 1, 2, 3, or
more conservative substitutions,
a heavy chain variable region CDR3 comprising the
amino acid sequence of SEQ ID NO: 3 or an amino acid
sequence differing from SEQ ID NO: 3 by 1, 2, 3, or
more conservative substitutions,
a light chain variable region CDR1 comprising the amino
acid sequence of SEQ ID NO: 4 or an amino acid
sequence differing from SEQ ID NO: 4 by 1, 2, 3, or
more conservative substitutions,
a light chain variable region CDR2 comprising the amino
acid sequence of SEQ ID NO: 5 or an amino acid
sequence differing from SEQ ID NO: 5 by 1, 2, 3, or
more conservative substitutions, and
a light chain variable region CDR3 comprising the amino
acid sequence of SEQ ID NO: 6 or an amino acid
sequence differing from SEQ ID NO: 6 by 1, 2, 3, or
more conservative substitutions.

Preferably, said antibody or antigen binding fragment
comprises one or more and preferably each of:
  a. a heavy chain variable region CDR1 comprising the
     amino acid sequence of SEQ ID NO: 1;
  b. a heavy chain variable region CDR2 comprising the
     amino acid sequence of SEQ ID NO: 2;
  c. a heavy chain variable region CDR3 comprising the
     amino acid sequence of SEQ ID NO: 3;
  d. a light chain variable region CDR1 comprising the
     amino acid sequence of SEQ ID NO: 4;
  e. a light chain variable region CDR2 comprising the
     amino acid sequence of SEQ ID NO: 5;
  f. a light chain variable region CDR3 comprising the
     amino acid sequence of SEQ ID NO: 6

Preferably said antibody has a heavy chain according to
SEQ ID NO: 7. Further preferably said antibody has a light
chain according to SEQ ID NO: 8. More preferably, the
heavy chain is chosen from any of SEQ ID NO: 10, 12, 14,
16, 18 or 20. More preferably, the light chain is chosen from
any of SEQ ID NO: 22, 24, 26, 30.

The invention further relates to an antibody or antigen
binding fragment thereof that binds to human CTLA-4
comprising a light chain immunoglobulin, a heavy chain
immunoglobulin or both a light chain and a heavy chain
immunoglobulin selected from the group consisting of:
  a. an antibody or antigen binding fragment thereof comprising a variable heavy chain comprising the amino acid sequence of SEQ ID NO: 7 and/or a variable light chain comprising the amino acid sequence of SEQ ID NO: 8;
  b. an antibody or antigen binding fragment thereof comprising a variable heavy chain comprising the amino acid sequence of SEQ ID NO: 10, 12, 14, 16, 18 or 20 and/or a variable light chain comprising the amino acid sequence of SEQ ID NO: 22, 24, 26 or 30;
  c. an antibody or antigen binding fragment thereof comprising a variable heavy chain comprising at least 90%, 95%, 96%, 97%, 98% or 99% identity any one of SEQ ID NO: 10, 12, 14, 16, 18 or 20 and/or a variable light chain comprising at least 90%, 95%, 96%, 97%, 98% or 99% identity to any one of SEQ ID NO: 22, 24, 26 or 30; and
  d. an antibody or antigen binding fragment thereof comprising a variable heavy chain comprising at least 90%, 95%, 96%, 97%, 98% or 99% identity any one of SEQ ID NO: 10, 12, 14, 16, 18 or 20 and/or a variable light chain comprising at least 90%, 95%, 95%, 96%, 97%, 98% or 99% identity to any one of SEQ ID NO: 22, 24, 26 or 30, wherein any sequence variations occur in the framework regions of the antibody or antigen binding fragment;
  e. an antibody or antigen binding fragment thereof comprising a variable heavy chain comprising 1, 2, 3, 4, 5, 6, 7, 8, 9 or 10 amino acid substitution with respect to any one of SEQ ID NO: 10, 12, 14, 16, 18 or 20 and/or a variable light chain 1, 2, 3, 4, 5, 6, 7, 8, 9 or 10 amino acid substitution with respect to any one of SEQ ID NO: 22, 24, 26 or 30; and
  f. an antibody or antigen binding fragment thereof comprising a variable heavy chain comprising 1, 2, 3, 4, 5, 6, 7, 8, 9 or 10 amino acid substitution with respect to any one of SEQ ID NO: 10, 12, 14, 16, 18 or 20 and/or a variable light chain 1, 2, 3, 4, 5, 6, 7, 8, 9 or 10 amino acid substitution with respect to any one of SEQ ID NO: 22, 24, 26 or 30, wherein any said substitutions occur in the framework regions of the antibody or antigen binding fragment.

Preferably, said antibody or antigen binding fragment has
at least one of the following characteristics:
  a) binds to human CTLA-4 with a KD value of at least about $1 \times 10^{-9}$ M as determined by surface plasmon resonance (e.g., BIACORE) or a similar technique (e.g. KinExa or OCTET);
  b) blocks the binding of hCTLA-4 to hCD80 with an $IC_{50}$ of about 100 nM or lower;
  c) blocks the binding of hCTLA-4 to hCD86 with an $IC_{50}$ of about 100 nM or lower;
  d) binds to a different CTLA-4 epitope than ipilimumab or tremelimumab.

The invention further comprises an antibody or antigen
binding fragment thereof that binds to an epitope of human
CTLA-4 wherein said antibody or antigen binding fragment
does not bind to the mouse-human chimeric CTLA-4 molecule of SEQ ID NO: 44.

A further aspect of the invention is an antibody or antigen
binding fragment thereof that binds to the same epitope of
human CTLA-4 as an antibody comprising the variable
heavy chain of SEQ ID NO: 7 and the variable light chain
of SEQ ID NO: 8, wherein the antibody or fragment thereof
does not bind to the mouse-human chimeric CTLA-4 molecule of SEQ ID NO: 44 and has one, two, three, or all four
of the following characteristics:
  g. binds to human CTLA-4 with a KD value of at least about $1 \times 10^{-9}$ M as determined by surface plasmon resonance (e.g., BIACORE) or a similar technique (e.g. KinExa or OCTET);
  h. blocks the binding of hCTLA-4 to hCD80 with an $IC_{50}$ of about 100 nM or lower;
  i. blocks the binding of hCTLA-4 to hCD86 with an $IC_{50}$ of about 100 nM or lower;
  j. binds to a different CTLA-4 epitope than ipilimumab or tremelimumab.

A further aspect of the invention is an antibody or antigen
binding fragment thereof that binds to human CTLA-4,
wherein the antibody or antigen binding fragment binds to
an epitope of human CTLA4 comprising at least 8 contiguous residues of SFVCEYASPGKAT (SEQ ID NO: 53).

An antibody or antigen binding fragment thereof according to claim 34, wherein the epitope consists of SFVCEYASPGKAT (SEQ ID NO: 53).

An antibody or antigen binding fragment thereof that binds to human CTLA-4, wherein one or more mutations in human CTLA-4 within the sequence SFVCEYASPGKAT (SEQ ID NO: 53) prevent binding of the antibody to human CTLA4.

An antibody or antigen binding fragment thereof that competes with the antibody hCTLA4.27A for binding to human CTLA-4.

Preferably the antibody or antigen binding fragment of the present invention is a humanized antibody comprising two heavy chains and two light chains.

In another aspect, the present invention relates to an isolated polypeptide comprising the amino acid sequence of any one of SEQ ID NOs: 1-8, 10, 12, 14, 16, 18, 20, 22, 24, 26 or 30.

In a further aspect, the invention is directed to an isolated nucleic acid encoding: any one of the antibodies or antigen binding fragments of the invention, or any one of the polypeptides as defined above. The invention also encompasses an expression vector comprising such an isolated nucleic acid.

The invention also comprises a host cell comprising the antibody, binding fragment, polypeptide, polynucleotide or expression vector of the invention. Said host cell preferably is a *Pichia* cell or a Chinese hamster ovary cell.

In an embodiment of the invention, an antibody or antigen binding fragment of the invention is used in association with one or more cyclic dinucleotides or other STING pathway agonists. STING (stimulator of interferon genes, also known as TMEM173, MITA, ERIS, and MPYS) is a transmembrane protein localized to the ER that undergoes a conformational change in response to direct binding of cyclic dinucleotides (CDNs), resulting in a downstream signaling cascade involving TBK1 activation, IRF-3 phosphorylation, and production of IFN-β and other cytokines. The STING pathway in tumor-resident host antigen presenting cells is involved in the induction of a spontaneous CD8+ T cell response against tumor-derived antigens. Activation of this pathway and the subsequent production of IFN-β also reportedly contributes to the anti-tumor effect of radiation. STING agonists and their uses are described in, for example, US20060040887, US20080286296, US20120041057, US20140205653, WO2014179335, WO 2014179760, US20150056224, WO 2016096174, WO 2017011444, WO 2017027645, and WO 2017027646. wherein the compound is administered as a pharmaceutical composition comprising a pharmaceutically acceptable carrier. Sting agonists may be administered by one or more non-parenteral or parenteral routes. In some embodiments, the administration is subcutaneous, intramuscular, intradermal, mucosal, vaginal, cervical, peri-tumoral, intra-tumoral, or directly into the tumor-draining lymph node(s). In certain embodiments, the STING agonist and an antibody or antigen binding fragment of the invention are administered as separate administrations, e.g., at different times and/or by different routes of administration.

Another embodiment of the invention is formed by a composition comprising the antibody or antigen binding fragment of the invention and a pharmaceutically acceptable carrier, diluent, excipient or stabilizer. Preferably, said composition further comprises an agent selected from the group consisting of:

k. an anti-PD1 antibody or an antigen binding fragment thereof;
l. an anti-LAG3 antibody or an antigen binding fragment thereof;
m. an anti-TIGIT antibody or an antigen binding fragment thereof;
n. an anti-VISTA antibody or an antigen binding fragment thereof;
o. an anti-BTLA antibody or an antigen binding fragment thereof;
p. an anti-TIM3 antibody or an antigen binding fragment thereof;
q. an anti-CD27 antibody or an antigen binding fragment thereof;
r. an anti-HVEM antibody or an antigen binding fragment thereof;
s. an anti-CD70 antibody or an antigen binding fragment thereof;
t. an anti-CD137 antibody or an antigen binding fragment thereof;
u. an anti-OX40 antibody or an antigen binding fragment thereof;
v. an anti-CD28 antibody or an antigen binding fragment thereof;
w. an anti-PDL1 antibody or an antigen binding fragment thereof;
x. an anti-PDL2 antibody or an antigen binding fragment thereof;
y. an anti-GITR antibody or an antigen binding fragment thereof;
z. an anti-ICOS antibody or an antigen binding fragment thereof;
aa. an anti-SIRPα antibody or an antigen binding fragment thereof;
bb. an anti-ILT2 antibody or an antigen binding fragment thereof;
cc. an anti-ILT3 antibody or an antigen binding fragment thereof;
dd. an anti-ILT4 antibody or an antigen binding fragment thereof;
ee. an anti-ILT5 antibody or an antigen binding fragment thereof;
ff. an anti-4-1BB antibody or an antigen binding fragment thereof;
gg. an anti-NK2GA antibody or an antigen binding fragment thereof;
hh. an anti-NK2GC antibody or an antigen binding fragment thereof;
ii. an anti-NK2GE antibody or an antigen binding fragment thereof;
jj. an anti-TSLP antibody or an antigen binding fragment thereof,
kk. a STING agonist, and;
ll. an anti-IL10 antibody or an antigen binding fragment thereof.

Also preferably, in said composition the anti-PD1 antibody or an antigen binding fragment thereof is selected from the group consisting of: pembrolizumab or an antigen binding fragment thereof and nivolumab or an antigen binding fragment thereof.

In another embodiment the composition of the invention further comprises a compound selected from the group of ADU-S 100, melphalan, vincristine, fludarabine, chlorambucil, bendamustine, etoposide, doxorubicin, cyclophosphamide, cisplatin, immune modulating agents such as corticosteroids, for example dexamethasone or prednisolone, thalidomide analogs, for example thalidomide, lenalidomide or pomalidomide, kinase inhibitors, for example ibrutinib, idealisib, antibody targeting CD20, for example rituximab, ofatumab or obinotuzumab, antibody targeting CD52, for example alemtuzumab, antibody targeting CD38, for example daratumumab, antibody targeting IL-6 or IL-6 receptor, for example sarilumab or tocilizumab, antibody targeting CS-1, for example elotuzumab, antibody targeting BCMA, for example GSK2857916, antibody targeting BAFF or BLyss, for example tabalumab, bisphosphonates, for example pamidronate or zolendronic acid, bortezomid, or combinations thereof.

The present invention also relates to a method of producing an antibody or antigen binding fragment comprising:
mm. culturing a host cell comprising a polynucleotide encoding the heavy chain and/or the light chain of any one of the antibodies or antigen binding fragments of the invention under conditions favorable to expression of the polynucleotide; and
nn. optionally, recovering the antibody or antigen binding fragment from the host cell and/or culture medium.

In certain embodiments the host cell comprises an expression vector comprising such a polynucleotide, wherein the expression vector comprises control sequences operably linked to the polynucleotide which drive expression of the antibody or antigen binding fragment. In preferred embodiments, the polynucleotide comprises a secretion signal sequence which mediates secretion of the antibody or antigen binding fragment by the host cell.

A further aspect of the present invention is a method of treating cancer in a subject, preferably a human subject, comprising administering to the subject an effective amount of the antibody or antigen binding fragment of the invention, or of an expression vector which mediates expression of the antibody or antigen binding fragment within the subject, optionally in association with a further therapeutic agent or therapeutic procedure.

Also part of the invention is a method of treating an infection or infectious disease in a human subject, comprising administering to the subject an effective amount of the antibody or antigen binding fragment according to the invention, optionally in association with a further therapeutic agent or therapeutic procedure.

The invention further comprises a vaccine comprising the antibody or antigen binding fragment according to the invention and an antigen.

In another aspect, the invention comprises a method for detecting the presence of a CTLA-4 peptide or a fragment thereof in a sample comprising contacting the sample with an antibody or fragment of the invention and detecting the presence of a complex between the antibody or fragment and the peptide; wherein detection of the complex indicates the presence of the CTLA-4 peptide.

The invention also relates to a method of increasing the activity of an immune cell, comprising administering to a subject in need thereof an effective amount of an antibody or antigen binding fragment according to the invention, or of an expression vector which mediates expression of the antibody or antigen binding fragment within the subject. Preferably said method is used for:
oo. the treatment of cancer;
pp. the treatment of an infection or infectious disease; or
qq. as a vaccine adjuvant.

In another aspect, the invention is directed to an antibody or antigen binding fragment according the invention, or an expression vector which mediates expression of the antibody or antigen binding fragment within the subject for use in the preparation of a medicament to:
rr. increase immune cell activation;
ss. treat cancer; or
tt. treat an infection or infectious disease.

The invention comprises, in a following aspect, the use of the antibody or antigen binding fragment of the present invention for the manufacture of a medicament for the treatment of cancer for: increasing immune cell activation; treating cancer; or treating an infection or infectious disease.

The invention also comprises an antibody or antigen binding fragment thereof of the invention, wherein the fragment is a Fab, F(ab')2, Fv or a single chain Fv fragment (scFV).

In a following aspect, the antibody or antigen binding fragment thereof of the invention comprises a heavy chain constant region selected from IgG1, IgG2, IgG3 and IgG4, preferably IgG1 or IgG4, and a light chain constant region chosen from the light chain constant regions kappa or lambda. In the embodiment wherein the antibody or antigen binding fragment thereof comprises a human IgG4 heavy chain constant region, said IgG4 sequence preferably has a Ser→Pro mutation at position 228, as depicted in SEQ ID NO: 50.

The invention is also directed to a method of stimulating an immune response in a subject, comprising administering to a subject in need thereof the antibody or antigen binding fragment thereof of the invention in an amount effective to stimulate the immune response. Preferably, in such a method the antibody molecule is administered in combination with an agonist of one or more costimulatory molecules for example one or more molecules selected from the group consisting of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand. Alternatively, the antibody molecule is administered in combination with one or more inhibitors of an immune checkpoint molecule, for example one or more inhibitors selected from the group consisting of PD-1, PD-L1, PD-L2, TIM-3, LAG-3, CEACAM-1, CEACAM-5, VISTA, BTLA, TIGIT, LAIR1, CD160, 2B4 or TGFR In a further embodiment, the invention comprises a method of treating cancer wherein the cancer is selected from the group consisting of a lung cancer, a melanoma, a renal cancer, a liver cancer, a myeloma, a prostate cancer, a breast cancer, a colorectal cancer, a gastric cancer, a pancreatic cancer, a thyroid cancer, a hematological cancer, a lymphoma, a myeloma, or a leukemia, or a metastatic lesion of the cancer.

Also in relation to a method of treating cancer the invention also is directed to a method wherein the antibody molecule is administered in combination with one or more second therapeutic agents or procedures, for example wherein the second therapeutic agent or procedure is selected from the group consisting of chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy.

DETAILED DESCRIPTION

Figure 1:
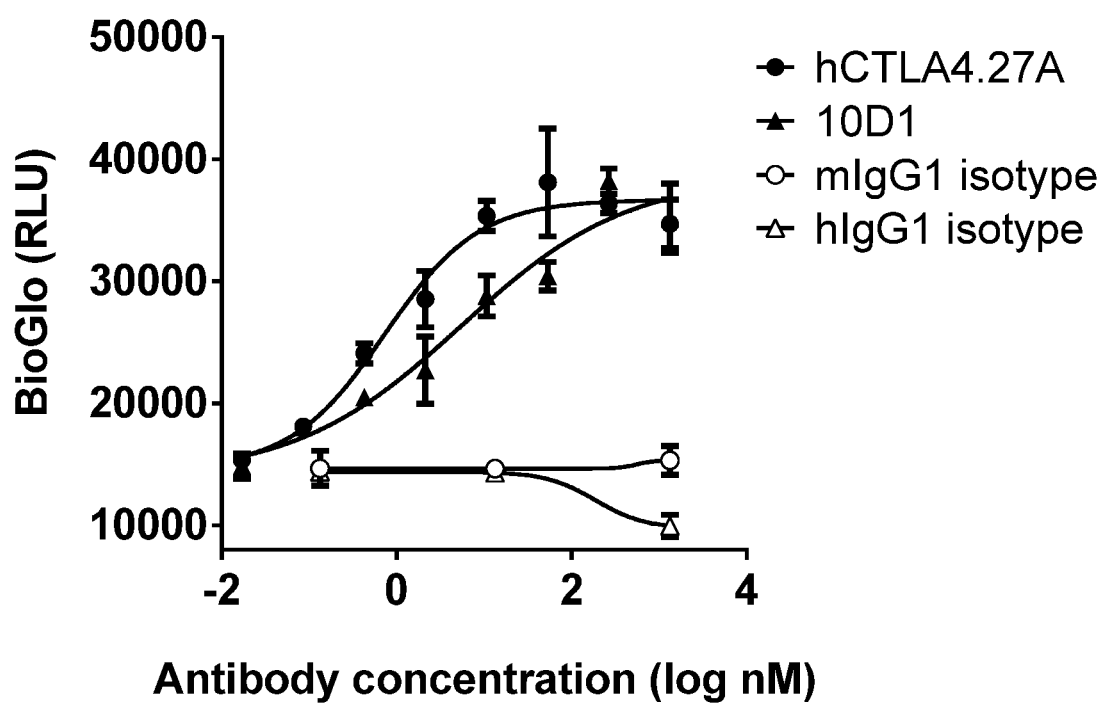
FIG. 1: Functionality of hCTLA4.27A antibody in the Jurkat-based reporter assay.

Throughout the detailed description and examples of the invention the following abbreviations will be used:
ADCC Antibody-dependent cellular cytotoxicity
CDC Complement-dependent cytotoxicity
CDR Complementarity determining region in the immunoglobulin variable regions, defined using the Kabat numbering system
CHO Chinese hamster ovary
$EC_{50}$ Concentration resulting in 50% of total binding
ELISA Enzyme-linked immunosorbent assay
FR Antibody framework region: the immunoglobulin variable regions excluding the CDR regions.
HRP Horseradish peroxidase
IFN interferon
$IC_{50}$ concentration resulting in 50% inhibition total signal
IgG Immunoglobulin G
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb or Mab or MAb Monoclonal antibody
SEB *Staphylococcus* Enterotoxin B
TT Tetanus toxoid
V region The segment of IgG chains which is variable in sequence between different antibodies. It extends to Kabat residue 109 in the light chain and 113 in the heavy chain.
VH Immunoglobulin heavy chain variable region
VL Immunoglobulin light chain variable region
VK Immunoglobulin kappa light chain variable region The following is a list of sequences referred to in the present specification (Table 1):

| Description | SEQ ID NO: | SEQUENCE |
|---|---|---|
| 27A heavy chain CDR1 (amino acid sequence) | 1 | TYWMN |
| 27A heavy chain CDR2 (amino acid sequence) | 2 | MIHPSDSETSLNQAFKD |
| 27A heavy chain CDR3 (amino acid sequence) | 3 | MGRRNPYYFDY |
| 27A light chain CDR1 (amino acid sequence) | 4 | RPSENLYTNLA |
| 27A light chain CDR2 (amino acid sequence) | 5 | GATNLAD |
| 27A light chain CDR3 (amino acid sequence) | 6 | QHLWGTPFT |
| Humanized 27 heavy chain variable region (consensus sequence) | 7 | EVQLX$_1$X$_2$X$_3$GX$_4$X$_5$X$_6$X$_7$X$_8$PGX$_9$SVKX$_{10}$SCKASGYSFTTYWM NWVX$_{11}$QX$_{12}$PGX$_{13}$GLEWX$_{14}$GMIHPSDSETSLNQAFKDX$_{15}$ X$_{16}$X$_{17}$X$_{18}$TX$_{19}$X$_{20}$X$_{21}$SX$_{22}$SX$_{23}$X$_{24}$YX$_{25}$X$_{26}$X$_{27}$SSLX$_{28}$X$_{29}$ED X$_{30}$AVYYCARX$_{31}$GRRNPYYFDYWGQGTX$_{32}$VTVSS wherein: X$_1$ = V, L X$_2$ = Q, E X$_3$ = S, A X$_4$ = A, P X$_5$ = V, E X$_6$ = L, V X$_7$ = A, V, K X$_8$ = R, K X$_9$ = A, T, S X$_{10}$ = I, V X$_{11}$ = K, R X$_{12}$ = R, A X$_{13}$ = K, Q X$_{14}$ = I, M X$_{15}$ = K, R X$_{16}$ = V, A X$_{17}$ = K, T X$_{18}$ = L, I, M X$_{19}$ = A, R X$_{20}$ = A, D X$_{21}$ = T, E, K X$_{22}$ = T, A X$_{23}$ = I, T X$_{24}$ = A, V X$_{25}$ = L, M |

| Description | SEQ ID NO: | SEQUENCE |
|---|---|---|
| | | $X_{26}$ = E, Q<br>$X_{27}$ = F, L<br>$X_{28}$ = R, T<br>$X_{29}$ = S, N<br>$X_{30}$ = S, T<br>$X_{31}$ = M, I<br>$X_{32}$ = L, T |
| Humanized 27 light chain variable region (consensus sequence) | 8 | DIQMTQX$_1$PSSLSASVGDX$_2$VTITCRPSENLYTNLAWYQQKP<br>GKAPKLLX$_3$YGATNLADGVPSRFSGSGSGTX$_4$X$_5$X$_6$LX$_7$ISSL<br>QX$_8$EDFATYYCQHLWGTPFTFGX$_9$GTKX$_{10}$EIK<br>wherein:<br>$X_1$ = S, A<br>$X_2$ = R, T<br>$X_3$ = L, I<br>$X_4$ = D, E<br>$X_5$ = Y, F<br>$X_6$ = T, S<br>$X_7$ = T, S<br>$X_8$ = P, S, A<br>$X_9$ = G, Q<br>$X_{10}$ = L, V |
| hCTLA4.27VH1 (nucleotide sequence) | 9 | GAGGTGCAGCTGCTGCAGTCTGGCGCTGTGCTGGCCAGACC<br>TGGCACCAGCGTGAAGATCAGCTGCAAGGCCAGCGGCTACA<br>GCTTCACCACCTACTGGATGAACTGGGTCAAGCAGCGGCCA<br>GGCCAGGGCCTGGAATGGATCGGAATGATCCACCCCAGCGA<br>CAGCGAGACAAGCCTGAACCAGGCCTTCAAGGACAAGGCCA<br>AGCTGACCGCCGCCACCTCTGCCTCTATCGCCTACCTGGAA<br>TTTTCCAGCCTGACCAACGAGGACAGCGCCGTGTACTACTG<br>CGCCCGGATGGGCAGACGGAACCCCTACTACTTCGACTACT<br>GGGGCCAGGGCACCCTCGTGACAGTGTCTAGC |
| hCTLA4.27VH1 (amino acid sequence) | 10 | EVQLLQSGAVLARPGTSVKISCKASGYSFTTYWMNWVKQRP<br>GQGLEWIGMIHPSDSETSLNQAFKDKAKLTAATSASIAYLE<br>FSSLTNEDSAVYYCARMGRRNPYYFDYWGQGTLVTVSS |
| hCTLA4.27VH2 (nucleotide sequence) | 11 | GAGGTGCAGCTGGTGCAGTCTGGCGCTGTGCTCGTGAAACC<br>TGGCGCCTCCGTGAAGGTGTCCTGCAAGGCCAGCGGCTACA<br>GCTTCACCACCTACTGGATGAACTGGGTGCGCCAGAGGCCT<br>GGCAAGGGCCTGGAATGGATCGGCATGATCCACCCCAGCGA<br>CAGCGAGACAAGCCTGAACCAGGCCTTCAAGGACAAAGTGA<br>CCATCACCGCCGACGAGAGCACCAGCACCGCCTACATGCAG<br>CTGAGCAGCCTGAGAAGCGAGGACACCGCCGTGTACTACTG<br>CGCCCGGATGGGCAGACGGAACCCCTACTACTTCGACTACT<br>GGGGCCAGGGCACCACCGTGACAGTGTCTAGC |
| hCTLA4.27VH2 (amino acid sequence) | 12 | EVQLVQSGAVLVKPGASVKVSCKASGYSFTTYWMNWVRQRP<br>GKGLEWIGMIHPSDSETSLNQAFKDKVTITADESTSTAYMQ<br>LSSLRSEDTAVYYCARMGRRNPYYFDYWGQGTTVTVSS |
| hCTLA4.27VH3 (nucleotide sequence) | 13 | GAGGTGCAGCTGGTGCAGTCTGGCGCCGTGGTGGCCAAGCC<br>TGGCAGCAGCGTGAAGGTGTCCTGTAAAGCCAGCGGCTACA<br>GCTTCACCACCTACTGGATGAACTGGGTGCGCCAGGCCCCT<br>GGACAGGGCCTGGAATGGATGGGCATGATCCACCCCAGCGA<br>CAGCGAGACAAGCCTGAACCAGGCCTTCAAGGACAGAGTGA<br>CCATCACCGCCGACAAGAGCACCAGCACCGCCTACATGGAA<br>CTGAGCAGCCTGACCAGCGAGGACACCGCCGTGTACTACTG<br>CGCCCGGATGGGCAGACGGAACCCCTACTACTTCGACTACT<br>GGGGCCAGGGCACCACCGTGACAGTGTCTAGC |
| hCTLA4.27VH3 (amino acid sequence) | 14 | EVQLVQSGAVVAKPGSSVKVSCKASGYSFTTYWMNWVRQAP<br>GQGLEWMGMIHPSDSETSLNQAFKDRVTITADKSTSTAYME<br>LSSLTSEDTAVYYCARMGRRNPYYFDYWGQGTTVTVSS |
| hCTLA4.27VH4 (nucleotide sequence) | 15 | GAGGTGCAGCTGGTGCAGTCTGGCGCCGAAGTGAAGAAACC<br>AGGCGCCAGCGTGAAGGTGTCCTGCAAGGCCAGCGGCTACA<br>GCTTCACCACCTACTGGATGAACTGGGTGCGCCAGGCCCCT<br>GGACAGGGCCTGGAATGGATGGGCATGATCCACCCCAGCGA<br>CAGCGAGACAAGCCTGAACCAGGCCTTCAAGGACAGAGTGA<br>CCATGACCCGGGACACCAGCACCTCCACCGTGTACATGGAA<br>CTGAGCAGCCTGCGGAGCGAGGACACCGCCGTGTACTACTG<br>CGCCCGGATGGGCAGACGGAACCCCTACTACTTCGACTACT<br>GGGGCCAGGGCACCCTCGTGACAGTGTCTAGC |

| Description | SEQ ID NO: | SEQUENCE |
|---|---|---|
| hCTLA4.27VH4 (amino acid sequence) | 16 | EVQLVQSGAEVKKPGASVKVSCKASGYSFTTYWMNWVRQAP<br>GQGLEWMGMIHPSDSETSLNQAFKDRVTMTRDTSTSTVYME<br>LSSLRSEDTAVYYCARMGRRNPYYFDYWGQGTLVTVSS |
| hCTLA4.27VH5 (nucleotide sequence) | 17 | GAGGTGCAGCTGCTGCAGGCTGGCGCTGTGCTGGCTAGACC<br>TGGCACCAGCGTGAAGATCAGCTGCAAGGCCAGCGGCTACA<br>GCTTCACCACCTACTGGATGAACTGGGTCAAGCAGAGGCCC<br>GGCAAGGGCCTGGAATGGATCGGCATGATCCACCCCAGCGA<br>CAGCGAGACAAGCCTGAACCAGGCCTTCAAGGACAAGGCCA<br>AGCTGACCGCCGCCACCTCTGCCTCTATCGCCTACCTGGAA<br>TTTTCCAGCCTGACCAACGAGGACAGCGCCGTGTACTACTG<br>CGCCCGGATCGGCAGACGGAACCCCTACTACTTCGACTACT<br>GGGGCCAGGGCACCCTCGTGACAGTGTCTAGC |
| hCTLA4.27VH5 (amino acid sequence) | 18 | EVQLLQAGAVLARPGTSVKISCKASGYSFTTYWMNWVKQRP<br>GKGLEWIGMIHPSDSETSLNQAFKDKAKLTAATSASIAYLE<br>FSSLTNEDSAVYYCARIGRRNPYYFDYWGQGTLVTVSS |
| hCTLA4.27VH6 (nucleotide sequence) | 19 | GAGGTGCAGCTGCTGGAATCTGGCCCTGAACTCGTGCGGCC<br>TGGCAGCAGCGTGAAGATCAGCTGTAAAGCCAGCGGCTACA<br>GCTTCACCACCTACTGGATGAACTGGGTCAAGCAGAGGCCC<br>GGCAAGGGCCTGGAATGGATCGGCATGATCCACCCCAGCGA<br>CAGCGAGACAAGCCTGAACCAGGCCTTCAAGGACAAAGTGA<br>AGCTGACCGCCGCCACCAGCGCCTCTATCGCCTACCTGGAA<br>TTTTCCAGCCTGCGGAACGAGGACAGCGCCGTGTACTACTG<br>CGCCCGGATGGGCAGACGGAACCCCTACTACTTCGACTACT<br>GGGGCCAGGGCACCCTCGTGACAGTGTCTAGC |
| hCTLA4.27VH6 (amino acid sequence) | 20 | EVQLLESGPELVRPGSSVKISCKASGYSFTTYWMNWVKQRP<br>GKGLEWIGMIHPSDSETSLNQAFKDKVKLTAATSASIAYLE<br>FSSLRNEDSAVYYCARMGRRNPYYFDYWGQGTLVTVSS |
| hCTLA4.27VL1 (nucleotide sequence) | 21 | GACATCCAGATGACCCAGAGCCCCAGCAGCCTGTCTGCCAG<br>CGTGGGCGACAGAGTGACCATCACCTGTCGGCCCAGCGAGA<br>ACCTGTACACCAACCTGGCCTGGTATCAGCAGAAGCCCGGC<br>AAGGCCCCCAAACTGCTGCTGTACGGCGCCACCAATCTGGC<br>CGATGGCGTGCCCAGCAGATTTTCCGGCTCTGGCAGCGGCA<br>CCGACTACACCCTGACCATCTCTAGCCTGCAGCCCGAGGAC<br>TTCGCCACCTACTACTGTCAGCACCTGTGGGGCACCCCCTT<br>CACCTTTGGCCAGGGCACCAAGCTGGAAATCAAG |
| hCTLA4.27VL1 (amino acid sequence) | 22 | DIQMTQSPSSLSASVGDRVTITCRPSENLYTNLAWYQQKPG<br>KAPKLLLYGATNLADGVPSRFSGSGSGTDYTLTISSLQPED<br>FATYYCQHLWGTPFTFGQGTKLEIK |
| hCTLA4.27VL2 (nucleotide sequence) | 23 | GACATCCAGATGACCCAGAGCCCCAGCAGCCTGTCTGCCAG<br>CGTGGGCGACAGAGTGACCATCACCTGTCGGCCCAGCGAGA<br>ACCTGTACACCAACCTGGCCTGGTATCAGCAGAAGCCCGGC<br>AAGGCCCCCAAGCTGCTGATCTACGGCGCCACCAATCTGGC<br>CGATGGCGTGCCCAGCAGATTTTCCGGCTCTGGCAGCGGCA<br>CCGAGTTCAGCCTGAGCATCTCTAGCCTGCAGCCCGAGGAC<br>TTCGCCACCTACTACTGTCAGCACCTGTGGGGCACCCCCTT<br>CACCTTTGGCGGCGGAACAAAGGTGGAAATCAAG |
| hCTLA4.27VL2 (amino acid sequence) | 24 | DIQMTQSPSSLSASVGDRVTITCRPSENLYTNLAWYQQKPG<br>KAPKLLIYGATNLADGVPSRFSGSGSGTEFSLSISSLQPED<br>FATYYCQHLWGTPFTFGGGTKVEIK |
| hCTLA4.27VL3 (nucleotide sequence) | 25 | GACATCCAGATGACCCAGAGCCCCAGCAGCCTGTCTGCCAG<br>CGTGGGCGATACCGTGACCATCACCTGTCGGCCCAGCGAGA<br>ACCTGTACACCAACCTGGCCTGGTATCAGCAGAAGCCCGGC<br>AAGGCCCCCAAACTGCTGCTGTACGGCGCCACCAATCTGGC<br>CGATGGCGTGCCCAGCAGATTTTCCGGCTCTGGCAGCGGCA<br>CCGACTACACCCTGACCATCTCTAGCCTGCAGAGCGAGGAC<br>TTCGCCACCTACTACTGTCAGCACCTGTGGGGCACCCCCTT<br>CACCTTTGGCCAGGGCACCAAGCTGGAAATCAAG |
| hCTLA4.27VL3 (amino acid sequence) | 26 | DIQMTQSPSSLSASVGDTVTITCRPSENLYTNLAWYQQKPG<br>KAPKLLLYGATNLADGVPSRFSGSGSGTDYTLTISSLQSED<br>FATYYCQHLWGTPFTFGQGTKLEIK |
| hCTLA4.27VL4 (nucleotide sequence) | 27 | GACATCCAGATGACCCAGAGCCCCAGCAGCCTGTCTGCCAG<br>CGTGGGCGACAGAGTGACCATCACCTGTCGGCCCAGCGAGA<br>ACCTGTACACCAACCTGGCCTGGTATCAGCAGAAGCCCGGC<br>AAGGCCCCTAAGCTGCTGCTGTACGGCGCCACCAATCTGGC |

| Description | SEQ ID NO: | SEQUENCE |
|---|---|---|
| | | CGATGGCGTGCCCAGCAGATTTTCCGGCTCTGGCAGCGGCA CCGACTACACCCTGACCATCTCTAGCCTGCAGCCCGAGGAC TTCGCCACCTACTACTGCCAGCACCTGTGGGGCACCCCCTT CACATTTGGCGGAGGCACCAAGCTGGAAATCAAG |
| hCTLA4.27VL4 (amino acid sequence) | 28 | DIQMTQSPSSLSASVGDRVTITCRPSENLYTNLAWYQQKPG KAPKLLLYGATNLADGVPSRFSGSGSGTDYTLTISSLQPED FATYYCQHLWGTPFTFGGGTKLEIK |
| hCTLA4.27VL5 (nucleotide sequence) | 29 | GACATCCAGATGACCCAGGCCCCTAGCAGCCTGTCTGCCAG CGTGGGCGACAGAGTGACCATCACCTGTCGGCCCAGCGAGA ACCTGTACACCAACCTGGCCTGGTATCAGCAGAAGCCCGGC AAGGCCCCCAAACTGCTGCTGTACGGCGCCACCAATCTGGC CGATGGCGTGCCCAGCAGATTTTCCGGCTCTGGCAGCGGCA CCGACTACACCCTGACAATCAGCTCCCTGCAGGCCGAGGAC TTCGCCACCTACTACTGTCAGCACCTGTGGGGCACCCCCTT CACCTTTGGCGGCGGAACAAAGCTGGAAATCAAG |
| hCTLA4.27VL5 (amino acid sequence) | 30 | DIQMTQAPSSLSASVGDRVTITCRPSENLYTNLAWYQQKPG KAPKLLLYGATNLADGVPSRFSGSGSGTDYTLTISSLQAED FATYYCQHLWGTPFTFGGGTKLEIK |
| hCTLA4.27A V$_H$ (nucleotide sequence) | 31 | caggtccaactgcagcagcctggggctgtactggtgaggcc tggagtttcagtgaagctgtcctgcaaggcttctggctact cccttcaccacctactggatgaactgggtgaagcagaggcct ggacaaggccttgagtggattggcatgattcatccttccga tagtgaaactagtttaaatcaggcgttcaaggacaaggcca cattgactatagacaaatcctccagcacagcctacatgcaa ctcagcagcccgacatctgaagactctgcggtctatttctg tgcaagaatgggacgtcgtaatcccattactttgactact ggggccaaggcaccactctcacagtctcctca |
| hCTLA4.27A V$_H$ (amino acid sequence) | 32 | QVQLQQPGAVLVRPGVSVKLSCKASGYSFTTYWMNWVKQRP GQGLEWIGMIHPSDSETSLNQAFKDKATLTIDKSSSTAYMQ LSSPTSEDSAVYFCARMGRRNPYYFDYWGQGTTLTVSS |
| hCTLA4.27A V$_L$ (nucleotide sequence) | 33 | gacatccaaatgactcagtctccagtctccctatctgtatc tgtgggagaaactgtcaccatcacatgtcgaccaagtgaga atctttatactaatttagcatggtatcaacagaaacaggga aaatctcctcagctcctggtctatggtgcaacaaacctagc agatggtgtgccatcaaggttcagtggcagtggatcaggga cacagtactccctcaggatcaacagcctgcagtctgaagat ttcgggacttattactgtcaacatttgtggggtactccttt cacgttcggctcggggacaaagttggaactaaaa |
| hCTLA4.27A V$_L$ (amino acid sequence) | 34 | DIQMTQSPVSLSVSVGETVTITCRPSENLYTNLAWYQQKQG KSPQLLVYGATNLADGVPSRFSGSGSGTQYSLRINSLQSED FGTYYCQHLWGTPFTFGSGTKLELK |
| full length open reading frame of hCTLA-4 (NCBI Reference Sequence: NM_005214.4) (nucleotide sequence) | 35 | atggcttgccttggatttcagcggcacaaggctcagctgaa cctggctaccaggacctggccctgcactctcctgtttttc ttctcttcatccctgtcttctgcaaagcaatgcacgtggcc cagcctgctgtggtactggccagcagccgaggcatcgcag cttttgtgtgtgagtatgcatctccaggcaaagccactgagg tccgggtgacagtgcttcggcaggctgacagccaggtgact gaagtctgtgcggcaacctacatgatggggaatgagttgac cttcctagatgattccatctgcacgggcaccctccagtggaa atcaagtgaacctcactatccaaggactgagggccatggac acgggactctacatctgcaaggtggagctcatgtacccacc gccatactacctgggcataggcaacggaacccagatttatg taattgatccagaaccgtgcccagattctgacttcctcctc tggatccttgcagcagttagttcggggttgttttttttatag cttctcctcacagctgtttctttgagcaaaatgctaaaga aaagaagccctcttacaacagggtctatgtgaaaatgccc ccaacagagccagaatgtgaaaagcaatttcagccttattt tattcccatcaat |
| full length open reading frame of hCTLA-4 (NCBI Reference Sequence: NM_005214.4) (amino acid sequence) | 36 | MACLGFQRHKAQLNLATRTWPCTLLFFLLFIPVFCKAMHVA QPAVVLASSRGIASFVCEYASPGKATEVRVTVLRQADSQVT EVCAATYMMGNELTFLDDSICTGTSSGNQVNLTIQGLRAMD TGLYICKVELMYPPPYYLGIGNGTQIYVIDPEPCPDSDFLL WILAAVSSGLFFYSFLLTAVSLSKMLKKRSPLTTGVYVKMP PTEPECEKQFQPYFIPIN |
| hCTLA-4 cDNA (Y166G and Y183G) | 37 | atggcttgccttggatttcagcggcacaaggctcagctgaa cctggctaccaggacctggccctgcactctcctgttttttc |

| Description | SEQ ID NO: | SEQUENCE |
|---|---|---|
| (Nucleotide sequence) | | ttctcttcatccctgtcttctgcaaagcaatgcacgtggcc cagcctgctgtggtactggccagcagccgaggcatcgccag ctttgtgtgtgagtatgcatctccaggcaaagccactgagg tccgggtgacagtgcttcggcaggctgacagccaggtgact gaagtctgtgcggcaacctacatgatggggaatgagttgac cttcctagatgattccatctgcacgggcacctccagtggaa atcaagtgaacctcactatccaaggactgagggccatggac acgggactctacatctgcaaggtggagctcatgtacccacc gccatactacctgggcataggcaacggaacccagatttatg taattgatccagaaccgtgcccagattctgacttcctcctc tggatccttgcagcagttagttcggggttgttttttatag cttttctcctcacagctgtttctttgagcaaaatgctaaaga aaagaagccctcttacaacaggggtcggtgtgaaaatgccc ccaacagagccagaatgtgaaaagcaatttcagcctggttt tattcccatcaat |
| hCTLA-4 cDNA (Y166G and Y183G) (amino acid sequence) | 38 | MACLGFQRHKAQLNLATRTWPCTLLFFLLFIPVFCKAMHVA QPAVVLASSRGIASFVCEYASPGKATEVRVTVLRQADSQVT EVCAATYMMGNELTFLDDSICTGTSSGNQVNLTIQGLRAMD TGLYICKVELMYPPPYYLGIGNGTQIYVIDPEPCPDSDFLL WILAAVSSGLFFYSFLLTAVSLSKMLKKRSPLTTGVGVKMP PTEPECEKQFQPGFIPIN |
| full length open reading frame of cynomolgus CTLA-4 (nucleotide sequence) | 39 | atggcttgccttggatttcagcggcacaaggctcggctcaa cctggctaccaggacccggccctacactctcctgttttctc ttctcttcatccctgtcttctccaaagcaatgcacgtggcc cagcctgctgtggtgctggccaacagccgagggatcgccag ctttgtgtgtgagtatgcatctccaggcaaagccactgagg tccgggtgacagtgcttcggcaggccgacagccaggtgact gaagtctgtgcggcaacgtacatgatggggaatgagttgac cttcctagatgattccatctgcacgggcacctccagtggaa atcaagtgaacctcactatccaaggactgagggctatggac acaggactctacatctgcaaggtggagctcatgtacccacc accatactacatgggcataggcaatggaacccagatttatg taattgatccagaaccgtgcccagattctgacttcctcctc tggatccttgcagcagttagttcggggttgttttttatag cttttctcctcacagctgtttctttgagcaaaatgctaaaga aaagaagccctctcacaacaggggtctatgtgaaaatgccc ccaacagagccagaatgtgaaaagcaatttcagccttattt tattcccatcaat |
| full length open reading frame of cynomolgus CTLA-4 (amino acid sequence) | 40 | MACLGFQRHKARLNLATRTRPYTLLFSLLFIPVFSKAMHVA QPAVVLANSRGIASFVCEYASPGKATEVRVTVLRQADSQVT EVCAATYMMGNELTFLDDSICTGTSSGNQVNLTIQGLRAMD TGLYICKVELMYPPPYYMGIGNGTQIYVIDPEPCPDSDFLL WILAAVSSGLFFYSFLLTAVSLSKMLKKRSPLTTGVYVKMP PTEPECEKQFQPYFIPIN |
| CTLA-4 human-mouse chimeric variant (human residues on strand 1, 2, 5 and 6 and mouse residues on strand 3, 4, 7, and 8) (Nucleotide sequence) | 41 | atggcctgcctgggcttccagagacacaaggcccagctgaa cctggccaccaggacctggccttgtaccctgctgttcttcc tgctgtttatccccgtgttctgcaaggccatgcacgtggcc cagcctgctgtggtgctggcctcttccagaggaatcgcctc cttcgtgtgcgagtacgcctccccccacaacaccgatgaag tgcgcgtgaccgtgctgcggcagaccaacgaccagatgacc gaagtgtgcgccaccaccttcaccgagaagaacgagctgac cttcctggacgactctatctgcaccggcacctccagcggca accaagtgaacctgacaatccagggcctgcgggccatggac accggcctgtacctgtgcaaggtggaactgatgtaccccc tcccctactcgtgggcatgggcaacggcacccagatctacg tgatcgaccccgagccttgccccgactccgactttctgctg tggatcctggctgccgtgtcctccggcctgttcttctactc tttcctgctgaccgccgtgtccctgtccaagatgctgaaga gcggtccccctgaccaccggcgtgggagtgaaaatgcct cccaccgagcccgagtgcgagaagcagttccagcccggctt catccccatcaac |
| CTLA-4 human-mouse chimeric variant (human residues on strand 1, 2, 5 and 6 and mouse residues on strand 3, 4, 7, and 8) (amino acid sequence) | 42 | MACLGFQRHKAQLNLATRTWPCTLLFFLLFIPVFCKAMHVA QPAVVLASSRGIASFVCEYASPHNTDEVRVTVLRQTNDQMT EVCATTFTEKNELTFLDDSICTGTSSGNQVNLTIQGLRAMD TGLYLCKVELMYPPPYFVGMGNGTQIYVIDPEPCPDSDFLL WILAAVSSGLFFYSFLLTAVSLSKMLKKRSPLTTGVGVKMP PTEPECEKQFQPGFIPIN |
| CTLA-4 human-mouse chimeric variant (mouse | 43 | atggcctgcctgggcttccagagacacaaggcccagctgaa cctggccaccaggacctggccttgtaccctgctgttcttcc |

| Description | SEQ ID NO: | SEQUENCE |
|---|---|---|
| residues on strand 1, 2, 5 and 6 and human residues on strand 3, 4, 7, and 8) (Nucleotide sequence) | | tgctgtttatccccgtgttctgcgaggccatccaagtgacc cagccctctgtggtgctggcctcttctcatggcgtggccag cttcccttgcgagtactcccatctggcaaggccaccgaag tgcgcgtgaccgtgctgagacaggccgactcccaagtgaca gaagtgtgcgccgccacctacatgatgggcaacaccgtggg ctttctggactacccttctgctccggcacccttcaacgagt ccagagtgaacctgacaatccagggcctgcgggccgtggat accggcctgtatatctgcaaggtggaactgatgtaccccc tccctactacctgggcatcggcaacggcacccagatctacg tgatcgaccccgagccttgccccgactccgactttctgctg tggatcctggccgccgtgtcctccggcctgttcttctactc tttcctgctgaccgctgtgtccctgtccaagatgctgaaga agcggtccccctgaccaccggcgtgggagtgaaaatgcct ccaccgagcccgagtgcgagaagcagttccagcccggctt catccccatcaac |
| CTLA-4 human-mouse chimeric variant (mouse residues on strand 1, 2, 5 and 6 and human residues on strand 3, 4, 7, and 8) (Nucleotide sequence) | 44 | MACLGFQRHKAQLNLATRTWPCTLLFFLLFIPVFCEAIQVT QPSVVLASSHGVASFPCEYSPSGKATEVRVTVLRQADSQVT EVCAATYMMGNTVGFLDYPFCSGTFNESRVNLTIQGLRAVD TGLYICKVELMYPPPYYLGIGNGTQIYVIDPEPCPDSDFLL WILAAVSSGLFFYSFLLTAVSLSKMLKKRSPLTTGVGVKMP PTEPECEKQFQPGFIPIN |
| full length open reading frame of mouse CTLA-4 (nucleotide sequence) | 45 | atggcttgtcttggactccggaggtacaaagctcaactgca gctgccttctaggacttggccttttgtagccctgctcactc ttcttttcatcccagtcttctctgaagccatacaggtgacc caaccttcagtggtgttggctagcagccatggtcgccag cttccatgtgaatattcaccatcacacaacactgatgagg tccgggtgactgtgctgcggcagacaaatgaccaaatgact gaggtctgtgccacgacattcacagagaagaatacagtggg cttcctagattacccttctgcagtggtacctttaatgaaa gcagagtgaacctcaccatccaaggactgagagctgttgac acgggactgtacctctgcaaggtggaactcatgtaccacc gccatactttgtgggcatgggcaacgggacgcagatttatg tcattgatccagaaccatgcccggattctgacttcctcctt tggatcctgtcgcagttagcttggggttgttttttttacag tttcctggtctctgctgtttctttgagcaagatgctaaaga aaagaagtcctcttacaacaggggtctatgtgaaaatgccc caacagagccagaatgtgaaaagcaatttcagccttattt tattcccatcaac |
| full length open reading frame of cynomolgus CTLA-4 (amino acid sequence) | 46 | MACLGLRRYKAQLQLPSRTWPFVALLTLLFIPVFSEAIQVT QPSVVLASSHGVASFPCEYSPSHNTDEVRVTVLRQTNDQMT EVCATTFTEKNTVGFLDYPFCSGTFNESRVNLTIQGLRAVD TGLYLCKVELMYPPPYFVGMGNGTQIYVIDPEPCPDSDFLL WILVAVSLGLFFYSFLVSAVSLSKMLKKRSPLTTGVYVKMP PTEPECEKQFQPYFIPIN |
| human IgG1 constant domain (nucleotide sequence) | 47 | gccagcacaaagggcccatcggtcttccccctggcaccctc ctccaagagcacctctgggggcacagcggccctgggctgcc tggtcaaggactacttccccgaaccggtgacggtgtcgtgg aactcaggcgccctgaccagcggcgtgcacaccttcccggc tgtcctacagtcctcaggactctactccctcagcagcgtgg tgaccgtgccctccagcagcttgggcacccagacctacatc tgcaacgtgaatcacaagcccagcaacaccaaggtggacaa gaaagttgagcccaaatcttgtgacaaaactcacacatgcc caccgtgcccagcacctgaactcctggggggaccgtcagtc ttcctcttccccccaaaacccaaggacaccctcatgatctc ccggacccctgaggtcacatgcgtggtggtggacgtgagcc acgaagaccctgaggtcaagttcaactggtacgtggacggc gtggaggtgcataatgccaagacaaagccgcgggaggagca gtacaacagcacgtaccgggtggtcagcgtcctcaccgtcc tgcaccaggactggctgaatggcaaggagtacaagtgcaag gtctccaacaaagccctcccagcccccatcgagaaaaccat ctccaaagccaaagggcagccccgagaaccacaggtgtaca ccctgcccccatcccgggatgagctgaccaagaaccaggtc agcctgacctgcctggtcaaaggcttctatcccagcgacat cgccgtggagtgggagagcaatgggcagccggagaacaact acaagaccacgcctcccgtgctggactccgacggctccttc ttcctctacagcaagctcaccgtggacaagagcaggtggca gcaggggaacgtcttctcatgctccgtgatgcatgaggctc tgcacaaccactacacgcagaagagcctctccctgtctccg ggtaaa |

| Description | SEQ ID NO: | SEQUENCE |
|---|---|---|
| human IgG1 constant domain (amino acid sequence) | 48 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSCDKTHTCPPCPAPELLGGPSV FLFPPKPKDTLMISRTPEVTCVVVDVSHEDPEVKFNWYVDG VEVHNAKTKPREEQYNSTYRVVSVLTVLHQDWLNGKEYKCK VSNKALPAPIEKTISKAKGQPREPQVYTLPPSRDELTKNQV SLTCLVKGFYPSDIAVEWESNGQPENNYKTTPPVLDSDGSF FLYSKLTVDKSRWQQGNVFSCSVMHEALHNHYTQKSLSLSP GK |
| human IgG4 S228P constant domain (nucleotide sequence) | 49 | gccagcacaaagggcccagcgtgttccctctggccccttg tagcagaagcaccagcgagtctacagccgcctgggctgcc tcgtgaaggactactttcccgagcccgtgaccgtgtcctgg aactctggcgctctgacaagcggcgtgcacacctttccagc cgtgctgcagagcagcggcctgtactctctgagcagcgtcg tgactgtgcccagcagctctctgggcaccaagacctacacc tgtaacgtggaccacaagcccagcaacaccaaggtggacaa gcgggtggaatctaagtacggccctccctgccctcctgcc cagccctgaatttctgggcggaccctccgtgttcctgttc cccccaaagcccaaggacaccctgatgatcagccggacccc cgaagtgacctgcgtggtggtggatgtgtcccaggaagatc ctgaggtgcagttcaattggtacgtggacggcgtggaagtg cacaacgccaagaccaagcctagagaggaacagttcaacag cacctaccgggtggtgtccgtgctgacagtgctgcaccagg actggctgaacggcaaagagtacaagtgcaaggtgtccaac aagggactgccagctccatcgagaaaaccatcagcaaggc caagggccagccccgcgaaccccaggtgtacacactgcctc caagccaggaagagatgaccaagaaccaggtgtccctgacc tgtctcgtgaaaggcttctaccctcgatatcgccgtgga atgggagagcaacggccagcccgagaacaactacaagacca cccccctgtgctggacagcgacggctcattcttcctgtac agcagactgaccgtggacaagagccggtggcaggaaggcaa cgtgttcagctgcagcgtgatgcacgaggccctgcacaacc actacacccagaagtccctgtctctgagcctgggcaaa |
| human IgG4 S228P constant domain (nucleotide sequence) | 50 | ASTKGPSVFPLAPCSRSTSESTAALGCLVKDYFPEPVTVSW NSGALTSGVHTFPAVLQSSGLYSLSSVVTVPSSSLGTKTYT CNVDHKPSNTKVDKRVESKYGPPCPPCPAPEFLGGPSVFLF PPKPKDTLMISRTPEVTCVVVDVSQEDPEVQFNWYVDGVEV HNAKTKPREEQFNSTYRVVSVLTVLHQDWLNGKEYKCKVSN KGLPSSIEKTISKAKGQPREPQVYTLPPSQEEMTKNQVSLT CLVKGFYPSDIAVEWESNGQPENNYKTTPPVLDSDGSFFLY SRLTVDKSRWQEGNVFSCSVMHEALHNHYTQKSLSLSLGK |
| human kappa constant domain (nucleotide sequence) | 51 | cggacagtggccgctcccagcgtgttcatcttcccacctag cgacgagcagctgaagtccggcacagccctctgtcgtgtgcc tgctgaacaacttctaccccccgcgaggccaaggtgcagtgg aaggtggacaatgccctgcagagcggcaacagccaggaaag cgtgaccgagcaggacagcaaggactccacctacagcctga gcagcaccctgacactgagcaaggccgactacgagaagcac aaggtgtacgcctgcgaagtgacccaccagggcctgtctag ccccgtgaccaagagcttcaaccggggcgagtgc |
| human kappa constant domain (amino acid sequence) | 52 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| hCTLA4.27A epitope on hCTLA-4 (amino acid sequence) | 53 | SFVCEYASPGKAT |
| CTLA-4 46-70 (amino acid sequence) | 54 | VLASSRGIASFVCEYASPGKATEVR |
| CTLA-4 49-56 (amino acid sequence) | 55 | ASSRGIASF |
| CTLA-4 66-70 (amino acid sequence) | 56 | ATEVR |
| CTLA-4 61-68 (amino acid sequence) | 57 | ASPGKATE |
| CTLA-4 46-76 (amino acid sequence) | 58 | VLASSRGIASFVCEYASPGKATEVRVTVLRQ |

-continued

| Description | SEQ ID NO: | SEQUENCE |
|---|---|---|
| rhCTLA-4/Fc/6His (amino acid sequence) | 59 | AMHVAQPAVVLASSRGIASFVCEYASPGKATEVRVTVLRQA DSQVTEVCAATYMMGNELTFLDDSICTGTSSGNQVNLTIQG LRAMDTGLYICKVELMYPPPYYLGIGNGTQIYVIDPEPCPD SDFIEGRMDPKSCDKTHTCPPCPAPELLGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALPA PIEKTISKAKGQPREPQVYTLPPSRDELTKNQVSLTCLVKG FYPSDIAVEWESNGQPENNYKTTPPVLDSDGSFFLYSKLTV DKSRWQQGNVFSCSVMHEALHNHYTQKSLSLSPGKHHHHHH |

"Treat" or "treating" means to administer a therapeutic agent, such as a composition containing any of the antibodies or antigen-binding fragments of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

The present invention includes anti-CTLA-4 antibodies and methods of use thereof. As used herein, the term "antibody" refers to any form of antibody that exhibits the desired biological activity. Thus, it is used in the broadest sense and specifically covers, but is not limited to, monoclonal antibodies (including full length monoclonal antibodies comprising two light chains and two heavy chains), polyclonal antibodies, multispecific antibodies (e.g., bispecific antibodies), humanized antibodies, fully human antibodies, chimeric antibodies and camelized single domain antibodies.

The present invention includes anti-CTLA-4 antigen-binding fragments and methods of use thereof. As used herein, unless otherwise indicated, "antibody fragment" or "antigen-binding fragment" refers to antigen-binding fragments of antibodies, i.e. antibody fragments that retain the ability to bind specifically to the antigen bound by the full-length antibody, e.g. fragments that retain one or more CDR regions. Examples of antigen-binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

The present invention includes anti-CTLA-4 Fab fragments and methods of use thereof. A "Fab fragment" is comprised of one light chain and the $C_H1$ and variable regions of one heavy chain. The heavy chain of a Fab molecule cannot form a disulfide bond with another heavy chain molecule. An "Fab fragment" can be the product of papain cleavage of an antibody.

The present invention includes anti-CTLA-4 antibodies and antigen-binding fragments thereof which comprise an Fc region and methods of use thereof. An "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

The present invention includes anti-CTLA-4 Fab' fragments and methods of use thereof. A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

The present invention includes anti-CTLA-4 F(ab')$_2$ fragments and methods of use thereof. A "F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab') 2 fragment thus is composed of two Fab' fragments that are held together by a disulfide bond between the two heavy chains. An "F(ab')$_2$ fragment" can be the product of pepsin cleavage of an antibody.

The present invention includes anti-CTLA-4 Fv fragments and methods of use thereof. The "Fv region" comprises the variable regions from both the heavy and light chains, but lacks the constant regions.

The present invention includes anti-CTLA-4 scFv fragments and methods of use thereof. The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen-binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

The present invention includes anti-CTLA-4 domain antibodies and methods of use thereof. A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The present invention includes anti-CTLA-4 bivalent antibodies and methods of use thereof. A "bivalent antibody" comprises two antigen-binding sites. In some instances, the two binding sites have the same antigen specificities. However, bivalent antibodies may be bispecific (see below).

The present invention includes anti-CTLA-4 camelized single domain antibodies and methods of use thereof. In certain embodiments, antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079).

In one embodiment, the present invention provides single domain antibodies comprising two $V_H$ domains with modifications such that single domain antibodies are formed.

The present invention includes anti-CTLA-4 diabodies and methods of use thereof. As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

Typically, an antibody or antigen-binding fragment of the invention which is modified in some way retains at least 10% of its binding activity (when compared to the parental antibody) when that activity is expressed on a molar basis. Preferably, an antibody or antigen-binding fragment of the invention retains at least 20%, 50%, 70%, 80%, 90%, 95% or 100% or more of the CTLA-4 binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

The present invention includes isolated anti-CTLA-4 antibodies and antigen-binding fragments thereof and methods of use thereof. "Isolated" antibodies or antigen-binding fragments thereof are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The present invention includes anti-CTLA-4 chimeric antibodies (e.g., human constant domain/mouse variable domain) and methods of use thereof. As used herein, a "chimeric antibody" is an antibody having the variable domain from a first antibody and the constant domain from a second antibody, where the first and second antibodies are from different species. (U.S. Pat. No. 4,816,567; and Morrison et al., (1984) *Proc. Natl. Acad. Sci. USA* 81: 6851-6855). Typically, the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g., mouse) antibody.

The present invention includes anti-CTLA-4 humanized antibodies and antigen-binding fragments thereof (e.g., rat or mouse antibodies that have been humanized) and methods of use thereof. The invention includes any humanized version of the hCTLA4.27A antibody as shown in the Examples. As used herein "27 antibody" and "hCTLA4.27" are used interchangeably to refer to an antibody comprising the VH region of SEQ ID NO: 7 and the VL region of SEQ ID NO: 8 more preferably, the VH region of any of SEQ ID NO: 10, 12, 14, 16, 18 or 20 and the VL region of any of SEQ ID NO: 22, 24, 26 or 30. As used herein, the term "humanized antibody" refers to forms of antibodies that contain sequences from both human and non-human (e.g., mouse or rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5th ed.; NIH Publ. No. 91-3242 (1991); Kabat (1978) *Adv. Prot. Chem.* 32:1-75; Kabat, et al., (1977) *J. Biol. Chem.* 252: 6609-6616; Chothia, et al., (1987) *J Mol. Biol.* 196:901-917 or Chothia, et al., (1989) *Nature* 342:878-883.

As used herein, the term "hypervariable region" refers to the amino acid residues of an antibody or antigen-binding fragment thereof that are responsible for antigen-binding. The hypervariable region comprises amino acid residues from a "complementarity determining region" or "CDR" (i.e. LCDR1, LCDR2 and LCDR3 in the light chain variable domain and HCDR1, HCDR2 and HCDR3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

"Isolated nucleic acid molecule" or "isolated polynucleotide" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

The antibodies of the present invention may comprise any combination of the heavy and light chains as defined in the present application and which are presented in SEQ ID NO: 7 and 8 and more preferably the heavy chains as presented in SEQ ID NO: 10, 12, 14, 16, 18 or 20 and the light chain as presented in SEQ ID NO: 22, 24, 26 and 30.

This means that the following combinations can be made:
An antibody with a heavy chain of SEQ ID NO: 10 and a light chain of SEQ ID NO: 22;
An antibody with a heavy chain of SEQ ID NO: 12 and a light chain of SEQ ID NO: 22;
An antibody with a heavy chain of SEQ ID NO: 14 and a light chain of SEQ ID NO: 22;
An antibody with a heavy chain of SEQ ID NO: 16 and a light chain of SEQ ID NO: 22;
An antibody with a heavy chain of SEQ ID NO: 18 and a light chain of SEQ ID NO: 22;
An antibody with a heavy chain of SEQ ID NO: 20 and a light chain of SEQ ID NO: 22;
An antibody with a heavy chain of SEQ ID NO: 10 and a light chain of SEQ ID NO: 24;
An antibody with a heavy chain of SEQ ID NO: 12 and a light chain of SEQ ID NO: 24;
An antibody with a heavy chain of SEQ ID NO: 14 and a light chain of SEQ ID NO: 24;
An antibody with a heavy chain of SEQ ID NO: 16 and a light chain of SEQ ID NO: 24;
An antibody with a heavy chain of SEQ ID NO: 18 and a light chain of SEQ ID NO: 24;
An antibody with a heavy chain of SEQ ID NO: 20 and a light chain of SEQ ID NO: 24;
An antibody with a heavy chain of SEQ ID NO: 10 and a light chain of SEQ ID NO: 26;
An antibody with a heavy chain of SEQ ID NO: 12 and a light chain of SEQ ID NO: 26;
An antibody with a heavy chain of SEQ ID NO: 14 and a light chain of SEQ ID NO: 26;
An antibody with a heavy chain of SEQ ID NO: 16 and a light chain of SEQ ID NO: 26;
An antibody with a heavy chain of SEQ ID NO: 18 and a light chain of SEQ ID NO: 26;
An antibody with a heavy chain of SEQ ID NO: 20 and a light chain of SEQ ID NO: 26;
An antibody with a heavy chain of SEQ ID NO: 10 and a light chain of SEQ ID NO: 30;
An antibody with a heavy chain of SEQ ID NO: 12 and a light chain of SEQ ID NO: 30;
An antibody with a heavy chain of SEQ ID NO: 14 and a light chain of SEQ ID NO: 30;
An antibody with a heavy chain of SEQ ID NO: 16 and a light chain of SEQ ID NO: 30;
An antibody with a heavy chain of SEQ ID NO: 18 and a light chain of SEQ ID NO: 30;
An antibody with a heavy chain of SEQ ID NO: 20 and a light chain of SEQ ID NO: 30.

Physical and Functional Properties of the
Exemplary Anti-CTLA-4 Antibodies

The present invention provides anti-CTLA-4 antibodies and antigen-binding fragments thereof having specified structural and functional features, and methods of use of the antibodies or antigen-binding fragments thereof in the treatment or prevention of disease (e.g., cancer or infectious disease). These all origin from the mouse antibody that has been found as described in the Examples, which antibody has the heavy chain of SEQ ID NO: 32 and the light chain of SEQ ID NO: 34 (the nucleotide sequences encoding for these are SEQ ID NO: 31 and 33, respectively).

This antibody and the humanize antibodies derived therefrom are characterized because they bind to human CTLA-4 (hCTLA-4) with an EC50 of less than 20 nM, preferably less than 1 nM and they are able to block the binding of hCTLA-4 to hCD80 or hCD86 with an IC50 of less than 100 nM, preferably less than 10 nM for hCD80 blocking and preferably less than 10 nM, more preferably less than 2.5 nM for hCD86 blocking. It should be remarked that the hCD80 blocking profile of the antibodies of the present invention lies in between the hCD80 blocking profiles of 10D1 (ipilimumab) and CP-675,206 (tremelimumab) (see FIG. 2). It differs from ipilimumab and tremelimumab because it binds to a different epitope on the CTLA-4 molecule. One of the differences is that the antibody or antigen binding fragment of the invention does not bind to the chimeric mouse-human CTLA4 molecule of which the sequence is provided in SEQ ID NO: 44 (see also FIG. 5), while 10D1 and CP-675,206 do bind There are several methods available for fine mapping antibody epitopes on target antigens, including: H/D-Ex Mass spec, X-ray crystallography, peptide array and site directed mutagenesis. For example, HDX (Hydrogen Deuterium Exchange) coupled with proteolysis and mass spectrometry can be used to determine the epitope of an antibody on a specific antigen Y. HDX-MS relies on the accurate measurement and comparison of the degree of deuterium incorporation by an antigen when incubated in $D_2O$ on its own and in presence of its antibody at various time intervals. Deuterium is exchanged with hydrogen on the amide backbone of the proteins in exposed areas whereas regions of the antigen bound to the antibody will be protected and will show less or no exchange after analysis by LC-MS/MS of proteolytic fragments.

The invention also comprises anti-CTLA-4 antibodies which bind to an epitope of human CTLA-4 but which do not bind to the mouse-human chimera CTLA-4 molecule of SEQ ID NO: 44.

In other embodiments, the invention provides antibodies or antigen-binding fragment thereof that bind human CTLA-4 (e.g., humanized antibodies) and has $V_L$ domains and $V_H$ domains with at least 80%, 85%, 90%, 95%, 96%, 97%, 98% or 99% sequence identity with the amino acid sequences of SEQ ID NOs: 7-30, preferably with at least 80%, 85%, 90%, 95%, 96%, 97%, 98% or 99% sequence identity with SEQ ID NOs: 10, 12, 14, 16, 18, 20, 22, 24, 26 or 30; wherein the variant exhibits the desired binding and properties, being the ability to bind to CTLA-4 and the ability to block CTLA-4 binding to CD80 and/or CD86. In other embodiments, the invention provides antibodies or antigen-binding fragment thereof that bind human CTLA-4 (e.g., humanized antibodies) and have $V_L$ domains and $V_H$ domains with at least 95% sequence identity with the amino acid sequences of SEQ ID NOs: 7-30, preferably with at least 80%, 85%, 90%, 95%, 96%, 97%, 98% or 99% sequence identity with SEQ ID NOs: 10, 12, 14, 16, 18, 20, 22, 24, 26 or 30. In other embodiments, the invention provides antibodies or antigen-binding fragment thereof that bind human CTLA-4 (e.g., humanized antibodies) and have $V_L$ domains and $V_H$ domains with at least 97% sequence identity with the amino acid sequences of SEQ ID NOs: 7-30, preferably with at least 80%, 85%, 90%, 95%, 96%, 97%, 98% or 99% sequence identity with SEQ ID NOs: 10, 12, 14, 16, 18, 20, 22, 24, 26 or 30. In other embodiments, the invention provides antibodies or antigen-binding fragment thereof that bind human CTLA-4 (e.g., humanized antibodies) and have $V_L$ domains and $V_H$ domains with at least 99% sequence identity with the amino acid sequences of SEQ ID NOs: 7-30, preferably with at least 80%, 85%, 90%, 95%, 96%, 97%, 98% or 99% sequence identity with SEQ ID NOs: 10, 12, 14, 16, 18, 20, 22, 24, 26 or 30.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 2.

TABLE 2

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table 2. Also provided are isolated polypeptides comprising the $V_L$ domains of the anti-CTLA-4 antibodies of the invention (e.g., SEQ ID NOs: 22, 24, 26, 30), and isolated polypeptides comprising the $V_H$ domains of the anti-CTLA-4 antibodies of the invention (e.g., SEQ ID NOs: 10, 12, 14, 16, 18, 20) having up to 0, 1, 2, 3, 4, 5, 6, 7, 8, 9, 10 or more amino acid substitutions.

In another embodiment, provided is an antibody or antigen-binding fragment thereof that binds human CTLA-4 and has $V_L$ domains and $V_H$ domains with at least 99% 98%, 97%, 96%, 95%, 90%, 85%, 80% or 75% sequence identity to one or more of the $V_L$ domains or $V_H$ domains described herein, and exhibits specific binding to CTLA-4. In another embodiment the binding antibody or antigen-binding fragment thereof of the present invention comprises $V_L$ and $V_H$ domains (with and without signal sequence) having up to 0, 1, 2, 3, 4, 5, 6, 7, 8, 9, 10, 11, 12, 13, 14, 15, 16, 17, 18, 19, 20, 21, 22, 23, 24, 25 or more amino acid substitutions, and exhibits specific binding to CTLA-4.

Polynucleotides and Polypeptides

The present invention further comprises the polynucleotides encoding any of the polypeptides or immunoglobulin chains of anti-CTLA-4 antibodies and antigen-binding fragments thereof of the invention. For example, the present invention includes the polynucleotides encoding the amino acids described in any one of SEQ ID NOs: 1-30.

In one embodiment, an isolated polynucleotide, for example DNA, encoding the polypeptide chains of the isolated antibodies or antigen-binding fragments set forth herein is provided. In one embodiment, the isolated polynucleotide encodes an antibody or antigen-binding fragment thereof comprising at least one mature immunoglobulin light chain variable ($V_L$) domain according to the invention and/or at least one mature immunoglobulin heavy chain variable ($V_H$) domain according to the invention. In some embodiments the isolated polynucleotide encodes both a light chain and a heavy chain on a single polynucleotide molecule, and in other embodiments the light and heavy chains are encoded on separate polynucleotide molecules. In another embodiment the polynucleotides further encodes a signal sequence.

In one embodiment, the invention comprises an isolated polynucleotide encoding an antibody heavy variable ($V_H$) domain or an antigen-binding fragment thereof comprising HCDR-1 (SEQ ID NO: 1), HCDR-2 (SEQ ID NO: 2) and HCDR-3 (SEQ ID NO: 3).

In one embodiment, the invention comprises an isolated polynucleotide encoding an antibody light chain variable ($V_L$) domain or an antigen-binding fragment thereof comprising LCDR-1 (SEQ ID NO: 4), LCDR-2 (SEQ ID NO: 5) and LCDR-3 (SEQ ID NO: 6).

In one embodiment, the invention comprises an isolated polynucleotide encoding the immunoglobulin heavy chain variable ($V_H$) domain of SEQ ID NO: 7.

In one embodiment, the invention comprises an isolated polynucleotide encoding the immunoglobulin light chain variable (VL) domain of SEQ ID NO: 8.

In one embodiment, the invention comprises an isolated polynucleotide according to any of SEQ ID NO: 9, 11, 13, 15, 17 or 19 encoding a humanized heavy chain In one embodiment, the invention comprises an isolated polynucleotide according to any of SEQ ID NO: 21, 23, 25 or 29 encoding a humanized light chain.

In a further embodiment of the invention an isolated polynucleotide is comprised which comprises an isolated polynucleotide according to any of SEQ ID NO: 9, 11, 13, 15, 17 or 19 encoding a humanized heavy chain and an isolated polynucleotide according to any of SEQ ID NO: 21, 23, 25 or 29 encoding a humanized light chain. All possible combinations of these are included. Accordingly, the invention comprises a polynucleotide comprising SEQ ID NO: 9 and SEQ ID NO: 21, a polynucleotide comprising SEQ ID NO: 11 and SEQ ID NO: 21, a polynucleotide comprising SEQ ID NO: 13 and SEQ ID NO: 21, a polynucleotide comprising SEQ ID NO: 15 and SEQ ID NO: 21, a polynucleotide comprising SEQ ID NO: 17 and SEQ ID NO: 21, a polynucleotide comprising SEQ ID NO: 19 and SEQ ID NO: 21, a polynucleotide comprising SEQ ID NO: 9 and SEQ ID NO: 23. a polynucleotide comprising SEQ ID NO: 11 and SEQ ID NO: 23, a polynucleotide comprising SEQ ID NO: 13 and SEQ ID NO: 23, a polynucleotide comprising SEQ ID NO: 15 and SEQ ID NO: 23, a polynucleotide comprising SEQ ID NO: 17 and SEQ ID NO: 23, a polynucleotide comprising SEQ ID NO: 19 and SEQ ID NO: 23, a polynucleotide comprising SEQ ID NO: 9 and SEQ ID NO: 25, a polynucleotide comprising SEQ ID NO: 11 and SEQ ID NO: 25, a polynucleotide comprising SEQ ID NO: 13 and SEQ ID NO: 25, a polynucleotide comprising SEQ ID NO: 15 and SEQ ID NO: 25, a polynucleotide comprising SEQ ID NO: 17 and SEQ ID NO: 25, a polynucleotide comprising SEQ ID NO: 19 and SEQ ID NO: 25, a polynucleotide comprising SEQ ID NO: 9 and SEQ ID NO: 29, a polynucleotide comprising SEQ ID NO: 11 and SEQ ID NO: 29, a polynucleotide comprising SEQ ID NO: 13 and SEQ ID NO: 29, a polynucleotide comprising SEQ ID NO: 15 and SEQ ID NO: 29, a polynucleotide comprising SEQ ID NO: 17 and SEQ ID NO: 29, and/or a polynucleotide comprising SEQ ID NO: 19 and SEQ ID NO: 29.

This present invention also provides vectors, e.g., expression vectors, such as plasmids, comprising the isolated polynucleotides of the invention, wherein the polynucleotide is operably linked to control sequences that are recognized by a host cell when the host cell is transfected with the vector. Also provided are host cells comprising a vector of the present invention and methods for producing the antibody or antigen-binding fragment thereof or polypeptide disclosed herein comprising culturing a host cell harboring an expression vector or a nucleic acid encoding the immunoglobulin chains of the antibody or antigen-binding fragment thereof in culture medium, and isolating the antigen or antigen-binding fragment thereof from the host cell or culture medium.

Also included in the present invention are polypeptides, e.g., immunoglobulin polypeptides, comprising amino acid sequences that are at least about 75% identical, 80% identical, more preferably at least about 90% identical and most preferably at least about 95% identical (e.g., 95%, 96%, 97%, 98%, 99%, 100%) to the amino acid sequences of the antibodies provided herein when the comparison is performed by a BLAST algorithm wherein the parameters of the algorithm are selected to give the largest match between the respective sequences over the entire length of the respective reference sequences (e.g. expect threshold: 10; word size: 3; max matches in a query range: 0; BLOSUM 62 matrix; gap costs: existence 11, extension 1; conditional compositional score matrix adjustment).

Sequence identity refers to the degree to which the amino acids of two polypeptides are the same at equivalent positions when the two sequences are optimally aligned.

The following references relate to BLAST algorithms often used for sequence analysis: BLAST ALGORITHMS: Altschul et al. (2005) *FEBS J.* 272(20): 5101-5109; Altschul, S. F., et al., (1990) *J. Mol. Biol.* 215:403-410; Gish, W., et al., (1993) *Nature Genet.* 3:266-272; Madden, T. L., et al., (1996) *Meth. Enzymol.* 266:131-141; Altschul, S. F., et al., (1997) *Nucleic Acids Res.* 25:3389-3402; Zhang, J., et al., (1997) *Genome Res.* 7:649-656; Wootton, J. C., et al., (1993) *Comput. Chem.* 17:149-163; Hancock, J. M. et al., (1994) *Comput. Appl. Biosci.* 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, *Natl. Biomed. Res. Found.*, Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, *Natl. Biomed. Res. Found.*, Washington, D.C.; Altschul, S. F., (1991) *J. Mol. Biol.* 219:555-565; States, D. J., et al., (1991) *Methods* 3:66-70; Henikoff, S., et al., (1992) *Proc. Natl. Acad. Sci. USA* 89:10915-10919; Altschul, S. F., et al., (1993) *J. Mol. Evol.* 36:290-300; ALIGNMENT STATISTICS: Karlin, S., et al., (1990) *Proc. Natl. Acad. Sci. USA* 87:2264-2268; Karlin, S., et al., (1993) *Proc. Natl. Acad. Sci. USA* 90:5873-5877; Dembo, A., et al., (1994) *Ann. Prob.* 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, New York.

Binding Affinity

By way of example, and not limitation, the antibodies and antigen-binding fragments disclosed herein may bind human CTLA-4 (NCBI Accession No. NM_005214.4) comprising the following amino acid sequence: (SEQ ID NO: 36):

MACLGFQRHKAQLNLATRTWPCTLLFFLLFIPVFCKAMHVAQPAVVLASS

RGIASFVCEYASPGKATEVRVTVLRQADSQVTEVCAATYMMGNELTFLDD

SICTGTSSGNQVNLTIQGLRAMDTGLYICKVELMYPPPYYLGIGNGTQIY

VIDPEPCPDSDFLLWILAAVSSGLFFYSFLLTAVSLSKMLKKRSPLTTGV

YVKMPPTEPECEKQFQPYFIPIN with a $K_D$ value of at least about $1 \times 10^{-9}$ M (i.e, a $K_D$ value of $1 \times 10^{-9}$ M or lower) as determined by surface plasmon resonance (e.g., BIACORE® (GE Healthcare Bio-Sciences AB)) or a similar technique (e.g. KinExa® (Sapidyne Instruments Inc.) or OCTET® (Molecular Devices, LLC)).

Immune Cell Activation

In some embodiments, the antibodies or antigen binding fragments of the invention increase the activity of an immune cell. The increase of the activity of an immune cell can be detected using any method known in the art. In one embodiment, the increase in activity of an immune cell can be detected by measuring the proliferation of the immune cell. For example, an increase in activity of a T cell can be detected by measuring the proliferation of the T cell or signal transduction events such as tyrosine phosphorylation of immune receptors or downstream kinases that transmit signals to transcriptional regulators. In other embodiments, the increase in activity of an immune cell can be detected by measuring CTL or NK cell cytotoxic function on specific target cells or IFNγ cytokine responses, which are associated with stimulation of anti-tumor immunity. In yet other embodiments, the increase in activity of an immune cell can be detected by measuring T cell activation ex vivo in a sample derived from the subject. In one embodiment, the increase in T cell activity is determined by: (i) measuring SEB (*Staphylococcus* Enterotoxin B) induced production of one or more pro-inflammatory cytokines selected from the group consisting of: IL-2, TNFα, IL-17, IFNγ, IL-1β, GM-CSF, RANTES, IL-6, IL-8, IL-5 and IL-13 or upregulation of membrane activation markers from a group consisting of: CD25 and CD69 or induction of proliferation using detection of blast formation by flow cytometry or 3H-incorporationor (ii) measuring mixed lymphocyte reactions or direct anti-CD3 mAb stimulation of T cell receptor (TCR) signaling to induce production of a cytokine selected from the group consisting of: IL-2, TNFα, IL-17, IFNγ, IL-1β, GM-CSF, RANTES, IL-6, IL-8, IL-5 and IL-13 or upregulation of membrane activation markers from a group consisting of: CD25 and CD69 or induction of proliferation using detection of blast formation by flow cytometry or 3H-incorporation. In certain embodiments, the anti-CTLA-4 antibody or antigen binding fragment thereof of the present invention will stimulate CD3+ T cells, when these are presented to Raji cells expressing CD80 and CD86, to produce pro-inflammatory cytokines selected from the group consisting of: IL-2, TNFα, IL-17, IFNγ, IL-1β, GM-CSF, RANTES, IL-6, IL-8, IL-5 and IL-13 or upregulation of membrane activation markers from a group consisting of: CD25 and CD69 or induction of proliferation using detection of blast formation by flow cytometry or 3H-incorporation. In certain embodiments, the anti-CTLA4 antibody or antigen binding fragment thereof of the present invention will stimulate production of IL-2 and/or IFNγ by activated T cells by at least 1.5 fold. As is clear from the experimental part, the T-cell activating characteristics of the antibodies of the present invention is about equal to the T-cell stimulating characteristics of the known prior art anti-hCTLA4 antibodies ipilimumab and tremelimumab.

Effector Function of Anti-hCTLA-4 Antibodies

In some embodiments, the anti-CTLA-4 antibodies or antigen binding fragments of the invention can deplete CTLA-4+ regulatory T cells. The ability of the antibodies to exert such an effector function can be determined using any method known in the art. In one embodiment the ability of the antibodies to induce Antibody-Dependent Cell-mediated Cytoxicity is determined using natural killer cells as effector cells and a cell line that stably expresses human CTLA-4. As shown in the experimental section, the hCTLA-4 antibodies with a human IgG1 Fc portion are able to induce ADCC on CTLA-4+ cells.

In another embodiment the ability of the antibodies to induce Complement-Dependent Cytoxicity is determined using human complement and a cell line that stably expresses human CTLA-4. As shown in the experimental section, the hCTLA-4 antibodies with a human IgG1 Fc portion are able to induce CDC on CTLA-4+ cells.

In another embodiment the ability of the antibodies to induce cell-mediated lysis can be determined using Non-classical CD14+CD16++ Monocytes that induce FcγRIIIA-Dependent Lysis of CTLA-4+ Tregs in the context of an hIgG1 CTLA-4 antibody such as ipilimumab (Romano et al; PNAS; 2015; 6140-6145; doi: 10.1073/pnas.1417320112)

Ability of Anti-hCTLA-4 Antibodies to Block Binding to hCD80 and hCD86

In some embodiments, the anti-CTLA-4 antibodies or antigen binding fragments of the invention are able to block binding of human CTLA-4 to human CD80 and/or human CD86. The ability to block binding of human CTLA-4 to human CD80 and/or human CD86 can be determined using any method known in the art. In one embodiment, the ability of the antibodies to block binding of human CTLA-4 to human CD80 and/or human CD86 is determined using an ELISA assay.

As is shown in the experimental section, the potency of blocking of CTLA-4 binding to human CD80 and/or human CD86 resembles the activities of the known anti-CTLA-4 antibodies ipilimumab and tremelimumab. It should be highlighted that the anti-CTLA-4 antibodies of the invention showed an intermediary efficacy in between the effects of ipilimumab and tremelimumab with respect to blocking of hCD80 (see FIG. 2).

Methods of Making Antibodies and
Antigen-Binding Fragments Thereof

Thus, the present invention includes methods for making an anti-CTLA-4 antibody or antigen-binding fragment thereof of the present invention comprising culturing a hybridoma cell that expresses the antibody or fragment under condition favorable to such expression and, optionally, isolating the antibody or fragment from the hybridoma and/or the growth medium (e.g. cell culture medium).

Monoclonal antibodies derived from animals other than rats and mice offer unique advantages. Many protein targets relevant to signal transduction and disease are highly conserved between mice, rats and humans, and can therefore be recognized as self-antigens by a mouse or rat host, making them less immunogenic. This problem may be avoided when using rabbit as a host animal. See, e.g., Rossi et al., *Am. J. Clin. Pathol.,* 124, 295-302, 2005.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. B-cells were cultured, as described by Steenbakkers et al., 1994, *Mol. Biol. Rep.* 19: 125-134.

B-cell clones from reactive supernatants are then immortalized, e.g. by mini-electrofusion following published procedures (Steenbakkers et al., 1992, *J. Immunol. Meth.* 152: 69-77; Steenbakkers et al., 1994, *Mol. Biol. Rep.* 19:125-34). Hybridomas are selected and cloned by limiting dilution.

The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Adjuvants that can be used in the methods of antibody generation include, but are not limited to, protein adjuvants; bacterial adjuvants, e.g., whole bacteria (BCG, *Corynebacterium parvum, Salmonella minnesota*) and bacterial components including cell wall skeleton, trehalose dimycolate, monophosphoryl lipid A, methanol extractable residue (MER) of tubercle *bacillus,* complete or incomplete Freund's adjuvant; viral adjuvants; chemical adjuvants, e.g., aluminum hydroxide, iodoacetate and cholesteryl hemisuccinateor; naked DNA adjuvants. Other adjuvants that can be used in the methods of the invention include, Cholera toxin, paropox proteins, MF-59 (Chiron Corporation; See also Bieg et al. (1999) "GAD65 And Insulin B Chain Peptide (9-23) Are Not Primary Autoantigens In The Type 1 Diabetes Syndrome Of The BB Rat," Autoimmunity, 31(1):15-24, which is incorporated herein by reference), MPL® (Corixa Corporation; See also Lodmell et al. (2000) "DNA Vaccination Of Mice Against Rabies Virus: Effects Of The Route Of Vaccination And The Adjuvant Monophosphoryl Lipid A (MPL)," Vaccine, 18: 1059-1066; Johnson et al. (1999) "3-O-Desacyl Monophosphoryl Lipid A Derivatives: Synthesis And Immunostimulant Activities," Journal of Medicinal Chemistry, 42: 4640-4649; Baldridge et al. (1999) "Monophosphoryl Lipid A (MPL) Formulations For The Next Generation Of Vaccines," Methods, 19: 103-107, all of which are incorporated herein by reference), RC-529 adjuvant (Corixa Corporation; the lead compound from Corixa's aminoalkyl glucosaminide 4-phosphate (AGP) chemical library, see also www.corixa.com), and DETOX™ adjuvant (Corixa Corporation; DETOX™ adjuvant includes MPL® adjuvant (monophosphoryl lipid A) and mycobacterial cell wall skeleton; See also Eton et al. (1998) "Active Immunotherapy With Ultraviolet B-Irradiated Autologous Whole Melanoma Cells Plus DETOX In Patients With Metastatic Melanoma," Clin. Cancer Res. 4(3):619-627; and Gupta et al. (1995) "Adjuvants For Human Vaccines—Current Status, Problems And Future Prospects," Vaccine, 13(14): 1263-1276, both of which are incorporated herein by reference).

Numerous publications discuss the use of phage display technology to produce and screen libraries of polypeptides for binding to a selected analyte. See, e.g, Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phages displaying a polypeptide with affinity to a target bind to the target and these phages are enriched by affinity screening to the target. The identity of polypeptides displayed from these phages can be determined from their respective genomes. Using this method, a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg et al. (1995) "Human Antibodies From Transgenic Mice," Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix/Amgen (Freemont, Calif.) and Medarex/BMS (Princeton, N.J.), Kymab (Cambridge, UK) and Merus (Utrecht, Netherlands) can be engaged to provide human antibodies directed against a selected antigen using technology similar to that described above.

The anti-CTLA-4 antibodies disclosed herein may also be produced recombinantly (e.g., in an *E. coli*/T7 expression system, a mammalian cell expression system or a lower eukaryote expression system). In this embodiment, nucleic acids encoding the antibody immunoglobulin molecules of the invention (e.g., $V_H$ or $V_L$) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as a *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside).

Monoclonal antibody preparations can be produced using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. One example of a method for recombinant production of antibodies is disclosed in U.S. Pat. No. 4,816,567.

Thus, the present invention includes recombinant methods for making an anti-CTLA-4 antibody or antigen-binding fragment thereof of the present invention, or an immunoglobulin chain thereof, comprising introducing a polynucleotide encoding one or more immunoglobulin chains of the antibody or fragment (e.g., heavy and/or light immunoglobulin chain); culturing the host cell (e.g., CHO or *Pichia* or *Pichia pastoris*) under condition favorable to such expression and, optionally, isolating the antibody or fragment or chain from the host cell and/or medium in which the host cell is grown.

Anti-CTLA-4 antibodies can also be synthesized by any of the methods set forth in U.S. Pat. No. 6,331,415.

Eukaryotic and prokaryotic host cells, including mammalian cells as hosts for expression of the antibodies or fragments or immunoglobulin chains disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Fungal cells include yeast and filamentous fungus cells including, for example, *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma*

*reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha*, any *Kluyveromyces* sp., *Candida albicans*, any *Aspergillus* sp., *Trichoderma reesei, Chrysosporium lucknowense*, any *Fusarium* sp., *Yarrowia lipolytica*, and *Neurospora crassa*. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody or fragment or chain in the host cells or secretion of the into the culture medium in which the host cells are grown.

A variety of host-expression vector systems may be utilized to express the antibodies of the invention. Such host-expression systems represent vehicles by which the coding sequences of the antibodies may be produced and subsequently purified, but also represent cells which may, when transformed or transfected with the appropriate nucleotide coding sequences, express the antibodies of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces, Pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphotic cells (see U.S. Pat. No. 5,807, 715), Per C.6 cells (rat retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited, to the *E. coli* expression vector pUR278 (Ruther et al. (1983) "Easy Identification Of cDNA Clones," EMBO J. 2:1791-1794), in which the antibody coding sequence may be ligated individually into the vector in frame with the lac Z coding region so that a fusion protein is produced; pIN vectors (Inouye et al. (1985) "Up-Promoter Mutations In The Lpp Gene Of *Escherichia coli*," Nucleic Acids Res. 13:3101-3110; Van Heeke et al. (1989) "Expression Of Human Asparagine Synthetase In *Escherichia coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts. (see e.g., see Logan et al. (1984) "Adenovirus Tripartite Leader Sequence Enhances Translation Of mRNAs Late After Infection," Proc. Natl. Acad. Sci. (U.S.A.) 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11:223-232), hypoxanthine-guanine phosphoribosyltransferase (Szybalska et al. (1962) "Genetics Of Human Cess Line. IV. DNA-Mediated Heritable Transformation Of A Biochemical Trait," Proc. Natl. Acad. Sci. (U.S.A.) 48:2026-2034), and adenine phosphoribosyltransferase (Lowy et al. (1980) "Isolation Of Transforming DNA: Cloning The Hamster Aprt Gene," Cell 22:817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplfiable Dominant-Acting Gene," Proc. Natl. Acad. Sci. (U.S.A.) 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. (U.S.A.) 78:1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. (U.S.A.) 78:2072-2076); neo, which confers resistance to the aminoglycoside G-418 (Tachibana et al. (1991) "Altered Reactivity Of Immunoglobutin Produced By Human-Human Hybridoma Cells Transfected By pSV2-Neo Gene," Cytotechnology 6(3):219-226; Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human gene therapy," Ann. Rev. Biochem. 62:191-217). Methods commonly known in the art of recombinant DNA technology which can be used are described in Ausubel et al. (eds.), 1993, CURRENT PROTOCOLS IN MOLECULAR BIOLOGY, John Wiley & Sons, NY; Kriegler, 1990, GENE TRANSFER AND EXPRESSION, A LABORATORY MANUAL, Stockton Press, NY; and in Chapters 12 and 13, Dracopoli et al. (eds), 1994, CURRENT PROTOCOLS IN HUMAN GENETICS, John Wiley & Sons, NY.; Colbere-Garapin et al. (1981) "A New Dominant Hybrid Selective Marker For Higher Eukaryotic Cells," J. Mol. Biol. 150:1-14; and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156).

The expression levels of an antibody of the invention can be increased by vector amplification (for a review, see Bebbington and Hentschel, "The Use Of Vectors Based On Gene Amplification For The Expression Of Cloned Genes In Mammaian Cells," in DNA CLONING, Vol. 3. (Academic Press, New York, 1987)). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al. (1983) "Expression And Amplification Of Engineered Mouse Dihydrofolate Reductase Minigenes," Mol. Cell. Biol. 3:257-266).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot (1986) "Expression And Amplification Of Engineered Mouse Dihydrofolate Reductase Minigenes," Nature 322:562-565; Kohler (1980) "Immunoglobulin Chain Loss In Hybridoma Lines," Proc. Natl. Acad. Sci. (U.S.A.) 77:2197-2199). The coding sequences for the heavy and light chains may comprise cDNA or genomic DNA.

Antibodies and antigen-binding fragments thereof and immunoglobulin chains can be recovered from the culture medium using standard protein purification methods. Further, expression of antibodies and antigen-binding fragments thereof and immunoglobulin chains of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell.

The present invention includes methods for purifying an anti-CTLA-4 antibody or antigen-binding fragment thereof of the present invention comprising introducing a sample comprising the antibody or fragment to a purification medium (e.g., cation exchange medium, anion exchange medium, hydrophobic exchange medium, affinity purification medium (e.g., protein-A, protein-G, protein-A/G, protein-L)) and either collecting purified antibody or fragment from the flow-through fraction of said sample that does not bind to the medium; or, discarding the flow-through fraction and eluting bound antibody or fragment from the medium and collecting the eluate. In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo (See for example, Shinkawa et al., *J. Biol. Chem.* 278: 3466-3473 (2003); U.S. Pat. Nos. 6,946,292 and 7,214,775). These antibodies with non-fucosylated N-glycans are not likely to be immunogenic because their carbohydrate structures are a normal component of the population that exists in human serum IgG.

The present invention includes bispecific and bifunctional antibodies and antigen-binding fragments having a binding specificity for CTLA-4 and another antigen such as, for example and antigen that plays a role in immune stimulation, such as, PD-1, PD-L1, TSLP, IL-10, 4-IBB, SIRP-alpha, ICOS, NKG2C, NKG2A, KR2DL and KIR3DL antigens, OX40, CD40, ITL-1 to ITL-8, GITR, CD137, CS1, CD27, APRIL, or LAG-3, or antigens that play a role in targeting to and recognition of cancer cells, such as EGFR (ERBB1), HER2 (ERBB2), ERBB3, CD19, CD20, CD30, CD33, CD52, CEA, alpha-fetoprotein, CC49, VEGF. VEGFR, HGFR (MET), CA-125, tenascin, integrin, FAB, IGF1R, EPHA3, TRAILR1, TRAILR2 or RANKL and methods of use thereof. In an embodiment of the invention, the anti-CTLA-4 chains comprise any one of the VH/VL sequences provided in SEQ ID NOs: 7-30 (or an antigen binding fragment of any of said sequences, such as provided in SEQ ID NOs: 1-6). A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai, et al., (1990) *Clin. Exp. Immunol.* 79: 315-321, Kostelny, et al., (1992) *J Immunol.* 148:1547-1553. In addition, bispecific antibodies may be formed as "diabodies" (Holliger, et al., (1993) *PNAS USA* 90:6444-6448) or as "Janusins" (Traunecker, et al., (1991) *EMBO J.* 10:3655-3659 and Traunecker, et al., (1992) *Int. J. Cancer Suppl.* 7:51-52). In addition, bispecific antibodies may be formed as "Duobodies" (Labrijn et al, PNAS 2013; 110(13):5145-5150).

The present invention further includes anti-CTLA-4 antigen-binding fragments of the anti-CTLA-4 antibodies disclosed herein. The antibody fragments include $F(ab)_2$ fragments, which may be produced by enzymatic cleavage of an IgG by, for example, pepsin. Fab fragments may be produced by, for example, reduction of $F(ab)_2$ with dithiothreitol or mercaptoethylamine.

Immunoglobulins may be assigned to different classes depending on the amino acid sequences of the constant domain of their heavy chains. In some embodiments, different constant domains may be appended to humanized $V_L$ and $V_H$ regions derived from the CDRs provided herein. There are at least five major classes of immunoglobulins: IgA, IgD, IgE, IgG and IgM, and several of these may be further divided into subclasses (isotypes), e.g. IgG1, IgG2, IgG3 and IgG4; IgA1 and IgA2. The invention comprises antibodies and antigen-binding fragments of any of these classes or subclasses of antibodies.

In one embodiment, the antibody or antigen-binding fragment comprises a heavy chain constant region, e.g. a human constant region, such as γ1, γ2, γ3, or γ4 human heavy chain constant region or a variant thereof. In another embodiment, the antibody or antigen-binding fragment comprises a light chain constant region, e.g. a human light chain constant region, such as lambda or kappa human light chain region or variant thereof. By way of example, and not limitation the human heavy chain constant region can be γ4 and the human light chain constant region can be kappa. In an alternative embodiment, the Fc region of the antibody is γ4 with a Ser228Pro mutation (Angal S. et al., 1993, *Mol Immunol.* 30: 105-108 position 241 is based on the Kabat numbering system).

In one embodiment, the antibody or antigen-binding fragment comprises a heavy chain constant region of the IgG1 subtype. In one embodiment, the antibody or antigen-binding fragment comprises a heavy chain constant region of the IgG2 subtype. In one embodiment, the antibody or antigen-binding fragment comprises a heavy chain constant region of the IgG4 subtype.

Antibody Engineering

Further included are embodiments in which the anti-CTLA-4 antibodies and antigen-binding fragments thereof are engineered antibodies to include modifications to framework residues within the variable domains of the parental hCTLA4.27A monoclonal antibody, e.g. to improve the properties of the antibody or fragment. Typically, such framework modifications are made to decrease the immunogenicity of the antibody or fragment. This is usually accomplished by replacing non-CDR residues in the variable domains (i.e. framework residues) in a parental (e.g. rodent) antibody or fragment with analogous residues from the immune repertoire of the species in which the antibody is to be used, e.g. human residues in the case of human therapeutics. Such an antibody or fragment is referred to as a "humanized" antibody or fragment. In some cases it is desirable to increase the affinity, or alter the specificity of an engineered (e.g. humanized) antibody. One approach is to "backmutate" one or more framework residues to the corresponding germline sequence. More specifically, an antibody or fragment that has undergone somatic mutation can contain framework residues that differ from the germline sequence from which the antibody is derived. Such residues can be identified by comparing the antibody or fragment framework sequences to the germline sequences from which the antibody or fragment is derived. Another approach is to revert to the original parental (e.g., rodent) residue at one or more positions of the engineered (e.g. humanized) antibody, e.g. to restore binding affinity that may have been lost in the process of replacing the framework residues. (See, e.g., U.S. Pat. No. 5,693,762, U.S. Pat. No. 5,585,089 and U.S. Pat. No. 5,530,101.)

In certain embodiments, the anti-CTLA-4 antibodies and antigen-binding fragments thereof are engineered (e.g. humanized) to include modifications to in the framework and/or CDRs to improve their properties. Such engineered changes can be based on molecular modelling. A molecular model for the variable region for the parental (non-human) antibody sequence can be constructed to understand the structural features of the antibody and used to identify potential regions on the antibody that can interact with the antigen. Conventional CDRs are based on alignment of immunoglobulin sequences and identifying variable regions. Kabat et al., (1991) *Sequences of Proteins of Immunological Interest*, Kabat, et al.; National Institutes of Health, Bethesda, Md.; 5$^{th}$ ed.; NIH Publ. No. 91-3242; Kabat (1978) *Adv. Prot. Chem.* 32:1-75; Kabat, et al., (1977) *J. Biol. Chem.* 252:6609-6616. Chothia and coworkers carefully examined conformations of the loops in crystal structures of antibodies and proposed hypervariable loops. Chothia, et al., (1987) *J Mol. Biol.* 196:901-917 or Chothia, et al., (1989) *Nature* 342:878-883. There are variations between regions classified as "CDRs" and "hypervariable loops". Later studies (Raghunathan et al, (2012) *J. Mol Recog.* 25, 3, 103-113) analyzed several antibody-antigen crystal complexes and observed that the antigen binding regions in antibodies do not necessarily conform strictly to the "CDR" residues or "hypervariable" loops. The molecular model for the variable region of the non-human antibody can be used to guide the selection of regions that can potentially bind to the antigen. In practice the potential antigen binding regions based on model differ from the conventional "CDR"s or "hyper variable" loops. Commercial scientific software such as Discovery Studio (BIOVIA, Dassault Systemes) can be used for molecular modeling. Human frameworks can be selected based on best matches with the non-human sequence both in the frameworks and in the CDRs. For FR4 (framework 4) in VH, VJ regions for the human germlines are compared with the corresponding non-human region. In the case of FR4 (framework 4) in VL, J-kappa and J-Lambda regions of human germline sequences are compared with the corresponding non-human region. Once suitable human frameworks are identified, the CDRs are grafted into the selected human frameworks. In some cases certain residues in the VL-VH interface can be retained as in the non-human (parental) sequence. Molecular models can also be used for identifying residues that can potentially alter the CDR conformations and hence binding to antigen. In some cases, these residues are retained as in the non-human (parental) sequence. Molecular models can also be used to identify solvent exposed amino acids that can result in unwanted effects such as glycosylation, deamidation and oxidation. Developability filters can be introduced early on in the design stage to eliminate/minimize these potential problems.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Pat. No. 7,125,689.

In particular embodiments, it will be desirable to change certain amino acids containing exposed side-chains to another amino acid residue in order to provide for greater chemical stability of the final antibody, so as to avoid deamidation or isomerization. The deamidation of asparagine may occur on NG, DG, NG, NS, NA, NT, QG or QS sequences and result in the creation of an isoaspartic acid residue that introduces a kink into the polypeptide chain and decreases its stability (isoaspartic acid effect). Isomerization can occur at DG, DS, DA or DT sequences. In certain embodiments, the antibodies of the present disclosure do not contain deamidation or asparagine isomerism sites.

For example, an asparagine (Asn) residue may be changed to Gln or Ala to reduce the potential for formation of isoaspartate at any Asn-Gly sequences, particularly within a CDR. A similar problem may occur at a Asp-Gly sequence. Reissner and Aswad (2003) *Cell. Mol. Life Sci.* 60:1281. Isoaspartate formation may debilitate or completely abrogate binding of an antibody to its target antigen. See, Presta (2005) *J. Allergy Clin. Immunol.* 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine and glutamine. See, Bischoff & Kolbe (1994) *J. Chromatog.* 662:261. In addition, any methionine residues (typically solvent exposed Met) in CDRs may be changed to Lys, Leu, Ala, or Phe or other amino acids in order to reduce the possibility that the methionine sulfur would oxidize, which could reduce antigen-binding affinity and also contribute to molecular heterogeneity in the final antibody preparation. Id. Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for CTLA-4, or other desired biological activity to unacceptable levels.

TABLE 3

Exemplary stabilizing CDR variants

| CDR Residue | Stabilizing Variant Sequence |
| --- | --- |
| Asn-Gly | Gln-Gly, Ala-Gly, or Asn-Ala |
| (N-G) | (Q-G), (A-G), or (N-A) |
| Asp-Gly | Glu-Gly, Ala-Gly or Asp-Ala |
| (D-G) | (E-G), (A-G), or (D-A) |
| Met (typically solvent exposed) (M) | Lys, Leu, Ala, or Phe (K), (L), (A), or (F) |
| Asn | Gln or Ala |
| (N) | (Q) or (A) |
| Asn-Pro | Gln-Pro, Ala-Pro, or Asn-Ala |
| (N-P) | (Q-P), (A-P), or (N-A) |

Antibody Engineering of the Fc Region

The antibodies (e.g., humanized antibodies) and antigen-binding fragments thereof disclosed herein (e.g., antibody 27A and humanized versions thereof) can also be engineered to include modifications within the Fc region, typically to alter one or more properties of the antibody, such as serum half-life, complement fixation, Fc receptor binding, and/or effector function (e.g., antigen-dependent cellular cytotoxicity). Furthermore, the antibodies and antigen-binding fragments thereof disclosed herein (e.g., antibody 27A and humanized versions thereof) can be chemically modified (e.g., one or more chemical moieties can be attached to the antibody) or be modified to alter its glycosylation, again to alter one or more properties of the antibody or fragment. Each of these embodiments is described in further detail below. The numbering of residues in the Fc region is that of the EU index of Kabat.

The antibodies and antigen-binding fragments thereof disclosed herein (e.g., antibody 27A and humanized versions thereof) also include antibodies and fragments with modified (or blocked) Fc regions to provide altered effector functions. See, e.g., U.S. Pat. No. 5,624,821; WO2003/086310; WO2005/120571; WO2006/0057702. Such modifications can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc regions. Changes to the Fc can also alter the half-life of antibodies in therapeutic antibodies, enabling less frequent dosing and thus increased convenience and decreased use of material. See Presta (2005) *J. Allergy Clin. Immunol.* 116:731 at 734-35.

In one embodiment, the antibody or antigen-binding fragment of the invention (e.g., antibody 27A and humanized versions thereof) is an IgG4 isotype antibody or fragment comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal S. et al., 1993, *Mol Immunol*. 30: 105-108; position 241 is based on the Kabat numbering system).

In one embodiment of the invention, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the Fc hinge region of an antibody or antigen-binding fragment of the invention (e.g., antibody 27A and humanized versions thereof) is mutated to decrease the biological half-life of the antibody or fragment. More specifically, one or more amino acid mutations are introduced into the CH2-CH3 domain interface region of the Fc-hinge fragment such that the antibody or fragment has impaired Staphylococcyl protein A (SpA) binding relative to native Fc-hinge domain SpA binding. This approach is described in further detail in U.S. Pat. No. 6,165,745.

In another embodiment, the antibody or antigen-binding fragment of the invention (e.g., antibody 27A and humanized versions thereof) is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody or antigen-binding fragment. For example, one or more amino acids selected from amino acid residues 234, 235, 236, 237, 297, 318, 320 and 322 can be replaced with a different amino acid residue such that the antibody has an altered affinity for an effector ligand and retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to decrease the ability of the antibody or antigen-binding fragment of the invention (e.g., antibody 27A and humanized versions thereof) to mediate antibody dependent cellular cytotoxicity (ADCC) and/or to decrease the affinity of the antibody or fragment for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) *J. Biol. Chem.* 276:6591-6604).

In one embodiment of the invention, the Fc region is modified to decrease the ability of the antibody of the invention (e.g., antibody 27A and humanized versions thereof) to mediate effector function and/or to increase anti-inflammatory properties by modifying residues 243 and 264. In one embodiment, the Fc region of the antibody or fragment is modified by changing the residues at positions 243 and 264 to alanine. In one embodiment, the Fc region is modified to decrease the ability of the antibody or fragment to mediate effector function and/or to increase anti-inflammatory properties by modifying residues 243, 264, 267 and 328.

Effector Function Enhancement

In some embodiments, the Fc region of an anti-CTLA-4 antibody is modified to increase the ability of the antibody or antigen-binding fragment to mediate effector function and/or to increase their binding to the Fcgamma receptors (FcγRs).

The term "Effector Function" as used herein is meant to refer to one or more of Antibody Dependent Cell-mediated Cytotoxic activity (ADCC), Complement-dependent cytotoxic activity (CDC) mediated responses, Fc-mediated phagocytosis or antibody dependent cellular phagocytosis (ADCP) and antibody recycling via the FcRn receptor.

The interaction between the constant region of an antigen binding protein and various Fc receptors (FcR) including FcgammaRI (CD64), FcgammaRII (CD32) and FcgammaRIII (CD16) is believed to mediate the effector functions, such as ADCC and CDC, of the antigen binding protein. The Fc receptor is also important for antibody cross-linking, which can be important for anti-tumor immunity.

Effector function can be measured in a number of ways including for example via binding of the FcgammaRIII to Natural Killer cells or via FcgammaRI to monocytes/macrophages to measure for ADCC effector function. For example an antigen binding protein of the present invention can be assessed for ADCC effector function in a Natural Killer cell assay. Examples of such assays can be found in Shields et al, 2001 *J. Biol. Chem., Vol.* 276, p 6591-6604; Chappel et al, 1993 *J. Biol. Chem., Vol* 268, p 25124-25131; Lazar et al, 2006 *PNAS,* 103; 4005-4010.

The ADCC or CDC properties of antibodies of the present invention, or their cross-linking properties, may be enhanced in a number of ways.

Human IgG1 constant regions containing specific mutations or altered glycosylation on residue Asn297 have been shown to enhance binding to Fc receptors. In some cases these mutations have also been shown to enhance ADCC and CDC (Lazar et al. *PNAS* 2006, 103; 4005-4010; Shields et al. *J Biol Chem* 2001, 276; 6591-6604; Nechansky et al. *Mol Immunol,* 2007, 44; 1815-1817).

In one embodiment of the present invention, such mutations are in one or more of positions selected from 239, 332 and 330 (IgG1), or the equivalent positions in other IgG isotypes. Examples of suitable mutations are S239D and I332E and A330L. In one embodiment, the antigen binding protein of the invention herein described is mutated at positions 239 and 332, for example S239D and I332E or in a further embodiment it is mutated at three or more positions selected from 239 and 332 and 330, for example S239D and I332E and A330L (EU index numbering).

In an alternative embodiment of the present invention, there is provided an antibody comprising a heavy chain constant region with an altered glycosylation profile such that the antigen binding protein has enhanced effector function. For example, wherein the antibody has enhanced ADCC or enhanced CDC or wherein it has both enhanced ADCC and CDC effector function. Examples of suitable methodologies to produce antigen binding proteins with an altered glycosylation profile are described in WO2003011878, WO2006014679 and EP1229125.

In a further aspect, the present invention provides "non-fucosylated" or "afucosylated" antibodies. Non-fucosylated antibodies harbour a tri-mannosyl core structure of complex-type N-glycans of Fc without fucose residue. These glycoengineered antibodies that lack core fucose residue from the Fc N-glycans may exhibit stronger ADCC than fucosylated equivalents due to enhancement of FcgammaRIIIa binding capacity.

The present invention also provides a method for the production of an antibody according to the invention comprising the steps of: a) culturing a recombinant host cell comprising an expression vector comprising the isolated nucleic acid as described herein, wherein the recombinant host cell does not comprise an alpha-1,6-fucosyltransferase; and b) recovering the antigen binding protein. The recombinant host cell may be not normally contain a gene encoding an alpha-1,6-fucosyltransferase (for example yeast host cells such as *Pichia* sp.) or may have been genetically modified to inactive an alpha-1,6-fucosyltransferase. Recombinant host cells which have been genetically modified to inactivate the FUT8 gene encoding an alpha-1,6-fucosyltransferase are available. See, e.g., the POTELLIGENT™ technology system available from BioWa, Inc. (Princeton, N.J.) in which CHOK1SV cells lacking a functional copy of the FUT8 gene produce monoclonal antibodies having enhanced antibody dependent cell mediated cytotoxicity (ADCC) activity that is increased relative to an identical monoclonal antibody produced in a cell with a functional FUT8 gene. Aspects of the POTELLIGENT™ technology system are described in U.S. Pat. No. 7,214,775, U.S. Pat. No. 6,946,292, WO0061739 and WO0231240. Those of ordinary skill in the art will also recognize other appropriate systems.

It will be apparent to those skilled in the art that such modifications may not only be used alone but may be used in combination with each other in order to further enhance effector function.

Production of Antibodies with Modified Glycosylation

In still another embodiment, the antibodies or antigen-binding fragments of the invention (e.g., antibody 27A and humanized versions thereof) comprise a particular glycosylation pattern. For example, an afucosylated or an aglycosylated antibody or fragment can be made (i.e., the antibody lacks fucose or glycosylation, respectively). The glycosylation pattern of an antibody or fragment may be altered to, for example, increase the affinity or avidity of the antibody or fragment for a CTLA-4 antigen. Such modifications can be accomplished by, for example, altering one or more of the glycosylation sites within the antibody or fragment sequence. For example, one or more amino acid substitutions can be made that result removal of one or more of the variable region framework glycosylation sites to thereby eliminate glycosylation at that site. Such aglycosylation may increase the affinity or avidity of the antibody or fragment for antigen. See, e.g., U.S. Pat. Nos. 5,714,350 and 6,350,861.

Antibodies and antigen-binding fragments disclosed herein (e.g., antibody 27A and humanized versions thereof) may further include those produced in lower eukaryote host cells, in particular fungal host cells such as yeast and filamentous fungi have been genetically engineered to produce glycoproteins that have mammalian- or human-like glycosylation patterns (See for example, Choi et al, (2003) *Proc. Natl. Acad. Sci.* 100: 5022-5027; Hamilton et al., (2003) *Science* 301: 1244-1246; Hamilton et al., (2006) *Science* 313: 1441-1443; Nett et al., *Yeast* 28(3):237-52 (2011); Hamilton et al., *Curr Opin Biotechnol.* October; 18(5):387-92 (2007)). A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. No. 7,029,872 and U.S. Pat. No. 7,449,308). These genetically modified host cells have been used to produce antibodies that have predominantly particular N-glycan structures (See for example, Li et al., (2006) *Nat. Biotechnol.* 24: 210-215).

In particular embodiments, the antibodies and antigen-binding fragments thereof disclosed herein (e.g., antibody 27A and humanized versions thereof) further include those produced in lower eukaryotic host cells and which comprise fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the antibodies and antigen-binding fragments thereof provided herein (e.g., antibody 27A and humanized versions thereof) may comprise antibodies or fragments having at least one hybrid N-glycan selected from the group consisting of $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition.

In particular embodiments, the antibodies and antigen-binding fragments thereof provided herein (e.g., antibody 27A and humanized versions thereof) comprise antibodies and fragments having at least one complex N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan are the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In one embodiment, the antibody and antigen binding fragments thereof provided herein comprise complex N-glycans, wherein at least 50%, 60%, 70%, 80%, 90%, 95%, 97%, 98%, 99%, or 100% of the complex N-glycans in comprise the structure $NANA_2Gal_2GlcNAc_2Man_3GlcNAc_2$, wherein such structure is afucosylated. Such structures can be produced, e.g., in engineered *Pichia pastoris* host cells.

In particular embodiments, the N-glycan is fucosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of $Man_5GlcNAc_2(Fuc)$, $GlcNAcMan_5GlcNAc_2(Fuc)$, $Man_3GlcNAc_2(Fuc)$, $GlcNAcMan_3GlcNAc_2(Fuc)$, $GlcNAc_2Man_3GlcNAc_2(Fuc)$, $GalGlcNAc_2Man_3GlcNAc_2(Fuc)$, $Gal_2GlcNAc_2Man_3GlcNAc_2(Fuc)$, $NANAGal_2GlcNAc_2Man_3GlcNAc_2(Fuc)$, and $NANA_2Gal_2GlcNAc_2Man_3GlcNAc_2(Fuc)$; in an α1,3-linkage or α1,4-linkage fucose to produce a glycoform selected from the group consisting of $GlcNAc(Fuc)Man_5GlcNAc_2$, $GlcNAc(Fuc)Man_3GlcNAc_2$, $GlcNAc_2(Fuc_{1-2})Man_3GlcNAc_2$, $GalGlcNAc_2(Fuc_{1-2})Man_3GlcNAc_2$, $Gal_2GlcNAc_2(Fuc1-2)Man_3GlcNAc_2$, $NANAGal_2GlcNAc_2(Fuc_{1-2})Man_3GlcNAc_2$, and $NANA_2Gal_2GlcNAc_2(Fuc_{1-2})Man_3GlcNAc_2$; or in an α1,2-linkage fucose to produce a glycoform selected from the group consisting of $Gal(Fuc)GlcNAc_2Man_3GlcNAc_2$, $Gal_2(Fuc_{1-2})GlcNAc_2Man_3GlcNAc_2$, $NANAGal_2(Fuc_{1-2})GlcNAc_2Man_3GlcNAc_2$, and $NANA_2Gal_2(Fuc_{1-2})GlcNAc_2Man_3GlcNAc_2$.

In further aspects, the antibodies (e.g., humanized antibodies) or antigen-binding fragments thereof comprise high mannose N-glycans, including but not limited to, $Man_8GlcNAc_2$, $Man_7GlcNAc_2$, $Man_6GlcNAc_2$, $Man_5GlcNAc_2$, $Man_4GlcNAc_2$, or N-glycans that consist of the $Man_3GlcNAc_2$ N-glycan structure.

In further aspects of the above, the complex N-glycans further include fucosylated and non-fucosylated bisected and multiantennary species.

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetylneuraminic acid (NANA)). The processing of the sugar groups occurs co-translationally in the lumen of the ER and continues post-translationally in the Golgi apparatus for N-linked glycoproteins.

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the $Man_3GlcNAc_2$ ("Man3") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as $Man_3GlcNAc_2$; the term "G-1" refers to an N-glycan structure that can be characterized as $GlcNAcMan_3GlcNAc_2$; the term "G0" refers to an N-glycan structure that can be characterized as $GlcNAc_2Man_3GlcNAc_2$; the term "G1" refers to an N-glycan structure that can be characterized as $GalGlcNAc_2Man_3GlcNAc_2$; the term "G2" refers to an N-glycan structure that can be characterized as $Gal_2GlcNAc_2Man_3GlcNAc_2$; the term "A1" refers to an N-glycan structure that can be characterized as $NANAGal_2GlcNAc_2Man_3GlcNAc_2$; and, the term "A2" refers to an N-glycan structure that can be characterized as $NANA_2Gal_2GlcNAc_2Man_3GlcNAc_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas $GlcNAc_{(2-4)}Man_3GlcNAc_2$, $Gal_{(1-4)}GlcNAc_{(2-4)}Man_3GlcNAc_2$, or $NANA_{(1-4)}Gal_{(1-4)}GlcNAc_{(2-4)}Man_3GlcNAc_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula $GlcNAc_3Man_3GlcNAc_2$ wherein each mannose residue is linked at its non-reducing end to a GlcNAc residue. In contrast, when a multiantennary N-glycan is characterized as $GlcNAc_3Man_3GlcNAc_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Antibody Physical Properties

The antibodies and antigen-binding fragments thereof disclosed herein (e.g., antibody 27A and humanized versions thereof) may further contain one or more glycosylation sites in either the light or heavy chain immunoglobulin variable region. Such glycosylation sites may result in increased immunogenicity of the antibody or fragment or an alteration of the pK of the antibody due to altered antigen-binding (Marshall et al. (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence.

Each antibody or antigen-binding fragment (e.g., 27A or humanized versions thereof) will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8.

Each antibody or antigen-binding fragment (e.g., 27A or humanized versions thereof) will have a characteristic melting temperature, with a higher melting temperature indicating greater overall stability in vivo (Krishnamurthy R and Manning M C (2002) *Curr Pharm Biotechnol* 3:361-71). In general, the $T_{M1}$ (the temperature of initial unfolding) may be greater than 60° C., greater than 65° C., or greater than 70° C. The melting point of an antibody or fragment can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9).

In a further embodiment, antibodies and antigen-binding fragments thereof (e.g., antibody 27A and humanized versions thereof) are selected that do not degrade rapidly. Degradation of an antibody or fragment can be measured using capillary electrophoresis (CE) and MALDI-MS (Alexander A J and Hughes D E (1995) *Anal Chem* 67:3626-32).

In a further embodiment, antibodies (e.g., antibody 27A and humanized versions thereof) and antigen-binding fragments thereof are selected that have minimal aggregation effects, which can lead to the triggering of an unwanted immune response and/or altered or unfavorable pharmacokinetic properties. Generally, antibodies and fragments are acceptable with aggregation of 25% or less, 20% or less, 15% or less, 10% or less, or 5% or less. Aggregation can be measured by several techniques, including size-exclusion column (SEC), high performance liquid chromatography (HPLC), and light scattering.

Antibody Conjugates

The anti-CTLA-4 antibodies and antigen-binding fragments thereof disclosed herein (e.g., antibody 27A and humanized versions thereof) may also be conjugated to a chemical moiety. The chemical moiety may be, inter alia, a polymer, a radionuclide or a cytotoxic factor. In particular embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The antibodies and antigen-binding fragments thereof disclosed herein (e.g., antibody 27A and humanized versions thereof) may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe.

The antibodies and antigen-binding fragments disclosed herein (e.g., antibody 27A and humanized versions thereof) may also be PEGylated, for example to increase its biological (e.g., serum) half-life. To PEGylate an antibody or fragment, the antibody or fragment, typically is reacted with a reactive form of polyethylene glycol (PEG), such as a reactive ester or aldehyde derivative of PEG, under conditions in which one or more PEG groups become attached to the antibody or antibody fragment. In particular embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody or fragment to be PEGylated is an aglycosylated antibody or fragment. Methods for PEGylating proteins are known in the art and can be applied to the antibodies of the invention. See, e.g., EP 0 154 316 and EP 0 401 384.

The antibodies and antigen-binding fragments disclosed herein (e.g., antibody 27A and humanized versions thereof) may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibodies and antigen-binding fragments thereof of the invention (e.g., antibody 27A and humanized versions thereof) may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *momordica charantia* inhibitor, curcin, crotin, *saponaria officinalis* inhibitor, mitogellin, restrictocin, phenomycin, and enomycin.

Any method known in the art for conjugating the antibodies and antigen-binding fragments thereof of the invention (e.g., antibody 27A and humanized versions thereof) to the various moieties may be employed, including those methods described by Hunter, et al., (1962) *Nature* 144:945; David, et al., (1974) *Biochemistry* 13:1014; Pain, et al., (1981) *J. Immunol. Meth.* 40:219; and Nygren, J., (1982)

*Histochem. and Cytochem.* 30:407. Methods for conjugating antibodies and fragments are conventional and very well known in the art.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGel® resins (Rapp Polymere GmbH), AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dinitrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

Therapeutic Uses of Anti-CTLA-4 Antibodies

Further provided are methods for treating subjects, including human subjects, in need of treatment with the isolated antibodies or antigen-binding fragments thereof disclosed herein (e.g., antibody 27A and humanized versions thereof). In one embodiment of the invention, such subject suffers from an infection or an infectious disease. In another embodiment of the invention, such subject suffers from cancer. In one embodiment the cancer is, e.g., osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer (e.g., non-small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment of the invention, the cancer is metastatic cancer, e.g., of the varieties described above.

In an embodiment, the invention provides methods for treating subjects using an anti-CTLA-4 antibody or antigen-binding fragment thereof of the invention (e.g., antibody 27A and humanized versions thereof), wherein the subject suffers from a viral infection. In one embodiment, the viral infection is infection with a virus selected from the group consisting of human immunodeficiency virus (HIV), hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus.

In an embodiment, the invention provides methods for treating subjects using an anti-CTLA-4 antibody or antigen-binding fragment thereof of the invention, wherein the subject suffers from a bacterial infection. In one embodiment, the bacterial infection is infection with a bacteria selected from the group consisting of *Chlamydia trachomatis*, rickettsial bacteria such as *Ehrlichia, Orientia* and *Ricekettsia*, mycobacteria, such as *Mycobacterium leprae*, or *Mycobacterium lepromatosis*, staphylococci, such as *Staphylococcus aureus*, streptococci, pneumonococci, meningococci and gonococci, *Klebsiella, Proteus, Serratia, Pseudomonas, Legionella, Corynebacterium diphtheriae, Salmonella*, bacilli, *Vibrio cholerae, Clostridium tetan, Clostridium botulinum, Bacillus anthracis, Yersinia pestis, Haemophilus influenza, Actinomyces, Leptospira, Treponema, Shigella, Chlamydophila psittaci* and *Borriella*.

In an embodiment, the invention provides methods for treating subjects using an anti-CTLA-4 antibody or antigen-binding fragment thereof of the invention, wherein the subject suffers from a fungal infection. In one embodiment, the fungal infection is infection with a fungus selected from the group consisting of *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizopus*), *Sporothrix schenkii, Blastomyces dermatitidis, Paracoccidioides brasiliensis, Coccidioides immitis* and *Histoplasma capsulatum*.

In an embodiment, the invention provides methods for treating subjects using an anti-CTLA-4 antibody or antigen-binding fragment thereof of the invention, wherein the subject suffers from a parasitic infection. In one embodiment, the parasitic infection is infection with a parasite selected from the group consisting of *Entamoeba histolytica, Balantidium coli, Naegleria fowleri, Acanthamoeba, Giar-* dia lambia, *Cryptosporidium, Pneumocystis carinii, Plasmodium vivax, Babesia microti, Trypanosoma brucei, Trypanosoma cruzi, Leishmania donovani, Toxoplasma gondii* and *Nippostrongylus brasiliensis*.

A "subject" may be a mammal such as a human, dog, cat, horse, cow, mouse, rat, monkey (*Macaca fascicularis* (cynomolgus monkey)) or rabbit. In preferred embodiments of the invention, the subject is a human subject.

In certain embodiments, the methods and compositions described herein are administered in combination with one or more of other antibody molecules, STING agonists, chemotherapy, other anti-cancer therapy (e.g., targeted anti-cancer therapies, gene therapy, viral therapy, RNA therapy bone marrow transplantation, nanotherapy, or oncolytic drugs), cytotoxic agents, immune-based therapies (e.g., cytokines or cell-based immune therapies), surgical procedures (e.g., lumpectomy or mastectomy) or radiation procedures, or a combination of any of the foregoing. The additional therapy may be in the form of adjuvant or neoadjuvant therapy. In some embodiments, the additional therapy is an enzymatic inhibitor (e.g., a small molecule enzymatic inhibitor) or a metastatic inhibitor. Exemplary cytotoxic agents that can be administered in combination with include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation (e.g., gamma irradiation). In other embodiments, the additional therapy is surgery or radiation, or a combination thereof. In other embodiments, the additional therapy is a therapy targeting one or more of PI3K/AKT/mTOR pathway, an HSP90 inhibitor, or a tubulin inhibitor. Alternatively, or in combination with the aforesaid combinations, the methods and compositions described herein can be administered in combination with one or more of: an immunomodulator (e.g., an activator of a costimulatory molecule or an inhibitor of an inhibitory molecule, e.g., an immune checkpoint molecule); a vaccine, e.g., a therapeutic cancer vaccine; or other forms of cellular immunotherapy.

In particular embodiments, the antibodies or antigen-binding fragments thereof disclosed herein (e.g., antibody 27A or humanized versions thereof) may be used alone, or in association with other, further therapeutic agents and/or therapeutic procedures, for treating or preventing any disease such as cancer, e.g., as discussed herein, in a subject in need of such treatment or prevention. Compositions, e.g., pharmaceutical compositions comprising a pharmaceutically acceptable carrier, comprising such antibodies and fragments in association with further therapeutic agents are also part of the present invention.

In particular embodiments, the antibodies or antigen-binding fragments thereof disclosed herein (e.g., antibody 27A and humanized versions thereof) may be used alone, or in association with tumor vaccines.

In particular embodiments, the antibodies or antigen-binding fragments thereof disclosed herein (e.g., antibody 27A and humanized versions thereof) may be used alone, or in association with chemotherapeutic agents.

In particular embodiments, the antibodies or antigen-binding fragments thereof disclosed herein (e.g., antibody 27A and humanized versions thereof) may be used alone, or in association with radiation therapy.

In particular embodiments, the antibodies or antigen-binding fragments thereof disclosed herein (e.g., antibody 27A and humanized versions thereof) may be used alone, or in association with targeted therapies. Examples of targeted therapies include: hormone therapies, signal transduction inhibitors (e.g., EGFR inhibitors, such as cetuximab (Erbitux® (ImClone LLC)) and erlotinib (Tarceva® (OSI Pharmaceuticals))); HER2 inhibitors (e.g., trastuzumab (Herceptin® (Genentech Inc.)) and pertuzumab (Perjeta® (Genentech Inc.))); BCR-ABL inhibitors (such as imatinib (Gleevec® (Novartis AG)) and dasatinib (Sprycel® (Bristol-Myers Squibb Company))); ALK inhibitors (such as crizotinib (Xalkori® (Pfizer Inc.)) and ceritinib (Zykadia® (Novartis AG))); BRAF inhibitors (such as vemurafenib (Zelboraf® (Genentech Inc.)) and dabrafenib (Tafinlar® (Novartis Pharma AG))), gene expression modulators, apoptosis inducers (e.g., bortezomib (Velcade® (Millennium Pharmaceuticals Inc.)) and carfilzomib (Kyprolis® (Onyx Phramaceuticals, Inc.))), angiogenesis inhibitors (e.g., bevacizumab (Avastin® (Genentech, Inc.)) and ramucirumab (Cyramza® (InClone LLC)), monoclonal antibodies attached to toxins (e.g., brentuximab vedotin (Adcetris® (Seattle Genetics, Inc.)) and ado-trastuzumab emtansine (Kadcyla® (Genentech, Inc.))).

In particular embodiments, the anti-CTLA-4 antibodies or antigen-binding fragments thereof of the invention (e.g., antibody 27A and humanized versions thereof) may be used in combination with an anti-cancer therapeutic agent or immunomodulatory drug such as an immunomodulatory receptor inhibitor, e.g., an antibody or antigen-binding fragment thereof that specifically binds to the receptor.

Thus, the present invention includes compositions comprising an anti-CTLA-4 antibody or antigen-binding fragment thereof of the present invention (e.g., antibody 27A and humanized versions thereof) in association with one or more of PD-1/PD-L1 blocking antibodies: pembrolizumab, nivolumab, pidilizumab, REGN2810, MEDI-0680, PDR-001, SHR-1210, BGB-A317, PF-06801591, TSR-042, atezoluzimab, durvalumab, BMS-936559; as well as methods for treating or preventing cancer in a subject comprising administering an effective amount of the anti-CTLA-4 antibody or antigen-binding fragment thereof and one or more of pembrolizumab, nivolumab, pidilizumab, REGN2810 to the subject. Optionally, the subject is also administered a further therapeutic agent.

In an embodiment of the invention, an anti-CTLA-4 antibody or antigen-binding fragment thereof of the present invention (e.g., antibody 27A and humanized versions thereof) is in association with an isolated antibody encoding the heavy and light chain of pembrolizumab.

In an embodiment of the invention, an anti-CTLA-4 antibody) or antigen-binding fragment thereof of the present invention (e.g., antibody 27A and humanized versions thereof) is in association with an isolated antibody encoding the heavy and light chain of nivolumab.

In an embodiment of the invention, an anti-CTLA-4 antibody or antigen-binding fragment thereof of the invention (e.g., antibody 27A and humanized versions thereof) is in association with one or more of: anti-PD1 antibody (e.g., pembrolizumab, nivolumab, pidilizumab (CT-011)), anti-PDL1 antibody, anti-TIGIT antibody, anti-CD27 antibody, anti-CS1 antibody (e.g., elotuzumab), anti-KIR2DL1/2/3 antibody (e.g., lirilumab), anti-CD137 antibody (e.g., urelumab), anti-GITR antibody (e.g., TRX518), anti-PD-L1 antibody (e.g., BMS-936559, MSB0010718C or MPDL3280A), anti-PD-L2 antibody, anti-ILT1 antibody, anti-ILT2 antibody, anti-ILT3 antibody, anti-ILT4 antibody, anti-ILT5 antibody, anti-ILT6 antibody, anti-ILT7 antibody, anti-ILT8 antibody, anti-CD40 antibody, anti-OX40 antibody, anti-ICOS, anti-SIRPα, anti-KIR2DL1 antibody, anti- KIR2DL2/3 antibody, anti-KIR2DL4 antibody, anti-KIR2DL5A antibody, anti-KIR2DL5B antibody, anti-KIR3DL1 antibody, anti-KIR3DL2 antibody, anti-KIR3DL3 antibody, anti-NKG2A antibody, anti-NKG2C antibody, anti-NKG2E antibody, anti-4-1BB antibody (e.g., PF-05082566), anti-TSLP antibody, anti-IL-10 antibody, anti-APRIL (e.g. BION1301), anti-CD38 (daratumumab), anti-IL-10 or PEGylated IL-10, or any small organic molecule inhibitor of such targets.

In an embodiment of the invention, an anti-CTLA-4 antibody or antigen-binding fragment thereof of the invention (e.g., antibody 27A or a humanized version thereof) is in association with an anti-PD1 antibody.

In an embodiment of the invention, an anti-CTLA-4 antibody or antigen-binding fragment thereof of the invention (e.g., antibody 27A or a humanized version thereof) is in association with an anti-PDL1 antibody (e.g., BMS-936559, MSB0010718C or MPDL3280A).

In an embodiment of the invention, an anti-CTLA-4 antibody or antigen-binding fragment thereof of the invention (e.g., antibody 27A or a humanized version thereof) is in association with an anti-CD27 antibody.

In an embodiment of the invention, an anti-CTLA-4 antibody or antigen-binding fragment thereof of the invention (e.g., antibody 27A or a humanized version thereof) is in association with an anti-CS1 antibody.

In an embodiment of the invention, an anti-CTLA-4 antibody or antigen-binding fragment thereof of the invention (e.g., antibody 27A or a humanized version thereof) is in association with an anti-KIR2DL1/2/3 antibody.

In an embodiment of the invention, an anti-CTLA-4 antibody or antigen-binding fragment thereof of the invention (e.g., antibody 27A or a humanized version thereof) is in association with an anti-CD137 (e.g., urelumab) antibody.

In an embodiment of the invention, an anti-CTLA-4 antibody or antigen-binding fragment thereof of the invention (e.g., antibody 27A or a humanized version thereof) is in association with an anti-GITR (e.g., TRX518) antibody.

In an embodiment of the invention, an anti-CTLA-4 antibody or antigen-binding fragment thereof of the invention (e.g., antibody 27A or a humanized version thereof) is in association with an anti-PD-L2 antibody.

In an embodiment of the invention, an anti-CTLA-4 antibody or antigen-binding fragment thereof of the invention (e.g., antibody 27A or a humanized version thereof) is in association with an anti-ITL1 antibody.

In an embodiment of the invention, an anti-CTLA-4 antibody or antigen-binding fragment thereof of the invention (e.g., antibody 27A or a humanized version thereof) is in association with an anti-ITL2 antibody.

In an embodiment of the invention, an anti-CTLA-4 antibody or antigen-binding fragment thereof of the invention (e.g., antibody 27A or a humanized version thereof) is in association with an anti-ITL3 antibody.

In an embodiment of the invention, an anti-CTLA-4 antibody or antigen-binding fragment thereof of the invention (e.g., antibody 27A or a humanized version thereof) is in association with an anti-ITL4 antibody.

In an embodiment of the invention, an anti-CTLA-4 antibody or antigen-binding fragment thereof of the invention (e.g., antibody 27A or a humanized version thereof) is in association with an anti-ITL5 antibody.

In an embodiment of the invention, an anti-CTLA-4 antibody or antigen-binding fragment thereof of the invention (e.g., antibody 27A or a humanized version thereof) is in association with an anti-ITL6 antibody.

In an embodiment of the invention, an anti-CTLA-4 antibody or antigen-binding fragment thereof of the invention (e.g., antibody 27A or a humanized version thereof) is in association with an anti-ITL7 antibody.

In an embodiment of the invention, an anti-CTLA-4 antibody or antigen-binding fragment thereof of the invention (e.g., antibody 27A or a humanized version thereof) is in association with an anti-ITL8 antibody.

In an embodiment of the invention, an anti-CTLA-4 antibody or antigen-binding fragment thereof of the invention (e.g., antibody 27A or a humanized version thereof) is in association with an anti-CD40 antibody.

In an embodiment of the invention, an anti-CTLA-4 antibody or antigen-binding fragment thereof of the invention (e.g., antibody 27A or a humanized version thereof) is in association with an anti-OX40 antibody.

In an embodiment of the invention, an anti-CTLA-4 antibody or antigen-binding fragment thereof of the invention (e.g., antibody 27A or a humanized version thereof) is in association with an anti-KIR2DL1 antibody.

In an embodiment of the invention, an anti-CTLA-4 antibody or antigen-binding fragment thereof of the invention (e.g., antibody 27A or a humanized version thereof) is in association with an anti-KIR2DL2/3 antibody.

In an embodiment of the invention, an anti-CTLA-4 antibody or antigen-binding fragment thereof of the invention (e.g., antibody 27A or a humanized version thereof) is in association with an anti-KIR2DL4 antibody.

In an embodiment of the invention, an anti-CTLA-4 antibody or antigen-binding fragment thereof of the invention (e.g., antibody 27A or a humanized version thereof) is in association with an anti-KIR2DL5A antibody.

In an embodiment of the invention, an anti-CTLA-4 antibody or antigen-binding fragment thereof of the invention (e.g., antibody 27A or a humanized version thereof) is in association with an anti-KIR2DL5B antibody.

In an embodiment of the invention, an anti-CTLA-4 antibody or antigen-binding fragment thereof of the invention (e.g., antibody 27A or a humanized version thereof) is in association with an anti-KIR3DL1 antibody.

In an embodiment of the invention, an anti-CTLA-4 antibody or antigen-binding fragment thereof of the invention (e.g., antibody 27A or a humanized version thereof) is in association with an anti-KIR3DL2 antibody.

In an embodiment of the invention, an anti-CTLA-4 antibody or antigen-binding fragment thereof of the invention (e.g., antibody 27A or a humanized version thereof) is in association with an anti-KIR3DL3 antibody.

In an embodiment of the invention, an anti-CTLA-4 antibody or antigen-binding fragment thereof of the invention (e.g., antibody 27A or a humanized version thereof) is in association with an anti-NKG2A antibody.

In an embodiment of the invention, an anti-CTLA-4 antibody or antigen-binding fragment thereof of the invention (e.g., antibody 27A or a humanized version thereof) is in association with an anti-NKG2C antibody.

In an embodiment of the invention, an anti-CTLA-4 antibody or antigen-binding fragment thereof of the invention (e.g., antibody 27A or a humanized version thereof) is in association with an anti-ICOS antibody.

In an embodiment of the invention, an anti-CTLA-4 antibody or antigen-binding fragment thereof of the invention (e.g., antibody 27A or a humanized version thereof) is in association with an anti-SIRPα antibody.

In an embodiment of the invention, an anti-CTLA-4 antibody or antigen-binding fragment thereof of the invention (e.g., antibody 27A or a humanized version thereof) is in association with an anti-4-1BB antibody.

In an embodiment of the invention, an anti-CTLA-4 antibody or antigen-binding fragment thereof of the invention (e.g., antibody 27A or a humanized version thereof) is in association with an anti-IL-10 antibody.

In an embodiment of the invention, an anti-CTLA-4 antibody or antigen-binding fragment thereof of the invention (e.g., antibody 27A or a humanized version thereof) is in association with an anti-TSLP antibody.

In an embodiment of the invention, an anti-CTLA-4 antibody or antigen-binding fragment thereof of the invention (e.g., antibody 27A or a humanized version thereof) is in association with IL-10 or PEGylated IL-10.

In an embodiment of the invention, an anti-CTKLA-4 antibody or antigen-binding fragment thereof of the invention is in association with a Tim-3 pathway antagonist, preferably as part of a pharmaceutical composition.

In an embodiment of the invention, an anti-CTLA-4 antibody or antigen-binding fragment thereof of the invention is in association with a Vista pathway antagonist, preferably as part of a pharmaceutical composition.

In an embodiment of the invention, an anti-CTLA-4 antibody or antigen-binding fragment thereof of the invention is in association with a BTLA pathway antagonist, preferably as part of a pharmaceutical composition.

In an embodiment of the invention, an anti-CTLA-4 antibody or antigen-binding fragment thereof of the invention is in association with a LAG-3 pathway antagonist, preferably as part of a pharmaceutical composition.

In an embodiment of the invention, an anti-CTLA-4 antibody or antigen-binding fragment thereof of the invention is in association with a TIGIT pathway antagonist, preferably as part of a pharmaceutical composition.

In an embodiment of the invention, an anti-CTLA-4 antibody or antigen-binding fragment thereof of the invention is in association with a STING agonist, preferably as part of a pharmaceutical composition. The cyclic-di-nucleotides (CDNs) cyclic-di-AMP (produced by *Listeria monocytogenes* and other bacteria) and its analogs cyclic-di-GMP and cyclic-GMP-AMP are recognized by the host cell as a pathogen associated molecular pattern (PAMP), which bind to the pathogen recognition receptor (PRR) known as Stimulator of INterferon Genes (STING). STING is an adaptor protein in the cytoplasm of host mammalian cells which activates the TANK binding kinase (TBK1)—IRF3 and the NF-kappaB signaling axis, resulting in the induction of IFN-β and other gene products that strongly activate innate immunity. It is now recognized that STING is a component of the host cytosolic surveillance pathway (Vance et al., 2009), that senses infection with intracellular pathogens and in response induces the production of IFN-β, leading to the development of an adaptive protective pathogen-specific immune response consisting of both antigen-specific CD4+ and CD8+ T cells as well as pathogen-specific antibodies. Examples of cyclic purine dinucleotides are described in some detail in, for example: U.S. Pat. Nos. 7,709,458 and 7,592,326; patent applications WO2007/054279, WO2014/093936, and WO2014/189805; and Yan et al., Bioorg. Med. Chem Lett. 18: 5631 (2008).

In some embodiments, the antibodies or antigen binding fragments of the invention increase the activity of an immune cell. The increase of the activity of an immune cell can be detected using any method known in the art. In one embodiment, the increase in activity of an immune cell can be detected by measuring the proliferation of the immune cell. For example, an increase in activity of a T cell can be detected by measuring the proliferation of the T cell or signal transduction events such as tyrosine phosphorylation of immune receptors or downstream kinases that transmit signals to transcriptional regulators. In other embodiments, the increase in activity of an immune cell can be detected by measuring CTL or NK cell cytotoxic function on specific target cells or IFNγ cytokine responses, which are associated with stimulation of anti-tumor immunity. In yet other embodiments, the increase in activity of an immune cell can be detected by measuring T cell activation ex vivo in a sample derived from the subject. In one embodiment, the increase in T cell activity is determined by: (i) measuring SEB (*Staphylococcus* Enterotoxin B) induced production of one or more pro-inflammatory cytokines selected from the group consisting of: IL-2, TNFα, IL-17, IFNγ, IL-1β, GM-CSF, RANTES, IL-6, IL-8, IL-5 and IL-13; or (ii) measuring mixed lymphocyte reactions or direct anti-CD3 mAb stimulation of T cell receptor (TCR) signaling to induce production of a cytokine selected from the group consisting of: IL-2, TNFα, IL-17, IFNγ, IL-1β, GM-CSF, RANTES, IL-6, IL-8, IL-5 and IL-13. In certain embodiments, the anti-CTLA-4 antibody or antigen binding fragment thereof of the present invention will stimulate antigen-specific T-cell production of IL-2 and/or IFNγ and/or upregulation of CD25 and/or CD69 by at least 1.5 fold. In certain embodiments, the anti-CTLA-4 antibody or antigen binding fragment thereof of the present invention will stimulate CD3+ T cells, when these are presented to Raji cells expressing CD80 and CD86, to produce pro-inflammatory cytokines selected from the group consisting of: IL-2, TNFα, IL-17, IFNγ, IL-1β, GM-CSF, RANTES, IL-6, IL-8, IL-5 and IL-13.

Additional agents which are beneficial to raising a cytolytic T cell response may be used in combination with the anti-CTLA-4 antibody or antigen binding fragment thereof of the present invention. These include, without limitation, B7 costimulatory molecule, interleukin-2, interferon-γ, GM-CSF, PD-1 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions.

Compositions for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts.

The composition can comprise a bacterial cell that is transformed to express the polypeptide or to deliver a polynucleoteide which is subsequently expressed in cells of the vaccinated individual. Adjuvants, such as aluminum hydroxide or aluminum phosphate, can be added to increase the ability of the vaccine to trigger, enhance, or prolong an immune response.

The composition can comprise a bacterial cell that is transformed to express the polypeptide or to deliver a polynucleotide which is subsequently expressed in cells of the vaccinated individual. A number of bacterial species have been developed for use as vaccines and can be used as a vaccine platform in present invention, including, but not limited to, *Shigella flexneri, Escherichia coli, Listeria monocytogenes, Yersinia enterocolitica, Salmonella typhimurium, Salmonella typhi* or *mycobacterium* species. This list is not meant to be limiting. The present invention contemplates the use of attenuated, commensal, and/or killed but metabolically active bacterial strains as vaccine platforms. In preferred embodiments the bacterium is *Listeria monocytogenes*.

In an embodiment of the invention, an anti-CTLA-4 antibody or antigen-binding fragment thereof of the invention with an inactivated tumor cell vaccine. By "inactivated tumor cell vaccine" is meant a tumor cell (either "autologous" or "allogeneic" to the patient) which has been treated to prevent division of the cells. For purposes of the present invention, such cells preserve their immunogenicity and their metabolic activity. Such tumor cells are genetically modified to express a transgene which is expressed within a patient as part of cancer therapy. Thus, a composition or vaccine of the invention comprises neoplastic (e.g., tumor) cells that are autologous or allogeneic to the patient undergoing treatment and is most preferably the same general type of tumor cell as is afflicting the patient. For example, a patient suffering from melanoma will typically be administered a genetically modified cell derived from a melanoma. Methods for inactivating tumor cells for use in the present invention, such as the use of irradiation, are well known in the art.

In some embodiments, the inactivated tumor cells of the present invention are modified to express and secrete one or more heat shock proteins. For example, gp96-Ig fusion proteins can be expressed and secreted to stimulate an immune response (Yamazaki et al., The Journal of Immunology, 1999, 163:5178-5182; Strbo et al., Immunol Res. 2013 December; 57(1-3):311-25). In some embodiments the inactivated tumor cells are modified to express and secrete a gp96-Ig fusion protein.

The inactivated tumor cells of the present invention are administered to the patient together with one or more costimulatory molecules or agents. A preferred costimulatory agent comprises one or more cytokines which stimulate dendritic cell induction, recruitment, and/or maturation. Methods for assessing such costimulatory agents are well known in the literature. Induction and maturation of DCs is typically assessed by increased expression of certain membrane molecules such as CD80 and CD86, and/or secretion of pro-inflammatory cytokines, such as IL-12 and type I interferons following stimulation.

In preferred embodiments, the inactivated tumor cells themselves are modified to express and secrete one or more cytokines which stimulate dendritic cell induction, recruitment, and/or maturation. The present invention is described in exemplary terms with regard to the use of GM-CSF. Thus, by way of example, the tumor cell may express a transgene encoding GM-CSF as described in U.S. Pat. Nos. 5,637,483, 5,904,920, 6,277,368 and 6,350,445, as well as in US Patent Publication No. 20100150946. A form of GM-CSF-expressing genetically modified cancer cells or a "cytokine-expressing cellular vaccine" for the treatment of pancreatic cancer is described in U.S. Pat. Nos. 6,033,674 and 5,985,290.

Other suitable cytokines which may be expressed by such inactivated tumor cells and/or bystander cells instead of, or together with, GM-CSF include, but are not limited to, one or more of CD40 ligand, FLT-3 ligand, IL-12, CCL3, CCL20, and CCL21. This list is not meant to be limiting.

In an embodiment of the invention, an anti-CTLA-4 antibody or antigen-binding fragment thereof of the invention is administered in conjunction with one or more vaccines intended to stimulate an immune response to one or more predetermined antigens. The antigen(s) may be administered directly to the individual, or may be expressed within the individual from, for example, a tumor cell vaccine (e.g., GVAX) which may be autologous or allogenic, a dendritic cell vaccine, a DNA vaccine, an RNA vaccine, a viral-based vaccine, a bacterial or yeast vaccine (e.g., a *Listeria monocytogenes* or *Saccharomyces cerevisiae*), etc. See, e.g., Guo et al., Adv. Cancer Res. 2013; 119: 421-475; Obeid et al., Semin Oncol. 2015 August; 42(4): 549-561. Examples of target antigens that may find use in the invention are listed in the following table. The target antigen may also be a fragment or fusion polypeptide comprising an immunologically active portion of the antigens listed in the table. This list is not meant to be limiting.

TABLE 4

List of antigens for use in combination with the anti-CTLA-4 antibody or antigen-binding fragment thereof of the invention as described herein

| Antigen | Reference |
|---|---|
| Tumor antigens | |
| Mesothelin | GenBank ® Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank ® Acc. Nos. NM_000378; NP_000369). WT-1 isoform B (GenBank ® Acc. Nos. NM_024424; NP_077742). WT-1 isoform C (GenBank ® Acc. Nos. NM_024425; NP_077743). WT-1 isoform D (GenBank ® Acc. Nos. NM_024426; NP_077744). |
| Stratum corneum chymotryptic enzyme (SCCE), and variants thereof. | GenBank ® Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein B (MICB). | See, e.g., Groh, et al. (2005) Proc. Natl. Acad. Sci. USA 102: 6461-6466; GenBank ® Acc. Nos. NM_000247; BC_016929; AY750850; NM_005931. |

TABLE 4-continued

List of antigens for use in combination with the anti-CTLA-4 antibody or antigen-binding fragment thereof of the invention as described herein

| Antigen | Reference |
|---|---|
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank ® Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank ® Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank ® Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank ® Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank ® Acc. No. BC096178; BC096176; BC096175. |
| Proteinase 3. | GenBank ® Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | GenBank ® Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |

TABLE 4-continued

List of antigens for use in combination with the anti-CTLA-4 antibody or antigen-binding fragment thereof of the invention as described herein

| Antigen | Reference |
|---|---|
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank ® Acc. Nos. P01112; P01116; M54969; M54968; P01111; P01112; K00654. See also, e.g., GenBank ® Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank ® Acc. No. NM_206956; NM_206955; NM_206954; NM_206953; NM_006115; NM_005367; NM_004988; AY148486; U10340; U10339; M77481. See, e g., Suzuki, et al. (1999) J. Immunol. 163: 2783-2791. |
| Survivin | GenBank ® Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |

TABLE 4-continued

| List of antigens for use in combination with the anti-CTLA-4 antibody or antigen-binding fragment thereof of the invention as described herein | |
|---|---|
| Antigen | Reference |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank ® Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank ® Acc. No. NM_001922. (see also, e.g., Bronte, et al. (2000) Cancer Res. 60: 253-258). |
| Gp100/pmel-17. | GenBank ® Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank ® Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published Pat. Appl. No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See, e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank ® Accession Nos. NP_004422, AAH37166, and AAA53375 (human); GenBank ® Accession Nos. NP_034269 (mouse), AAH06954 (mouse), XP_345597 (rat), and BAB63910 (chicken). |
| EGFRvIII | See, e.g., WO/2012/068360 |
| | *Francisella tularensis* antigens |
| *Francisella tularensis* A and B. | Complete genome of subspecies Schu S4 (GenBank ® Acc. No. AJ749949); of subspecies Schu 4 (GenBank ® Acc. No. NC_006570). Outer membrane protein (43 kDa) Bevanger, et al. (1988) J. Clin. |

TABLE 4-continued

List of antigens for use in combination with the anti-CTLA-4 antibody or antigen-binding fragment thereof of the invention as described herein

| Antigen | Reference |
|---|---|
| | Microbiol. 27: 922-926; Porsch-Ozcurumez, et al. (2004) Clin. Diagnostic. Lab. Immunol. 11: 1008-1015). Antigenic components of *F. tularensis* include, e.g., 80 antigens, including 10 kDa and 60 kDa chaperonins (Havlasova, et al. (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |
| Malarial antigens | |
| Circumsporozoite protein (CSP); SSP2; HEP17; Exp-1 orthologs found in P. falciparum; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank ® Acc. No. AB121024). SSP2 (see, e.g., GenBank ® Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank ® Acc. No. X96399; X96397). MSP1 (see, e.g., GenBank ® Acc. No. X03371). RESA (see, e.g., GenBank ® Acc. No. X05181; X05182). |
| Apical membrane antigen 1 (AMA1). | See, e.g., Gupta, et al. (2005) Protein Expr. Purif. 41: 186-198. AMA1 (see, e.g., GenBank ® Acc. No. A'13; AJ494905; AJ490565). |
| Viruses and viral antigens | |
| Hepatitis A | GenBank ® Acc. Nos., e.g., NC_001489; AY644670; X83302; K02990; M14707. |
| Hepatitis B | Complete genome (see, e.g., GenBank ® Acc. Nos. AB214516; NC_003977; AB205192; AB205191; AB205190; AJ748098; AB198079; AB198078; AB198076; AB074756). |
| Hepatitis C | Complete genome (see, e.g., GenBank ® Acc. Nos. NC_004102; AJ238800; AJ238799; AJ132997; AJ132996; AJ000009; D84263). |
| Hepatitis D | GenBank ® Acc. Nos, e.g. NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank ® Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank ® Acc. Nos. AY563954; AY563953. HTLV type II (see, e.g., GenBank ® Acc. Nos. L03561; Y13051; AF139382). |
| Coronaviridae, including Coronaviruses, such as SARS-coronavirus (SARS-CoV), and Toroviruses. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank ® Acc. Nos. AY348314; NC_004718; AY394850). |
| Rubella virus. | GenBank ® Acc. Nos. NC_001545; AF435866. |
| Mumps virus, including the genotypes A, C, D, G, H, and I. | See, e.g., Orvell, etal. (2002) J. Gen. Virol. 83: 2489-2496. See, e.g., GenBank ® Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank ® Acc. Nos. AY421768; AY790926: X67706. |

TABLE 4-continued

List of antigens for use in combination with the anti-CTLA-4 antibody or
antigen-binding fragment thereof of the invention as described herein

| Antigen | Reference |
| --- | --- |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank ® Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78: 855-867. Human enterovirus A (GenBank ® Acc. Nos. NC_001612); human enterovirus B (NC_001472); human enterovirus C (NC_001428); human enterovirus D (NC_001430). Simian enterovirus A (GenBank Acc. No. NC_003988). |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank ® Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank ® Acc. No. NC_003899; AY722102); Western equine encephalitis (NC_003908). |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank ® Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virol. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank ® Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank ® Acc. No. V01555). |
| Reovirus, including serotypes and strains 1, 2, and 3, type 1 Lang, type 2 Jones, and type 3 Dearing. | See, e.g., Barthold, et al. (1993) Lab. Anim Sci. 43: 425-430; Roner, et al. (1995) Proc. Natl. Acad. Sci. USA 92: 12362-12366; Kedl, et al. (1995) J. Virol. 69: 552-559. GenBank ® Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank ® Acc. No. X17403. |
| Rhinovirus, including all serotypes. | Human rhinovirus 2 (GenBank ® Acc. No. X02316); Human rhinovirus B (GenBank ® Acc. No. NC_001490); Human rhinovirus 89 (GenBank ® Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |

TABLE 4-continued

List of antigens for use in combination with the anti-CTLA-4 antibody or antigen-binding fragment thereof of the invention as described herein

| Antigen | Reference |
| --- | --- |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank ® Acc. No. NC_001608). Ebola virus (see, e.g., GenBank ® Acc. Nos. NC_006432; AY769362; NC_002549; AF272001; AF086833). |
| Arenaviruses, including lymphocytic choriomeningitis (LCM) virus, Lassa virus, Junin virus, and Machupo virus. | Junin virus, segment S (GenBank ® Acc. No. NC_005081); Junin virus, segment L (GenBank ® Acc. No. NC_005080). |
| Rabies virus. | See, e.g., GenBank ® Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank ® Acc. Nos. AB195673; AY762084). Dengue virus type 2 (see, e.g., GenBank ® Acc. No. NC_001474; AY702040; AY702039; AY702037). Dengue virus type 3 (see, e.g., GenBank ® Acc. Nos. AY923865; AT858043). Dengue virus type 4 (see, e.g., GenBank ® Acc. Nos. AY947539; AY947539; AF326573). Sindbis virus (see, e.g., GenBank ® Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank ® Acc. Nos. NC_001611; Y16780; X72086; X69198). |
| Yellow fever. | See, e.g., GenBank ® Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank ® Acc. No. NC_005222 and NC_005219 (Hantavirus). See also, e.g., GenBank ® Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank ® Acc. Nos NC_001474 and AY702040 (Dengue). GenBank ® Acc. Nos. NC_001563 and AY603654. |
| Measles virus. | See, e.g., GenBank ® Acc. Nos. AB040874 and AY486084. |
| Human parainfluenzaviruses (HPV), including HPV types 1-56. | Human parainfluenza virus 2 (see, e.g., GenBank ® Acc. Nos. AB176531; NC003443). Human parainfluenza virus 3 (see, e.g., GenBank ® Acc. No. NC_001796). |
| Influenza virus, including influenza virus types A, B, and C. | Influenza nucleocapsid (see, e.g., GenBank ® Acc. No. AY626145). Influenza hemagglutinin (see, e.g., GenBank ® Acc. Nos. AY627885; AY555153). Influenza neuraminidase (see, e.g., GenBank ® Acc. Nos. AY555151; AY577316). Influenza matrix protein 2 (see, e.g., GenBank ® Acc. Nos. AY626144(. Influenza basic protein 1 (see, e.g., GenBank ® Acc. No. AY627897). Influenza polymerase acid protein (see, e.g., GenBank ® Acc. No. AY627896). Influenza nucleoprotein (see, e.g., GenBank ® Acc. Nno. AY627895). |
| Influenza A viruses of various subtypes that originate from other species:, e.g., swine influenza viruses (SIV) (e.g. H1N1) and avian influenza virus (AIV) (e.g. H5N1; H7N7; H9N2) | Hemagglutinin of H1N1 (GenBank ® Acc. No. S67220). Influenza A virus matrix protein (GenBank ® Acc. No. AY700216). Influenza virus A H5H1 nucleoprotein (GenBank ® Acc. No. AY646426). H1N1 haemagglutinin (GenBank ® Acc. No. D00837). See also, GenBank Acc. Nos. BD006058; BD006055; BD006052. See also, e.g., Wentworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank ® Acc. Nos. AY353550; NC_001803; NC001781). |
| Rotaviruses, including human rotaviruses A to E, bovine rotavirus, rhesus | Human rotavirus C segment 8 (GenBank ® Acc. No. AJ549087); Human rotavirus G9 strain outer capsid protein (see, e.g., GenBank Acc. No. DQ056300); Human rotavirus B strain non-structural |

TABLE 4-continued

List of antigens for use in combination with the anti-CTLA-4 antibody or antigen-binding fragment thereof of the invention as described herein

| Antigen | Reference |
|---|---|
| monkey rotavirus, and human-RVV reassortments. | protein 4 (see, e.g., GenBank ® Acc. No. AY548957); human rotavirus A strain major inner capsid protein (see, e.g., GenBank ® Acc. No. AY601554). |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank ® Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank ® Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank ® Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis, Streptococcus pyogenes* (Group A Strep), *Streptococcus agalactia* (Group B Strep), *Streptococcus pneumonia, Staphylococcus aureus, Escherichia coli, Haemophilus influenzae, Neisseria meningitidis, Neisseria gonorrheae, Vibrio cholerae, Salmonella* species (including *typhi, typhimurium*), *enterica* (including *Helicobactor pylori Shigella flexneri* and other Group D *shigella* species), *Burkholderia mallei, Burkholderia pseudomallei, Klebsiella pneumonia, Clostridium* species (including *C. difficile*), *Vibrio parahaemolyticus* and *V. vulnificus*. This list is not meant to be limiting.

In an embodiment of the invention, an anti-CTLA-4 antibody or antigen-binding fragment thereof of the invention (e.g., antibody 27A or a humanized version thereof) is in association with one or more of an inhibitor (e.g., a small organic molecule or an antibody or antigen-binding fragment thereof) such as: an MTOR (mammalian target of rapamycin) inhibitor, a cytotoxic agent, a platinum agent, an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a RANKL (Receptor activator of nuclear factor kappa-B ligand) inhibitor, an ERK inhibitor, a MAP Kinase inhibitor, an AKT inhibitor, a MEK inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, or a farnesyl protein transferase inhibitor.

In an embodiment of the invention, an anti-CTLA-4 antibody or antigen-binding fragment thereof of the invention (e.g., antibody 27A or a humanized version thereof) is in association with any one or more of: 13-cis-retinoic acid, 3-[5-(methylsulfonylpiperadinemethyl)-indolyl]-quinolone, 4-hydroxytamoxifen, 5-deoxyuridine, 5'-deoxy-5-fluorouridine, 5-fluorouracil, 6-mecaptopurine, 7-hydroxystaurosporine, A-443654, abirateroneacetate, abraxane, ABT-578, acolbifene, ADS-100380, ALT-110, altretamine, amifostine, aminoglutethimide, amrubicin, Amsacrine, anagrelide, anastrozole, angiostatin, AP-23573, ARQ-197, arzoxifene, AS-252424, AS-605240, asparaginase, AT-9263, atrasentan, axitinib, AZD1152, *Bacillus* Calmette-Guerin (BCG) vaccine, batabulin, BC-210, besodotox, bevacizumab, bicalutamide, Bio111, BIO140, bleomycin, BMS-214662, BMS-247550, BMS-275291, BMS-310705, bortezimib, buserelin, busulfan, calcitriol, camptothecin, canertinib, capecitabine, carboplatin, carmustine, CC8490, Cediranib, CG-1521, CG-781, chlamydocin, chlorambucil, chlorotoxin, cilengitide, cimitidine, cisplatin, cladribine, clodronate, COL-3, CP-724714, cyclophosphamide, cyproterone, cyproteroneacetate, cytarabine, cytosinearabinoside, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, docetaxel, dovitinib, doxorubicin, droloxifene, edotecarin, yttrium-90 labeled-edotreotide, edotreotide, EKB-569, EMD 121974, endostatin, enzalutamide, enzastaurin, epirubicin, epithilone B, ERA-923, Erbitux, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, Fulvestrant, galeterone, gefitinib, gemcitabine, gimatecan, goserelin, goserelin acetate, gossypol, GSK461364, GSK690693, HMR-3339, hydroxyprogesteronecaproate, hydroxyurea, IC87114, idarubicin, idoxyfene, ifosfamide, IM862, imatinib, IMC-1C11, INCB24360, INO1001, interferon, interleukin-12, ipilimumab, irinotecan, JNJ-16241199, ketoconazole, KRX-0402, lapatinib, lasofoxifene, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY317615, marimastat, mechlorethamine, medroxyprogesteroneacetate, megestrolacetate, melphalan, mercaptopurine, mesna, methotrexate, mithramycin, mitomycin, mitotane, mitoxantrone, tozasertib, MLN8054, neovastat, Neratinib, neuradiab, nilotinib, nilutimide, nolatrexed, NVP-BEZ235, oblimersen, octreotide, ofatumumab, oregovomab, orteronel, oxaliplatin, paclitaxel, palbociclib, pamidronate, panitumumab, pazopanib, PD0325901, PD184352, PEG-interferon, pemetrexed, pentostatin, perifosine, phenylalaninemustard, PI-103, pictilisib, PIK-75, pipendoxifene, PKI-166, plicamycin, porfimer, prednisone, procarbazine, progestins, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, thioguanine, thiotepa, ticilimumab, tipifarnib, tivozanib, TKI-258, TLK286, topotecan, toremifene citrate, trabectedin, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vinblastine, vincristine, vindesine, vinorelbine, vitaxin, vitespan, vorinostat, VX-745, wortmannin, Xr311, zanolimumab, ZK186619, ZK-304709, ZM336372, ZSTK474.

In an embodiment of the invention, an anti-CTLA-4 antibody or antigen-binding fragment thereof of the invention (e.g., antibody 27A or a humanized version thereof) is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, N.C.), granisetron (sold as Kytril® by Hoffmann-La Roche Inc.; Nutley, N.J.), ondansetron (sold as Zofran® by Glaxosmithkline; Research Triangle Park, N.C.), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment of the invention, an anti-CTLA-4 antibody or antigen-binding fragment thereof of the invention (e.g., antibody 27A or a humanized version thereof) is in association with an agent which treats or prevents such a deficiency, such as, e.g., filgrastim, PEG-filgrastim, erythropoietin, epoetin alfa or darbepoetin alfa.

In an embodiment of the invention, an anti-CTLA-4 antibody or antigen-binding fragment thereof of the invention (e.g., antibody 27A or a humanized version thereof) is administered in association with anti-cancer radiation therapy. For example, in an embodiment of the invention, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In an embodiment of the invention, the radiation therapy is proton beam therapy: a type of conformal therapy that bombards the diseased tissue with protons instead of X-rays. In an embodiment of the invention, the radiation therapy is conformal external beam radiation therapy: a procedure that uses advanced technology to tailor the radiation therapy to an individual's body structures. In an embodiment of the invention, the radiation therapy is brachytherapy: the temporary placement of radioactive materials within the body, usually employed to give an extra dose—or boost—of radiation to an area.

In an embodiment of the invention, a surgical procedure that can be applied in association with an anti-CTLA-4 antibody or antigen-binding fragment thereof of the invention (e.g., antibody 27A or a humanized version thereof) is surgical tumorectomy.

The term "in association with" indicates that the components administered in a method of the present invention (e.g., an anti-CTLA-4 antibody or antigen-binding fragment thereof of the invention (e.g., antibody 27A or a humanized version thereof) along with pembrolizumab) can be formulated into a single composition for simultaneous delivery or formulated separately into two or more compositions (e.g., a kit). Each component can be administered to a subject at a different time than when the other component is administered; for example, each administration may be given non-simultaneously (e.g., separately or sequentially) at several intervals over a given period of time. Moreover, the separate components may be administered to a subject by the same or by a different route.

Experimental and Diagnostic Uses

The anti-CTLA-4 antibody or antigen-binding fragment thereof of the invention (e.g., antibody 27A or a humanized version thereof) may be used as affinity purification agent. In this process, the anti-CTLA-4 antibodies and antigen-binding fragments thereof are immobilized on a solid phase such a Sephadex, glass or agarose resin or filter paper, using methods well known in the art. The immobilized antibody or fragment is contacted with a sample containing the CTLA-4 protein (or a fragment thereof) to be purified, and thereafter the support is washed with a suitable solvent that will remove substantially all the material in the sample except the CTLA-4 protein, which is bound to the immobilized antibody or fragment. Finally, the support is washed with a solvent which elutes the bound CTLA-4 (e.g., protein A). Such immobilized antibodies and fragments form part of the present invention.

Further provided are antigens for generating secondary antibodies which are useful for example for performing Western blots and other immunoassays discussed herein.

Anti-CTLA-4 antibodies (e.g., humanized antibodies) and antigen-binding fragments thereof may also be useful in diagnostic assays for CTLA-4 protein, e.g., detecting its expression in specific cells, tissues, or serum, e.g., tumor cells such as melanoma cells. Such diagnostic methods may be useful in various disease diagnoses.

The present invention includes ELISA assays (enzyme-linked immunosorbent assay) incorporating the use of an anti-CTLA-4 antibody or antigen-binding fragment thereof disclosed herein (e.g., antibody 27A or a humanized version thereof).

For example, such a method comprises the following steps:

(a) coat a substrate (e.g., surface of a microtiter plate well, e.g., a plastic plate) with anti-CTLA-4 antibody or antigen-binding fragment thereof;
(b) apply a sample to be tested for the presence of CTLA-4 to the substrate;
(c) wash the plate, so that unbound material in the sample is removed;
(d) apply detectably labeled antibodies (e.g., enzyme-linked antibodies) which are also specific to the CTLA-4 antigen;
(e) wash the substrate, so that the unbound, labeled antibodies are removed;
(f) if the labeled antibodies are enzyme linked, apply a chemical which is converted by the enzyme into a fluorescent signal; and
(g) detect the presence of the labeled antibody.

Detection of the label associated with the substrate indicates the presence of the CTLA-4 protein.

In a further embodiment, the labeled antibody or antigen-binding fragment thereof is labeled with peroxidase which react with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody or fragment is labeled with a detectable radioisotope (e.g., $^3$H) which can be detected by scintillation counter in the presence of a scintillant.

An anti-CTLA-4 antibody or antigen-binding fragment thereof of the invention (e.g., antibody 27A or a humanized version thereof) may be used in a Western blot or immune-protein blot procedure. Such a procedure forms part of the present invention and includes e.g.:

(1) optionally transferring proteins from a sample to be tested for the presence of CTLA-4 (e.g., from a PAGE or SDS-PAGE electrophoretic separation of the proteins in the sample) onto a membrane or other solid substrate using a method known in the art (e.g., semi-dry blotting or tank blotting); contacting the membrane or other solid substrate to be tested for the presence of bound CTLA-4 or a fragment thereof with an anti-CTLA-4 antibody or antigen-binding fragment thereof of the invention.

Such a membrane may take the form of a nitrocellulose or vinyl-based (e.g., polyvinylidene fluoride (PVDF)) membrane to which the proteins to be tested for the presence of CTLA-4 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-CTLA-4 antibody or fragment, the membrane is optionally blocked, e.g., with non-fat dry milk or the like so as to bind non-specific protein binding sites on the membrane.

(2) washing the membrane one or more times to remove unbound anti-CTLA-4 antibody or fragment and other unbound substances; and
(3) detecting the bound anti-CTLA-4 antibody or fragment.

Detection of the bound antibody or fragment indicates that the CTLA-4 protein is present on the membrane or substrate and in the sample. Detection of the bound antibody or fragment may be by binding the antibody or fragment with a secondary antibody (an anti-immunoglobulin antibody) which is detectably labeled and, then, detecting the presence of the secondary antibody.

The anti-CTLA-4 antibodies and antigen-binding fragments thereof disclosed herein (e.g., antibody 27A and humanized versions thereof) may also be used for immuno-histochemistry. Such a method forms part of the present invention and comprises, e.g., (1) contacting a cell (e.g., a tumor cell such as a melanoma cell) to be tested for the presence of CTLA-4 protein with an anti-CTLA-4 antibody or antigen-binding fragment thereof of the invention; and
(2) detecting the antibody or fragment on or in the cell.

If the antibody or fragment itself is detectably labeled, it can be detected directly. Alternatively, the antibody or fragment may be bound by a detectably labeled secondary antibody which is detected.

Certain anti-CTLA-4 antibodies and antigen-binding fragments thereof disclosed herein (e.g., antibody 27A and humanized versions thereof) may also be used for in vivo tumor imaging. Such a method may include injection of a radiolabeled anti-CTLA-4 antibody or antigen-binding fragment thereof into the body of a patient to be tested for the presence of a tumor associated with CTLA-4 expression (e.g., which expresses CTLA-4, for example, on tumor-infiltrating lymphocytes) followed by nuclear imaging of the body of the patient to detect the presence of the labeled antibody or fragment e.g., at loci comprising a high concentration of the antibody or fragment which are bound to the tumor. The detection of the loci indicates the presence of the CTLA-4$^+$ cells in the tumor.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 (See e.g., Gordon et al., (2005) International Rev. Neurobiol. 67:385-440).

Pharmaceutical Compositions and Administration

To prepare pharmaceutical or sterile compositions of the anti-CTLA-4 antibodies and antigen-binding fragments of the invention (e.g., antibody 27A and humanized versions thereof), the antibody or antigen-binding fragment thereof is admixed with a pharmaceutically acceptable carrier or excipient. See, e.g., *Remington's Pharmaceutical Sciences and U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the antibodies of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an anti-CTLA-4 antibody or antigen-binding fragment thereof of the invention (e.g., antibody 27A or humanized versions thereof) in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the anti-CTLA-4 antibodies or antigen-binding fragments thereof of the invention (e.g., antibody 27A and humanized versions thereof) can be administered by an invasive route such as by injection. In further embodiments of the invention, an anti-CTLA-4 antibody or antigen-binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The present invention provides a vessel (e.g., a plastic or glass vial, e.g., with a cap or a chromatography column, hollow bore needle or a syringe cylinder) comprising any of the antibodies or antigen-binding fragments of the invention (e.g., antibody 27A and humanized versions thereof) or a pharmaceutical composition thereof. The present invention also provides an injection device comprising any of the antibodies or antigen-binding fragments of the invention (e.g., antibody 27A and humanized versions thereof) or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an autoinjector) which, for example, includes a cylinder or barrel for holding fluid to be injected (e.g., antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$ and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the anti-CTLA-4 antibody or antigen-binding fragment of the invention (e.g., antibody 27A and humanized versions thereof) in a local rather than systemic manner, for example, via injection of the antibody or fragment directly into a tumor. Furthermore, one may administer the antibody or fragment in a targeted drug delivery system, for example, in a liposome coated with a tissue-specific antibody, targeting, for example, a tumor e.g., characterized by immunopathology. The liposomes will be targeted to and taken up selectively by the afflicted tissue. Such methods and liposomes are part of the present invention.

The administration regimen depends on several factors, including the serum or tissue turnover rate of the therapeutic antibody or antigen-binding fragment, the level of symptoms, the immunogenicity of the therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies or fragments is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies are may be desirable.

Antibodies or antigen-binding fragments thereof disclosed herein (e.g., antibody 27A and humanized versions thereof) may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:151-144). Doses may also be provided to achieve a pre-determined target concentration of anti-CTLA-4 antibody in the subject's serum, such as 0.1, 0.3, 1, 3, 10, 30, 100, 300 µg/ml or more. In other embodiments, An anti-CTLA-4 antibody of the present invention is administered, e.g., subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, the term "effective amount" refer to an amount of an anti-CTLA-4 or antigen-binding fragment thereof of the invention (e.g., antibody 27A and humanized versions thereof) that, when administered alone or in combination with an additional therapeutic agent to a cell, tissue, or subject, is effective to cause a measurable improvement in one or more symptoms of disease, for example cancer or the progression of cancer. An effective dose further refers to that amount of the antibody or fragment sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

Further provided are kits comprising one or more components that include, but are not limited to, an anti-CTLA-4 antibody or antigen-binding fragment, as discussed herein (e.g., antibody 27A or a humanized version thereof) in association with one or more additional components including, but not limited to a pharmaceutically acceptable carrier and/or a therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an anti-CTLA-4 antibody or antigen-binding fragment thereof of the invention (e.g., antibody 27A or a humanized version thereof) or a pharmaceutical composition thereof in one container (e.g., in a sterile glass or plastic vial) and a pharmaceutical composition thereof and/or a therapeutic agent in another container (e.g., in a sterile glass or plastic vial).

In another embodiment, the kit comprises a combination of the invention, including an anti-CTLA-4 antibody or antigen-binding fragment thereof of the invention (e.g., humanized 27A) along with a pharmaceutically acceptable carrier, optionally in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Detection Kits and Therapeutic Kits

As a matter of convenience, an anti-CTLA-4 antibody or antigen-binding fragment thereof of the invention (e.g., antibody 27A and humanized versions thereof) can be provided in a kit, i.e., a packaged combination of reagents in predetermined amounts with instructions for performing the diagnostic or detection assay. Where the antibody or fragment is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments of the invention, the signal generating means may come pre-associated with an antibody or fragment of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemilluminescent or chromogenic product or the reduction of a chemilluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising an anti-CTLA-4 antibody (e.g., humanized antibody) or antigen-binding fragment thereof packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating cancer and comprises an anti-CTLA-4 antibody (e.g., humanized antibody) or antigen-binding fragment thereof and a further therapeutic agent or a vaccine. The kit may optionally further include a syringe for parenteral, e.g., intravenous, administration. In another aspect, the kit comprises an anti-CTLA-4 antibody (e.g., humanized antibody) or antigen-binding fragment thereof and a label attached to or packaged with the container describing use of the antibody or fragment with the vaccine or further therapeutic agent. In yet another aspect, the kit comprises the vaccine or further therapeutic agent and a label attached to or packaged with the container describing use of the vaccine or further therapeutic agent with the anti-CTLA-4 antibody or fragment. In certain embodiments, an anti-CTLA-4 antibody and vaccine or further therapeutic agent are in separate vials or are combined together in the same pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein may also be prepared that comprise at least one of the antibody, peptide, antigen-binding fragment, or polynucleotide disclosed herein and instructions for using the composition as a detection reagent or therapeutic agent. Containers for use in such kits may typically comprise at least one vial, test tube, flask, bottle, syringe or other suitable container, into which one or more of the detection and/or therapeutic composition(s) may be placed, and preferably suitably aliquoted. Where a second therapeutic agent is also provided, the kit may also contain a second distinct container into which this second detection and/or therapeutic composition may be placed. Alternatively, a plurality of compounds may be prepared in a single pharmaceutical composition, and may be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

PREFERRED EMBODIMENTS

The following are preferred embodiments of the present invention, and are exemplary in nature.

Embodiment 1

An antibody or antigen binding fragment thereof that binds to human CTLA-4, wherein the antibody or antigen binding fragment comprises one or more of the polypeptide sequences defined in a-f, and optionally each of the polypeptide sequences defined in a-c and/or each of the polypeptide sequences defined in d-f:
a. a heavy chain variable region CDR1 comprising the amino acid sequence of SEQ ID NO: 1, or an amino acid sequence differing from SEQ ID NO: 1 by 1, 2, 3, or more conservative substitutions;
b. a heavy chain variable region CDR2 comprising the amino acid sequence of SEQ ID NO: 2, or an amino acid sequence differing from SEQ ID NO: 2 by 1, 2, 3, or more conservative substitutions;
c. a heavy chain variable region CDR3 comprising the amino acid sequence of SEQ ID NO: 3, or an amino acid sequence differing from SEQ ID NO: 3 by 1, 2, 3, or more conservative substitutions;
d. a light chain variable region CDR1 comprising the amino acid sequence of SEQ ID NO: 4, or an amino acid sequence differing from SEQ ID NO: 4 by 1, 2, 3, or more conservative substitutions;
e. a light chain variable region CDR2 comprising the amino acid sequence of SEQ ID NO: 5, or an amino acid sequence differing from SEQ ID NO: 5 by 1, 2, 3, or more conservative substitutions, and
f. a light chain variable region CDR3 comprising the amino acid sequence of SEQ ID NO: 6, or an amino acid sequence differing from SEQ ID NO: 6 by 1, 2, 3, or more conservative substitutions.

Embodiment 2

The antibody or antigen binding fragment of embodiment 1, wherein the antibody or antigen binding fragment comprises one or more of the polypeptide sequences defined in a-f, and optionally each of the polypeptide sequences defined in a-c and/or each of the polypeptide sequences defined in d-f:
a. a heavy chain variable region CDR1 comprising the amino acid sequence of SEQ ID NO: 1;
b. a heavy chain variable region CDR2 comprising the amino acid sequence of SEQ ID NO: 2;
c. a heavy chain variable region CDR3 comprising the amino acid sequence of SEQ ID NO: 3;
d. a light chain variable region CDR1 comprising the amino acid sequence of SEQ ID NO: 4;
e. a light chain variable region CDR2 comprising the amino acid sequence of SEQ ID NO: 5;
f. a light chain variable region CDR3 comprising the amino acid sequence of SEQ ID NO: 6

Embodiment 3

An antibody or antigen binding fragment thereof that binds to human CTLA-4 comprising a light chain immunoglobulin, a heavy chain immunoglobulin or both a light chain and a heavy chain immunoglobulin selected from the group consisting of:
a. an antibody or antigen binding fragment thereof comprising a variable heavy chain comprising the amino acid sequence of SEQ ID NO: 7 and/or a variable light chain comprising the amino acid sequence of SEQ ID NO: 8;
b. an antibody or antigen binding fragment thereof comprising a variable heavy chain comprising the amino acid sequence of SEQ ID NO: 10, 12, 14, 16, 18 or 20 and/or a variable light chain comprising the amino acid sequence of SEQ ID NO: 22, 24, 26 or 30;
c. an antibody or antigen binding fragment thereof comprising a variable heavy chain comprising at least 90%, 95%, 96%, 97%, 98% or 99% identity any one of SEQ ID NO: 10, 12, 14, 16, 18 or 20 and/or a variable light chain comprising at least 90%, 95%, 96%, 97%, 98% or 99% identity to any one of SEQ ID NO: 22, 24, 26 or 30; and
d. an antibody or antigen binding fragment thereof comprising a variable heavy chain comprising at least 90%, 95%, 96%, 97%, 98% or 99% identity any one of SEQ ID NO: 10, 12, 14, 16, 18 or 20 and/or a variable light chain comprising at least 90%, 95%, 95%, 96%, 97%, 98% or 99% identity to any one of SEQ ID NO: 22, 24, 26 or 30, wherein any sequence variations occur in the framework regions of the antibody or antigen binding fragment;
e. an antibody or antigen binding fragment thereof comprising a variable heavy chain comprising 1, 2, 3, 4, 5, 6, 7, 8, 9 or 10 amino acid substitution with respect to any one of SEQ ID NO: 10, 12, 14, 16, 18 or 20 and/or a variable light chain comprising 1, 2, 3, 4, 5, 6, 7, 8, 9 or 10 amino acid substitution with respect to any one of SEQ ID NO: 22, 24, 26 or 30; and
f. an antibody or antigen binding fragment thereof comprising a variable heavy chain comprising 1, 2, 3, 4, 5, 6, 7, 8, 9 or 10 amino acid substitution with respect to any one of SEQ ID NO: 10, 12, 14, 16, 18 or 20 and/or a variable light chain comprising 1, 2, 3, 4, 5, 6, 7, 8, 9 or 10 amino acid substitution with respect to any one of SEQ ID NO: 22, 24, 26 or 30, wherein any said substitutions occur in the framework regions of the antibody or antigen binding fragment.

Embodiment 4

The antibody or antigen binding fragment of embodiment 3, wherein the antibody or fragment thereof has one, two, three, or all four of the following characteristics:
i. binds to human CTLA-4 with a KD value of at least about $1 \times 10^{-9}$ M as determined by surface plasmon resonance (e.g., BIACORE) or a similar technique (e.g. KinExa or OCTET);
ii. blocks the binding of hCTLA-4 to hCD80 with an IC50 of about 100 nM or lower;
iii. blocks the binding of hCTLA-4 to hCD86 with an IC50 of about 100 nM or lower;
iv. binds to a different CTLA-4 epitope than ipilimumab or tremelimumab.

Embodiment 5

An antibody or antigen binding fragment thereof that binds to an epitope of human CTLA-4 wherein said antibody or antigen binding fragment does not bind to the mouse-human chimeric CTLA-4 molecule of SEQ ID NO: 44.

Embodiment 6

An antibody or antigen binding fragment thereof that binds to the same epitope of human CTLA-4 as an antibody comprising the variable heavy chain of SEQ ID NO: 7 and the variable light chain of SEQ ID NO: 8, wherein the antibody or fragment thereof does not bind to the mouse-human chimeric CTLA-4 molecule of SEQ ID NO: 44 and has at least one of the following characteristics:
a. binds to human CTLA-4 with a KD value of at least about $1 \times 10^{-9}$ M as determined by surface plasmon resonance (e.g., BIACORE) or a similar technique (e.g. KinExa or OCTET);
b. blocks the binding of hCTLA-4 to hCD80 with an IC50 of about 100 nM or lower;

c. blocks the binding of hCTLA-4 to hCD86 with an IC50 of about 100 nM or lower;
d. binds to a different CTLA-4 epitope than ipilimumab or tremelimumab.

Embodiment 7

An antibody or antigen binding fragment thereof that binds to human CTLA-4, wherein the antibody or antigen binding fragment binds to an epitope of human CTLA4 comprising at least 8 contiguous residues of SFVCEYAS-PGKAT (SEQ ID NO: 53).

Embodiment 8

An antibody or antigen binding fragment thereof according to embodiment 7, wherein the epitope consists of SFVC-EYASPGKAT (SEQ ID NO: 53).

Embodiment 9

An antibody or antigen binding fragment thereof that binds to human CTLA-4, wherein one or more mutations in human CTLA-4 within the sequence SFVCEYASPGKAT (SEQ ID NO: 53) prevent binding of the antibody to human CTLA4.

Embodiment 10

An antibody or antigen binding fragment thereof that competes with the antibody hCTLA4.27A for binding to human CTLA-4.

Embodiment 11

The antibody or antigen binding fragment of any of the above embodiments, which is a humanized antibody comprising two heavy chains and two light chains.

Embodiment 12

An isolated polypeptide comprising the amino acid sequence of any one of SEQ ID NOs: 1-8, 10, 12, 14, 16, 18, 20, 22, 24, 26 or 30.

Embodiment 13

An isolated nucleic acid encoding: any one of the antibodies or antigen binding fragments of any of embodiments 1-11, or any one of the polypeptides of embodiment 12.

Embodiment 14

An expression vector comprising the isolated nucleic acid of embodiment 13.

Embodiment 15

A host cell comprising the antibody, binding fragment, polypeptide, polynucleotide or expression vector of any of embodiments 1-14.

Embodiment 16

The host cell of embodiment 15, which is a *Pichia* cell or a Chinese hamster ovary cell.

Embodiment 17

A composition comprising the antibody or antigen binding fragment of any of embodiments 1-11 and a pharmaceutically acceptable carrier, diluent, excipient or stabilizer.

Embodiment 18

The composition of embodiment 17, further comprising an agent selected from the group consisting of:
an anti-PD1 antibody or an antigen binding fragment thereof;
an anti-LAG3 antibody or an antigen binding fragment thereof;
an anti-TIGIT antibody or an antigen binding fragment thereof;
an anti-VISTA antibody or an antigen binding fragment thereof;
an anti-BTLA antibody or an antigen binding fragment thereof;
an anti-TIM3 antibody or an antigen binding fragment thereof;
an anti-CD27 antibody or an antigen binding fragment thereof;
an anti-HVEM antibody or an antigen binding fragment thereof;
an anti-CD70 antibody or an antigen binding fragment thereof;
an anti-CD137 antibody or an antigen binding fragment thereof;
an anti-OX40 antibody or an antigen binding fragment thereof;
an anti-CD28 antibody or an antigen binding fragment thereof;
an anti-PDL1 antibody or an antigen binding fragment thereof;
an anti-PDL2 antibody or an antigen binding fragment thereof;
an anti-GITR antibody or an antigen binding fragment thereof;
an anti-ICOS antibody or an antigen binding fragment thereof;
an anti-SIRPα antibody or an antigen binding fragment thereof;
an anti-ILT2 antibody or an antigen binding fragment thereof;
an anti-ILT3 antibody or an antigen binding fragment thereof;
an anti-ILT4 antibody or an antigen binding fragment thereof;
an anti-ILT5 antibody or an antigen binding fragment thereof;
an anti-4-1BB antibody or an antigen binding fragment thereof;
an anti-NK2GA antibody or an antigen binding fragment thereof;
an anti-NK2GC antibody or an antigen binding fragment thereof;
an anti-NK2GE antibody or an antigen binding fragment thereof;
an anti-TSLP antibody or an antigen binding fragment thereof,
A STING agonist; and
an anti-IL10 antibody or an antigen binding fragment thereof.

Embodiment 19

The composition of embodiment 17, wherein the anti-PD1 antibody or an antigen binding fragment thereof is selected from the group consisting of: pembrolizumab or an antigen binding fragment thereof and nivolumab or an antigen binding fragment thereof.

Embodiment 20

The composition of embodiment 17, further comprising a compound selected from the group of ADU-S100, melphalan, vincristine, fludarabine, chlorambucil, bendamustine, etoposide, doxorubicin, cyclophosphamide, cisplatin, immune modulating agents such as corticosteroids, for example dexamethasone or prednisolone, thalidomide analogs, for example thalidomide, lenalidomide or pomalidomide, kinase inhibitors, for example ibrutinib, idealisib, antibody targeting CD20, for example rituximab, ofatumab or obinotuzumab, antibody targeting CD52, for example alemtuzumab, antibody targeting CD38, for example daratumumab, antibody targeting IL-6 or IL-6 receptor, for example sarilumab or tocilizumab, antibody targeting CS-1, for example elotuzumab, antibody targeting BCMA, for example GSK2857916, antibody targeting BAFF or BLyss, for example tabalumab, bisphosphonates, for example pamidronate or zolendronic acid, bortezomid, or combinations thereof.

Embodiment 21

A method of producing an antibody or antigen binding fragment comprising:
culturing a host cell comprising a polynucleotide encoding the heavy chain and/or the light chain of an antibody or antigen binding fragment of any of embodiments 1-11 under conditions favorable to expression of the polynucleotide; and
optionally, recovering the antibody or antigen binding fragment from the host cell and/or culture medium.

Embodiment 22

A method of treating cancer in a subject, preferably a human subject, comprising administering to the subject an effective amount of the antibody or antigen binding fragment of any of embodiments 1-11, or of an expression vector which mediates expression of the antibody or antigen binding fragment within the subject, optionally in association with a further therapeutic agent or therapeutic procedure.

Embodiment 23

A method of treating an infection or infectious disease in a subject, preferably a human subject, comprising administering to the subject an effective amount of the antibody or antigen binding fragment of any of embodiments 1-11, or of an expression vector which mediates expression of the antibody or antigen binding fragment within the subject, optionally in association with a further therapeutic agent or therapeutic procedure.

Embodiment 24

A vaccine comprising the antibody or antigen binding fragment of any of embodiments 1-11 and an antigen.

Embodiment 25

A method for detecting the presence of a CTLA-4 peptide or a fragment thereof in a sample comprising contacting the sample with an antibody or fragment of any of embodiments 1-11 and detecting the presence of a complex between the antibody or fragment and the peptide; wherein detection of the complex indicates the presence of the CTLA-4 peptide.

Embodiment 26

A method of increasing the activity of an immune cell, comprising administering to a subject in need thereof an effective amount of an antibody or antigen binding fragment according to any of embodiments 1-11, or of an expression vector which mediates expression of the antibody or antigen binding fragment within the subject.

Embodiment 27

The method of embodiment 26, wherein said method is used for:
treatment of cancer;
treatment of an infection or infectious disease; or
as a vaccine adjuvant.

Embodiment 28

An antibody or antigen binding fragment according to any of embodiments 1-11, or an expression vector which mediates expression of the antibody or antigen binding fragment within the subject, for use in the preparation of a medicament to:
increase immune cell activation;
treat cancer; or
treat an infection or infectious disease.

Embodiment 29

Use of the antibody or antigen binding fragment of any of embodiments 1-11 for the manufacture of a medicament for the treatment of cancer for: increasing immune cell activation; treating cancer; or treating an infection or infectious disease.

Embodiment 30

The antibody or antigen binding fragment thereof of any of embodiments 1-11, wherein the fragment is a Fab, F(ab')2, Fv or a single chain Fv fragment (scFV).

Embodiment 31

The antibody or antigen binding fragment thereof of any of embodiments 1-11, which comprises a heavy chain constant region selected from IgG, IgG2, IgG3 and IgG4, preferably IgG1 or IgG4, and a light chain constant region chosen from the light chain constant regions kappa or lambda.

Embodiment 32

The antibody or antigen binding fragment thereof of embodiment 31, which comprises a human IgG4 heavy chain constant region with e Ser→Pro mutation at position 228 of SEQ ID NO: 50

Embodiment 33

A method of stimulating an immune response in a subject, comprising administering to a subject in need thereof the antibody or antigen binding fragment thereof of any of embodiments 1-11 in an amount effective to stimulate the immune response.

Embodiment 34

A method of treating cancer according to embodiment 22, wherein the cancer is selected from the group consisting of a lung cancer, a melanoma, a renal cancer, a liver cancer, a myeloma, a prostate cancer, a breast cancer, a colorectal cancer, a gastric cancer, a pancreatic cancer, a thyroid cancer, a hematological cancer, a lymphoma, a myeloma, or a leukemia, or a metastatic lesion of the cancer.

Embodiment 35

A method of treating cancer according to embodiment 22, wherein the antibody molecule is administered in combination with one or more therapeutic agents or procedures, wherein the second therapeutic agent or procedure is selected from the group consisting of a STING agonist, chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy.

Embodiment 36

A method according to embodiment 35, wherein the antibody molecule is administered in combination with an agonist of one or more costimulatory molecules selected from the group consisting of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

Embodiment 37

A method according to embodiment 35, wherein the antibody molecule is administered in combination with one or more inhibitors of an immune checkpoint molecule selected from the group consisting of PD-1, PD-L1, PD-L2, TIM-3, LAG-3, CEACAM-1, CEACAM-5, VISTA, BTLA, TIGIT, LAIR1, CD160, 2B4 or TGFR.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature* Biotechnol. 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, 2$^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank®, Vector NTI® Suite (Informax, Inc, Bethesda, Md.); GCG Wisconsin Package (Accelrys, Inc., San Diego, Calif.); DeCypher® (Time-Logic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLES

The following examples serve to illustrate the present invention. These examples are in no way intended to limit the scope of the invention.

Example 1: Immunization and Selection of Anti-hCTLA-4 Antibodies

To isolate antibodies against the human CTLA-4 protein mice were immunized with an expression construct encoding hCTLA-4. To generate this construct, cDNA encoding the full length open reading frame of hCTLA-4 (NCBI Reference Sequence: NM_005214.4, SEQ ID NO: 35) was subcloned into the pCI-neo vector (Promega, Madison, Wis.). Mice were immunized by gene gun immunization using a Helios Gene gun (BioRad, Hercules, Calif.) and DNA coated gold bullets (BioRad) following manufacturer's instructions. Briefly, 1 am gold particles were coated with pCI-neo-CTLA-4 cDNA and commercial expression vectors for mouse Flt3L and mouse GM-CSF in a 2:1:1 ratio (both from Aldevron, Fargo, N. Dak.). A total of 1 µg of plasmid DNA was used to coat 500 µg of gold particles. Specifically, 7-8 weeks old female BALB/C mice were immunized in the ears with a gene gun, receiving 4 administration cycles in both ears. Approximately, a 1:125-625 anti-hCTLA-4 titer was detected by flow Cytometry in mouse serum after three DNA immunizations. For this screening CHO-K1 cells were used, that were transiently transfected with the pCI-neo-CTLA-4 construct, using Lipofectamine 2000 (Invitrogen). Transfected cells were cultured overnight and a subsequently single cell suspension was obtained using cell dissocation solution (Sigma). $7.5*10^5$ cells were incubated with each sample of the diluted mouse sera for 30 minutes at 4° C. Then, cells were washed with Phosphate-buffered Saline (PBS)/2% Fetal Bovine serum (FBS) and stained with FITC-labelled goat-anti-mouse IgG (BD Pharmingen) for 30 minutes at 4° C. Again cells were washed with PBS/2% FBS followed by resuspension in PBS/2% FBS and antibody-bound cells were detected based on their FITC-labelling, assessed by flow cytometry (FACS Canto II; BD Biosciences). Mice that demonstrated reactivity against hCTLA-4 were immunized for a final, fourth time and sacrificed four days later. Erythrocyte-depleted spleen and lymph-node cell populations were prepared as described previously (Steenbakkers et al., 1992, *J. Immunol. Meth.* 152: 69-77; Steenbakkers et al., 1994, *Mol. Biol. Rep.* 19: 125-134) and frozen at −140° C.

For B-cell selection and CELISA purposes, CHO-K1.hCTLA-4 stable cell-lines were generated by transfecting CHO-K1 cells (American Type Culture Collection) with pCI-neo vector encoding a mutant hCTLA-4 cDNA (Y166G and Y183G, SEQ ID NO: 37). Stable clones were obtained by limiting dilution.

To select anti-hCTLA-4 antibody producing B-cells, a selection strategy was designed and developed that preferentially bound B-cells expressing antibodies that bind to hCTLA-4. Splenocyte and lymph nodes were harvested from the hCTLA-4 immunized mice and isolated cells were incubated with CHO-K1.hCTLA-4 cells that were irradiated at 3,000 RAD. After 1 hour unbound cells were removed with multiple wash steps using culture medium. Subsequently CHO-K1.hCTLA-4 cells with bound lymphocytes were harvested with dissociation buffer. Bound B-cells were cultured, as described by Steenbakkers et al., 1994, *Mol. Biol. Rep.* 19: 125-134. Briefly, selected B-cells were mixed with 7.5% (v/v) T-cell supernatant and 50,000 irradiated (2,500 RAD) EL-4 B5 feeder cells in a final volume of 200 µl medium in a 96-well flat-bottom tissue culture plates. On day eight, supernatants were screened for hCTLA-4 reactivity by CELISA as described below.

CHO-K1.hCTLA-4 cells were seeded in culture medium (DMEM-F12 (Gibco) with 10% Fetal Bovine Serum (Hyclone) and Pen/Strep (Gibco)) in tissue culture plates and cultured at 37° C., 5% $CO_2$ and 95% humidity until they were confluent. Subsequently, culture medium was removed and cells were incubated for 1 hour at 37° C., 5% $CO_2$ and 95% humidity with supernatants from the B cell cultures. Next, cells were washed with PBS/0.05% Tween (PBST) and incubated for 1 hour at 37° C., 5% $CO_2$ and 95% humidity with goat-anti-mouse IgG-HRP (Southern Biotechnology). Subsequently, cells were washed 3 times with PBST and anti-hCTLA-4 immunoreactivity was visualized with TMB Stabilized Chromagen (Invitrogen). Reactions were stopped with 0.5 M $H_2SO_4$ and absorbances were read at 450 and 610 nm.

In addition, supernatants were evaluated for hCTLA-4/hCD80 interaction blockade using a Homogeneous Time Resolved Fluorescence (HTRF) assay format. Supernatants were co-incubated with biotinylated recombinant hCD80 in HTRF buffer (PBS/0.53M Kaliumfluoride/0.1% BSA). Recombinant human CTLA-4/Fc was added in combination with the detection reagents Streptavidin K (Donor) and anti-human Fc D2 (Acceptor). The complete mixtures were incubated at room temperature (RT) for 3 hours and subsequently fluorescence was measured at a wavelength of 615 and 665 nM using a Victor2 reader (Perkin Elmer). hCTLA-4 binding to hCD80 results in a fluorescent signal in this setup which was set a 100%. Supernatants containing blocking antibodies reduced fluorescence.

B-cell clones from the hCTLA-4 reactive supernatants, which were shown to block the hCTLA-4/hCD80 interaction were immortalized by mini-electrofusion following published procedures (Steenbakkers et al., 1992, *J. Immunol. Meth.* 152: 69-77; Steenbakkers et al., 1994, *Mol. Biol. Rep.* 19:125-34). Briefly, B-cells were mixed with $10^6$ Sp2/0-Ag14 myeloma cells in Electrofusion Isomolar Buffer (Eppendorf). Electrofusions were performed in a 50 μL fusion chamber by an alternating electric field of 30 s, 1 MHz, 15 Vrms followed by a square, high field pulse of 10 μs, 3 kV/cm and again by an alternating electric field of 30 s, 1 MHz, 15 Vrms. Content of the chamber was transferred to hybridoma selective medium and plated in a 96-well plate under limiting dilution conditions. On day 12 following the electrofusion, hybridoma supernatants were screened for hCTLA-4 binding activity, as described above. Hybridomas that secreted antibodies in the supernatant that bound hCTLA-4 were subcloned by limited dilution to safeguard their integrity and stability. Stable hybridomas were cultured in serum-free media for 7-10 days; supernatants were harvested and antibodies were purified using MabSelect Sure Protein A resin according to the manufacturer's instructions (GE Healthcare). Antibody concentrations were quantified using spectrophotometry. Supernatants of the hybridoma cultures were used to isotype the hybridomas. In short, isotyping was done using a mouse monoclonal antibody isotyping kit (Biorad) based on a dipstick with immobilized goat-anti-mouse antibody bands to each of the common mouse isotypes and light chains. Recovered antibodies were all identified as mouse IgG1. Antibody sequences were elucidated by sequencing of variable regions of the mouse IgG1 hybridoma material, using the following method: the total RNA of the hybridoma cells was extracted, which allowed cDNA synthesis. Rapid Amplification of cDNA Ends (RACE) was performed that allowed cloning of positive fragments in a TOPO (ThermoFisher) vector. TOPO clones were sequenced and sequences were annotated using VBASE2 (http://www.vbase2.org).

In experiments binding and blocking was compared to 10D1 (US20020086014) or CP-675,206 (WO2007113648), which were expressed as human IgG1 kappa and IgG2 kappa, respectively. Plasmids encoding VH and VL constructs were transiently expressed by transfection into FreeStyle 293-F human embryonic kidney cells (HEK293T/17, ATCC-CRL-11268), using 293fectin transfection reagent (Invitrogen) following the manufacturer's instructions. Supernatants (30 ml) were harvested after 7 days and antibodies were purified using MabSelect Sure Protein A resin according to the manufacturer's instructions (GE Healthcare). Buffer was exchanged for 10 mM Histidine, 100 mM NaCl pH 5.5 buffer using Zeba desalting columns (Thermo Scientific). The concentration of purified antibodies was determined based on OD280 (Nanodrop ND-1000). Endotoxin level was determined by LAL-test according to the manufacturer's instructions (Lonza).

hCTLA-4 antibodies were characterized for binding to hCTLA-4, *Macaca fascicularis* (cynomolgus) CTLA-4 and blockade of ligand binding (hCD80/hCD86). Next, in vitro functionality was determined using a Jurkat-based reporter assay (Promega), following the manufacturer's procedures. In short, Raji cells expressing hCD80/hCD86 were co-incubated with Jurkat T cells stably expressing membrane CTLA-4 and an IL2-RE-luciferase reporter. To this mixture a mouse anti-human CD3 antibody (BD Pharmingen) and goat anti-mouse IgG antibody (Thermo Fisher) were added followed by a dilution range of hCTLA-4 mouse antibodies (starting at 200 μg/ml and the dilutions thereof). After six hours of incubation at 37° C., 5% $CO_2$ and 95% humidity IL-2 promoter activity was detected by addition of Bio-Glo™ substrate (Promega) and using an Envision reader (Perkin Elmer). As shown in FIG. 1, hCTLA4.27A more potently enhances IL-2 promoter as compared to 10D1.

Example 2: Humanized Antibody Design and CDR Grafting

The mouse hCTLA4.27A antibody was humanized by CDR-grafting technology (see e.g. U.S. Pat. No. 5,225,539 and Williams, D. G. et al., 2010, *Antibody Engineering*, volume 1, Chapter 21).

First, human germline sequences were identified using IgBLAST (Ye J. et al., 2013, Nucleic Acids Res. 41:W34-40). For the hCTLA4.27A VH human germline sequence, V-gene IGHV1-46*01 was identified (62.2% identity) and for the VL human germline sequence IGKV1-NL1*01 was identified (68.4% identity). These two germline sequences were used to directly graft the mouse CDRs, resulting in the following two cDNA constructs: SEQ ID NO: 15 ($V_H$, encoding SEQ ID NO: 16) and SEQ ID NO: 27 ($V_L$, encoding SEQ ID NO: 28). Next, a database was constructed containing all human sequences available in the IMGT database (Lefranc, M.-P. et al., 1999, *Nucleic Acid Res.* 27:209-212) identifying 82,958 individual sequences. These sequences were queried using TBLASTN (2.2.30+) to identify template sequences that demonstrated the highest identify to the framework of hCTLA4.27A $V_H$ and $V_L$ sequences. Three $V_H$ and three $V_L$ sequences were identified that demonstrated a similarity score of 70% or higher and that displayed similar CDR lengths, preferably identical to those in hCTLA4.27A $V_H$ CDR1, CDR2, CDR3 and $V_L$ CDR1, CDR2 and CDR3, respectively.

For the heavy chain, the frameworks encoded by GenBank (Benson, D. A. et al., 2013, Nucleic Acids Res. 41(D1):D36-42) accession # L39130, DI109259, and DD431634 were selected as templates for straight grafting of the hCTLA4.27A $V_H$ CDRs, resulting in the following cDNA constructs: SEQ ID NO: 9, 11 and 13. respectively. For the light chain, the frameworks encoded by GenBank accession # AB063955, DI112350, and AB363305 were selected as templates for straight grafting of the hCTLA4.27A $V_L$ CDRs, resulting in the following cDNA constructs: SEQ ID NO: 21, 23 and 25. Framework and CDR definition were those as described by Kabat et al.

To study the effect of humanized framework residues on the structure of the Fv, a homology model of the mouse hCTLA4.27A Fv was made using the 'Antibody Modeling Cascade' (default parameters) within Discovery Studio 4.5. The homology model was built on basis of PDB ID 3V7A.

The CDRs were grafted in silico to study residues that are close to any of the CDRs and which might affect the loop conformation, referred as Vernier residues. Residues that might affect the loop conformation, and which are within <5 Å to the CDR surface were identified and substituted with the mouse amino acid at this position. The resulting templates were checked for the presence of post translational modification (PTM) motifs using Discovery Studio 4.5 and where possible (i.e. non-CDR, non-Vernier residues) changed to prevent a PTM. For the heavy chain, removal of the predicted sequence PTM motifs and structural considerations (i.e. rigidity of the backbone) in the hCTLA4.27A $V_H$ resulted in the design of two additional constructs: SEQ ID NO: 17 and 19. For the light chain the PTM removal resulted in the following construct: SEQ ID NO: 29.

CDRs were grafted on each of the identified templates, expressed as a human IgG4 (SEQ ID NO: 50), kappa (SEQ ID NO: 52) antibody cloned in the pcDNA3.1(+) vector and transient transfection in HEK293 Free-style cells. An IgG4 version of humanized antibodies was produced, with the stabilizing Adair mutation (Angal S. et al., 1993, *Mol Immunol.* 30: 105-108), where Serine 228 is converted to Proline.

The hCTLA4.27IgG1 was also expressed as a human IgG1 (SEQ ID NO: 48), kappa antibody (SEQ ID NO: 52) cloned in the pcDNA3.1(+) vector and transiently transfected in HEK293 Free-style cells. The plasmids encoding the human IgG1 heavy chain and light chain constructs were mixed in a 1:1 ratio (1280 μg in total) and transiently expressed by transfection into FreeStyle 293-F human embryonic kidney cells (HEK293T/17, ATCC-CRL-11268), using 293fectin transfection reagent (Invitrogen) following the manufacturer's instructions. Supernatant (1250 ml) were harvested after 7 days and hCTLA4.27IgG1 was purified using MabSelect Sure Protein A resin according to the manufacturer's instructions (GE Healthcare). Buffer was exchanged for 10 mM Histidine, 100 mM NaCl pH 5.5 buffer using Zeba desalting columns (Thermo Scientific). The concentration of purified hCTLA4.27IgG1 was determined based on OD280 (Nanodrop ND-1000).

In addition, the mouse hCTLA4.27A $V_H$ and $V_L$ (SEQ ID NO: 32 and 34) were expressed as a chimeric human IgG1 (hCTLA4.27A.C1) and IgG4 (hCTLA4.27A.C4), kappa antibody, cloned in the pcDNA3.1(+) vector and transient transfection in HEK293 Free-style cells.

Example 3: Synthesis, Expression and Purification of Humanized Constructs

The plasmids encoding the heavy chain and light chain constructs were mixed in a 1:1 ratio (30 μg in total) and transiently expressed by transfection into FreeStyle 293-F human embryonic kidney cells (HEK293T/17, ATCC-CRL-11268), using 293fectin transfection reagent (Invitrogen) following the manufacturer's instructions. Supernatants (30 ml) were harvested after 7 days and antibodies were purified using MabSelect Sure Protein A resin according to the manufacturer's instructions (GE Healthcare). Buffer was exchanged for 10 mM Histidine, 100 mM NaCl pH 5.5 buffer using Zeba desalting columns (Thermo Scientific). The concentration of purified antibodies was determined based on OD280 (Nanodrop ND-1000). Endotoxin level was determined by LAL-test according to the manufacturer's instructions (Lonza).

Example 4: Binding of Humanized CTLA-4 Antibodies

Binding of the humanized antibodies to hCTLA-4 was studied in CELISA format. CHO-K1.hCTLA-4 cells were seeded in culture medium (DMEM-F12 (Gibco) with 10% Fetal Bovine Serum (Hyclone) and Pen/Strep (Gibco)) in tissue culture plates and cultured at 37° C., 5% $CO_2$ and 95% humidity until they were confluent. Subsequently, culture medium was removed and cells were incubated for 1 hour at 37° C., 5% $CO_2$ and 95% humidity with purified hCTLA-4 antibodies (10 μg/ml and dilutions thereof). Next, cells were washed with PBS/0.05% Tween (PBST) and incubated for 1 hour at 37° C., 5% $CO_2$ and 95% humidity with goat-anti-human IgG-HRP (Southern Biotechnology) or goat-anti-mouse IgG-HRP (Southern Biotechnology). Subsequently, cells were washed 3 times with PBST and anti-hCTLA-4 immunoreactivity was visualized with TMB Stabilized Chromagen (Invitrogen). Reactions were stopped with 0.5 M $H_2SO_4$ and absorbances were read at 450 and 610 nm. EC50 values, the concentration at which 50% of the total binding signal is observed, were calculated using Graphpad Prism 6. In Table 5 the EC50 values of the humanized hCTLA4.27 antibodies are depicted.

TABLE 5

Binding of humanized hCTLA4.27 antibodies, parental and chimeric antibodies to human CTLA-4 expressed on CHO-K1.hCTLA-4 cells. EC50 values represent the concentration at which 50% of the total binding signal is observed (average and SD were calculated from values of two independent experiment).

| Antibody | hCTLA-4 Binding EC50 (nM) | |
|---|---|---|
| | Average | SD |
| hCTLA4.27H1L1 | 0.037 | 0.015 |
| hCTLA4.27H1L2 | 0.040 | 0.013 |
| hCTLA4.27H1L3 | 0.045 | 0.028 |
| hCTLA4.27H1L5 | 0.046 | 0.037 |
| hCTLA4.27H2L1 | 0.042 | 0.041 |
| hCTLA4.27H2L2 | 0.044 | 0.003 |
| hCTLA4.27H2L3 | 0.051 | 0.002 |
| hCTLA4.27H2L5 | 0.045 | 0.010 |
| hCTLA4.27H3L1 | 0.070 | 0.006 |
| hCTLA4.27H3L2 | 0.065 | 0.008 |
| hCTLA4.27H3L3 | 0.101 | 0.010 |
| hCTLA4.27H3L5 | 0.082 | 0.022 |
| hCTLA4.27H4L1 | 0.070 | 0.010 |

TABLE 5-continued

Binding of humanized hCTLA4.27 antibodies, parental and chimeric antibodies to human CTLA-4 expressed on CHO-K1.hCTLA-4 cells. EC50 values represent the concentration at which 50% of the total binding signal is observed (average and SD were calculated from values of two independent experiment).

| Antibody | hCTLA-4 Binding EC50 (nM) | |
| --- | --- | --- |
| | Average | SD |
| hCTLA4.27H4L2 | 0.047 | 0.008 |
| hCTLA4.27H4L3 | 0.051 | 0.006 |
| hCTLA4.27H4L5 | 0.061 | 0.002 |
| hCTLA4.27H5L1 | 0.029 | 0.016 |
| hCTLA4.27H5L2 | 0.042 | 0.032 |
| hCTLA4.27H5L3 | 0.042 | 0.010 |
| hCTLA4.27H5L5 | 0.035 | 0.011 |
| hCTLA4.27H6L1 | 0.044 | 0.003 |
| hCTLA4.27H6L2 | 0.027 | 0.004 |
| hCTLA4.27H6L3 | 0.028 | 0.004 |
| hCTLA4.27H6L5 | 0.036 | 0.005 |
| hCTLA4.27A | 0.048 | 0.005 |
| hCTLA4.27A.C1 | 0.022 | 0.009 |
| hCTLA4.27A.C4 | 0.033 | 0.005 |

Variants with the L4 light chain did not bind to human CTLA-4

Binding of the hCTLA-4 antibodies to cynomolgus CTLA-4 (SEQ ID NO: 40) was confirmed using CHO-K1 cells (American Type Culture Collection, Manassas, Va.) that had been transiently transfected with cDNA encoding the full length open reading frame of cynomolgus CTLA-4 (SEQ ID NO: 39), subcloned into the pCI-neo vector (Promega). CHO-K1.cynoCTLA-4 cells were seeded in tissue culture plates and incubated at 37° C., 5% $CO_2$ and 95% humidity for until cell layers were confluent. Subsequently culture medium was removed and cells were incubated for 1 hour with purified hCTLA-4 antibodies (10 µg/ml and dilutions thereof) at 37° C., 5% $CO_2$ and 95% humidity. Next, cells were washed with PBST and incubated for 1 hour at 37° C. with goat-anti-human IgG-HRP (Jackson Immuno Research). Subsequently, cells were washed 3 times with PBST and anti-CTLA-4 immunoreactivity was visualized with TMB Stabilized Chromagen (Invitrogen). Reactions were stopped with 0.5 M H2SO4 and absorbances were read at 450 and 610 nm.

Binding of hCTLA4.27 humanized antibodies to CTLA-4 expressed on human CD3+ T cells was confirmed by flow cytometry. Human CD3+ T cells were isolated from human buffy coat as follows. First, the Buffy coat was diluted to a total volume of 180 ml with PBS at room temperature. After mixing the cell suspension, aliquotes were loaded on a Ficoll-Paque Plus gradient in Sepmate tubes (Stemcell Technologies) and centrifuged at 1200 g for 10 min, at 20° C. without a brake. Next, plasma was removed by aspiration and PBMCs were recovered from the plasma/Ficoll interface. PBMCs were washed three times in PBS. Subsequently, CD3+ T cell isolation was conducted with magnetic beads (CD3+ T-cell Biotin-Ab cocktail; Miltenyi Biotec). Next, T cells were stimulated with αCD3/αCD28 coated beads (Thermo Fisher Scientific) for 48 hours. First T-cell stimulation was confirmed by detection of blast formation using flow cytometry. Binding of hCTLA4.27 humanized antibodies was assessed after fixation and permeabilization of T cells with Cytofix/Cytoperm (BD). Cells were washed twice in perm/wash buffer (BD), incubated with the hCTLA4.27 humanized antibodies, washed three times, and finally incubated with a FITC-labelled Goat-anti-human-hIgG detection antibody (Southern Biotech). After this labeling procedure, cells were washed two times, resuspended in FACS buffer and analysed by flow Cytometry on the FACS Canto II (BD). Data were processed and analysed with Flowjo Software.

Binding of hCTLA4.27 humanized antibodies to CTLA-4 expressed on *Macaca fascicularis* (cynomolgus) PBMCs was confirmed by flow cytometry. To this end cynomolgus blood was diluted 1:1 with PBS and added to 50 ml tubes containing 13 ml Lymphoprep 95%/PBS 5%. Cells were centrifuged for 30 minutes at 450 g and 20° C. without brake. Next, plasma was removed by aspiration and PBMCs were recovered from the plasma/Ficoll interface. PBMCs were washed twice times in PBS. Cells were frozen in liquid nitrogen and retrieved from the freezer on the day of the experiment. Since endogenous expression of CTLA-4 on resting immune cells is low, the thawed PBMCs were stimulated with αCD3/αCD28/αCD2 coated beads (Milteny Biotec) for 48 hours. Subsequently, stimulation of the PBMCs was confirmed by detection of blast formation using flow cytometry. Next, the cells were analyzed by flow cytometry for intracellular binding of hCTLA4.27 antibodies.

Example 5: Blockade of hCD80 Binding to hCTLA-4 by Humanized hCTLA4.27 Antibodies hCD80 blockade was assessed in CELISA format for the full panel of humanized hCTLA4.27 antibodies. CHO-K1.hCTLA-4 cells were seeded in tissue culture plates and incubated at 37° C., 5% $CO_2$ and 95% humidity in culture medium. Once the cells were confluent culture medium was removed and cells were incubated for 1 hour with the humanized hCTL4.27 antibody variants (10 µg/ml and dilutions thereof) at 37° C., 5% $CO_2$ and 95% humidity. Next, cells were washed with PBS/0.05% Tween-20 (PBST) and incubated for 1 hour at 37° C., 5% $CO_2$ and 95% humidity with biotinylated recombinant hCD80/Fc-protein. Cells were then washed with PBST followed by addition of Streptavidin-HRP conjugate on the cells, which was incubated for 1 hour at 37° C., 5% $CO_2$ and 95% humidity. Subsequently cells were washed three times with PBST and binding of hCD80/Fc-protein was visualized with TMB Stabilized Chromagen (Invitrogen). Reactions were stopped with 0.5 M $H_2SO_4$ and absorbances were read at 450 and 610 nm. IC50 values for the blockade of hCD80 were calculated from this data and are represented in Table 6. IC50 values represent the concentration at which half of the inhibition is observed.

TABLE 6

Blockade of hCD80 binding by humanized hCTLA4.27 antibodies, parental and chimeric antibodies. IC50 values represent the concentration at which half of the inhibition is observed (average and SD were calculated from values of two independent experiment).

| Antibody | hCD80 Blocking IC50 (nM) | |
| --- | --- | --- |
| | Average | SD |
| hCTLA4.27H1L1 | 2.546 | 1.003 |
| hCTLA4.27H1L2 | 2.716 | 1.193 |
| hCTLA4.27H1L3 | 3.127 | 0.764 |
| hCTLA4.27H1L5 | 3.444 | 1.048 |
| hCTLA4.27H2L1 | 2.982 | 1.000 |
| hCTLA4.27H2L2 | 2.586 | 0.872 |
| hCTLA4.27H2L3 | 2.969 | 0.519 |
| hCTLA4.27H2L5 | 2.722 | 0.197 |

TABLE 6-continued

Blockade of hCD80 binding by humanized hCTLA4.27 antibodies, parental and chimeric antibodies. IC50 values represent the concentration at which half of the inhibition is observed (average and SD were calculated from values of two independent experiment).

| Antibody | hCD80 Blocking IC50 (nM) | |
|---|---|---|
| | Average | SD |
| hCTLA4.27H3L1 | 2.519 | 0.806 |
| hCTLA4.27H3L2 | 2.061 | 0.399 |
| hCTLA4.27H3L3 | 3.365 | 1.821 |
| hCTLA4.27H3L5 | 3.666 | 1.468 |
| hCTLA4.27H4L1 | 3.331 | 1.720 |
| hCTLA4.27H4L2 | 2.519 | 0.706 |
| hCTLA4.27H4L3 | 3.257 | 2.375 |
| hCTLA4.27H4L5 | 3.077 | 2.272 |
| hCTLA4.27H5L1 | 5.388 | 4.397 |
| hCTLA4.27H5L2 | 10.334 | n.a. |

TABLE 6-continued

Blockade of hCD80 binding by humanized hCTLA4.27 antibodies, parental and chimeric antibodies. IC50 values represent the concentration at which half of the inhibition is observed (average and SD were calculated from values of two independent experiment).

| Antibody | hCD80 Blocking IC50 (nM) | |
|---|---|---|
| | Average | SD |
| hCTLA4.27H5L3 | 2.574 | 0.513 |
| hCTLA4.27H5L5 | 1.912 | 0.255 |
| hCTLA4.27H6L1 | 2.056 | 0.482 |
| hCTLA4.27H6L2 | 1.805 | 0.622 |
| hCTLA4.27H6L3 | 1.821 | 1.089 |
| hCTLA4.27H6L5 | 2.571 | 1.163 |
| hCTLA4.27A | 2.175 | 0.249 |
| hCTLA4.27A.C1 | 1.535 | 0.471 |
| hCTLA4.27A.C4 | 1.611 | 0.395 |

1) Variants with the L4 light chain did not bind CTLA-4

Example 6: hCTLA4.27 Affinity, Binding to hCTLA-4 and its Blocking Abilities of the hCD80/hCD86 Interaction Compared to 10D1 (Ipilimumab) and CP-675,206 (Tremelimumab)

hCTLA4.27 binding kinetics and equilibrium binding constants were profiled using bio-light interferometry on the Octet RED96 and compared to several antibodies known in the art. First, anti-hCTLA-4 mAbs were coupled to amine-reactive second generation biosensors (Fortebio) using standard amine chemistry. hCTLA-4 binding to and dissociation from the biosensors was then observed at various hCTLA-4 concentrations. Amine-reactive biosensors were pre-wet by immersing them in wells containing 0.1M MES pH=5.5 for 10 minutes. The biosensors were then activated using a 0.1M NHS/0.4M EDC mixture for 5 minutes. Antibodies were coupled by immersing the biosensors in a solution of 2.5 or 12 ug/mL antibody in 0.1M MES for 7.5 minutes. The biosensor surface was quenched using a solution of IM ethanolamine for 5 minutes. Biosensors were equilibrated in Octet kinetics buffer (ForteBio) for 5 minutes. Association of rhCTLA-4/Fc (R&D Systems) was observed by placing the biosensors in wells containing various rhCTLA-4/Fc concentrations (2.5-40 nM) and monitoring interferometry for 15 minutes. Dissociation was measured after transfer of the biosensors into kinetics buffer and monitoring of the interferometry signal for 45 minutes. The assay was run with a plate temperature of 30° C. The observed on and off rates (kon and kdis) were fit using a 1:1 binding global fit model comprising all concentrations tested, and the equilibrium binding constant KD was calculated. As shown in Table 7: hCTLA4.27 has similar binding affinity as control antibodies.

TABLE 7

Affinities of hCTLA4.27 formatted as human IgG1 and human IgG4 in relation to control antibodies 10D1 and CP-675,206

| | KD (M) | KD error | kon(1/Ms) | kon Error | kdis(1/s) | kdis Error |
|---|---|---|---|---|---|---|
| hCTLA4.27A | 2.0E−09 | 1.7E−09 | 5.0E+05 | 3.4E+05 | 4.5E−04 | 1.7E−04 |
| hCTLA4.27IgG1 | 4.0E−09 | 3.7E−09 | 2.3E+05 | 1.8E+05 | 2.5E−04 | 1.3E−04 |
| hCTLA4.27IgG4 | 1.2E−09 | 1.9E−10 | 5.7E+05 | 4.0E+05 | 6.4E−04 | 4.1E−04 |
| 10D1 | 1.2E−09 | 5.9E−10 | 4.1E+05 | 6.2E+04 | 4.4E−04 | 1.7E−04 |
| CP-675,206 | 3.4E−09 | 2.6E−09 | 1.0E+05 | 4.2E+04 | 2.4E−04 | 1.3E−04 |

Next, binding of hCTLA4.27 antibodies to hCTLA-4 and its blocking abilities of the hCD80/hCD86 interaction were compared to 10D1 and CP-675,206 in CELISA format. In short, CELISA for hCTLA-4 binding was performed on CHO-K1.hCTLA-4 cells. Detection of bound antibody was done with goat-anti-mouse IgG HRP (Southern Biotech) for the mouse hCTLA4.27A and goat-anti-human IgG-HRP (Southern Biotech) for the hCTLA4.27A chimeric hIgG1 and hIgG4 and control antibodies respectively. For the assessment of hCD80 and hCD86 blockade CHO-K1.hCTLA-4 cells were seeded in tissue culture plates and incubated at 37° C., 5% $CO_2$ and 95% humidity in culture medium. Once the cells were confluent culture medium was removed and cells were incubated for 1 hour with the hCTL4.27 antibodies and control antibodies (10 μg/ml and dilutions thereof) at 37° C., 5% $CO_2$ and 95% humidity. Next, cells were washed with PBS/0.05% Tween-20 (PBST) and incubated for 1 hour at 37° C., 5% $CO_2$ and 95% humidity with biotinylated recombinant hCD80/Fc-protein or hCD86/Fc protein. Cells were then washed with PBST followed by addition of Streptavidin-HRP conjugate on the cells, which was incubated for 1 hour at 37° C., 5% $CO_2$ and 95% humidity. Subsequently cells were washed three times with PBST and binding of hCD80/Fc-protein or hCD86/Fc-protein was visualized with TMB Stabilized Chromagen (Invitrogen). Reactions were stopped with 0.5 M $H_2SO_4$ and absorbances were read at 450 and 610 nm. IC50 values represent the concentration at which half of the inhibition is observed.

Figure 2:
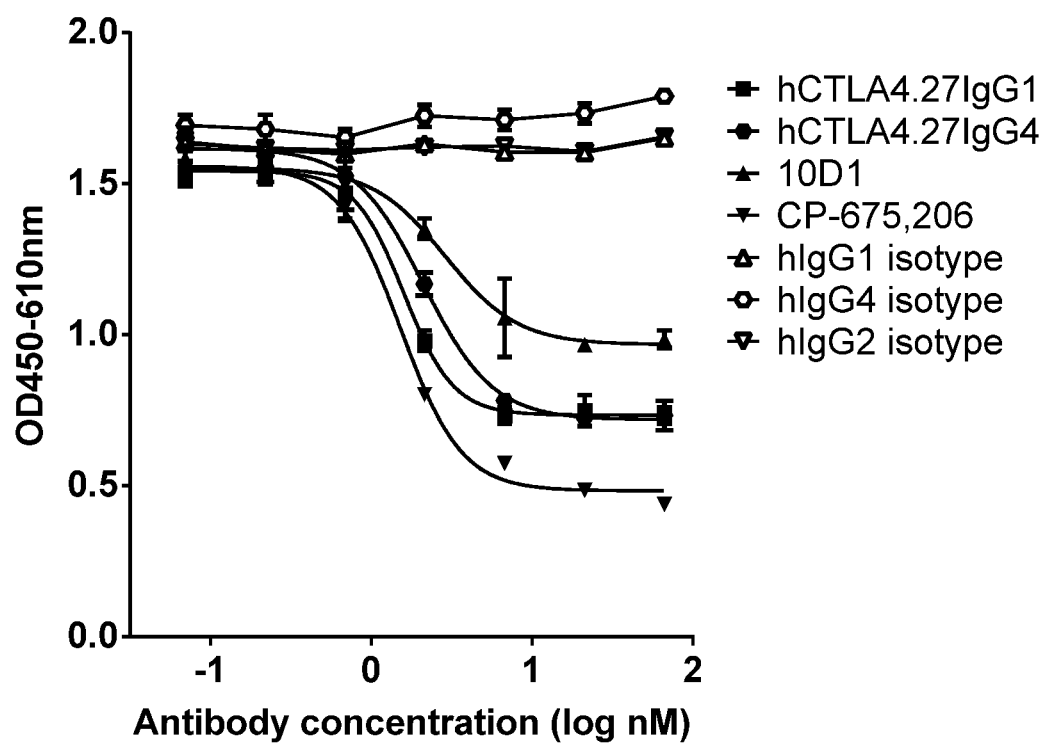
FIG. 2: Differential hCD80 blocking profile of hCTLA4.27 antibodies.

As depicted in FIG. 2 the hCD80 blocking profile of hCTLA4.27IgG1 and hCTLA4.27IgG4 antibodies lies between the hCD80 profiles of ipilimumab and tremelimumab. Thus although IC50 values are comparable, the efficacy plateau differs.

TABLE 8

Binding of hCTLA4.27A, hCTLA4.27A chimeric hIgG1 and hIgG4 and control antibodies to hCTLA-4 and their blocking abilities of the hCD80/hCD86 interaction. EC50 values represent the concentration at which 50% of the total binding signal is observed. IC50 values represent the concentration at which half of the inhibition is observed (averages and SDs were calculated from values of two independent experiments).

| | hCTLA-4 Binding EC50 (nM) | | hCD80 Blocking IC50 (nM) | | hCD86 Blocking IC50 (nM) | |
|---|---|---|---|---|---|---|
| | Average | SD | Average | SD | Average | SD |
| hCTLA4.27A | 0.053 | 0.010 | 2.715 | 0.328 | 2.167 | 0.307 |
| hCTLA4.27A.C1 | 0.034 | 0.001 | 1.454 | 0.565 | 1.175 | 0.040 |
| hCTLA4.27A.C4 | 0.053 | 0.013 | 1.597 | 0.359 | 1.205 | 0.031 |
| 10D1 | 0.053 | 0.006 | 3.253 | 0.517 | 2.309 | 0.012 |
| CP-675,206 | 0.037 | 0.006 | 1.754 | 0.234 | 1.690 | 0.194 |

Example 7: Functionality of Humanized hCTLA4.27 Antibodies in the Human PBMC SEB Assay To confirm the functionality of humanized hCTLA4.27 in primary immune cells, PBMCs were isolated from buffy coats of human donor blood. First, the buffy coat was diluted and mixed to a total volume of 180 ml with PBS at room temperature. Aliquots were loaded on a Ficoll-Paque® Plus (Pharmacia Fine Chemicals, Inc.) gradient in Sepmate tubes (Stemcell Technologies) and centrifuged at 1200 g for 10 min, at 20° C. without a brake. Next, plasma was removed by aspiration and PBMCs were recovered from the plasma/Ficoll interface. PBMCs were washed three times in PBS before use in the assay. PBMCs were seeded at $2*10^5$ cells per well. Subsequently humanized hCTLA4.27 and control antibodies were diluted in RPMI 1640 medium (Gibco) supplemented with 10% Fetal Calf Serum and added in a concentration range starting at 100 ug/ml with square root 10 dilution steps. *Staphylococcus* Enterotoxin B (Sigma) diluted in RPMI 1640 medium supplemented with 10% Fetal Calf Serum was added at a concentration of 10 µg/ml. Plates were incubated for seventy-two hours at 37° C., 5% $CO_2$ and 95% humidity, followed by isolation of supernatants.

Figure 3:
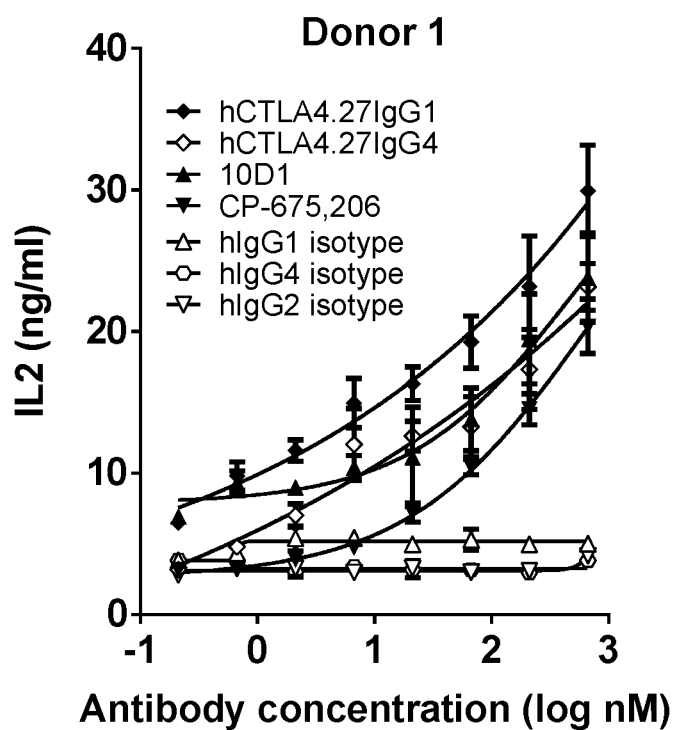
FIG. 3: Induction of IL2 production by hCTLA4.27 antibodies in the PBMC SEB assay.

IL-2 secretion was detected in the supernatant as a measure of immune activation. Supernatants were cleared from any cell material by centrifugation and added to Nunc maxisorp ELISA plates that had been coated with anti-hIL-2 antibody (BD Pharmingen) in PBS by incubation at 4° C. for a minimal period of 16 hours. Prior to addition of the supernatant, wells were emptied and blocked with PBS/1% BSA for one hour at Room Temperature (RT). Supernatants were incubated in the anti-hIL-2 coated plates for one hour at RT after which plates were washed three times with PBST (PBS with 0.05% Tween 20). Subsequently, 0.5 µg/ml of anti-hIL2-biotin (BD Pharmingen) was added in PBST/0.5% BSA and incubated for one hour at RT. After three washes with PBST, 1:5000 diluted streptavidin-HRP (BD Pharmingen) was added in PBST/0.5% BSA. After six washes with PBST, IL-2 was detected by addition of TMB stabilized chromogen (Invitrogen). Reactions were stopped with 0.5 M $H_2SO_4$ and absorbances were read at 450 and 610 nm. In this assay, recombinant human IL-2 (Sigma) was used as a reference to quantify IL-2 protein levels in the supernatants. FIG. 3 shows that hCTLA4.27 antibodies enhance immune activation.

Example 8: hCTLA4.27 in Effector Function Assays

The ability of the chimeric hCTLA4.27A antibodies: hCTLA4.27A.C1 and hCTLA4.27A.C4 to induce Antibody-Dependent Cell-mediated Cytotoxicity (ADCC) and Complement-Dependent Cytotoxicity (CDC) was studied. For the ADCC assay, human NK cells were used as effector cells. NK cells were isolated from human blood. Buffy coats were enriched for NK cells with the Rosette SEP NK enrichment cocktail (Stemcell Technologies). Subsequent the buffy coat was mixed 1:1 with PBS/2% FBS and layered on Ficol Paque plus (GE Healthcare). After centrifugation the interphase was collected and cells were washed with PBS/2% FBS. Characterization of the isolated NK cells by flow cytometry confirmed CD16 and CD56 expression.

Figure 4A:
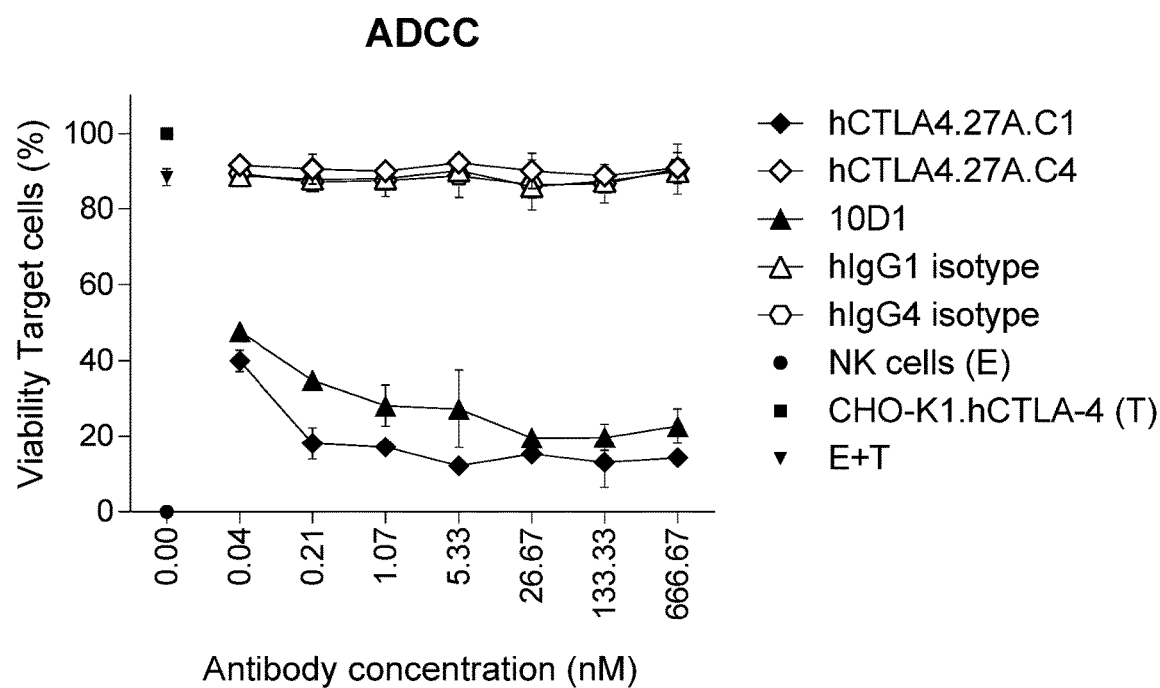
FIG. 4A: hCTLA4.27 and control antibodies: effector function in the ADCC assay.

CHO-K1.hCTLA-4 were used as target cells and seeded in a flat bottom cell culture plate together with NK cells in an effector:target ratio of 10:1. hCTLA4.27 antibodies or control antibodies (10D1 or isotype-matched control antibodies (hIgG1, hIgG4)) were added (100 µg/ml and dilutions thereof). Plates were incubated overnight at 37° C., 5% $CO_2$ and 95% humidity. After overnight incubation, cells were washed with PBST (PBS and 0.01% Tween-20) and incubated in RPMI (Gibco) supplemented with 10% Fetal Bovine Serum (Hyclone) and 1% Pen/Strep (Gibco) incubated at 37° C., 5% $CO_2$ and 95% humidity for 30 minutes. Subsequently Celltiter 96 Aqueous One solution (Promega) was added followed by 3 hours incubation at 37° C., 5% $CO_2$ and 95% humidity. Cell viability was assessed by analyzing the OD492-690 using an iEMS reader (Labsystems). As shown in FIG. 4A, hCTLA4.27A.C1 induced NK-mediated cell lysis in two different donors, while formatted as an hIgG4 it was not able to induce cytotoxicity.

Figure 4B:
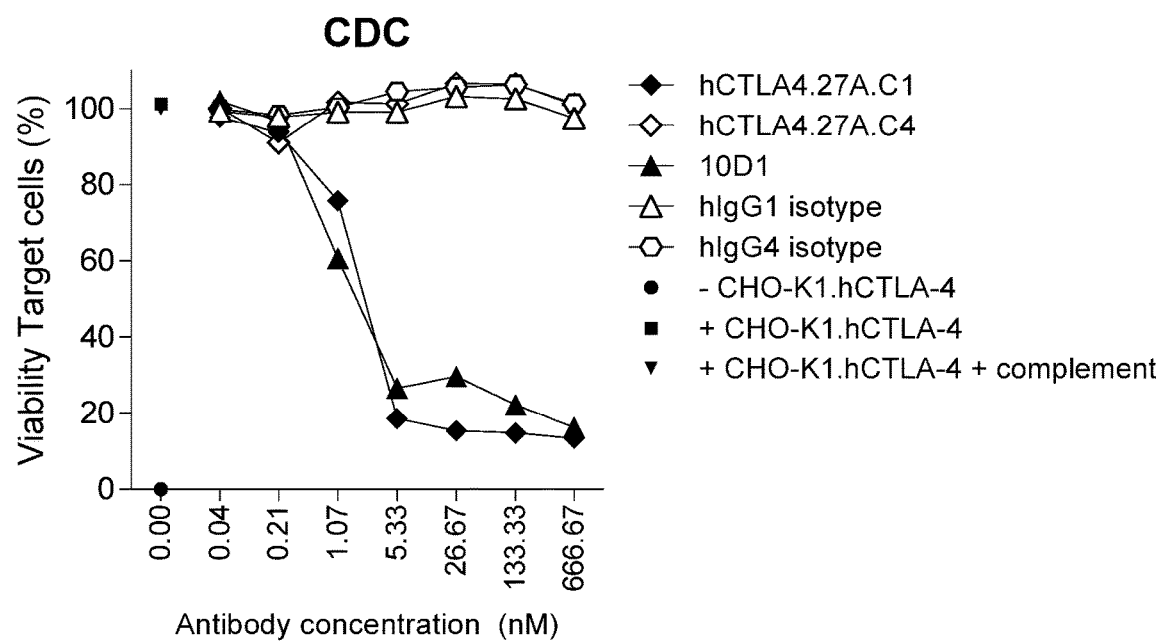
FIG. 4B: hCTLA4.27 and control antibodies: effector function in the CDC assay.

To assess Complement-dependent Cytotoxicity a concentration range of hCTLA4.27 antibodies was added to confluent monolayers of CHO-K1.hCTLA-4 target cells. After a 15 minutes incubation period 50% human complement serum (Sigma) was added to the cells. After 3.5 hours incubation cells were washed with PBST (PBS and 0.01% Tween-20), incubated with supplemented RPMI (Gibco) and incubated at 37° C., 5% $CO_2$ and 95% humidity for 30 minutes. Subsequently Celltiter 96 Aqueous One solution (Promega) was added followed by 3 hours incubated at 37° C., 5% $CO_2$ and 95% humidity. Cell viability was assessed by analyzing the OD492-690 in an iEMS reader (Labsystems). As shown in FIG. 4B, hCTLA4.27A.C1 does induce Complement-mediated cell lysis in the CDC assay, while formatted as an hIgG4 it does not induce complement-mediated cell cytotoxicity.

Example 9: Cross Competition of hCTLA4.27 and Control Antibodies

To characterize the difference in binding site of hCTLA4.27 compared to 10D1 (ipilimumab) and CP-675,206 (tremelimumab) competition between the antibodies was profiled using bio-light interferometry as described previously. Amine-reactive biosensors were pre-wet by immersing them in wells containing 0.1M MES pH=5.5 for 10 minutes. The biosensors were then activated using a 0.1M NHS/0.4M EDC mixture for 5 minutes. hCTLA4.27 formatted as human IgG1 or human IgG4 was coupled by immersing the biosensors in a solution of 12 μg/ml mAb in 0.1M MES for 7.5 minutes. The biosensor surface was quenched using a solution of 1M ethanolamine for 5 minutes. Biosensors were equilibrated in OCTET® kinetics buffer (ForteBio) for 5 minutes. Association of rhCTLA-4/Fc was observed by placing the biosensors in wells containing a fixed concentration rhCTLA-4/Fc (12 μg/ml) and monitoring interferometry for 15 minutes. Next, for an additional 2 minutes the same anti-hCTLA-4 mAb as coupled to the biosensor was allowed to bind, to ensure binding of all available rhCTLA-4/Fc binding sites. Competition or non-competition was determined by placing the biosensors for 5 minutes in wells containing a fixed concentration (6 μg/ml) of another or the same anti-hCTLA-4 mAb or a reference well containing kinetics buffer only. In this direct competition assay, binding of hCTLA4.27 to rhCTLA-4 does not block binding of control antibodies to rhCTLA-4/Fc as shown in Table 9.

TABLE 9

Cross competition of hCTLA4.27 and control antibodies. Binding of the second antibody in nm shift, zero or negative value means no binding is observed.

| Coupled antibody | Binding of second antibody (in nm shift) | | | |
|---|---|---|---|---|
|  | hCTLA4.27IgG1 | hCTLA4.27IgG4 | 10D1 | CP-675,206 |
| hCTLA4.27IgG1 | −0.0144 | −0.0164 | 0.0534 | 0.0877 |
| hCTLA4.27IgG4 | −0.0096 | −0.0132 | 0.0395 | 0.0714 |

Example 10: Binding to Human/Mouse CTLA-4 Exchange Mutants

The difference in binding regions between hCTLA4.27 in comparison to 10D1 and CP-675,206 was confirmed using two hCTLA-4 mutants. hCTLA-4 mutants were designed which were half human and half mouse. Based on the fold of CTLA-4, an Ig-like V-type (immunoglobulin-like) domain, the protein can be divided into two subdomains: one containing beta-strand 1, 2, 5, and 6, including connecting loops and one containing beta-strand 3, 4, 7, and 8, including connecting loops. The human-mouse variant (SEQ ID NO: 42, Hum-Mou-CTLA-4) contains human residues on strand 1, 2, 5 and 6 and mouse residues (SEQ ID NO: 46) on strand 3, 4, 7, and 8. The mouse-human variant (SEQ ID NO: 44, Mou-Hum-CTLA-4) contains mouse residues on strand 1, 2, 5 and 6 and human residues on strand 3, 4, 7, and 8.

Figure 5:
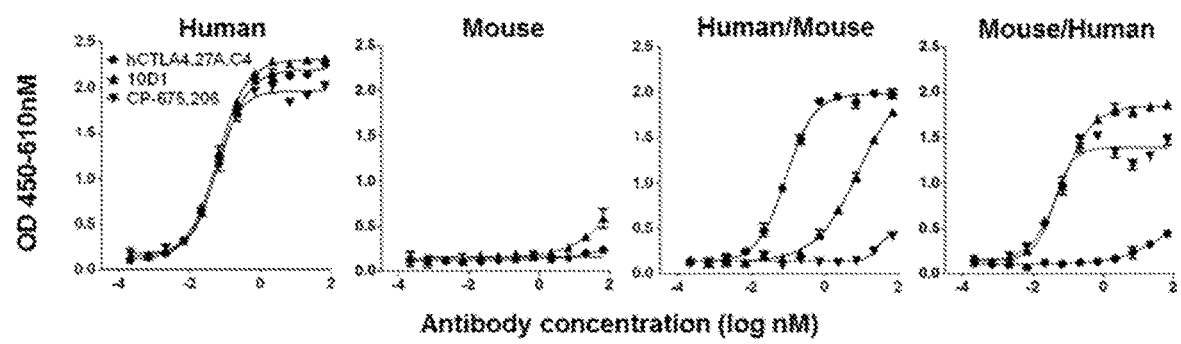
FIG. 5: Unique binding profile of hCTLA4.27A chimeric hIgG4 to human/mouse CTLA-4 exhange mutants.

The cDNAs encoding these constructs (SEQ ID NO: 41 and 43, respectively) were synthesized and subcloned into the pCI-Neo vector (GeneArt). Binding of hCTLA4.27A chimeric hIgG4 (hCTLA4.27A.C4), 10D1 and CP-675,206 to the exchange mutants was tested using CELISA. To this end CHO-K1 cells were transiently transfected, using Lipofectamine 2000 (Invitrogen), with the pCI-Neo vectors expressing human CTLA-4 (hCTLA-4), mouse CTLA-4 (mCTLA-4) (SEQ ID NO: 45), Hum-Mou-CTLA-4, and Mou-Hum-CTLA-4 respectively. The transfected cells were cultured at 37° C., 5% $CO_2$ and 95% humidity in medium (DMEM-F12 (Gibco) with 5% New Born Calf serum (Biowest) and Pen/Strep (Gibco)) until confluent. Subsequently, cells were trypsinized and seeded in tissue culture plates and cultured at 37° C., 5% $CO_2$ and 95% humidity in culture medium until confluent. Then, culture medium was removed and cells were incubated for 1 hour at 37° C., 5% $CO_2$ and 95% humidity with hCTLA-4 antibodies. Next, cells were washed with PBS/0.05% Tween (PBST) and incubated for 1 hour at 37° C., 5% $CO_2$ and 95% humidity with 1:2,000 goat-anti-human IgG-HRP (Jackson Immunoresearch). After that, cells were washed 3 times with PBST and anti-CTLA-4 immunoreactivity was visualized with TMB Stabilized Chromagen (Invitrogen). Reactions were stopped with 0.5 M $H_2SO_4$ and absorbances were read at 450 and 610 nm. hCTLA4.27A.C4 showed binding to the human-mouse exchange mutant, while 10D1 and CP-675,206 could bind to the mouse-human exchange mutant (FIG. 5).

Example 11: Mapping the Interaction Interface Between hCTLA-4 and hCTLA4.27A

The binding epitope of hCTLA4.27A to hCTLA-4 was elucidated by a procedure that involves deuterated chemical crosslinking followed by enzymatic digesting and detection using mass spectrometry. First, antibody hCTLA4.27A and antigen rhCTLA-4/Fc/6His (R&D systems; SEQ ID NO: 59) were incubated to promote binding and integrity and aggregation level were verified by Ultraflex III MALDI ToF mass spectrometer (Bruker) equipped with a HM4 interaction module (CovalX). For these control experiments a dilution series of 10 μL samples of antibody or antigen (1 to 128 fold dilution, starting at 1 mg/mL) was prepared. Of each sample, 9 μL was submitted to cross-linking using K200 MALDI MS analysis kit, according to the manufacturer's instructions (CovalX) and incubated for 180 minutes, while 1 μL was directly used for mass spectrometry analysis (High-Mass MALDI). The mass spectrometry analysis showed the antibody and antigen had the expected molecular weight, 152.25 kDa (160.94 kDa with cross-linker) and 88.25 kDa (95.19 kDa with cross-linker) respectively. For characterization of the antigen-antibody complex, a mixture was made with a 2-fold excess of antigen (antigen:antibody ratio 4 μM:2 μM). A 9 μL sample of the antigen-antibody mixture was submitted to cross-linking using K200 MALDI MS analysis kit, according to the manufacturer's instructions, while 1 μL was directly used for mass spectrometry analysis. The detected mass of the antibody (149.916 kDa) and antigen (88.211) correspond to the molecular weight as detected previously. The antigen-antibody complexes, after crosslinking, were detected as two non-covalent complexes with a 1:1 (239.113 kDa) and 1:2 (326.415 kDa) stoichiometry (hCTLA4.27A: rhCTLA-4/Fc). Antibody and antigen bound non-covalently, non-covalent aggregates or non-specific multimers were not detected.

Next, peptide mass fingerprinting of rhCTLA-4/Fc was performed. Samples were submitted to ASP-N, trypsin, chymotrypsin, elastase and thermolysin (Roche Diagnostic) proteolysis, following the manufacturer's instructions followed by analysis by nLC-LTQ Orbitrap MS/MS using an Ultimate 3000 (Dionex) system in line with a LTQ Orbitrap XL mass spectrometer (Thermo Scientific). The result of this proteolysis array resulted in 92.52% of the sequence being covered by the identified peptides.

Figure 6:
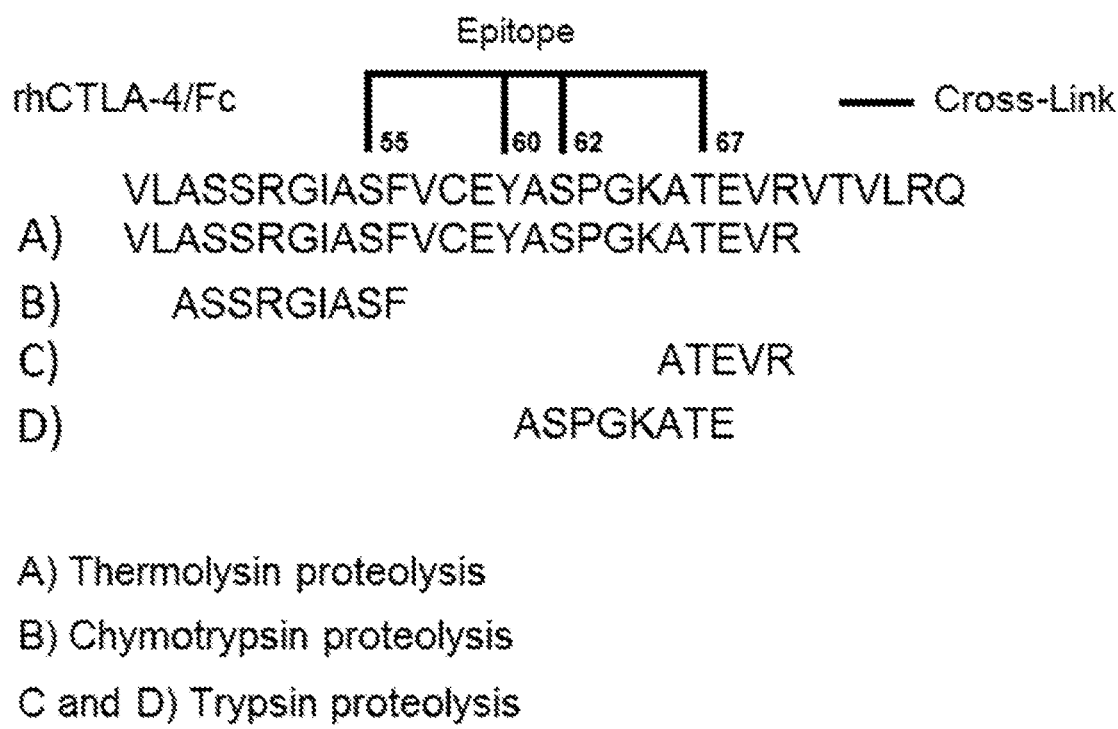
FIG. 6 depicts epitope mapping results of hCTLA4.27A binding to rhCTLA-4/Fc. Crosslinked peptides detected by different proteolysis approaches are SEQ ID NO: 54-57. hCTLA-4 residues 46-76 (SEQ ID NO: 58) are shown for reference.

To determine the epitope of the antibody hCTLA4.27A on rhCTLA-4/Fc antigen with high resolution, the antibody/antigen complex (antigen:antibody ratio 4 µM:2 µM) was incubated with deuterated cross-linkers d0/d12 (K200 MALDI Kit) for 180 minutes and subjected to multi-enzymatic cleavage with the enzymes ASP-N, trypsin, chymotrypsin, elastase and thermolysin. After enrichment of the cross-linked peptides, the samples were analyzed by high-resolution mass spectrometry (nLC-Orbitrap MS) and the data generated were analyzed using XQuest [Y. J. Lee, Mol. BioSyst., 2008, 4, 816-823] and Stavrox [Götze M et al. J Am Soc Mass Spectrom. 2012 January; 23(1):76-87]. Cross-linked peptides resulting from these different proteolysis approaches are shown in FIG. 6. The binding epitope of hCTLA4.27A was identified as SFVCEYASPGKAT (SEQ ID NO: 53), and is distinctly different from epitopes of anti-CTLA-4 antibodies 10D1 (Ramagopal et al. PNAS 2017; 114(21): E4223-E4232) and CP-675,206 (Lee et al. Nat Commun. 2016; 7: 13354).

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains.

The invention illustratively described herein suitably may be practiced in the absence of any element or elements, limitation or limitations which is not specifically disclosed herein. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. An antibody or antigen binding fragment thereof that binds to human Cytotoxic T Lymphocyte Antigen 4 (CTLA-4) comprising the sequence set forth in SEQ ID NO: 36, wherein the antibody or antigen binding fragment comprises each of the polypeptide sequences defined in a-c and each of the polypeptide sequences defined in d-f:
   a. a heavy chain variable region CDR1 comprising the amino acid sequence of SEQ ID NO: 1;
   b. a heavy chain variable region CDR2 comprising the amino acid sequence of SEQ ID NO: 2;
   c. a heavy chain variable region CDR3 comprising the amino acid sequence of SEQ ID NO: 3;
   d. a light chain variable region CDR1 comprising the amino acid sequence of SEQ ID NO: 4;
   e. a light chain variable region CDR2 comprising the amino acid sequence of SEQ ID NO: 5, and
   f. a light chain variable region CDR3 comprising the amino acid sequence of SEQ ID NO: 6;

or an isolated nucleic acid encoding the antibody or antigen binding fragment thereof; an expression vector comprising an isolated nucleic acid encoding the antibody or antigen binding fragment thereof; a host cell expressing an isolated nucleic acid encoding the antibody or antigen binding fragment thereof; or a composition comprising the antibody or antigen binding fragment thereof and a pharmaceutically acceptable carrier, diluent, excipient or stabilizer.

2. The antibody or antigen binding fragment of claim 1, wherein the antibody or antigen binding fragment is humanized.

3. An antibody or antigen binding fragment thereof according to claim 1 selected from the group consisting of:
   a. an antibody or antigen binding fragment thereof comprising a variable heavy chain comprising the amino acid sequence of SEQ ID NO: 7 and a variable light chain comprising the amino acid sequence of SEQ ID NO: 8;
   b. an antibody or antigen binding fragment thereof comprising a variable heavy chain comprising the amino acid sequence of SEQ ID NO: 10, 12, 14, 16, 18 or 20 and a variable light chain comprising the amino acid sequence of SEQ ID NO: 22, 24, 26 or 30;
   c. an antibody or antigen binding fragment thereof comprising a variable heavy chain comprising at least 90%, 95%, 96%, 97%, 98% or 99% identity any one of SEQ ID NO: 10, 12, 14, 16, 18 or 20 and a variable light chain comprising at least 90%, 95%, 96%, 97%, 98% or 99% identity to any one of SEQ ID NO: 22, 24, 26 or 30; and
   d. an antibody or antigen binding fragment thereof comprising a variable heavy chain comprising at least 90%, 95%, 96%, 97%, 98% or 99% identity any one of SEQ ID NO: 10, 12, 14, 16, 18 or 20 and a variable light chain comprising at least 90%, 95%, 95%, 96%, 97%, 98% or 99% identity to any one of SEQ ID NO: 22, 24, 26 or 30, wherein any sequence variations occur in the framework regions of the antibody or antigen binding fragment or an isolated nucleic acid encoding the antibody or antigen binding fragment thereof; an expression vector comprising an isolated nucleic acid encoding the antibody or antigen binding fragment thereof; a host cell expressing an isolated nucleic acid encoding the antibody or antigen binding fragment thereof; or a composition comprising the antibody or antigen binding fragment thereof and a pharmaceutically acceptable carrier, diluent, excipient or stabilizer.

4. The antibody or antigen binding fragment of claim 3, wherein the antibody or fragment thereof has the following characteristics:
   i. binds to human CTLA-4 with a KD value of at least about 1×10-9 M as determined by surface plasmon resonance;
   ii. blocks the binding of human CTLA-4 to hCD80 with an IC50 of about 100 nM or lower;
   iii. blocks the binding of human CTLA-4 to hCD86 with an IC50 of about 100 nM or lower; and
   iv. binds to a different human CTLA-4 epitope than ipilimumab or tremelimumab.

5. A method of producing an antibody or antigen binding fragment comprising:
   culturing a host cell comprising one or more polynucleotides encoding any one of the antibodies or antigen binding fragments of claim 1 under conditions favorable to expression of the polynucleotide; and
   optionally, recovering the antibody or antigen binding fragment from the host cell and/or culture medium.

6. A method of producing an antibody or antigen binding fragment comprising:
   culturing a host cell comprising one or more polynucleotides encoding any one of the antibodies or antigen binding fragments of claim 3 under conditions favorable to expression of the polynucleotide; and optionally, recovering the antibody or antigen binding fragment from the host cell and/or culture medium.

7. A method of treating cancer in a subject comprising administering to the subject an effective amount of the antibody or antigen binding fragment of claim 1, or of an expression vector which mediates expression of the antibody or antigen binding fragment within the subject, optionally in association with a further therapeutic agent or therapeutic procedure.

8. A method of treating cancer in a subject comprising administering to the subject an effective amount of the antibody or antigen binding fragment of claim 3, or of an expression vector which mediates expression of the antibody or antigen binding fragment within the subject, optionally in association with a further therapeutic agent or therapeutic procedure.

9. A method according to claim 7, wherein the subject is a human.

10. A method according to claim 8, wherein the subject is a human.

* * * * *